United States Patent
Patel et al.

(10) Patent No.: US 9,775,627 B2
(45) Date of Patent: Oct. 3, 2017

(54) SYSTEMS AND METHODS FOR CREATING CURVED PATHS THROUGH BONE AND MODULATING NERVES WITHIN THE BONE

(71) Applicant: Relievant Medsystems, Inc., Redwood City, CA (US)

(72) Inventors: Samit Patel, San Francisco, CA (US); Richard C. Pellegrino, Leesburg, VA (US); Robert Flager, Pleasanton, CA (US)

(73) Assignee: Relievant Medsystems, Inc., Redwood City, CA (US)

(*) Notice: Subject to any disclaimer, the term of this patent is extended or adjusted under 35 U.S.C. 154(b) by 395 days.

(21) Appl. No.: 14/440,050

(22) PCT Filed: Nov. 1, 2013

(86) PCT No.: PCT/US2013/068012
§ 371 (c)(1),
(2) Date: Apr. 30, 2015

(87) PCT Pub. No.: WO2014/071161
PCT Pub. Date: May 8, 2014

(65) Prior Publication Data
US 2015/0297246 A1    Oct. 22, 2015

Related U.S. Application Data

(60) Provisional application No. 61/722,750, filed on Nov. 5, 2012.

(51) Int. Cl.
*A61B 17/16*    (2006.01)
*A61B 17/17*    (2006.01)
(Continued)

(52) U.S. Cl.
CPC ...... *A61B 17/1642* (2013.01); *A61B 17/1671* (2013.01); *A61B 17/1757* (2013.01);
(Continued)

(58) Field of Classification Search
CPC ............ A61B 17/1671; A61B 17/1757; A61B 17/3472; A61B 17/3478; A61B 17/1642
See application file for complete search history.

(56) References Cited

U.S. PATENT DOCUMENTS 3,845,771 A    11/1974    Vise
3,920,021 A    11/1975    Hiltebrandt
(Continued)

FOREIGN PATENT DOCUMENTS

EP    0040658    12/1981
EP    0584959    3/1994
(Continued)

OTHER PUBLICATIONS

Ullrich, Jr. Peter F., "Lumbar Spinal Fusion Surgery" Jan. 9, 2013, Spine-Health (available via wayback machine Internet archive at http://web.archive.org/web/20130109095419/http://www/spine-health.come/treatement/spinal-fusion/lumbar-spinal-fusion-surgery.
(Continued)

*Primary Examiner* — Christian Sevilla
(74) *Attorney, Agent, or Firm* — Knobbe, Martens, Olson & Bear LLP

(57) ABSTRACT

System and methods for channeling a path into bone include a trocar having a proximal end, distal end and a central channel disposed along a central axis of the trocar. The trocar includes a distal opening at or near the distal end of the trocar. The system includes a curved cannula sized to be received in the central channel, and having a curved distal end configured to be extended laterally outward from the
(Continued)

distal opening in a curved path extending away from the trocar. The curved cannula has a central passageway having a diameter configured allow a probe to be delivered through the central passageway to a location beyond the curved path.

20 Claims, 62 Drawing Sheets

(51) Int. Cl.
 A61B 17/88 (2006.01)
 A61B 17/34 (2006.01)
 A61B 18/14 (2006.01)
 A61B 17/00 (2006.01)
 A61B 17/32 (2006.01)
 A61B 18/02 (2006.01)
 A61B 18/06 (2006.01)
 A61B 18/18 (2006.01)
 A61B 18/20 (2006.01)
 A61B 18/00 (2006.01)
 A61B 18/16 (2006.01)

(52) U.S. Cl.
 CPC ...... *A61B 17/3472* (2013.01); *A61B 17/3478* (2013.01); *A61B 17/8805* (2013.01); *A61B 18/1492* (2013.01); *A61B 17/320068* (2013.01); *A61B 18/02* (2013.01); *A61B 18/06* (2013.01); *A61B 18/1815* (2013.01); *A61B 18/20* (2013.01); *A61B 2017/00261* (2013.01); *A61B 2017/00314* (2013.01); *A61B 2017/00331* (2013.01); *A61B 2018/0044* (2013.01); *A61B 2018/00577* (2013.01); *A61B 2018/00994* (2013.01); *A61B 2018/162* (2013.01); *A61B 2018/1807* (2013.01)

(56) References Cited

U.S. PATENT DOCUMENTS

| | | |
|---|---|---|
| 4,044,774 A | 8/1977 | Corgin et al. |
| 4,116,198 A | 9/1978 | Roos |
| 4,312,364 A | 1/1982 | Convert et al. |
| 4,448,198 A | 5/1984 | Turner |
| 4,573,448 A | 3/1986 | Kambin |
| 4,657,017 A | 4/1987 | Sorochenko |
| 4,679,561 A | 7/1987 | Doss |
| 4,754,757 A | 7/1988 | Feucht |
| 4,907,589 A | 3/1990 | Cosman |
| 4,950,267 A | 8/1990 | Ishihara et al. |
| 4,959,063 A | 9/1990 | Kojima |
| 4,963,142 A | 10/1990 | Loertscher |
| 4,966,144 A | 10/1990 | Rochkind et al. |
| 5,061,266 A | 10/1991 | Hakky |
| 5,080,660 A | 1/1992 | Buelna |
| 5,084,043 A | 1/1992 | Hertzmann et al. |
| 5,098,431 A | 3/1992 | Rydell |
| 5,106,376 A | 4/1992 | Mononen et al. |
| 5,108,404 A | 4/1992 | Scholten et al. |
| 5,161,533 A | 11/1992 | Prass et al. |
| 5,190,546 A | 3/1993 | Jervis |
| 5,201,729 A | 4/1993 | Hertzmann et al. |
| 5,209,748 A | 5/1993 | Daikuzono |
| 5,222,953 A | 6/1993 | Dowlatshahi |
| 5,242,439 A | 9/1993 | Larsen et al. |
| 5,273,026 A | 12/1993 | Wilk |
| 5,281,213 A | 1/1994 | Milder et al. |
| 5,295,484 A | 3/1994 | Marcus et al. |
| 5,314,463 A | 5/1994 | Camps et al. |
| 5,320,617 A | 6/1994 | Leach |
| 5,350,377 A | 9/1994 | Winston et al. |
| 5,366,443 A | 11/1994 | Eggers et al. |
| 5,368,031 A | 11/1994 | Cline et al. |
| 5,374,265 A | 12/1994 | Sand |
| 5,391,197 A | 2/1995 | Burdette et al. |
| 5,405,376 A | 4/1995 | Mulier et al. |
| 5,419,767 A | 5/1995 | Eggers et al. |
| 5,431,649 A | 7/1995 | Mulier et al. |
| 5,433,739 A | 7/1995 | Sluijter et al. |
| 5,437,661 A | 8/1995 | Rieser |
| 5,441,499 A | 8/1995 | Fritzsch |
| 5,443,463 A | 8/1995 | Stern et al. |
| 5,458,596 A | 10/1995 | Lax et al. |
| 5,458,597 A | 10/1995 | Edwards et al. |
| 5,472,441 A | 12/1995 | Edwards et al. |
| 5,484,432 A | 1/1996 | Sand |
| 5,486,170 A | 1/1996 | Winston et al. |
| 5,514,130 A | 5/1996 | Baker |
| 5,540,681 A | 7/1996 | Strul et al. |
| 5,540,684 A | 7/1996 | Hassler, Jr. |
| 5,569,242 A | 10/1996 | Lax et al. |
| 5,571,147 A | 11/1996 | Sluijter et al. |
| 5,596,988 A | 1/1997 | Markle et al. |
| 5,609,151 A | 3/1997 | Mulier et al. |
| 5,620,479 A | 4/1997 | Diederich |
| 5,630,426 A | 5/1997 | Shmulewitz et al. |
| 5,630,837 A | 5/1997 | Crowley |
| 5,643,319 A | 7/1997 | Green et al. |
| 5,647,871 A | 7/1997 | Levine et al. |
| 5,672,173 A | 9/1997 | Gough et al. |
| 5,681,282 A | 10/1997 | Eggers et al. |
| 5,683,366 A | 11/1997 | Eggers et al. |
| 5,693,052 A | 12/1997 | Weaver |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,927 A | 12/1997 | Imran et al. |
| 5,700,262 A | 12/1997 | Acosta et al. |
| 5,720,287 A | 2/1998 | Chapelon et al. |
| 5,725,494 A | 3/1998 | Brisken |
| 5,728,062 A | 3/1998 | Brisken |
| 5,733,315 A | 3/1998 | Burdette et al. |
| 5,735,280 A | 4/1998 | Sherman et al. |
| 5,735,811 A | 4/1998 | Brisken |
| 5,735,847 A | 4/1998 | Gough et al. |
| 5,738,680 A | 4/1998 | Mueller et al. |
| 5,743,904 A | 4/1998 | Edwards |
| 5,746,737 A | 5/1998 | Saadat |
| 5,752,969 A | 5/1998 | Cunci et al. |
| 5,762,066 A | 6/1998 | Law et al. |
| 5,762,616 A | 6/1998 | Talish |
| 5,766,153 A | 6/1998 | Eggers et al. |
| 5,776,092 A | 7/1998 | Farin et al. |
| 5,785,705 A | 7/1998 | Baker |
| 5,800,378 A | 9/1998 | Edwards et al. |
| 5,807,237 A | 9/1998 | Tindel |
| 5,807,392 A | 9/1998 | Eggers |
| 5,807,395 A | 9/1998 | Mulier et al. |
| 5,810,764 A | 9/1998 | Eggers et al. |
| 5,817,021 A | 10/1998 | Reichenberger |
| 5,843,019 A | 12/1998 | Eggers et al. |
| 5,843,021 A | 12/1998 | Edwards et al. |
| 5,846,218 A | 12/1998 | Brisken et al. |
| 5,849,011 A | 12/1998 | Jones et al. |
| 5,855,576 A | 1/1999 | LeVeen et al. |
| 5,860,951 A | 1/1999 | Eggers et al. |
| 5,865,788 A | 2/1999 | Edwards et al. |
| 5,868,740 A | 2/1999 | LeVeen et al. |
| 5,871,469 A | 2/1999 | Eggers et al. |
| 5,871,470 A | 2/1999 | McWha |
| 5,871,481 A | 2/1999 | Kannenberg et al. |
| 5,873,855 A | 2/1999 | Eggers et al. |
| 5,873,877 A | 2/1999 | McGaffigan et al. |
| 5,876,398 A | 3/1999 | Mulier et al. |
| 5,888,198 A | 3/1999 | Eggers et al. |
| 5,891,095 A | 4/1999 | Eggers et al. |
| 5,895,370 A | 4/1999 | Edwards et al. |
| 5,902,272 A | 5/1999 | Eggers et al. |
| 5,904,681 A | 5/1999 | West, Jr. |
| 5,906,613 A | 5/1999 | Mulier et al. |
| 5,916,213 A | 6/1999 | Haissaguerre et al. |
| 5,916,214 A | 6/1999 | Cosio |

(56) References Cited

U.S. PATENT DOCUMENTS

| | | |
|---|---|---|
| 5,919,188 A | 7/1999 | Shearon et al. |
| 5,931,805 A | 8/1999 | Brisken |
| 5,935,123 A | 8/1999 | Edwards et al. |
| 5,938,582 A | 8/1999 | Ciamacco et al. |
| 5,941,722 A | 8/1999 | Chen |
| 5,941,876 A | 8/1999 | Nardella et al. |
| 5,944,715 A | 8/1999 | Goble et al. |
| 5,948,007 A | 9/1999 | Starkebaum et al. |
| 5,948,008 A | 9/1999 | Daikuzono |
| 5,954,716 A | 9/1999 | Sharkey et al. |
| 5,964,727 A | 10/1999 | Edwards et al. |
| 5,967,988 A | 10/1999 | Briscoe et al. |
| 5,983,141 A | 11/1999 | Sluijter et al. |
| 5,997,497 A | 12/1999 | Nita et al. |
| 6,001,095 A | 12/1999 | de la Rama et al. |
| 6,007,533 A | 12/1999 | Casscells et al. |
| 6,007,570 A | 12/1999 | Sharkey et al. |
| 6,012,457 A | 1/2000 | Lesh |
| 6,016,452 A | 1/2000 | Kasevich |
| 6,016,809 A | 1/2000 | Mulier et al. |
| 6,017,356 A | 1/2000 | Frederick et al. |
| 6,019,776 A | 2/2000 | Preissman et al. |
| 6,022,334 A | 2/2000 | Edwards et al. |
| 6,024,733 A | 2/2000 | Eggers et al. |
| 6,024,740 A | 2/2000 | Lesh et al. |
| 6,030,402 A | 2/2000 | Thompson et al. |
| 6,032,674 A | 3/2000 | Eggers et al. |
| 6,033,411 A | 3/2000 | Preissman et al. |
| 6,035,238 A | 3/2000 | Ingle et al. |
| 6,045,532 A | 4/2000 | Eggers et al. |
| 6,050,995 A | 4/2000 | Durgin |
| 6,053,172 A | 4/2000 | Hovda et al. |
| 6,053,909 A | 4/2000 | Shadduck |
| 6,063,078 A | 5/2000 | Wittkampf |
| 6,063,079 A | 5/2000 | Hovda et al. |
| 6,066,134 A | 5/2000 | Eggers et al. |
| 6,068,642 A | 5/2000 | Johnson et al. |
| 6,073,051 A | 6/2000 | Sharkey et al. |
| 6,086,585 A | 7/2000 | Hovda et al. |
| 6,090,105 A | 7/2000 | Zepeda et al. |
| 6,095,149 A | 8/2000 | Sharkey et al. |
| 6,099,499 A | 8/2000 | Ciamacco |
| 6,099,514 A | 8/2000 | Sharkey et al. |
| 6,102,046 A | 8/2000 | Weinstein et al. |
| 6,104,957 A | 8/2000 | Alo et al. |
| 6,105,581 A | 8/2000 | Eggers et al. |
| 6,106,454 A | 8/2000 | Berg et al. |
| 6,109,268 A | 8/2000 | Thapliyal et al. |
| 6,113,597 A | 9/2000 | Eggers et al. |
| 6,117,101 A | 9/2000 | Diederich et al. |
| 6,117,109 A | 9/2000 | Eggers et al. |
| 6,117,128 A | 9/2000 | Gregory |
| 6,120,467 A | 9/2000 | Schallhorn |
| 6,122,549 A | 9/2000 | Sharkey et al. |
| 6,139,545 A | 10/2000 | Utley et al. |
| 6,142,992 A | 11/2000 | Cheng et al. |
| 6,143,019 A | 11/2000 | Motamedi et al. |
| 6,146,380 A | 11/2000 | Racz et al. |
| 6,149,620 A | 11/2000 | Baker et al. |
| 6,159,194 A | 12/2000 | Eggers et al. |
| 6,159,208 A | 12/2000 | Hovda et al. |
| 6,161,048 A | 12/2000 | Sluijter et al. |
| 6,164,283 A | 12/2000 | Lesh |
| 6,165,172 A | 12/2000 | Farley et al. |
| 6,168,593 B1 | 1/2001 | Sharkey et al. |
| 6,176,857 B1 | 1/2001 | Ashley |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,190,383 B1 | 2/2001 | Schmaltz et al. |
| 6,193,715 B1 | 2/2001 | Wrublewski et al. |
| 6,203,542 B1 | 3/2001 | Ellsberry et al. |
| 6,206,842 B1 | 3/2001 | Tu et al. |
| 6,210,393 B1 | 4/2001 | Brisken |
| 6,210,402 B1 | 4/2001 | Olsen et al. |
| 6,210,415 B1 | 4/2001 | Bester |
| 6,221,038 B1 | 4/2001 | Brisken |
| 6,224,592 B1 | 5/2001 | Eggers et al. |
| 6,228,046 B1 | 5/2001 | Brisken |
| 6,228,078 B1 | 5/2001 | Eggers et al. |
| 6,228,082 B1 | 5/2001 | Baker et al. |
| 6,231,571 B1 | 5/2001 | Ellman et al. |
| 6,231,615 B1 | 5/2001 | Preissman |
| 6,235,020 B1 | 5/2001 | Cheng et al. |
| 6,235,024 B1 | 5/2001 | Tu |
| 6,238,391 B1 | 5/2001 | Olsen et al. |
| 6,238,393 B1 | 5/2001 | Mulier et al. |
| 6,241,665 B1 | 6/2001 | Negus et al. |
| 6,241,725 B1 | 6/2001 | Cosman |
| 6,245,064 B1 | 6/2001 | Lesh |
| 6,246,912 B1 | 6/2001 | Sluijter et al. |
| 6,254,553 B1 | 7/2001 | Lidgren et al. |
| 6,254,599 B1 | 7/2001 | Lesh et al. |
| 6,254,600 B1 | 7/2001 | Willink et al. |
| 6,258,086 B1 | 7/2001 | Ashley et al. |
| 6,259,952 B1 | 7/2001 | Sluijter |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,659 B1 | 7/2001 | Ross et al. |
| 6,267,770 B1 | 7/2001 | Truwit |
| 6,277,112 B1 | 8/2001 | Underwood et al. |
| 6,277,122 B1 | 8/2001 | McGahan et al. |
| 6,280,441 B1 | 8/2001 | Ryan |
| 6,283,961 B1 | 9/2001 | Underwood et al. |
| 6,287,114 B1 | 9/2001 | Meller et al. |
| 6,287,272 B1 | 9/2001 | Brisken et al. |
| 6,287,304 B1 | 9/2001 | Eggers et al. |
| 6,290,715 B1 | 9/2001 | Sharkey et al. |
| 6,296,619 B1 | 10/2001 | Brisken et al. |
| 6,296,636 B1 | 10/2001 | Cheng et al. |
| 6,296,638 B1 | 10/2001 | Davison et al. |
| 6,305,378 B1 | 10/2001 | Lesh et al. |
| 6,309,387 B1 | 10/2001 | Eggers et al. |
| 6,309,420 B1 | 10/2001 | Preissman |
| 6,312,408 B1 | 11/2001 | Eggers et al. |
| 6,312,426 B1 | 11/2001 | Goldberg et al. |
| 6,322,549 B1 | 11/2001 | Eggers et al. |
| 6,348,055 B1 | 2/2002 | Preissman |
| 6,355,032 B1 | 3/2002 | Hovda et al. |
| 6,356,790 B1 | 3/2002 | Maguire et al. |
| 6,363,937 B1 | 4/2002 | Hovda et al. |
| 6,379,351 B1 | 4/2002 | Thapliyal et al. |
| 6,383,190 B1 | 5/2002 | Preissman |
| 6,391,025 B1 | 5/2002 | Weinstein et al. |
| 6,416,507 B1 | 7/2002 | Eggers et al. |
| 6,416,508 B1 | 7/2002 | Eggers et al. |
| 6,423,059 B1 | 7/2002 | Hanson et al. |
| 6,432,103 B1 | 8/2002 | Ellsberry et al. |
| 6,436,060 B1 | 8/2002 | Talish |
| 6,451,013 B1 | 9/2002 | Bays et al. |
| 6,454,727 B1 | 9/2002 | Bubank et al. |
| 6,461,350 B1 | 10/2002 | Underwood et al. |
| 6,461,354 B1 | 10/2002 | Olsen et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,478,793 B1 | 11/2002 | Cosman et al. |
| 6,482,201 B1 | 11/2002 | Olsen et al. |
| 6,487,446 B1 | 11/2002 | Hill et al. |
| 6,494,902 B2 | 12/2002 | Hoey et al. |
| 6,500,173 B2 | 12/2002 | Underwood et al. |
| 6,505,075 B1 | 1/2003 | Weiner |
| 6,527,759 B1 | 3/2003 | Tachibana et al. |
| 6,540,741 B1 | 4/2003 | Underwood et al. |
| 6,544,261 B2 | 4/2003 | Ellsberry et al. |
| 6,557,559 B1 | 5/2003 | Eggers et al. |
| 6,558,385 B1 | 5/2003 | McClurken et al. |
| 6,560,486 B1 | 5/2003 | Osorio et al. |
| 6,562,033 B2 | 5/2003 | Shah et al. |
| 6,575,968 B1 | 6/2003 | Eggers et al. |
| 6,582,423 B1 | 6/2003 | Thapliyal et al. |

(56) References Cited

U.S. PATENT DOCUMENTS

| | | |
|---|---|---|
| 6,585,656 B2 | 7/2003 | Masters |
| 6,589,237 B2 | 7/2003 | Woloszko et al. |
| 6,595,990 B1 | 7/2003 | Weinstein et al. |
| 6,602,248 B1 | 8/2003 | Sharps et al. |
| 6,607,529 B1 | 8/2003 | Jones et al. |
| 6,622,731 B2 | 9/2003 | Daniel et al. |
| 6,632,193 B1 | 10/2003 | Davison et al. |
| 6,632,220 B1 | 10/2003 | Eggers et al. |
| 6,648,883 B2 | 11/2003 | Francischelli et al. |
| 6,659,106 B1 | 12/2003 | Hovda et al. |
| 6,663,627 B2 | 12/2003 | Francischelli et al. |
| 6,692,450 B1 | 2/2004 | Coleman |
| 6,699,240 B2 | 3/2004 | Francischelli |
| 6,699,242 B2 | 3/2004 | Heggeness |
| 6,709,432 B2 | 3/2004 | Ferek-Patric |
| 6,718,208 B2 | 4/2004 | Hill et al. |
| 6,723,087 B2 | 4/2004 | O'Neill et al. |
| 6,726,684 B1 | 4/2004 | Woloszko et al. |
| 6,736,810 B2 | 5/2004 | Hoey et al. |
| 6,736,835 B2 | 5/2004 | Pellegrino et al. |
| 6,745,079 B2 | 6/2004 | King |
| 6,746,447 B2 | 6/2004 | Davison et al. |
| 6,749,604 B1 | 6/2004 | Eggers et al. |
| 6,758,846 B2 | 7/2004 | Goble et al. |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,827,715 B2 | 12/2004 | Francischelli et al. |
| 6,827,716 B2 | 12/2004 | Ryan et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,852,091 B2 | 2/2005 | Edwards et al. |
| 6,863,672 B2 | 3/2005 | Reiley et al. |
| 6,875,219 B2 | 4/2005 | Arramon et al. |
| 6,881,214 B2 | 4/2005 | Cosman et al. |
| 6,896,674 B1 | 5/2005 | Woloszko et al. |
| 6,896,675 B2 | 5/2005 | Leung et al. |
| 6,907,884 B2 | 6/2005 | Pellegrino et al. |
| 6,915,806 B2 | 7/2005 | Pacek et al. |
| 6,922,579 B2 | 7/2005 | Taimisto et al. |
| 6,923,813 B2 | 8/2005 | Phillips et al. |
| 6,936,046 B2 | 8/2005 | Hissong et al. |
| 6,955,674 B2 | 10/2005 | Eick et al. |
| 6,960,204 B2 | 11/2005 | Eggers et al. |
| 6,962,589 B2 | 11/2005 | Mulier et al. |
| 6,974,453 B2 | 12/2005 | Woloszko et al. |
| 6,989,010 B2 | 1/2006 | Francischelli et al. |
| 6,997,941 B2 | 2/2006 | Sharkey et al. |
| 7,048,743 B2 | 5/2006 | Miller et al. |
| 7,090,672 B2 | 8/2006 | Underwood et al. |
| 7,104,989 B2 | 9/2006 | Skarda |
| 7,131,969 B1 | 11/2006 | Hovda et al. |
| 7,177,678 B2 | 2/2007 | Osorio et al. |
| 7,179,255 B2 | 2/2007 | Lettice et al. |
| 7,186,234 B2 | 3/2007 | Dahla et al. |
| 7,192,428 B2 | 3/2007 | Eggers et al. |
| 7,201,731 B1 | 4/2007 | Lundquist et al. |
| 7,201,750 B1 | 4/2007 | Eggers et al. |
| 7,211,055 B2 | 5/2007 | Diederich et al. |
| 7,217,268 B2 | 5/2007 | Eggers et al. |
| 7,250,048 B2 | 7/2007 | Francischelli et al. |
| 7,258,690 B2 | 8/2007 | Sutton et al. |
| 7,270,659 B2 | 9/2007 | Ricart et al. |
| 7,270,661 B2 | 9/2007 | Dahla et al. |
| 7,276,063 B2 | 10/2007 | Davison et al. |
| 7,294,127 B2 | 11/2007 | Leung et al. |
| 7,305,264 B2 | 12/2007 | Larson et al. |
| 7,306,596 B2 | 12/2007 | Hillier et al. |
| 7,318,823 B2 | 1/2008 | Sharps et al. |
| 7,326,203 B2 | 2/2008 | Papineau et al. |
| 7,331,956 B2 | 2/2008 | Hovda et al. |
| 7,331,957 B2 | 2/2008 | Woloszko et al. |
| RE40,156 E | 3/2008 | Sharps et al. |
| 7,346,391 B1 | 3/2008 | Osorio et al. |
| 7,386,350 B2 | 6/2008 | Vilims |
| 7,387,625 B2 | 6/2008 | Hovda et al. |
| 7,393,351 B2 | 7/2008 | Woloszko et al. |
| 7,422,585 B1 | 9/2008 | Eggers et al. |
| 7,429,262 B2 | 9/2008 | Woloszko et al. |
| 7,435,247 B2 | 10/2008 | Woloszko et al. |
| 7,435,250 B2 | 10/2008 | Francischelli et al. |
| 7,442,191 B2 | 10/2008 | Hovda et al. |
| 7,468,059 B2 | 12/2008 | Eggers et al. |
| 7,480,533 B2 | 1/2009 | Cosman et al. |
| 7,502,652 B2 | 3/2009 | Gaunt et al. |
| 7,503,920 B2 | 3/2009 | Siegal |
| 7,507,236 B2 | 3/2009 | Eggers et al. |
| 7,546,164 B2 | 6/2009 | King |
| 7,553,307 B2 | 6/2009 | Bleich et al. |
| 7,555,343 B2 | 6/2009 | Bleich |
| 7,593,778 B2 | 9/2009 | Chandran et al. |
| 7,645,277 B2 | 1/2010 | McClurken et al. |
| 7,678,111 B2 | 3/2010 | Mulier et al. |
| 7,708,733 B2 | 5/2010 | Sanders et al. |
| 7,738,968 B2 | 6/2010 | Bleich |
| 7,740,631 B2 | 6/2010 | Bleich et al. |
| 7,749,218 B2 | 7/2010 | Pellegrino et al. |
| 7,749,220 B2 | 7/2010 | Schmaltz et al. |
| 7,819,826 B2 | 10/2010 | Diederich et al. |
| 7,819,869 B2 | 10/2010 | Godara et al. |
| 7,824,398 B2 | 11/2010 | Woloszko et al. |
| 7,824,404 B2 | 11/2010 | Godara et al. |
| 7,850,685 B2 | 12/2010 | Kunis et al. |
| 7,857,813 B2 | 12/2010 | Schmitz et al. |
| 7,896,870 B2 | 3/2011 | Arless et al. |
| 7,901,403 B2 | 3/2011 | Woloszko et al. |
| 7,909,827 B2 | 3/2011 | Reiley et al. |
| 7,914,526 B2 | 3/2011 | Lehmann et al. |
| 7,917,222 B1 | 3/2011 | Osorio et al. |
| 7,918,849 B2 | 4/2011 | Bleich et al. |
| 7,918,874 B2 | 4/2011 | Seigal |
| 7,945,331 B2 | 5/2011 | Vilims |
| 7,951,140 B2 | 5/2011 | Arless et al. |
| 7,959,634 B2 | 6/2011 | Sennett |
| 7,963,915 B2 | 6/2011 | Bleich |
| 8,021,401 B2 | 9/2011 | Carl et al. |
| 8,034,052 B2 | 10/2011 | Podhajsky |
| 8,062,290 B2 | 11/2011 | Buysse et al. |
| 8,066,702 B2 | 11/2011 | Rittman, III et al. |
| 8,083,736 B2 | 12/2011 | McClurken et al. |
| 8,100,896 B2 | 1/2012 | Podhajsky |
| 8,128,633 B2 | 3/2012 | Linderman et al. |
| 8,162,933 B2 | 4/2012 | Francischelli et al. |
| 8,172,846 B2 | 5/2012 | Brunnett et al. |
| 8,182,477 B2 | 5/2012 | Orszulak et al. |
| 8,192,424 B2 | 6/2012 | Woloszko |
| 8,192,435 B2 | 6/2012 | Bleich et al. |
| 8,265,747 B2 | 9/2012 | Rittman, III et al. |
| 8,282,628 B2 | 10/2012 | Paul et al. |
| 8,292,887 B2 | 10/2012 | Woloszko et al. |
| 8,323,279 B2 | 12/2012 | Dahla et al. |
| 8,348,946 B2 | 1/2013 | McClurken et al. |
| 8,355,799 B2 | 1/2013 | Marion et al. |
| 8,361,067 B2 | 1/2013 | Pellegrino et al. |
| 8,414,509 B2 | 4/2013 | Diederich et al. |
| 8,414,571 B2 | 4/2013 | Pellegrino et al. |
| 8,419,730 B2 | 4/2013 | Pellegrino et al. |
| 8,419,731 B2 | 4/2013 | Pellegrino et al. |
| 8,425,507 B2 | 4/2013 | Pellegrino et al. |
| 8,444,640 B2 | 5/2013 | Demarais et al. |
| 8,454,594 B2 | 6/2013 | Demarais et al. |
| 8,475,449 B2 | 7/2013 | Werneth et al. |
| 8,486,063 B2 | 7/2013 | Werneth et al. |
| 8,504,147 B2 | 8/2013 | Deem et al. |
| 8,535,309 B2 | 9/2013 | Pellegrino et al. |
| 8,579,903 B2 | 11/2013 | Carl |
| 8,597,301 B2 | 12/2013 | Mitchell |
| 8,613,744 B2 | 12/2013 | Pellegrino et al. |
| 8,617,156 B2 | 12/2013 | Werneth et al. |
| 8,623,014 B2 | 1/2014 | Pellegrino et al. |
| 8,628,528 B2 | 1/2014 | Pellegrino et al. |
| 8,644,941 B2 | 2/2014 | Rooney et al. |
| 8,657,814 B2 | 2/2014 | Werneth et al. |

(56) References Cited

U.S. PATENT DOCUMENTS

| | | |
|---|---|---|
| 8,676,309 B2 | 3/2014 | Deem et al. |
| 8,690,884 B2 | 4/2014 | Linderman et al. |
| 8,747,359 B2 | 6/2014 | Pakter et al. |
| 8,747,398 B2 | 6/2014 | Behnke |
| 8,758,349 B2 | 6/2014 | Germain et al. |
| 8,771,276 B2 | 7/2014 | Linderman |
| 8,774,913 B2 | 7/2014 | Demarais et al. |
| 8,774,924 B2 | 7/2014 | Weiner |
| 8,795,270 B2 | 8/2014 | Drake |
| 8,808,284 B2 | 8/2014 | Pellegrino et al. |
| 8,821,488 B2 | 9/2014 | Stewart et al. |
| 8,845,631 B2 | 9/2014 | Werneth et al. |
| 8,882,755 B2 | 11/2014 | Leung et al. |
| 8,882,759 B2 | 11/2014 | Manley et al. |
| 8,882,764 B2 | 11/2014 | Pellegrino et al. |
| 8,894,658 B2 | 11/2014 | Linderman et al. |
| 8,926,620 B2 | 1/2015 | Chasmawala et al. |
| 8,968,288 B2 | 3/2015 | Brannan |
| 8,989,859 B2 | 3/2015 | Deem et al. |
| 8,992,522 B2 | 3/2015 | Pellegrino et al. |
| 8,992,523 B2 | 3/2015 | Pellegrino et al. |
| 9,017,325 B2 | 4/2015 | Pellegrino et al. |
| 9,023,038 B2 | 5/2015 | Pellegrino et al. |
| 9,028,488 B2 | 5/2015 | Goshayeshgar |
| 9,028,538 B2 | 5/2015 | Paul et al. |
| 9,039,701 B2 | 5/2015 | Pellegrino et al. |
| 9,044,245 B2 | 6/2015 | Condie et al. |
| 9,044,254 B2 | 6/2015 | Ladtkow et al. |
| 9,044,575 B2 | 6/2015 | Beasley et al. |
| 9,095,359 B2 | 8/2015 | Behnke, II et al. |
| 9,113,896 B2 | 8/2015 | Mulier et al. |
| 9,113,911 B2 | 8/2015 | Sherman |
| 9,113,925 B2 | 8/2015 | Smith et al. |
| 9,119,647 B2 | 9/2015 | Brannan |
| 9,119,650 B2 | 9/2015 | Brannan et al. |
| 9,125,671 B2 | 9/2015 | Germain et al. |
| 9,131,597 B2 | 9/2015 | Taft et al. |
| 9,151,680 B2 | 10/2015 | Brannan |
| 9,155,895 B2 | 10/2015 | Wacnik et al. |
| 9,161,805 B2 | 10/2015 | Isenberg |
| 9,161,814 B2 | 10/2015 | Brannan et al. |
| 9,168,078 B2 | 10/2015 | Linderman et al. |
| 9,168,085 B2 | 10/2015 | Juzkiw |
| 9,173,676 B2 | 11/2015 | Pellegrino et al. |
| 9,173,700 B2 | 11/2015 | Godara et al. |
| 9,179,970 B2 | 11/2015 | Utley et al. |
| 9,186,197 B2 | 11/2015 | McKay |
| 9,192,308 B2 | 11/2015 | Brannan et al. |
| 9,198,684 B2 | 12/2015 | Arthur et al. |
| 9,226,756 B2 | 1/2016 | Teisen et al. |
| 9,238,139 B2 | 1/2016 | Degiorgio et al. |
| 9,241,760 B2 | 1/2016 | Godara et al. |
| 9,247,992 B2 | 2/2016 | Ladtkow et al. |
| 9,247,993 B2 | 2/2016 | Ladtkow et al. |
| 9,248,278 B2 | 2/2016 | Crosby et al. |
| 9,248,289 B2 | 2/2016 | Bennett et al. |
| 9,254,168 B2 | 2/2016 | Palanker |
| 9,254,386 B2 | 2/2016 | Lee et al. |
| 9,259,241 B2 | 2/2016 | Pellegrino et al. |
| 9,259,248 B2 | 2/2016 | Leuthardt et al. |
| 9,259,269 B2 | 2/2016 | Ladtkow et al. |
| 9,259,569 B2 | 2/2016 | Brounstein et al. |
| 9,259,577 B2 | 2/2016 | Kaula et al. |
| 9,265,522 B2 | 2/2016 | Pellegrino et al. |
| 9,265,557 B2 | 2/2016 | Sherman et al. |
| 9,277,969 B2 | 3/2016 | Brannan et al. |
| 9,282,988 B2 | 3/2016 | Goshayeshgar |
| 9,289,607 B2 | 3/2016 | Su et al. |
| 9,295,517 B2 | 3/2016 | Peyman et al. |
| 9,295,841 B2 | 3/2016 | Fang et al. |
| 9,301,723 B2 | 4/2016 | Brannan et al. |
| 9,301,804 B2 | 4/2016 | Bonn |
| 9,302,117 B2 | 4/2016 | De Vincentiis |
| 9,308,036 B2 | 4/2016 | Robinson |
| 9,308,045 B2 | 4/2016 | Kim et al. |
| 9,314,252 B2 | 4/2016 | Schaller et al. |
| 9,314,613 B2 | 4/2016 | Mashiach |
| 9,314,618 B2 | 4/2016 | Imran et al. |
| 9,333,144 B2 | 5/2016 | Baxter et al. |
| 9,333,339 B2 | 5/2016 | Weiner |
| 9,333,361 B2 | 5/2016 | Li et al. |
| 9,333,373 B2 | 5/2016 | Imran |
| 9,339,655 B2 | 5/2016 | Carbunaru |
| 9,345,530 B2 | 5/2016 | Ballakur et al. |
| 9,345,537 B2 | 5/2016 | Harrison et al. |
| 9,345,538 B2 | 5/2016 | Deem et al. |
| 9,351,739 B2 | 5/2016 | Mahoney et al. |
| 9,358,067 B2 | 6/2016 | Lee et al. |
| 9,358,396 B2 | 6/2016 | Holley |
| 9,364,286 B2 | 6/2016 | Werneth et al. |
| 9,370,348 B2 | 6/2016 | Tally et al. |
| 9,370,392 B2 | 6/2016 | Sharonov |
| 9,370,398 B2 | 6/2016 | Ladtkow et al. |
| 9,375,274 B2 | 6/2016 | Reid |
| 9,375,275 B2 | 6/2016 | Lee et al. |
| 9,375,278 B2 | 6/2016 | Behnke, II et al. |
| 9,375,279 B2 | 6/2016 | Brannan |
| 9,375,283 B2 | 6/2016 | Arts et al. |
| 9,381,045 B2 | 7/2016 | Donner et al. |
| 9,381,050 B2 | 7/2016 | Lee et al. |
| 9,381,359 B2 | 7/2016 | Parramon et al. |
| 9,387,094 B2 | 7/2016 | Manrique et al. |
| 9,393,416 B2 | 7/2016 | Rooney et al. |
| 9,398,931 B2 | 7/2016 | Wittenberger et al. |
| 9,399,144 B2 | 7/2016 | Howard |
| 9,403,038 B2 | 8/2016 | Tyler |
| 9,409,023 B2 | 8/2016 | Burdick et al. |
| 9,414,884 B2 | 8/2016 | Faehndrich et al. |
| 9,421,064 B2 | 8/2016 | Pellegrino et al. |
| 9,421,123 B2 | 8/2016 | Lee et al. |
| 9,421,371 B2 | 8/2016 | Pless et al. |
| 9,421,378 B2 | 8/2016 | Lian et al. |
| 9,439,721 B2 | 9/2016 | Werneth et al. |
| 9,445,859 B2 | 9/2016 | Pageard |
| 9,446,229 B2 | 9/2016 | Omar-Pasha |
| 9,446,235 B2 | 9/2016 | Su et al. |
| 9,452,286 B2 | 9/2016 | Cowan et al. |
| 9,456,836 B2 | 10/2016 | Boling et al. |
| 9,457,182 B2 | 10/2016 | Koop |
| 9,468,485 B2 | 10/2016 | Wittenberger et al. |
| 9,468,495 B2 | 10/2016 | Kunis et al. |
| 9,474,906 B2 | 10/2016 | Sachs et al. |
| 9,486,279 B2 | 11/2016 | Pellegrino et al. |
| 9,486,447 B2 | 11/2016 | Peterson et al. |
| 9,486,621 B2 | 11/2016 | Howard et al. |
| 9,492,657 B2 | 11/2016 | Gerber |
| 9,492,664 B2 | 11/2016 | Peterson |
| 9,504,372 B2 | 11/2016 | Kim |
| 9,504,518 B2 | 11/2016 | Condie et al. |
| 9,504,530 B2 | 11/2016 | Hartmann et al. |
| 9,504,818 B2 | 11/2016 | Moffitt et al. |
| 9,511,229 B2 | 12/2016 | Bradley |
| 9,511,231 B1 | 12/2016 | Kent et al. |
| 9,517,200 B2 | 12/2016 | Bleier |
| 9,526,507 B2 | 12/2016 | Germain |
| 9,526,551 B2 | 12/2016 | Linderman |
| 9,532,828 B2 | 1/2017 | Condie et al. |
| 9,549,772 B2 | 1/2017 | Carl |
| 9,550,041 B2 | 1/2017 | Bedell |
| 9,555,037 B2 | 1/2017 | Podhajsky |
| 9,566,449 B2 | 2/2017 | Perryman et al. |
| 9,572,976 B2 | 2/2017 | Howard et al. |
| 9,572,986 B2 | 2/2017 | Moffitt |
| 9,579,518 B2 | 2/2017 | Gertner |
| RE46,356 E | 4/2017 | Pellegrino et al. |
| 9,610,117 B2 | 4/2017 | Germain |
| 2001/0001314 A1 | 5/2001 | Davison et al. |
| 2001/0001811 A1 | 5/2001 | Burney et al. |
| 2001/0020167 A1 | 9/2001 | Woloszko et al. |
| 2001/0023348 A1 | 9/2001 | Ashley et al. |
| 2001/0025176 A1 | 9/2001 | Ellsberry et al. |
| 2001/0025177 A1 | 9/2001 | Woloszko et al. |
| 2001/0029370 A1 | 10/2001 | Hovda et al. |
| 2001/0029373 A1 | 10/2001 | Baker et al. |

(56) References Cited

U.S. PATENT DOCUMENTS

| | | |
|---|---|---|
| 2001/0032001 A1 | 10/2001 | Ricart et al. |
| 2001/0047167 A1 | 11/2001 | Heggeness |
| 2001/0049522 A1 | 12/2001 | Eggers et al. |
| 2001/0051802 A1 | 12/2001 | Woloszko et al. |
| 2001/0056280 A1 | 12/2001 | Underwood et al. |
| 2002/0016600 A1 | 2/2002 | Cosman |
| 2002/0019626 A1 | 2/2002 | Sharkey et al. |
| 2002/0026186 A1 | 2/2002 | Woloszko et al. |
| 2002/0052600 A1 | 5/2002 | Davison et al. |
| 2002/0068930 A1 | 6/2002 | Tasto et al. |
| 2002/0095144 A1 | 7/2002 | Carl |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0120259 A1 | 8/2002 | Lettice et al. |
| 2002/0147444 A1 | 10/2002 | Shah et al. |
| 2002/0151885 A1 | 10/2002 | Underwood et al. |
| 2002/0188284 A1 | 12/2002 | To et al. |
| 2002/0188290 A1 | 12/2002 | Sharkey et al. |
| 2002/0193789 A1 | 12/2002 | Underwood et al. |
| 2003/0009164 A1 | 1/2003 | Woloszko et al. |
| 2003/0014047 A1 | 1/2003 | Woloszko et al. |
| 2003/0028189 A1 | 2/2003 | Woloszko et al. |
| 2003/0040742 A1 | 2/2003 | Underwood et al. |
| 2003/0055418 A1 | 3/2003 | Tasto et al. |
| 2003/0083592 A1 | 5/2003 | Faciszewski |
| 2003/0084907 A1 | 5/2003 | Pacek et al. |
| 2003/0097126 A1 | 5/2003 | Woloszko et al. |
| 2003/0097129 A1 | 5/2003 | Davison et al. |
| 2003/0130655 A1 | 7/2003 | Woloszko et al. |
| 2003/0158545 A1 | 8/2003 | Hovda et al. |
| 2003/0181963 A1 | 9/2003 | Pellegrino et al. |
| 2003/0208194 A1 | 11/2003 | Hovda et al. |
| 2003/0216725 A1 | 11/2003 | Woloszko et al. |
| 2003/0216726 A1 | 11/2003 | Eggers et al. |
| 2003/0225364 A1 | 12/2003 | Kraft |
| 2004/0006339 A1 | 1/2004 | Underwood et al. |
| 2004/0024399 A1 | 2/2004 | Sharps et al. |
| 2004/0054366 A1 | 3/2004 | Davison et al. |
| 2004/0064137 A1 | 4/2004 | Pellegrino et al. |
| 2004/0068242 A1 | 4/2004 | McGuckin, Jr. |
| 2004/0087937 A1 | 5/2004 | Eggers et al. |
| 2004/0116922 A1 | 6/2004 | Hovda et al. |
| 2004/0133124 A1 | 7/2004 | Bates et al. |
| 2004/0162559 A1 | 8/2004 | Arramon |
| 2004/0186544 A1 | 9/2004 | King |
| 2004/0193151 A1 | 9/2004 | To et al. |
| 2004/0220577 A1 | 11/2004 | Cragg et al. |
| 2004/0225228 A1 | 11/2004 | Ferree |
| 2004/0230190 A1 | 11/2004 | Dahla et al. |
| 2005/0004634 A1 | 1/2005 | Ricart et al. |
| 2005/0010095 A1 | 1/2005 | Stewart et al. |
| 2005/0010203 A1 | 1/2005 | Edwards et al. |
| 2005/0010205 A1 | 1/2005 | Hovda et al. |
| 2005/0055096 A1 | 3/2005 | Serhan et al. |
| 2005/0177210 A1 | 8/2005 | Leung et al. |
| 2005/0177211 A1 | 8/2005 | Leung et al. |
| 2005/0182417 A1 | 8/2005 | Pagano |
| 2005/0192564 A1 | 9/2005 | Cosman et al. |
| 2005/0209659 A1 | 9/2005 | Pellegrino et al. |
| 2005/0234445 A1 | 10/2005 | Conquergood et al. |
| 2005/0267552 A1 | 12/2005 | Conquergood et al. |
| 2005/0278007 A1 | 12/2005 | Godara |
| 2005/0283148 A1 | 12/2005 | Janssen et al. |
| 2006/0004369 A1 | 1/2006 | Patel et al. |
| 2006/0064101 A1 | 3/2006 | Arramon |
| 2006/0095026 A1 | 5/2006 | Ricart et al. |
| 2006/0095028 A1 | 5/2006 | Bleich |
| 2006/0106375 A1 | 5/2006 | Werneth et al. |
| 2006/0106376 A1 | 5/2006 | Godara et al. |
| 2006/0122458 A1 | 6/2006 | Bleich |
| 2006/0129101 A1 | 6/2006 | McGuckin |
| 2006/0178670 A1 | 8/2006 | Woloszko et al. |
| 2006/0206128 A1 | 9/2006 | Conquergood et al. |
| 2006/0206129 A1 | 9/2006 | Conquergood et al. |
| 2006/0206130 A1 | 9/2006 | Conquergood et al. |
| 2006/0206132 A1 | 9/2006 | Conquergood et al. |
| 2006/0206133 A1 | 9/2006 | Conquergood et al. |
| 2006/0206134 A1 | 9/2006 | Conquergood et al. |
| 2006/0206166 A1 | 9/2006 | Weiner |
| 2006/0229625 A1 | 10/2006 | Truckai et al. |
| 2006/0253117 A1 | 11/2006 | Hovda et al. |
| 2006/0259026 A1 | 11/2006 | Godara et al. |
| 2006/0264957 A1 | 11/2006 | Cragg et al. |
| 2006/0265014 A1 | 11/2006 | Demarais et al. |
| 2006/0276749 A1 | 12/2006 | Selmon et al. |
| 2007/0027449 A1 | 2/2007 | Godara et al. |
| 2007/0055316 A1 | 3/2007 | Godara et al. |
| 2007/0118142 A1 | 5/2007 | Krueger et al. |
| 2007/0129715 A1 | 6/2007 | Eggers et al. |
| 2007/0142791 A1 | 6/2007 | Yeung et al. |
| 2007/0142842 A1 | 6/2007 | Krueger et al. |
| 2007/0149966 A1 | 6/2007 | Dahla et al. |
| 2007/0179497 A1 | 8/2007 | Eggers et al. |
| 2007/0260237 A1 | 11/2007 | Sutton et al. |
| 2008/0004621 A1 | 1/2008 | Dahla et al. |
| 2008/0004675 A1 | 1/2008 | King et al. |
| 2008/0009847 A1 | 1/2008 | Ricart et al. |
| 2008/0021447 A1 | 1/2008 | Davison et al. |
| 2008/0021463 A1* | 1/2008 | Georgy ............. A61B 17/8811 606/262 |
| 2008/0058707 A1 | 3/2008 | Ashley et al. |
| 2008/0065062 A1 | 3/2008 | Leung et al. |
| 2008/0091207 A1 | 4/2008 | Truckai et al. |
| 2008/0114364 A1 | 5/2008 | Goldin et al. |
| 2008/0119844 A1 | 5/2008 | Woloszko et al. |
| 2008/0119846 A1 | 5/2008 | Rioux |
| 2008/0132890 A1 | 6/2008 | Woloszko et al. |
| 2008/0161804 A1 | 7/2008 | Rioux et al. |
| 2008/0275458 A1 | 11/2008 | Bleich et al. |
| 2008/0281322 A1 | 11/2008 | Sherman et al. |
| 2008/0294166 A1 | 11/2008 | Goldin et al. |
| 2009/0030308 A1 | 1/2009 | Bradford et al. |
| 2009/0069807 A1 | 3/2009 | Eggers et al. |
| 2009/0105775 A1 | 4/2009 | Mitchell et al. |
| 2009/0112278 A1 | 4/2009 | Wingeier et al. |
| 2009/0118731 A1 | 5/2009 | Young et al. |
| 2009/0131867 A1 | 5/2009 | Liu et al. |
| 2009/0131886 A1 | 5/2009 | Liu et al. |
| 2009/0149878 A1 | 6/2009 | Truckai et al. |
| 2009/0222053 A1 | 9/2009 | Gaunt et al. |
| 2009/0312764 A1 | 12/2009 | Marino |
| 2010/0010392 A1 | 1/2010 | Skelton et al. |
| 2010/0016929 A1 | 1/2010 | Prochazka |
| 2010/0023006 A1 | 1/2010 | Ellman |
| 2010/0023065 A1 | 1/2010 | Welch et al. |
| 2010/0082033 A1 | 4/2010 | Germain |
| 2010/0094269 A1 | 4/2010 | Pellegrino et al. |
| 2010/0114098 A1 | 5/2010 | Carl |
| 2010/0145424 A1 | 6/2010 | Podhajsky et al. |
| 2010/0185082 A1 | 7/2010 | Chandran et al. |
| 2010/0185161 A1 | 7/2010 | Pellegrino et al. |
| 2010/0211076 A1 | 8/2010 | Germain et al. |
| 2010/0222777 A1 | 9/2010 | Sutton et al. |
| 2010/0261989 A1 | 10/2010 | Boseck et al. |
| 2010/0261990 A1 | 10/2010 | Gillis et al. |
| 2010/0298832 A1 | 11/2010 | Lau et al. |
| 2010/0324506 A1* | 12/2010 | Pellegrino ........... A61B 17/3472 604/272 |
| 2011/0022133 A1 | 1/2011 | Diederich et al. |
| 2011/0034884 A9 | 2/2011 | Pellegrino et al. |
| 2011/0040362 A1 | 2/2011 | Godara et al. |
| 2011/0077628 A1 | 3/2011 | Hoey et al. |
| 2011/0087314 A1 | 4/2011 | Diederich et al. |
| 2011/0118735 A1 | 5/2011 | Abou-Marie et al. |
| 2011/0196361 A1 | 8/2011 | Vilims |
| 2011/0264098 A1 | 10/2011 | Cobbs |
| 2011/0276001 A1 | 11/2011 | Schultz et al. |
| 2011/0295261 A1 | 12/2011 | Germain |
| 2011/0319765 A1 | 12/2011 | Gertner et al. |
| 2012/0029420 A1 | 2/2012 | Vilims |
| 2012/0123427 A1* | 5/2012 | McGuckin, Jr. ... A61B 17/3417 606/93 |
| 2012/0136346 A1 | 5/2012 | Condie et al. |

(56) References Cited

U.S. PATENT DOCUMENTS

| | | |
|---|---|---|
| 2012/0136348 A1 | 5/2012 | Condie et al. |
| 2012/0172858 A1 | 7/2012 | Harrison et al. |
| 2012/0172859 A1 | 7/2012 | Condie et al. |
| 2012/0196251 A1 | 8/2012 | Taft et al. |
| 2012/0197344 A1 | 8/2012 | Taft et al. |
| 2012/0203219 A1 | 8/2012 | Evans et al. |
| 2012/0226273 A1 | 9/2012 | Nguyen et al. |
| 2012/0239050 A1 | 9/2012 | Linderman |
| 2012/0265186 A1 | 10/2012 | Burger et al. |
| 2012/0330180 A1 | 12/2012 | Pellegrino et al. |
| 2012/0330300 A1 | 12/2012 | Pellegrino et al. |
| 2012/0330301 A1 | 12/2012 | Pellegrino et al. |
| 2013/0006232 A1 | 1/2013 | Pellegrino et al. |
| 2013/0006233 A1 | 1/2013 | Pellegrino et al. |
| 2013/0012933 A1 | 1/2013 | Pellegrino et al. |
| 2013/0012935 A1 | 1/2013 | Pellegrino et al. |
| 2013/0012936 A1 | 1/2013 | Pellegrino et al. |
| 2013/0012951 A1 | 1/2013 | Linderman |
| 2013/0079810 A1 | 3/2013 | Isenberg |
| 2013/0103022 A1 | 4/2013 | Sutton et al. |
| 2013/0231654 A1 | 9/2013 | Germain |
| 2013/0261507 A1 | 10/2013 | Diederich et al. |
| 2013/0324994 A1 | 12/2013 | Pellegrino et al. |
| 2013/0324996 A1 | 12/2013 | Pellegrino et al. |
| 2013/0324997 A1 | 12/2013 | Pellegrino et al. |
| 2013/0345765 A1 | 12/2013 | Brockman et al. |
| 2014/0031715 A1 | 1/2014 | Sherar et al. |
| 2014/0039500 A1 | 2/2014 | Pellegrino et al. |
| 2014/0046245 A1 | 2/2014 | Cornacchia |
| 2014/0066913 A1 | 3/2014 | Sherman |
| 2014/0088575 A1 | 3/2014 | Loeb |
| 2014/0148801 A1 | 5/2014 | Asher et al. |
| 2014/0148805 A1 | 5/2014 | Stewart et al. |
| 2014/0171942 A1 | 6/2014 | Werneth et al. |
| 2014/0221967 A1 | 8/2014 | Childs et al. |
| 2014/0236144 A1 | 8/2014 | Krueger et al. |
| 2014/0243943 A1 | 8/2014 | Rao et al. |
| 2014/0257265 A1 | 9/2014 | Godara et al. |
| 2014/0271717 A1 | 9/2014 | Goshayeshgar et al. |
| 2014/0276728 A1 | 9/2014 | Goshayeshgar et al. |
| 2014/0276744 A1 | 9/2014 | Arthur et al. |
| 2014/0288544 A1 | 9/2014 | Diederich et al. |
| 2014/0288546 A1 | 9/2014 | Sherman et al. |
| 2014/0296850 A1 | 10/2014 | Condie et al. |
| 2014/0316405 A1 | 10/2014 | Pellegrino et al. |
| 2014/0324051 A1 | 10/2014 | Pellegrino et al. |
| 2014/0336630 A1 | 11/2014 | Woloszko et al. |
| 2014/0336667 A1 | 11/2014 | Pellegrino et al. |
| 2014/0364842 A1 | 12/2014 | Werneth et al. |
| 2015/0005614 A1 | 1/2015 | Heggeness et al. |
| 2015/0005767 A1 | 1/2015 | Werneth et al. |
| 2015/0045783 A1 | 2/2015 | Edidin |
| 2015/0057658 A1 | 2/2015 | Sutton et al. |
| 2015/0065945 A1 | 3/2015 | Zarins et al. |
| 2015/0073515 A1 | 3/2015 | Turovskiy et al. |
| 2015/0157402 A1 | 6/2015 | Kunis et al. |
| 2015/0164546 A1 | 6/2015 | Pellegrino et al. |
| 2015/0196358 A1 | 7/2015 | Goshayeshgar |
| 2015/0216588 A1 | 8/2015 | Deem et al. |
| 2015/0231417 A1 | 8/2015 | Metcalf et al. |
| 2015/0272655 A1 | 10/2015 | Condie et al. |
| 2015/0335349 A1 | 11/2015 | Pellegrino et al. |
| 2015/0335382 A1 | 11/2015 | Pellegrino et al. |
| 2015/0342660 A1 | 12/2015 | Nash |
| 2015/0342670 A1 | 12/2015 | Pellegrino et al. |
| 2015/0359586 A1 | 12/2015 | Heggeness |
| 2015/0374432 A1 | 12/2015 | Godara et al. |
| 2015/0374992 A1 | 12/2015 | Crosby et al. |
| 2015/0374995 A1 | 12/2015 | Foreman et al. |
| 2016/0000601 A1 | 1/2016 | Burger et al. |
| 2016/0001096 A1 | 1/2016 | Mishelevich |
| 2016/0002627 A1 | 1/2016 | Bennett et al. |
| 2016/0008593 A1 | 1/2016 | Cairns |
| 2016/0008618 A1 | 1/2016 | Omar-Pasha |
| 2016/0008628 A1 | 1/2016 | Morries et al. |
| 2016/0016012 A1 | 1/2016 | Youn et al. |
| 2016/0022988 A1 | 1/2016 | Thieme et al. |
| 2016/0022994 A1 | 1/2016 | Moffitt et al. |
| 2016/0024208 A1 | 1/2016 | MacDonald et al. |
| 2016/0029930 A1 | 2/2016 | Plumley et al. |
| 2016/0030276 A1 | 2/2016 | Spanyer |
| 2016/0030408 A1 | 2/2016 | Levin |
| 2016/0030748 A1 | 2/2016 | Edgerton et al. |
| 2016/0030765 A1 | 2/2016 | Towne et al. |
| 2016/0051831 A1 | 2/2016 | Lundmark et al. |
| 2016/0059007 A1 | 3/2016 | Koop |
| 2016/0074068 A1 | 3/2016 | Patwardhan |
| 2016/0074279 A1 | 3/2016 | Shin |
| 2016/0074661 A1 | 3/2016 | Lipani |
| 2016/0081716 A1 | 3/2016 | Boling et al. |
| 2016/0095721 A1 | 4/2016 | Schell et al. |
| 2016/0106985 A1 | 4/2016 | Zhu |
| 2016/0106994 A1 | 4/2016 | Crosby et al. |
| 2016/0113704 A1 | 4/2016 | Godara et al. |
| 2016/0115173 A1 | 4/2016 | Bois et al. |
| 2016/0136310 A1 | 5/2016 | Bradford et al. |
| 2016/0144182 A1 | 5/2016 | Bennett et al. |
| 2016/0144187 A1 | 5/2016 | Caparso et al. |
| 2016/0158551 A1 | 6/2016 | Kent et al. |
| 2016/0166835 A1 | 6/2016 | De Ridder |
| 2016/0175586 A1 | 6/2016 | Edgerton et al. |
| 2016/0199097 A1 | 7/2016 | Linderman et al. |
| 2016/0213927 A1 | 7/2016 | McGee et al. |
| 2016/0220393 A1 | 8/2016 | Slivka et al. |
| 2016/0220638 A1 | 8/2016 | Dony et al. |
| 2016/0220672 A1 | 8/2016 | Chalasani et al. |
| 2016/0228131 A1 | 8/2016 | Brockman et al. |
| 2016/0228696 A1 | 8/2016 | Imran et al. |
| 2016/0235471 A1 | 8/2016 | Godara et al. |
| 2016/0235474 A1 | 8/2016 | Prisco et al. |
| 2016/0243353 A1 | 8/2016 | Ahmed |
| 2016/0246944 A1 | 8/2016 | Jain et al. |
| 2016/0250469 A1 | 9/2016 | Kim et al. |
| 2016/0250472 A1 | 9/2016 | Carbunaru |
| 2016/0262830 A1 | 9/2016 | Werneth et al. |
| 2016/0271405 A1 | 9/2016 | Angara et al. |
| 2016/0278791 A1 | 9/2016 | Pellegrino et al. |
| 2016/0278846 A1 | 9/2016 | Harrison et al. |
| 2016/0279190 A1 | 9/2016 | Watts et al. |
| 2016/0279408 A1 | 9/2016 | Grigsby et al. |
| 2016/0279411 A1 | 9/2016 | Rooney et al. |
| 2016/0279441 A1 | 9/2016 | Imran |
| 2016/0302925 A1 | 10/2016 | Keogh et al. |
| 2016/0310739 A1 | 10/2016 | Burdick et al. |
| 2016/0317053 A1 | 11/2016 | Srivastava |
| 2016/0317211 A1 | 11/2016 | Harrison et al. |
| 2016/0317621 A1 | 11/2016 | Bright |
| 2016/0324541 A1 | 11/2016 | Pellegrino et al. |
| 2016/0324677 A1 | 11/2016 | Hyde et al. |
| 2016/0325100 A1 | 11/2016 | Lian et al. |
| 2016/0339251 A1 | 11/2016 | Kent et al. |
| 2016/0354093 A1 | 12/2016 | Pellegrino et al. |
| 2016/0354233 A1 | 12/2016 | Sansone et al. |
| 2016/0367797 A1 | 12/2016 | Eckermann |
| 2016/0367823 A1 | 12/2016 | Cowan et al. |
| 2016/0375259 A1 | 12/2016 | Davis et al. |
| 2017/0001026 A1 | 1/2017 | Schwarz et al. |
| 2017/0007277 A1 | 1/2017 | Drapeau et al. |
| 2017/0014169 A1 | 1/2017 | Dean et al. |
| 2017/0027618 A1 | 2/2017 | Lee et al. |
| 2017/0028198 A1 | 2/2017 | Degiorgio et al. |
| 2017/0028201 A1 | 2/2017 | Howard |
| 2017/0035483 A1 | 2/2017 | Crainich et al. |
| 2017/0036009 A1 | 2/2017 | Hughes et al. |
| 2017/0036025 A1 | 2/2017 | Sachs et al. |
| 2017/0036033 A9 | 2/2017 | Perryman et al. |
| 2017/0042834 A1 | 2/2017 | Westphal et al. |
| 2017/0049503 A1 | 2/2017 | Cosman |
| 2017/0049507 A1 | 2/2017 | Cosman |
| 2017/0049513 A1 | 2/2017 | Cosman |
| 2017/0050017 A1 | 2/2017 | Cosman |
| 2017/0050021 A1 | 2/2017 | Cosman |
| 2017/0050024 A1 | 2/2017 | Bhadra et al. |
| 2017/0128080 A1 | 5/2017 | Torrie |

(56) References Cited

U.S. PATENT DOCUMENTS

FOREIGN PATENT DOCUMENTS

| | | |
|---|---|---|
| EP | 0597463 | 5/1994 |
| EP | 0880938 A1 | 12/1998 |
| EP | 1013228 | 6/2000 |
| EP | 1059067 | 12/2000 |
| EP | 1059087 | 12/2000 |
| JP | 06-47058 | 2/1994 |
| JP | 10-290806 | 11/1998 |
| JP | 2001-037760 | 2/2001 |
| JP | 2005-169012 | 6/2005 |
| WO | WO96/36289 | 11/1996 |
| WO | WO98/27876 | 7/1998 |
| WO | WO98/34550 | 8/1998 |
| WO | WO 99/19025 | 4/1999 |
| WO | WO 99/44519 | 9/1999 |
| WO | WO 99/48621 | 9/1999 |
| WO | WO 00/21448 | 4/2000 |
| WO | WO 00/33909 | 6/2000 |
| WO | WO 00/49978 | 8/2000 |
| WO | WO 00/56237 | 9/2000 |
| WO | WO 00/67648 | 11/2000 |
| WO | WO 00/67656 | 11/2000 |
| WO | WO01/01877 | 1/2001 |
| WO | WO01/45579 | 6/2001 |
| WO | WO01/57655 | 8/2001 |
| WO | WO02/05699 | 1/2002 |
| WO | WO02/05897 | 1/2002 |
| WO | WO02/28302 | 4/2002 |
| WO | WO02/054941 | 7/2002 |
| WO | WO02/067797 | 9/2002 |
| WO | WO02/096304 | 12/2002 |
| WO | WO2007/031264 | 3/2007 |
| WO | WO 2008/001385 | 1/2008 |
| WO | WO2008/008522 | 1/2008 |
| WO | WO2008/121259 | 10/2008 |
| WO | WO 2008/140519 | 11/2008 |
| WO | WO2013/101772 | 7/2013 |
| WO | WO2013/134452 | 9/2013 |
| WO | WO2014/141207 | 9/2014 |

OTHER PUBLICATIONS

Bailey, Jeannie F., "Innervation Patterns of PGP 9.5-Positive Nerve Fibers within the Human Lumbar Vertebra, Journal of Anatomy", (2011) 218, pp. 263-270, Sari Francisco, California.
Fras M.D., Christian et al., "Substance P-containing Nerves withing the Human Vertebral Body: An Immunohistochemical Study of the Basivertebral Nerve", The Spine Journal 3, 2003, pp. 63-67.
A Novel Approach for Treating Chronic Lower Back Pain, Abstract for Presentation at North American Spine Society 26th Annual Meeting in Chicago, IL on Nov. 4, 2011.
Antonacci, M. Darryl et al.; Innervation of the Human Vertebral Body: A Histologic Study; Journal of Spinal Disorder, vol. 11, No. 6, pp. 526-531, 1998 Lippincott Williams & Wilkins, Philadelphia.
Arnoldi, Carl C.; Intraosseous Hypertension—A Possible Cause of Low Back Pain?; Clinical Orthopedics and Related Research, No. 115, Mar.-Apr. 1976.
Bergeron et al., "Fluoroscopic-guided radiofrequency ablation of the basivertebral nerve: application and analysis with multiple imaging modalities in an ovine model," Thermal Treatment of Tissue: Energy Delivery and Assessment III, edited by Thomas P. Ryan, Proceedings of SPIE, vol. 5698 (SPIE, Bellingham, WA, 2005) pp. 156-167.
Bogduk, Nikolai, et al.; Technical Limitations to the efficacy of Radiofrequency Neurotomy for Spinal Pain; Neurosurgery vol. 20, No. 4, 1987.
Choy, Daniel SS.J. et al.; Percutaneous Laser Disc Decompression, A New Therapeutic Modality; Spine vol. 17, No. 8, 1992.
Cosman, E.R. et al., Theoretical Aspects of Radiofrequency Lesions in the Dorsal Root Entry Zone. Neurosurgery, vol. 1, No. 6, 1984, pp. 945-950.
Deardorff, Dana L. et al.; Ultrasound applicators with internal cooling for interstitial thermal therapy; SPIE vol. 3594, 1999.
Dupuy, D.E. et al. Radiofrequency ablation of spinal tumors: Temperature distribution in the spinal canal AJR, vol. 175, pp. 1263-1266, Nov. 2000.
Dupuy, Damian E.; Radiofrequency Ablation: An Outpatient Percutaneous Treatment; Medicine and Health/Rhode Island vol. 82, No. 6, Jun. 1999.
Deramond, H. et al., Temperature Elevation Caused by Bone Cement Polymerization During Vertebroplasty, Bone, Aug. 1999, pp. 17S-21S, vol. 25, No. 2, Supplement.
Diederich, C. J. et al., "IDTT Therapy in Cadaveric Lumbar Spine: Temperature and thermal dose distributions, Thermal Treatment of Tissue: Energy Delivery and Assessment," Thomas P. Ryan, Editor, Proceedings of SPIE vol. 4247:104-108 (2001).
Diederich, Chris J. et al.; Ultrasound Catheters for Circumferential Cardiac Ablation; SPIE vol. 3594 (1999).
Esses, Stephen I. et al.; Intraosseous Vertebral Body Pressures; Spine vol. 17 No. 6 Supplement 1992.
FDA Response to 510(k) Submission by Relievant Medsystems, Inc. submitted on Sep. 27, 2007 (date stamped on Oct. 5, 2007) and associated documents.
Goldberg, S.N. et al., Tissue ablation with radiofrequency: Effect of probe size, gauge, duration, and temperature on lesion volume, Acad. Radiol., vol. 2, pp. 399-404 (1995).
Hanai, Kenji et al.; Simultaneous Measurement of Intraosseous and Cerebrospinal Fluid Pressures in the Lumbar Region; Spine vol. 10, No. 1, 1985.
Heggeness, Michael H. et al., The Trabecular Anatomy of Thoracolumbar Vertebrae: Implications for Burst Fractures, Journal of Anatomy, 1997, pp. 309-312, vol. 191, Great Britain.
Heggeness, Michael H. et al. Discography Causes End Plate Deflection; Spine vol. 18, No. 8, pp. 1050-1053, 1993, J.B. Lippincott Company.
Hoopes et al., "Radiofrequency Ablation of the Basivertebral Nerve as a Potential Treatment of Back Pain: Pathologic Assessment in an Ovine Model," Thermal Treatment of Tissue: Energy Delivery and Assessment III, edited by Thomas P. Ryan, Proceedings of SPIE, vol. 5698 (SPIE, Bellingham, WA, 2005) pp. 168-180.
Houpt, Jonathan C. et al.; Experimental Study of Temperature Distributions and Thermal Transport During Radiofrequency Current Therapy of the Intervertebral Disc; Spine vol. 21, No. 15, pp. 1808-1813, 1996, Lippincott-Raven Publishers.
Kleinstueck, Frank S. et al.; Acute Biomechanical and Histological Effects of Intradiscal Electrothermal Therapy on Human Lumbar Discs; Spine vol. 26, No. 20, pp. 2198-2207; 2001, Lippincott Williams & Wilkins, Inc.
Kopecky, Kenyon K. et al. "Side-Exiting Coaxial Needle for Aspiration Biopsy" —AJR—1996; 167, pp. 661-662.
Lehmann, Justus F. et al.; Selective Heating Effects of Ultrasound in Human Beings; Archives of Physical Medicine & Rehabilitation Jun. 1966.
Letcher, Frank S. et al.; The Effect of Radiofrequency Current and Heat on Peripheral Nerve Action Potential in the Cat; U.S. Naval Hospital, Philadelphia, PA. (1968).
Lundskog, Jan; Heat and Bone Tissue—/an experimental investigation of the thermal properties of bone tissue and threshold levels for thermal injury; Scandinavian Journal of Plastic and Reconstructive Surgery Supplemental 9, From the Laboratory of Experimental Biology, Department of anatomy, University of Gothenburg, Gothenburg, Sweden, Goteborg 1972.
Martin, J.B. et al., Vertebroplasty: Clinical Experience and Follow-up Results, Bone, Aug. 1999, pp. 11S-15S, vol. 25, No. 2, Supplement.
Massad, Malek M.D. et al.; Endoscopic Thoracic Sympathectomy: Evaluation of Pulsatile Laser, Non-Pulsatile Laser, and Radiofrequency-Generated Thermocoagulation; Lasers in Surgery and Medicine; 1991; pp. 18-25.
Mehta, Mark et al.; The treatment of chronic back pain; Anaesthesia, 1979, vol. 34, pp. 768-775.
Nau, William H., Ultrasound interstitial thermal therapy (USITT) in the prostate; SPIE vol. 3594, Jan. 1999.

(56) References Cited

OTHER PUBLICATIONS

Rashbaum, Ralph F.; Radiofrequency Facet Denervation a Treatment alternative in Refractory Low Back Pain with or without Leg Pain; Orthopedic Clinics of North America—vol. 14, No. 3, Jul. 1983.
Rosenthal, D.I., Seminars in Musculoskeletal Radiology, vol. 1, No. 2., pp. 265-272 (1997).
Ryan et al., "Three-Dimensional Finite Element Simulations of Vertebral Body Thermal Treatment," Thermal Treatment of Tissue: Energy Delivery and Assessment III, edited by Thomas P. Ryan, Proceedings of SPIE, vol. 5698 (SPIE, Bellingham, WA, 2005) pp. 137-155.
Shealy, C. Norman; Percutaneous radiofrequency denervation of spinal facets Treatment for chronic back pain and sciatica; Journal of Neurosurgery/vol. 43/Oct. 1975.
Sherman, Mary S.; The Nerves of Bone, The Journal of Bone and Joint Surgery, Apr. 1963, pp. 522-528, vol. 45-A, No. 3.
Solbiati, L. et al. Hepatic metastases: Percutaneous radio-frequency ablation with cooled-tip electrodes. Interventional Radiology, vol. 205, No. 2, pp. 367-373 (1997).
Stanton, Terry, "Can Nerve Ablation Reduce Chronic Back Pain?" AAOS Now Jan. 2012.
The AVAmax System—Cardinal Health Special Procedures, Lit. No. 25P0459-01—www.cardinal.com (copyright 2007).
Tillotson, L. et al. Controlled thermal injury of bone: Report of a percutaneous technique using radiofrequency electrode and generator. Investigative Radiology, Nov. 1989, pp. 888-892.
Troussier, B. et al.; Percutaneous Intradiscal Radio-Frequency Thermocoagulation a Cadaveric Study; Spine vol. 20, No. 15, pp. 1713-1718, 1995, Lippincott-Raven Publishers.

* cited by examiner

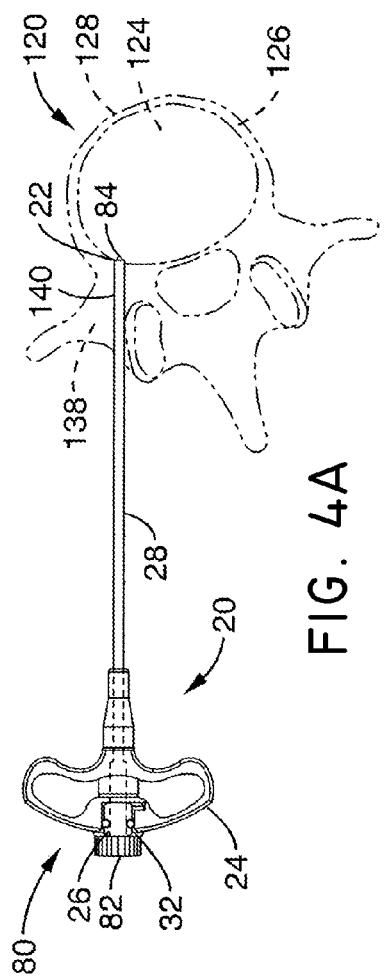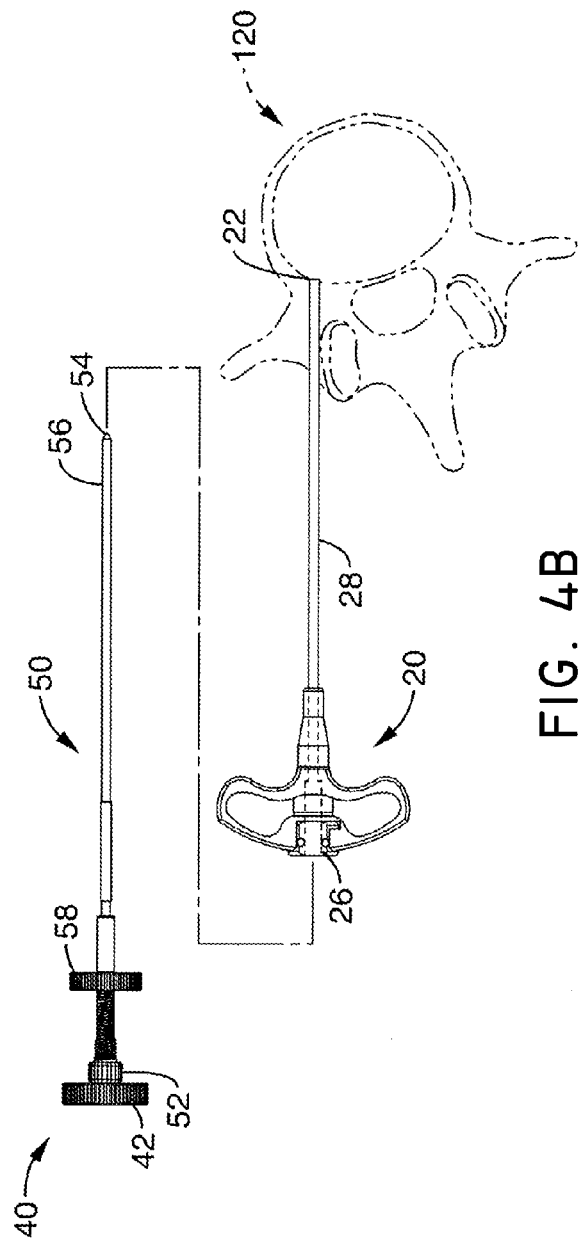
FIG. 4A
FIG. 4B

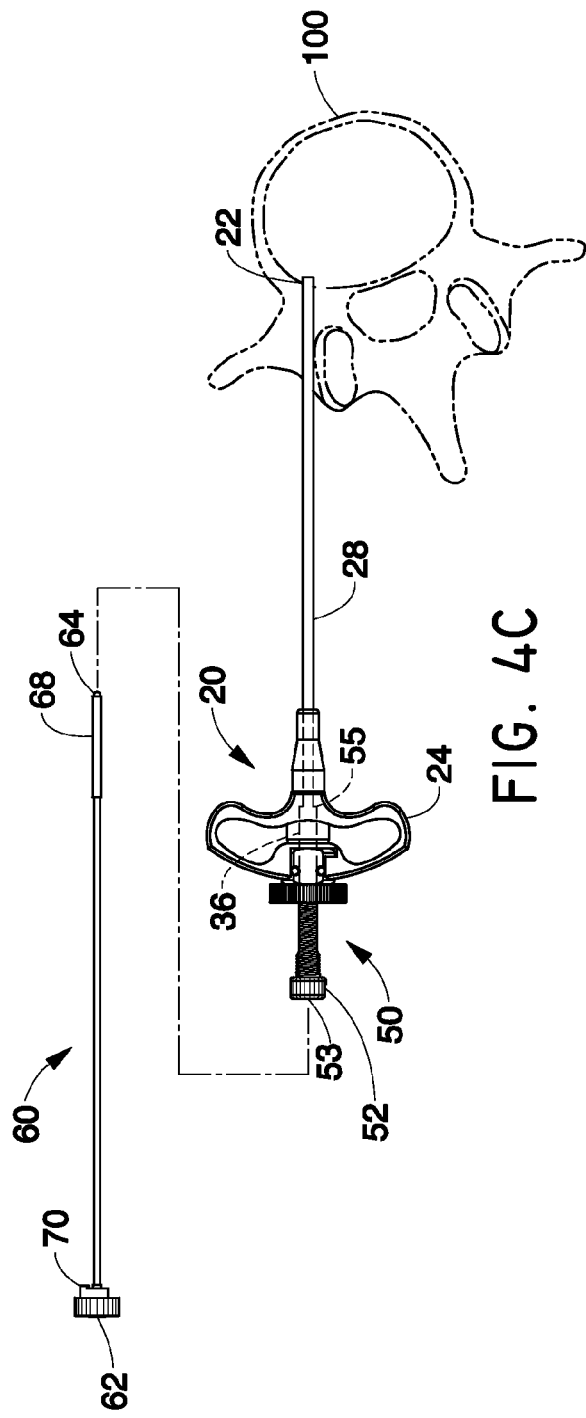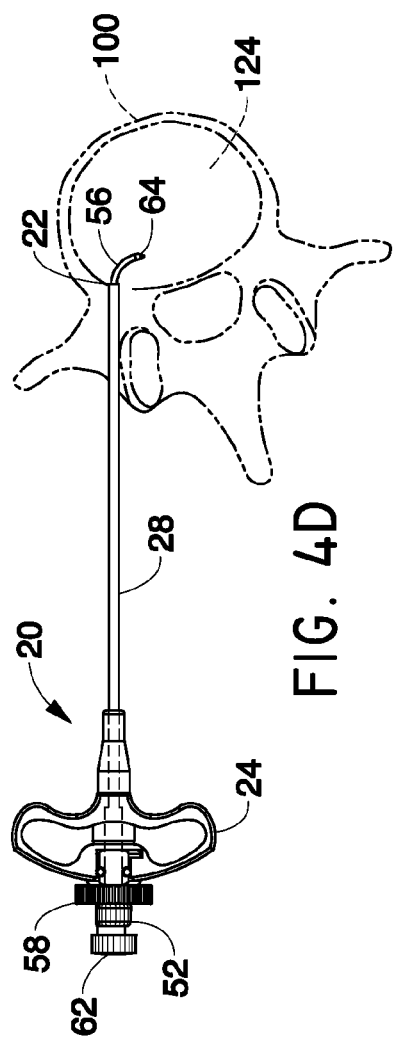
FIG. 4C
FIG. 4D

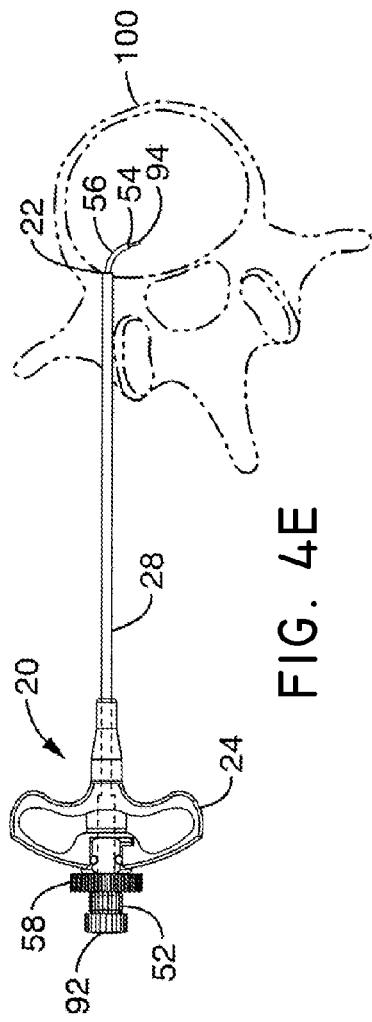
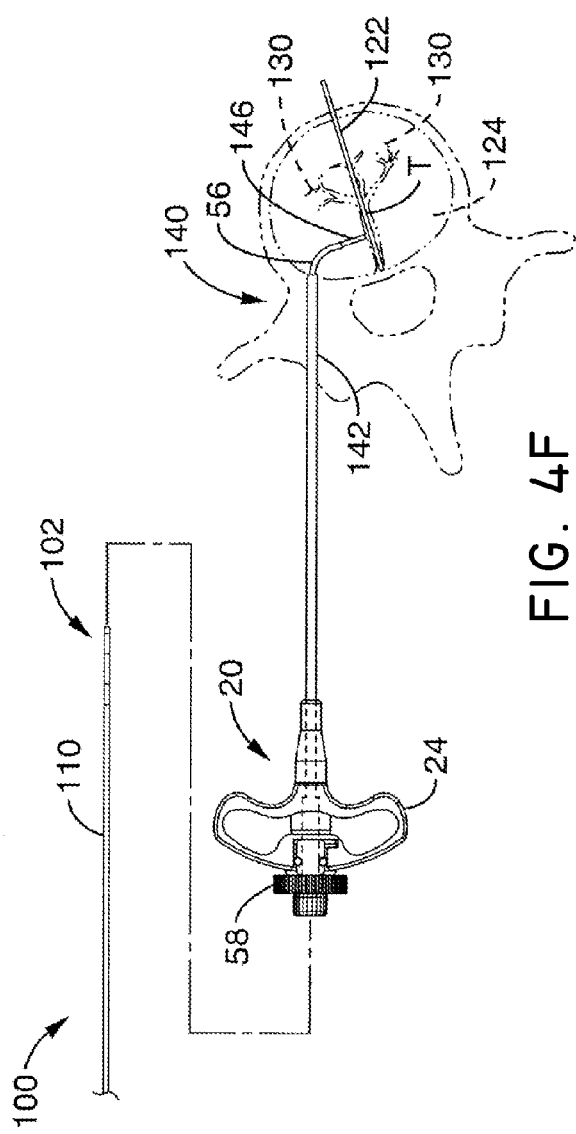
FIG. 4E
FIG. 4F

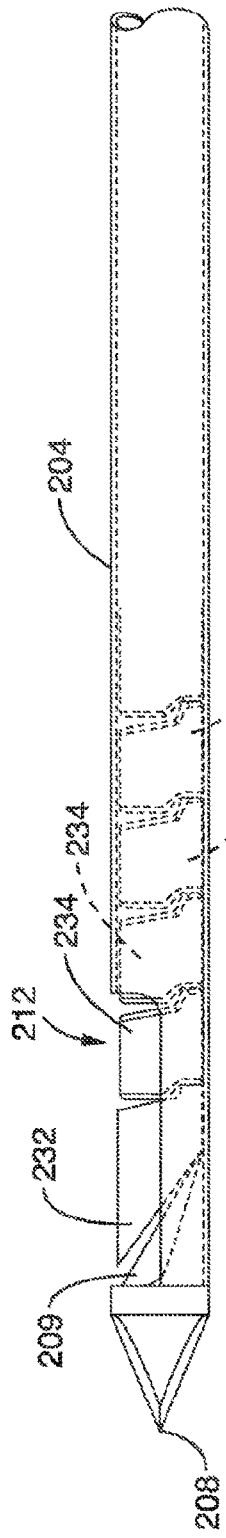
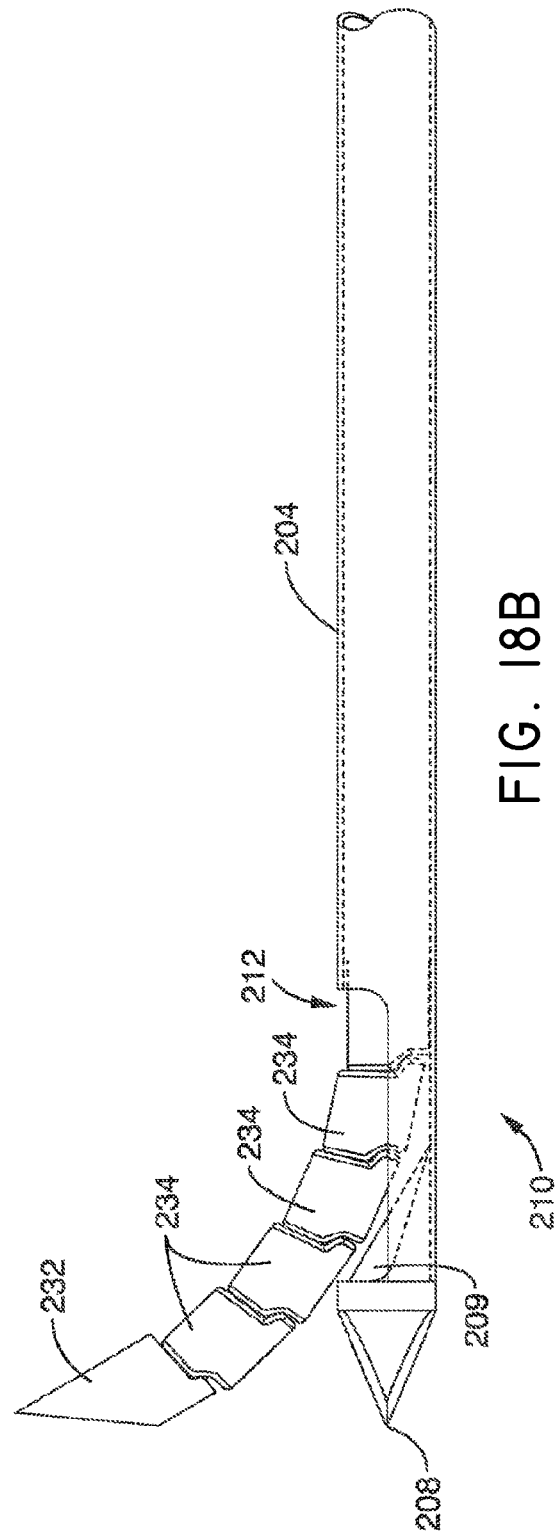
FIG. 18A
FIG. 18B

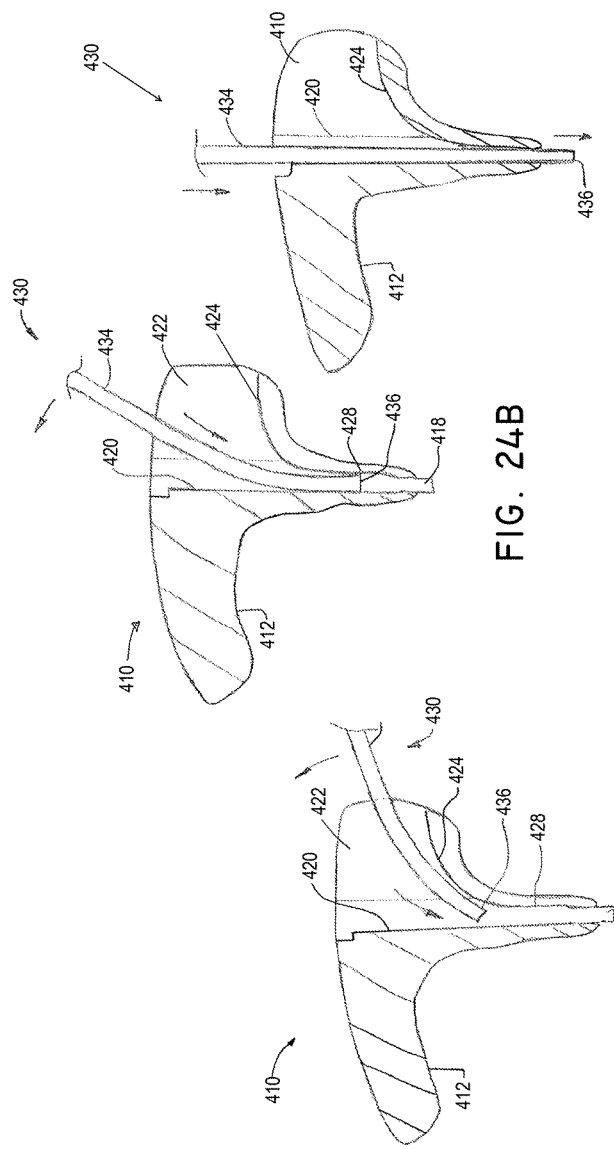

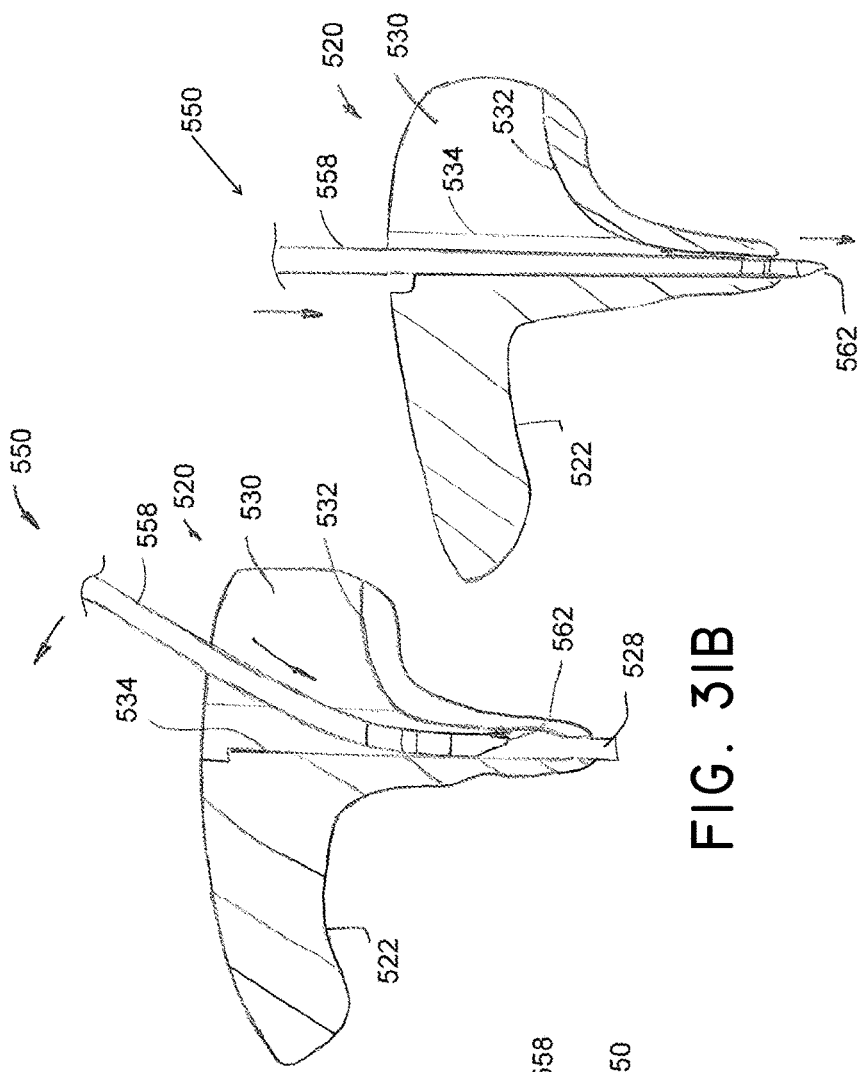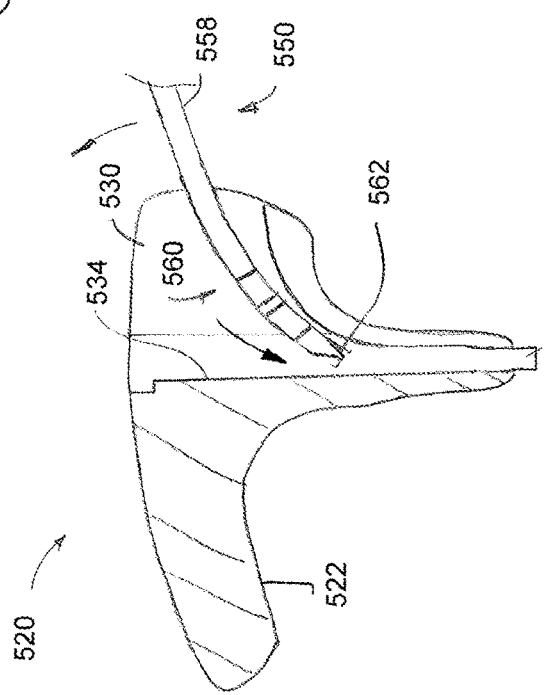

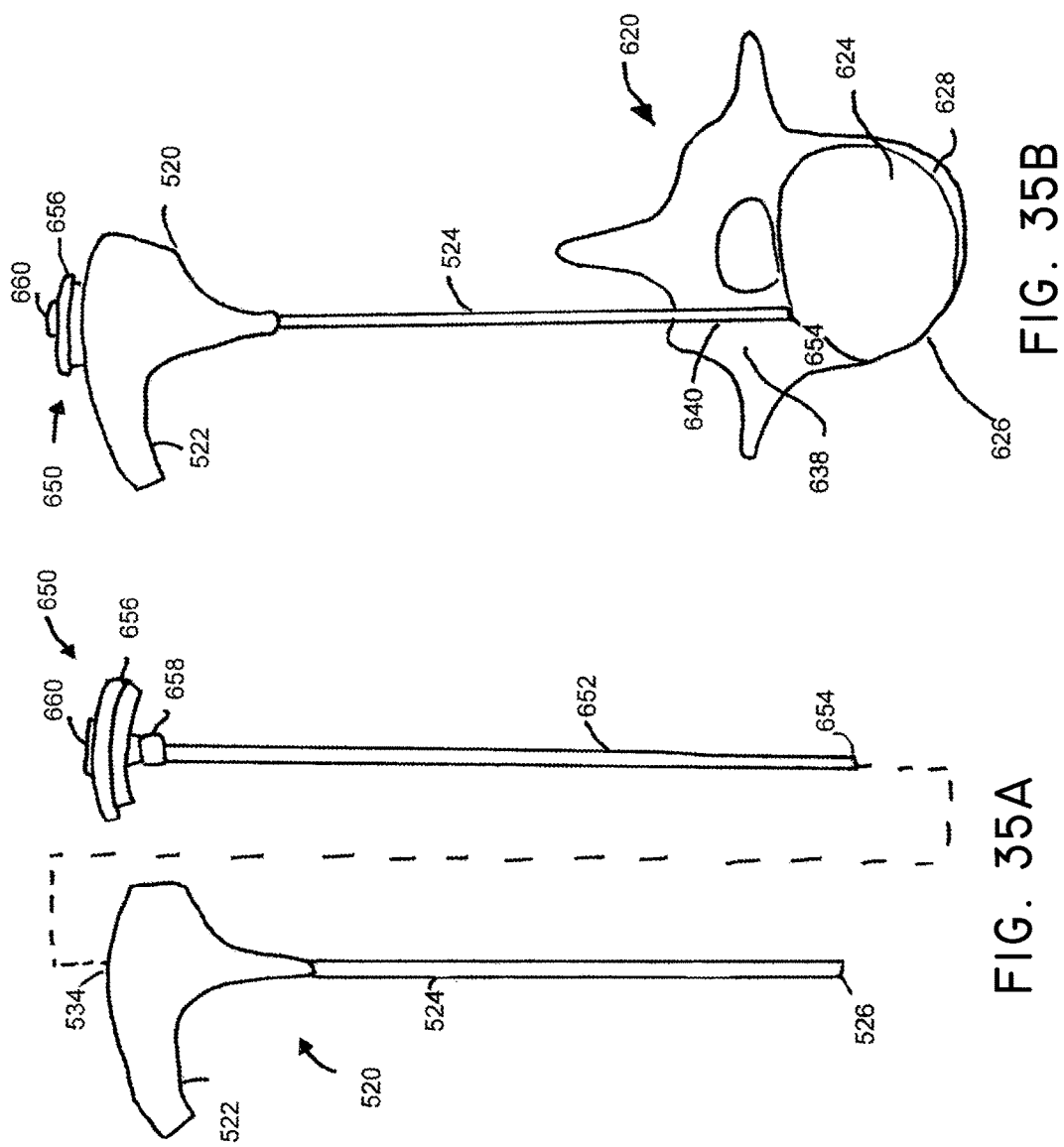

SYSTEMS AND METHODS FOR CREATING CURVED PATHS THROUGH BONE AND MODULATING NERVES WITHIN THE BONE

FIELD

Various embodiments of the invention pertain generally to generating passageways through tissue and to treatment or monitoring of intraosseous nerves ("ION"s), and more particularly to creating paths in bone and to treatment (e.g., modulation) of basivertebral nerves within vertebral bodies of the spine.

BACKGROUND

Back pain is a very common health problem worldwide and is a major cause for work-related disability benefits and compensation. Back pain may arise from strained muscles, ligaments, or tendons in the back and/or structural problems with bones or spinal discs. The back pain may be acute or chronic. Treatments for chronic back pain vary widely and include physical therapy and exercise, chiropractic treatments, rest, pharmacological therapy such as pain relievers or anti-inflammatory medications, and surgical intervention such as vertebral fusion, discectomy or disc repair. Existing treatments can be costly, addictive, temporary, ineffective, and/or can increase the pain or require long recovery times.

SUMMARY

Although accessing the vertebral segments of the spine through the pedicle and into the lateral/anterior section of the body of the vertebra is a primary method of placing a treatment device or neuromodulation device (e.g. a bone cement delivery device, a chemical agent delivery device, and/or an RF probe) into the vertebra, it can be difficult to place a probe in the posterior midline section of the vertebra. Furthermore, accessing the posterior midline section of the S1 segment of the spine can be difficult with a straight linear access route. In one embodiment, a probe or other treatment device (e.g., neuromodulation device) advantageously may be capable of navigating to the posterior section of the S1 vertebral segment, as well as to the same target area within a lumbar vertebral segment. In addition, in accordance with several embodiments, vertebral segments in the cervical and thoracic regions of the spine may also be targeted.

In order to accurately and predictably place a treatment device (e.g., neuromodulation device such as an energy or fluid delivery catheter or probe) in the posterior section of a lumbar vertebral body, a sacral vertebral body or other level vertebral body, the device or probe may navigate to the target area through varying densities of bone in some embodiments. However, due to the varying densities of bone, it can be difficult to navigate a device or probe in bone and ensure its positioning will be in the posterior (e.g., posterior to the midline) or posterior midline section of the vertebral body. The neuromodulation devices described herein can be configured to perform any of the method steps recited herein.

Several embodiments of the invention are directed to systems and methods to deploy and navigate a flexible treatment instrument, such as a neuromodulation device (e.g., a radiofrequency (RF) bipolar probe, a microwave energy delivery device, or a fluid or agent delivery device) within bone. In accordance with several embodiments, a system and method for generating a path in bone that predictably follows a predetermined curved path are provided. Several embodiments herein are primarily directed to navigating through the bone of a vertebral member of the spine, and particularly to treat the basivertebral nerve (BVN) of a vertebral member. The treatment may also be applied to any tissue segment of the body.

In accordance with several embodiments, this invention advantageously facilitates navigation of a curve or angle within varying densities of cancellous bone and creation of a straight channel at the end of the navigated curve or angle.

In accordance with several embodiments, a method of therapeutically treating a vertebral body having an outer cortical bone region and an inner cancellous bone region, and a basivertebral nerve having a trunk extending from the outer cortical bone region of the vertebral body into the inner cancellous region of the vertebral body and a plurality of branches extending from the trunk to define a basivertebral nerve junction or terminus, comprises the steps of: a) inserting one or more energy devices into the vertebral body, and b) exclusively depositing energy within the inner cancellous bone region of the vertebral body between, but exclusive of, the basivertebral nerve junction and the outer cortical bone region, to denervate the basivertebral nerve. In some embodiments, the method comprises depositing, or delivering, energy, fluid, or other substance at or proximate (e.g., posterior to) the basivertebral nerve junction, or terminus. In some embodiments, a delivery probe for delivering a non-energy therapeutic is provided instead of, or in addition to, the energy device.

In some embodiments, a tube-within-tube system comprises a deployable curved tube (e.g. comprised of Nitinol or other flexible, elastic, or shape memory material) that deploys from a straight cannula. The tube can be pre-curved to create an angular range of approximately 0° to approximately 180° (e.g., from approximately 45° to approximately 110°, from approximately 15° to approximately 145°, from approximately 30° to approximately 120°, from approximately 60° to approximately 90°, from approximately 10° to approximately 45°, overlapping ranges thereof, or any angle within the recited ranges), when fully deployed from the straight cannula. The design of the curve can be such that a flexible element (e.g., probe carrying a treatment device) can navigate through the angular range of deployment of the curved tube. The curved tube can allow the flexible element to navigate through a curve within cancellous bone tissue without veering off towards an unintended direction.

Cancellous bone density varies from person to person. Therefore, creating a curved channel within varying density cancellous bone may not predictably or accurately support and contain a treatment device as it tries to navigate the curved channel. With some embodiments, the flexible element is deployed into the bone through the curved tube, which supports the flexible element as it traverses through the curve, thereby preventing the flexible element from channeling its own path. When the flexible element (e.g., energy or agent delivery probe) departs from the tube, it can do so in a linear direction towards the target zone or location. In accordance with several embodiments, this design allows the user to predictably and accurately deploy the flexible element (e.g., treatment device) towards the target zone or location regardless of the density of the cancellous bone.

One embodiment of the invention comprises a system for channeling a path into bone. The system may comprise a trocar having a central channel and an opening at its distal tip, and a cannula sized to be received in the central channel and to be delivered to the distal opening. The cannula may comprise a deflectable or deformable tip with a preformed curve such that the tip straightens while being delivered through the trocar and transitions to a curve (e.g., regains its preformed curve) upon exiting and extending past the distal opening of the trocar to generate a curved path in the bone corresponding to the preformed curve of the deflectable or deformable tip. At least the distal tip or distal section of the cannula may comprise a resiliently deformable material (such as Nitinol or other shape memory material). The cannula may comprise a central passageway or lumen having an internal diameter configured to allow a treatment device to be delivered through the central passageway to a location beyond the curved path in the bone.

In one embodiment, the system further includes a straight stylet configured to be installed in the trocar, wherein the straight stylet comprises a sharp distal tip that is configured to extend beyond the distal opening of the trocar to pierce the bone as the trocar is being delivered to a treatment location within the bone (e.g., within the inner cancellous bone region of a vertebral body).

Additional embodiments of the system may further include one or more straightening stylets configured to be introduced in the cannula, wherein the straightening stylet comprises a rigid construction configured to straighten the distal tip of the curved cannula when positioned in the trocar. In some embodiments, the straightening stylet further comprises a sharp distal end to pierce the bone, and the straightening stylet and curved cannula are installed or inserted in the trocar in place of the straight stylet as the trocar is delivered into the bone.

In some embodiments, the system further comprises a curved stylet having an outer radius sized to fit within the central passageway of the curved cannula. The curved stylet is configured to be installed or inserted in the curved cannula while the curved cannula is extended past the distal opening of the trocar, the curved stylet configured to block the distal opening of the curved cannula while being delivered into the bone. In some embodiments the curved stylet advantageously has a curved distal end corresponding to the curve of the curved cannula.

In one embodiment, the curved stylet has a sharp distal tip configured to extend past the curved cannula to pierce the bone as the cannula is delivered past the distal opening of the trocar. The curved stylet may also advantageously comprise an angled distal tip configured to further support and maintain the curved stylet radius as it is delivered past the distal opening of the trocar and into bone. The curved stylet and the curved cannula may have mating proximal ends (e.g., visual indicia or corresponding physical mating elements) that align the curve of the curved stylet with the curve of the curved cannula. In one embodiment, the angled distal tip is blunt or non-sharp.

In one embodiment, the system further includes a straight channeling stylet configured to be installed in the curved cannula after removing the curved stylet, wherein the straight channeling stylet is flexibly deformable to navigate the curved cannula yet retain a straight form upon exiting the curved cannula. The straight channeling stylet may have a length longer than the curved cannula such that it creates a linear path beyond the distal end of the curved cannula when fully extended. Curved and/or straightening stylets may be used for non-spinal embodiments.

In accordance with several embodiments, a method for channeling a path into bone to a treatment location in the body of a patient is provided. The method includes, in one embodiment, inserting a trocar having a central channel and an opening at its distal tip into a region of bone at or near the treatment location, and delivering a cannula through the central channel and to the distal opening. In one embodiment, the cannula comprises a deflectable or deformable tip with a preformed curve such that the tip straightens while being delivered through the trocar and transitions to a curve (e.g., regains its preformed curve) upon exiting the trocar, and extending the cannula past the distal opening of the trocar to generate a curved path in the bone corresponding to the preformed curve of the deflectable tip. In some embodiments, a treatment device may be delivered through a central passageway or lumen in the cannula to the treatment location beyond the curved path. The treatment device may facilitate or effect energy delivery, fluid delivery, delivery of an agent, etc.

In one embodiment, inserting a trocar into a region of bone comprises inserting a stylet into the trocar such that the stylet extends beyond the distal opening of the trocar, and inserting the stylet and trocar simultaneously into the region of bone such that the stylet pierces the bone as the trocar is being delivered to a treatment location.

In one embodiment, delivering a cannula through the central channel comprises inserting a straightening stylet into the central passageway of the cannula and inserting the straightening stylet and straightened cannula simultaneously into the trocar. In one embodiment, the straightening stylet comprises a rigid construction configured to straighten the curved distal tip of the cannula. In one embodiment, the straightening stylet further comprises a sharp distal end to pierce the bone. In one embodiment, the straightening stylet and cannula are installed simultaneously along with the trocar as the trocar is delivered into the bone.

In one embodiment, extending the cannula past the distal opening is performed by inserting a curved stylet into the central passageway of the curved cannula such that a distal tip of the curved stylet extends to at least the distal opening of the curved cannula and simultaneously extending the curved cannula and curved stylet from the distal end of the trocar such that the curved stylet blocks the distal opening of the curved cannula while being delivered into the bone.

In some embodiments, the curved stylet has a curved distal end corresponding to the curve of the curved cannula such that the curved stylet reinforces the curved shape of the curved cannula as the curved cannula is extended past the distal opening of the trocar. The curved stylet may have a sharp distal tip so that when the curved stylet extends past the distal opening of the curved cannula the curved stylet is configured to pierce the cancellous bone tissue as the curved cannula is delivered past the distal opening of the trocar. In some embodiments, the distal tip of the curved stylet is angled and/or blunt.

In accordance with some embodiments, the curved stylet is then removed from the curved cannula, and a straight channeling stylet is inserted into the curved distal end of the cannula. The straight channeling stylet can be flexibly deformable to navigate the curved cannula, yet retain a straight form upon exiting the curved cannula. The straight channeling stylet can advantageously be longer than the curved cannula to create a linear channel beyond the distal tip of the curved cannula.

In some embodiments, the trocar is inserted through a cortical bone region and into a cancellous bone region of a vertebral body, and the curved cannula is extended though at least a portion of the cancellous bone region to a location at or near a target treatment location. A target treatment location may comprise a basivertebral nerve within the vertebra, and treatment may be delivered to the target treatment location to modulate (e.g., denervate, ablate, stimulate, block, disrupt) at least a portion of the basivertebral nerve (e.g., terminus or junction or a portion of the basivertebral nerve between the terminus or junction and the posterior wall). In one embodiment, a portion of the basivertebral nerve is modulated by delivering focused, therapeutic heating (e.g., a thermal dose) to an isolated region of the basivertebral nerve. In another embodiment, a portion of the basivertebral nerve is modulated by delivering an agent to the treatment region to isolate treatment to that region. In accordance with several embodiments of the invention, the treatment is advantageously focused on a location of the basivertebral nerve that is upstream of one or more branches of the basivertebral nerve.

Several embodiments may include a kit for channeling a path into bone. The kit comprises a trocar having a central channel and opening at its distal tip, and a cannula selected from a set of cannulas sized to be received in the central channel and delivered to the distal opening. The cannula may have a deflectable or deformable distal tip with a preformed curve such that the tip straightens while being delivered through the trocar and regains its preformed curve upon exiting and extending past the distal opening of the trocar to generate a curved path in the bone corresponding to the preformed curve of the deflectable tip. The cannula may comprise a central passageway or lumen having an internal diameter configured to allow a treatment device to be delivered through the central passageway or lumen to a location beyond the curved path within bone, wherein the set of cannulas comprises one or more cannulas that have varying preformed curvatures at the distal tip.

In some embodiments, the one or more cannulas have a varying preformed radius at the distal tip. In addition, the one or more cannulas may each have distal tips that terminate at varying angles with respect to the central channel of the trocar. The length of the distal tips may also be varied. The angle of the distal tip with respect to the central channel of the trocar may vary from 0 degrees to 180 degrees. In accordance with several embodiments, t (e.g., from 10 degrees to 60 degrees, from 15 degrees to 45 degrees, from 20 degrees to 80 degrees, from 30 degrees to 90 degrees, from 20 degrees to 120 degrees, from 15 degrees to 150 degrees, overlapping ranges thereof, or any angle between the recited ranges). The kit may further include a straight stylet configured to be installed in the trocar, the straight stylet comprising a sharp distal tip that is configured to extend beyond the distal opening of the trocar to pierce the bone as the trocar is being delivered to a treatment location within the bone. The kits may be adapted for non-spinal embodiments.

In some embodiments, the kit includes a set of curved stylets having an outer radius sized to fit within the central passageway of the curved cannula, wherein each curved stylet is configured to be installed in the curved cannula while the curved cannula is extended past the distal opening of the trocar. The curved stylet may be configured to block the distal opening of the curved cannula while being delivered into the bone. In one embodiment, each curved stylet may have a varying curved distal end corresponding to the curve of a matching curved cannula in the set of curved cannulas.

In some embodiments, the kit includes a set of straight channeling stylets wherein one of the set of stylets is configured to be installed in the cannula after removing the curved stylet. The straight channeling stylet can be flexibly deformable to navigate the curved cannula yet retain a straight form upon exiting the curve cannula. Each of the straight channeling stylets can have a varying length longer than the curved cannula such that the straight channeling stylet creates a predetermined-length linear path beyond the distal end of the curved cannula when fully extended.

In accordance with several embodiments, a system for channeling a path into bone comprising a trocar with a proximal end, a distal end and a central channel disposed along a central axis of the trocar and extending from the proximal end toward the distal end is provided. The trocar, in one embodiment, comprises a radial opening at or near the distal end of the trocar, the radial opening being in communication with the central channel. In some embodiments, the system further comprises a curveable or steerable cannula sized to be received in said central channel and delivered from the proximal end toward said radial opening. In several embodiments, the curveable cannula comprises a curveable and/or steerable distal end configured to be extended laterally outward from the radial opening in a curved path extending away from the trocar, and a central passageway having a diameter configured allow a treatment device (e.g., probe, catheter) to be delivered through the central passageway to a location beyond the curved path.

In several embodiments, the curveable cannula comprises a proximal end having a proximal body. In one embodiment, the proximal end of the trocar comprises a housing. The housing may comprise a proximal recess configured to allow reciprocation (e.g., alternating back-and-forth motion or other oscillatory motion) of the proximal body of the curveable cannula. The proximal recess of the housing may be in communication with the central channel of the trocar. In several embodiments, a proximal body of the curveable cannula is configured to be releasably restrained with respect to translation within the trocar housing. In several embodiments, the system comprises a probe sized to fit within the central channel of the cannula. The probe may comprise a proximal end configured to be releasably restrained with respect to translation within the proximal body of the curveable cannula. In one embodiment, the probe comprises mating threads that mate with corresponding mating threads of a distal recess of the drive nut so as to allow controlled translation of the probe with respect to the drive nut.

In several embodiments, a spine therapy system is provided. In one embodiment, the system comprises a trocar having a proximal end, a distal end and a central channel. The central channel can be disposed along a central axis of the trocar and extend from the proximal end toward the distal end. In one embodiment, the trocar comprises a radial opening at or near the distal end of the trocar, the radial opening being in communication with the central channel. In one embodiment, the trocar is configured to be deployed through a cortical bone region and into a cancellous bone region of a vertebral body. In one embodiment, a curveable cannula is configured (e.g., sized) to be received in said central channel and delivered from the proximal end toward the radial opening. The curveable cannula may comprise a central passageway and a curveable and/or steerable distal end configured to be extended laterally outward from the radial opening in a curved path extending away from the trocar. The curved path may be generated through at least a portion of the cancellous bone region of the vertebral body. In one embodiment, a treatment device or probe is configured to be delivered through the central passageway to a location beyond the curved path. The trocar, curveable cannula, and/or treatment device can have a sharp distal end or tip configured to penetrate bone tissue. In some embodiments, the distal ends of the trocar, curveable cannula, and/or treatment device are rounded or blunt. In some embodiments, the distal ends of the trocar or curved or curveable cannula have a full radius on the inside and/or outside diameter to prevent other devices from catching when being pulled back into the distal end after being delivered out of the distal end.

In accordance with several embodiments, a method for channeling a path into bone to a treatment location in the body of a patient is provided. The bone may be within or proximal a vertebral body, or may be non-spinal (e.g., knee or other joints). In one embodiment, the method comprises inserting a trocar into a region of bone near the treatment location. In one embodiment, the trocar comprises a proximal end, a distal end, and a central channel disposed between the two ends. In one embodiment, the method comprises delivering a curveable cannula through the central channel and to a radial opening at or near the distal end of the curveable cannula. In one embodiment, the method comprises deploying the curveable cannula laterally outward from the radial opening in a curved path extending away from the trocar. In one embodiment, the method comprises steering the curveable cannula (e.g., via a pull cord coupled to the distal tip of the curveable cannula or via other steering mechanisms) to bias the curveable cannula in the curved path. Energy and/or another diagnostic or therapeutic agent is then optionally delivered to the treatment location.

In accordance with several embodiments, a method of treating back pain is provided. In some embodiments, the method comprises identifying a vertebral body for treatment (e.g., a target for treatment of chronic back pain). In some embodiments, the method comprises identifying a treatment zone, area or site within the inner cancellous bone region of the vertebral body. In some embodiments, the treatment zone, area or site is within a posterior section of the vertebral body (e.g., posterior to an anterior-posterior midline). In some embodiments, the treatment zone comprises a location corresponding to the mid-height of the vertebra from an anterior-posterior view. In some embodiments, a border of the treatment zone is at least 1 cm (e.g., between 1-2 cm, 2-3 cm, 3-4 cm, or more) from the posterior wall of the vertebral body. In some embodiments, the treatment zone is determined by measuring the distance from the posterior wall to the basivertebral foramen as a percentage of the total distance from the posterior wall to the anterior wall of the vertebral body.

In some embodiments, identifying a treatment zone is performed preoperatively using imaging methods such as magnetic resonance imaging (MRI) or computed tomography (CT) imaging modalities. In some embodiments, the treatment zone, site, or location corresponds to a location that is about mid-height between the superior and inferior endplate surfaces of the vertebral body (which may be identified by imaging methods from an anterior-posterior view). In some embodiments, the treatment zone, site or location is identified by measuring the distance from the posterior wall of the vertebral body to the basivertebral foramen from images (e.g., anteroposterior and/or lateral MRI or CT images) of the vertebral body as a percentage of the total distance from the posterior wall to the anterior wall of the vertebral body. In some embodiments, inserting the neuromodulation device within the treatment zone is performed under visualization (e.g., using fluoroscopy). In some embodiments, positioning a distal end portion of the neuromodulation device within the treatment zone comprises positioning the distal end portion (and any active elements such as electrodes located at the distal end portion) at a location corresponding to the measured distance percentage described above. In some embodiments, the percentage is a standardized distance percentage that is not individually measured for the individual subject or vertebral body being treated. In some embodiments, the treatment zone, site, or location corresponds to a location at or proximate (e.g., posterior to) a terminus of the basivertebral foramen.

In some embodiments, the method comprises inserting a curved cannula through the outer cortical bone region of the vertebral body and into the inner cancellous bone region of the vertebral body. The curved cannula can comprise a flexible catheter, tube, or other conduit having a pre-curved or steerable distal end. The curved cannula may comprise Nitinol, PEEK, or other thermoplastic, shape memory or resiliently deformable material. In some embodiments, the method comprises inserting a neuromodulation device within the curved cannula. The neuromodulation device can comprise an energy delivery device, a fluid delivery device, or an agent delivery device. The fluid may or may not comprise an agent, such as a chemical agent. In one embodiment, the chemical agent comprises a lytic agent.

In various embodiments, the energy delivery device is configured to deliver radiofrequency energy, microwave energy, light energy, thermal energy, ultrasonic energy, and/or other forms of electromagnetic energy, and/or combinations of two or more thereof. In accordance with several embodiments, the energy is configured to heat tissue within bone (e.g., a vertebral body) sufficient to modulate (e.g., denervate, ablate) intraosseous nerves (e.g., basivertebral nerves or other nerves located partially or fully within bone). In other embodiments, the energy is configured to treat tissue outside the spine, for example in non-spinal joints or in non-orthopedic applications (e.g., cardiac, pulmonary, renal, or treatment of other organs and/or their surrounding nerves). The temperature of the energy may be in the range of between 40° C. and 100° C., between 50° C. and 95° C., between 60° C. and 80° C., between 75° C. and 95° C., between 80° C. and 90° C., overlapping ranges thereof, or any temperature between the recited ranges. In some embodiments, the temperature and length of treatment can be varied as long as the thermal dose is sufficient to modulate (e.g., at least temporarily denervate, ablate, block, disrupt) the nerve. In some embodiments, the length of treatment (e.g., delivery of energy) ranges from about 5 to about 30 minutes (e.g., about 5 to 15 minutes, about 10 to 20 minutes, about 15 to 25 minutes, about 20 to 30 minutes, overlapping ranges thereof, 15 minutes, or about any other length of time between the recited ranges). In some embodiments, the neuromodulation device comprises a sensor to measure nerve conduction of the nerve at the treatment zone.

The energy delivery device may comprise one or more probes (e.g., a radiofrequency probe). In some embodiments, the probe comprises one or more electrodes configured to generate a current to heat tissue within bone. In one embodiment, the probe comprises a bipolar probe having two electrodes. The two electrodes may comprise an active electrode and a return electrode. In one embodiment, the active electrode comprises a tip electrode positioned at the distal tip of the radiofrequency probe and the return electrode comprises a ring electrode spaced proximally from the active electrode with insulation material between the two electrodes. In one embodiment, the return electrode comprises a tip electrode positioned at the distal tip of the probe (e.g., a radiofrequency probe) and the active electrode comprises a ring electrode spaced proximally from the return electrode. The two electrodes may be spaced about 1 mm, 2 mm, 3 mm, 4 mm, 5 mm, 6 mm, 7 mm, 8 mm, 9 mm or 1 cm apart. In various embodiments, the electrodes comprise cylindrical electrodes, tip electrodes, plate electrodes, curved electrodes, circular electrodes, or other shapes. In some embodiments, the electrodes comprise an electrode array. In various embodiments, the frequency of the energy can be between about 100 kHz and 1 MHz, between 400 kHz and 600 kHz, between 300 kHz and 500 kHz, between 350 kHz and 600 kHz, between 450 kHz and 600 kHz, overlapping ranges thereof, or any frequency within the recited ranges.

In one embodiment, the energy delivery device comprises an ultrasound probe having one or more ultrasound transducers. The ultrasound probe may be configured to deliver high-intensity focused ultrasonic energy, low-intensity ultrasonic energy or other forms of ultrasonic energy sufficient to modulate the nerve. The ultrasound energy may be used for cavitation or non-cavitation. In one embodiment, the energy delivery device comprises a laser or light energy delivery device configured to deliver light energy sufficient to modulate the nerve. In one embodiment, the energy delivery device is configured to deliver radiation sufficient to modulate the nerve. In one embodiment, the energy delivery device comprises a microwave energy delivery device comprising one or more microwave antennas configured to deliver microwave energy sufficient to effect modulation of the nerve.

In one embodiment, a fluid delivery device is used to effect a temperature change in a location in the disc. For example, the fluid delivery device may be used to deliver a cryoablative fluid. In another embodiment, the fluid delivery device may be used to deliver a cooling fluid to cool a region in conjunction with a therapy that generates heat. In some embodiments, a distal portion of the curved cannula is shaped so as to guide a distal end of the neuromodulation device towards the midline of the vertebral body (or other treatment area outside the spine). In some embodiments, a proximal end of the fluid delivery device is coupled to a fluid source or reservoir (e.g., syringe, fluid pump). In some embodiments, the fluid delivery device comprises a catheter, tube, sleeve, needle, cannula, wicking device, or other conduit configured to deliver fluid. The fluid may comprise neurolytic agents, chemotherapy agents, radioactive substances, medications, drugs, pharmaceuticals, alcohols, acids, solvents, cooling agents, nerve blocking agents, and/or other chemical agents.

In some embodiments, the method comprises advancing the distal end of the neuromodulation device out of a distal opening of said cannula and into the inner cancellous bone region of the vertebral body or treatment area. The distal opening may be an axial opening or a radial opening. In some embodiments, the method comprises positioning the distal end of said neuromodulation device within, at or proximate the treatment zone, area site, or location of the vertebral body or treatment area.

In some embodiments, the method comprises effecting modulation of at least a portion of a nerve (e.g., basivertebral nerve or intraosseous nerve) using the neuromodulation device. The modulation (e.g., neuromodulation) can comprise partial or complete and/or temporary or permanent blocking, disruption, denervation or ablation of the nerve. In various embodiments, the modulation comprises radiofrequency ablation, microwave energy ablation, chemical ablation, cryoablation, ultrasonic ablation, acoustic ablation, laser ablation, thermal ablation, thermal heating, cooling, mechanical severing, neuromodulation, and/or stimulation of the nerve. In one embodiment, stimulation of the nerve is performed to block the travel of signals indicative of pain. Stimulation may comprise mechanical, electrical, or electromechanical stimulation and may be performed by any of the modalities or methods described herein with reference to ablation or modulation. The stimulation may be continuous or pulsed. In various embodiments, the modulation may be performed by a radioactive implant or by an external radiation beam (e.g., electron beam, gamma-knife, etc.).

In accordance with several embodiments, a method of treating pain (e.g., back pain) is provided. In some embodiments, the method comprises identifying a treatment zone, such as a vertebral body for treatment (e.g., an identified source of pain or location likely to treat pain). In some embodiments, the treatment zone comprises a basivertebral residence zone within which a portion of the basivertebral nerve (e.g., main trunk, junction, terminus of basivertebral foramen, etc.) is likely to reside. In some embodiments, the treatment zone is identified without knowing the precise location of the basivertebral nerve. In some embodiments, the method comprises identifying a treatment zone, site, region or location within the inner cancellous bone region within a posterior section of the vertebral body. The posterior section may comprise a section posterior to an anterior-posterior midline or a region within a distance between about 10% and about 50%, between about 20% and about 50%, between about 10% and about 40% of the distance from the posterior wall. In some embodiments, the method comprises inserting a distal end portion of the neuromodulation device (e.g., energy and/or fluid delivery probe), and any active elements disposed thereon, within or proximate the treatment zone. In some embodiments, the method comprises thermally inducing modulation of a function of a basivertebral nerve within the vertebral body with the energy delivery probe.

In some embodiments, the method comprises generating a curved path within the inner cancellous bone region towards a midline of the vertebral body with a cannula having a pre-curved distal end portion to facilitate access to the posterior section of the vertebral body. In some embodiments, insertion of the neuromodulation device through a curved cannula allows for access straight through (e.g., concentrically through) the pedicle in a transpedicular approach instead of an off-center access, which may be difficult for some levels of vertebrae due to anatomic constraints. In some embodiments, the method comprises inserting the neuromodulation device within the curved path created by the cannula. In some embodiments, the cannula is shaped so as to guide a distal end portion of the neuromodulation device towards the midline of the vertebral body. In some embodiments, the method comprises inserting a stylet within the cannula that is adapted to penetrate bone tissue of the vertebral body beyond the curved path created by the cannula.

In accordance with several embodiments, a method of therapeutically heating a vertebral body to treat back pain is provided, In some embodiments, the method comprises identifying a residence zone of a basivertebral nerve within the inner cancellous bone region of the vertebral body. In some embodiments, the method comprises inserting two electrodes into the vertebral body. In some embodiments, the method comprises positioning the two electrodes within or proximate the residence zone. In some embodiments, the method comprises generating a heating zone between the two electrodes to heat the basivertebral nerve. For example, a first electrode may be activated to generate a current between the first electrode and a second electrode. The current may generate heat within the bone tissue. The heating zone may comprise an inner resistive heating zone and an outer conductive heating zone. In some embodiments, the heating zone is configured to have a radius or diameter between about 0.5 cm and 2 cm (e.g., 0.5 cm, 0.6 cm, 0.7 cm, 0.8 cm, 0.9 cm, 1 cm, 1.1 cm, 1.2 cm, 1.3 cm, 1.4 cm, 1.5 cm, 1.6 cm, 1.7 cm, 1.8 cm, 1.9 cm, 2 cm). In accordance with several embodiments, forming heating zones (and in some cases, lesions) of a specific size and shape can be improved by adjusting parameters such as diameter and active length of electrodes, initial and steady-state power input, length of treatment, and device control temperature.

In some embodiments, inserting two electrodes into the vertebral body comprises inserting a first energy delivery probe having a first electrode within the inner cancellous bone region and positioning a second energy delivery probe having a second electrode within the inner cancellous bone region. In some embodiments, inserting two electrodes into the vertebral body comprises inserting a single energy delivery probe having two electrodes within the inner cancellous bone region.

In some embodiments, positioning the two electrodes within or proximate the residence zone comprises positioning the electrodes at a location such that a single heating treatment modulates (e.g., denervates, ablates) the entire basivertebral nerve system without requiring separate downstream modulation (e.g., denervation, ablation) treatments. In some embodiments, positioning the two electrodes within or proximate the residence zone comprises positioning the two electrodes to straddle the residence zone. In some embodiments, positioning the two electrodes within or proximate the residence zone comprises positioning a first electrode on a first side of the vertebral body and positioning a second electrode on a second side of the vertebral body (wherein the first side and second side are on opposite sides of any line drawn through a midpoint of the vertebral body).

In accordance with several embodiments of the invention, methods and systems allow for positioning of a treatment device in contact with or in close proximity to a basivertebral nerve without knowing the precise location of the basivertebral nerve. In attempting to place at least one electrode in close proximity to the basivertebral nerve, the approaches disclosed in the teachings of the art are somewhat problematic. In particular, although the location of the basivertebral nerve is somewhat well known, the basivertebral nerve is radiolucent and so its precise location cannot be easily identified by an X-ray. Since the basivertebral nerve is also extremely thin, knowingly placing the electrode in close proximity to the basivertebral nerve may be problematic in some cases. Moreover, in one embodiment, since certain RF electrodes appear to heat only a fairly limited volume of bone, misplacement of the electrode vis-à-vis the basivertebral nerve may result in heating a volume of bone that does not contain the basivertebral nerve. "Close proximity" with regard to the intraosseous or basivertebral nerve can mean located at a position such that the nerve is modulated upon activation of the neuromodulation device or delivery of fluid or other substances by the neuromodulation device.

The terms "modulation" or "neuromodulation", as used herein, shall be given their ordinary meaning and shall also include ablation, permanent denervation, temporary denervation, disruption, blocking, inhibition, therapeutic stimulation, diagnostic stimulation, inhibition, necrosis, desensitization, or other effect on tissue. Neuromodulation shall refer to modulation of a nerve (structurally and/or functionally) and/or neurotransmission. Modulation is not limited to nerves and may include effects on other tissue.

Several embodiments of the invention relate to the production of a large but well-controlled heating zone within bone tissue to therapeutically treat (e.g., modulate) an ION within the heating zone. Other embodiments provide modulation of non-spinal tissue (e.g., nerves).

Accordingly, some embodiments of the invention are advantageous because they allow the clinician to create a sufficiently large heating zone for therapeutically treating the ION (e.g., basivertebral nerve) without requiring direct access to the ION. Some embodiments of the invention are particularly advantageous because such embodiments: (i) do not require knowing the precise location of the ION, (ii) do not require directly accessing the ION, and/or (iii) have a controlled heating profile that allows a clinician to avoid heating adjacent structures such as the healthy adjacent cancellous bone tissue, the spinal cord or opposing vertebral endplates.

In accordance with several embodiments, a system for channeling a path into bone is provided. The system may comprise a trocar comprising a proximal end, a distal end and a central channel. In one embodiment, the central channel is disposed along a central axis of the trocar and extends from the proximal end toward the distal end. In one embodiment, the trocar comprises a distal opening at or near the distal end of the trocar, the distal opening being in communication with the central channel. The system may comprise a curved cannula sized to be received in the central channel and delivered from the proximal end toward the distal opening of the trocar. In one embodiment, the curved cannula comprises a straight tubular body at a proximal end of the curved cannula and a curved distal end. The curved distal end may be configured to be extended laterally outward from the distal opening in a curved path extending away from the trocar; wherein the curved cannula comprises a central passageway having a diameter configured to allow a probe to be delivered through the central passageway to a location beyond the curved path.

In some embodiments, the distal end of the curved cannula is deformable so as to be delivered in a straight configuration through the trocar and deployed in a curved configuration outward from the distal opening at an angle with respect to the central axis. In various embodiments, the proximal end of the trocar comprises a handle having a proximal recess in communication with the central channel of the trocar to allow reciprocation of the curved cannula within the central channel and a lateral slot in communication with the proximal recess. In one embodiment, the lateral slot extends radially outward from the proximal recess at a proximal surface of the handle. The slot may be configured to allow insertion of the curved cannula such that a central axis of the straight tubular body is at an angle with respect to the central axis of the trocar when the curved distal end of the curved cannula is inserted into the proximal recess. In one embodiment, the curved cannula can be inserted within the trocar without requiring a straightening sleeve or other structure to straighten the curved cannula prior to insertion.

In one embodiment, the lateral slot comprises a curvilinear bottom surface configured to allow the curved distal end of the curved cannula to be slideably advanced into the proximal recess and the central channel, thereby facilitating ease of insertion of a curved instrument into a straight channel. In one embodiment, the curvilinear bottom surface of the lateral slot comprises a radius substantially matching the radius of the curved distal end of the curved cannula.

In several embodiments, the system comprises a curved stylet comprising a straight proximal body and a preformed curved distal end. In one embodiment, the curved cannula comprises a cannula channel configured to allow delivery of a treatment device to the location beyond the curved path.

The proximal end of the curved cannula may comprise a cannula handle having a central recess in communication with the cannula channel to allow reciprocation of the curved stylet within the cannula channel and a lateral cannula slot in communication with the central recess. In one embodiment, the cannula slot extends radially outward from the central recess at a proximal surface of the cannula handle such that the lateral cannula slot is configured to allow insertion of the curved stylet in a manner such that a central axis of the straight proximal body is at an angle with respect to a central axis of the cannula channel when the preformed curved distal end of the curved stylet is inserted into the central recess.

In some embodiments, the lateral cannula slot comprises a curvilinear bottom surface configured to allow the preformed curved distal end of the curved stylet to be slideably advanced into the central recess and cannula channel. The curvilinear bottom surface of the cannula handle may comprise a radius substantially matching the radius of the preformed curved distal end of the curved stylet. In some embodiments, the curved cannula comprises a stop nut threaded about a threaded portion distal to the cannula handle and proximal to the straight proximal body. In one embodiment, the stop nut is configured to have a first position on the threaded portion. The stop nut may be configured to restrain advancement of the curved cannula within the trocar such that the curved distal end of the cannula does not extend past the distal end of the trocar when the stop nut is in the first position. In one embodiment, the stop nut comprises a second position on the threaded portion configured to allow further translation of the curved cannula with respect to the trocar. The stop nut may be rotated or otherwise translated to the second position prior to extending the curved distal end of the curved cannula laterally outward from the distal opening of the trocar. In some embodiments, the system comprises a treatment probe (e.g., an RF energy delivery probe) configured to be delivered through the central passageway to a location at or beyond the curved path.

In accordance with several embodiments, a method for channeling a path into a vertebral body of a patient using the trocar, curved cannula and/or curved stylet described above is provided. The method comprises inserting a trocar into the vertebral body. The trocar may have any of the structural features of the trocars described herein (e.g., slotted handle) to facilitate insertion of a curved instrument without requiring straightening of the curved instrument prior to insertion, thereby reducing the number of steps and/or instruments in a spine therapy system. In some embodiments, the method comprises inserting the curved distal end of a curved cannula into a proximal recess of a trocar handle through a lateral slot of the trocar handle and such that a central axis of the straight tubular body of the curved cannula is at an angle with respect to the central axis of the trocar. In some embodiments, the method comprises advancing the curved cannula into the proximal recess of the trocar, thereby straightening the curved distal end of the curved cannula. In one embodiment, the method comprises advancing the curved cannula within the central channel of the trocar from the proximal end toward the distal opening of the trocar and extending the curved distal end of the curved cannula laterally outward from the distal opening of the trocar to generate a curved path radially outward from the trocar. In one embodiment, the method comprises delivering a treatment probe through the curved cannula to a location beyond the curved path.

In some embodiments, the method comprises retracting the curved stylet from the curved cannula and delivering a straight stylet into the curved cannula to generate a straight path beyond the curved path radially outward from the trocar. In some embodiments, the method comprises retracting the straight stylet from the curved cannula and delivering the treatment probe through the curved cannula to a location beyond the curved path.

In accordance with several embodiments, a system for delivering a self-guided treatment device into bone is provided. The system may comprise a trocar comprising a proximal end, a distal end and a central channel. In one embodiment, the central channel is disposed along a central axis of the trocar and extends from the proximal end toward the distal end and the trocar comprises a distal opening at or near the distal end of the trocar, the distal opening being in communication with the central channel. The system may also comprise a treatment probe sized to be received in the central channel and delivered from the proximal end toward the distal opening of the trocar. In one embodiment, the treatment probe comprises a stylet comprising a straight proximal end and a curved distal end. In one embodiment, the curved distal end is deformable so as to be delivered in a straight configuration through the trocar and deployed in a curved configuration outward from the distal opening at an angle with respect to the central axis of the trocar. In some embodiments, the curved distal end comprises a treatment device configured to deliver a therapeutic dose of energy to a treatment location.

In some embodiments, the curved distal end of the treatment probe comprises a sharpened distal tip configured to channel through a cancellous bone region of a vertebral body. In some embodiments, the therapeutic dose of energy delivered by the treatment device is configured to denervate a basivertebral nerve associated with the vertebral body. In one embodiment, the proximal end of the trocar comprises a handle comprising a proximal recess in communication with the central channel to allow reciprocation of the curved cannula within the central channel and a lateral slot in communication with the proximal recess. In one embodiment, the lateral slot extends radially outward from the proximal recess at a proximal surface of the handle of the trocar such that the lateral slot is configured to allow insertion of the treatment probe such that a central axis of the straight proximal end of the stylet is at an angle with respect to the central axis of the trocar when the curved distal end of the treatment probe is inserted into the proximal recess of the trocar. The lateral slot may comprise a curvilinear bottom surface configured to allow the curved distal end of the treatment probe to be slideably advanced into the proximal recess and the central channel of the trocar. In one embodiment, the curvilinear bottom surface comprises a radius substantially matching the radius of the curved distal end of the treatment probe.

In several embodiments, the system comprises a straight stylet comprising a straight proximal body and a sharpened distal end. The stylet may be configured to protrude from the distal opening of the trocar when installed in the trocar. In one embodiment, the stylet comprises a striking surface for advancing the trocar through a cortical bone region of the vertebral body. In one embodiment, the treatment probe comprises a handle having a striking surface for advancing the treatment probe through the cancellous bone region of the vertebral body.

In one embodiment, the distal end of the treatment probe comprises a plurality of circumferentially relieved sections. In one embodiment, the distal end of the treatment probe comprises a pair of ring electrodes forming a bipolar RF treatment device. In some embodiments, the stylet of the treatment probe comprises a longitudinal channel extending from the curved distal end to the straight proximal end, the channel configured to house a flexible lead coupled to the pair of ring electrodes. In one embodiment, the probe handle comprises a connector for coupling a power source to the flexible lead.

In accordance with several embodiments, a method for delivering a self-guided treatment device into bone is provided. The method may comprise inserting a trocar into bone. The trocar may comprise any of the structural features of the trocars described herein (e.g., slotted handle) to facilitate insertion of a curved instrument without requiring straightening of the curved instrument prior to insertion, thereby reducing the number of steps and/or instruments in a treatment system. In one embodiment, the method comprise inserting a curved distal end of a treatment probe (such as the treatment probes described above) into a proximal recess of the trocar through a lateral slot and such that a central axis of a straight tubular body of the treatment probe is at an angle with respect to the central axis of the trocar. The method may comprise advancing the treatment probe into the proximal recess of the trocar, thereby straightening the curved distal end of the treatment probe upon insertion rather than prior to insertion (e.g., with a sleeve or other constraint). In one embodiment, the method comprises advancing the treatment probe within the central channel of the trocar from the proximal end toward the distal opening of the trocar and extending the curved distal end of the treatment probe laterally outward from the distal opening of the trocar to generate a curved path radially outward from the trocar. In one embodiment, the method comprises delivering a therapeutic dose of energy to a treatment location within the bone. In some embodiments, the therapeutic dose of energy is configured to denervate a basivertebral nerve associated with the vertebral body. In one embodiment, delivering a therapeutic dose of energy to the treatment location comprises delivering RF energy to denervate the basivertebral nerve.

In several embodiments, the system may comprise a curved stylet comprising a straight proximal body and a curved distal end. The curved stylet may further comprise an inner core and an outer layer. In several embodiments, the inner core comprises an elastic metal alloy. In several embodiments, the outer layer comprises a polymer. In some embodiments, the diameter of the inner core is constant along the length of the inner core. In accordance with several embodiments, during manufacturing, the stiffness of the curved stylet can be altered by manipulating the diameter of the inner core, the wall thickness of the outer layer, or a combination thereof. The curved stylet may be configured to protrude from the distal opening of the trocar when installed in the trocar.

In accordance with several embodiments, a method for manufacturing a curved stylet is provided. The method may comprise providing an inner core, and in some embodiments, providing an inner core of a constant diameter. The method may comprise encasing at least a portion of the inner core with an outer layer. In several embodiments, the inner core comprises an elastic metal alloy. In several embodiments, the outer layer comprises a polymer. In some embodiment, the method may comprise manipulating the diameter of the inner core, the wall thickness of the outer layer, or a combination thereof in order to achieve desired stiffness.

The methods summarized above and set forth in further detail below describe certain actions taken by a practitioner; however, it should be understood that they can also include the instruction of those actions by another party. Thus, actions such as "delivering a therapeutic dose of energy" include "instructing the delivery of a therapeutic dose of energy." Further aspects of embodiments of the invention will be discussed in the following portions of the specification. With respect to the drawings, elements from one figure may be combined with elements from the other figures.

BRIEF DESCRIPTION OF THE DRAWINGS

Several embodiments of the invention will be more fully understood by reference to the following drawings which are for illustrative purposes only:

FIGS. 18A and 18B are side views of the distal end of embodiments of the system of FIG. 8 with the curveable cannula in a stowed and deployed position respectively.

FIGS. 24A through 24C show section views of embodiments of the trocar of FIG. 20 with the curved cannula at different possible stages of insertion within the trocar.

FIGS. 31A through 31C show section views of embodiments of the trocar of FIG. 30 with the curveable treatment device at different possible stages of insertion within the trocar.

FIGS. 35A-35C show embodiments of the self-guiding curveable treatment device of FIG. 27 through various possible stages of deployment through the vertebral body.

FIGS. 41A-41E illustrate embodiments of a steerable probe system comprising a steerable sleeve and a passively steered probe.

DETAILED DESCRIPTION

Several embodiments of the invention are directed to systems and methods to deploy and navigate a treatment instrument, such as a neuromodulation device (e.g., a radiofrequency (RF) bipolar energy delivery device, a microwave energy delivery device, or a fluid or agent delivery device) within bone. Although the systems and methods described herein are primarily directed to navigating through the bone of a vertebral member of the spine, and particularly to treat the basivertebral nerve (BVN) of a vertebral member, the treatment may be applied to any nerve and/or to any tissue segment of the body.

In accordance with several embodiments, the systems and methods of treating back pain or facilitating neuromodulation of intraosseous nerves described herein can be performed without surgical resection, without general anesthesia, and/or with virtually no blood loss. In some embodiments, the systems and methods of treating back pain or facilitating neuromodulation of intraosseous nerves described herein facilitate easy retreat if necessary. In accordance with several embodiments of the invention, successful treatment can be performed in challenging or difficult-to-access locations and access can be varied depending on bone structure. One or more of these advantages also apply to treatment of tissue outside of the spine (e.g., other orthopedic applications or other tissue).

Figure 1:
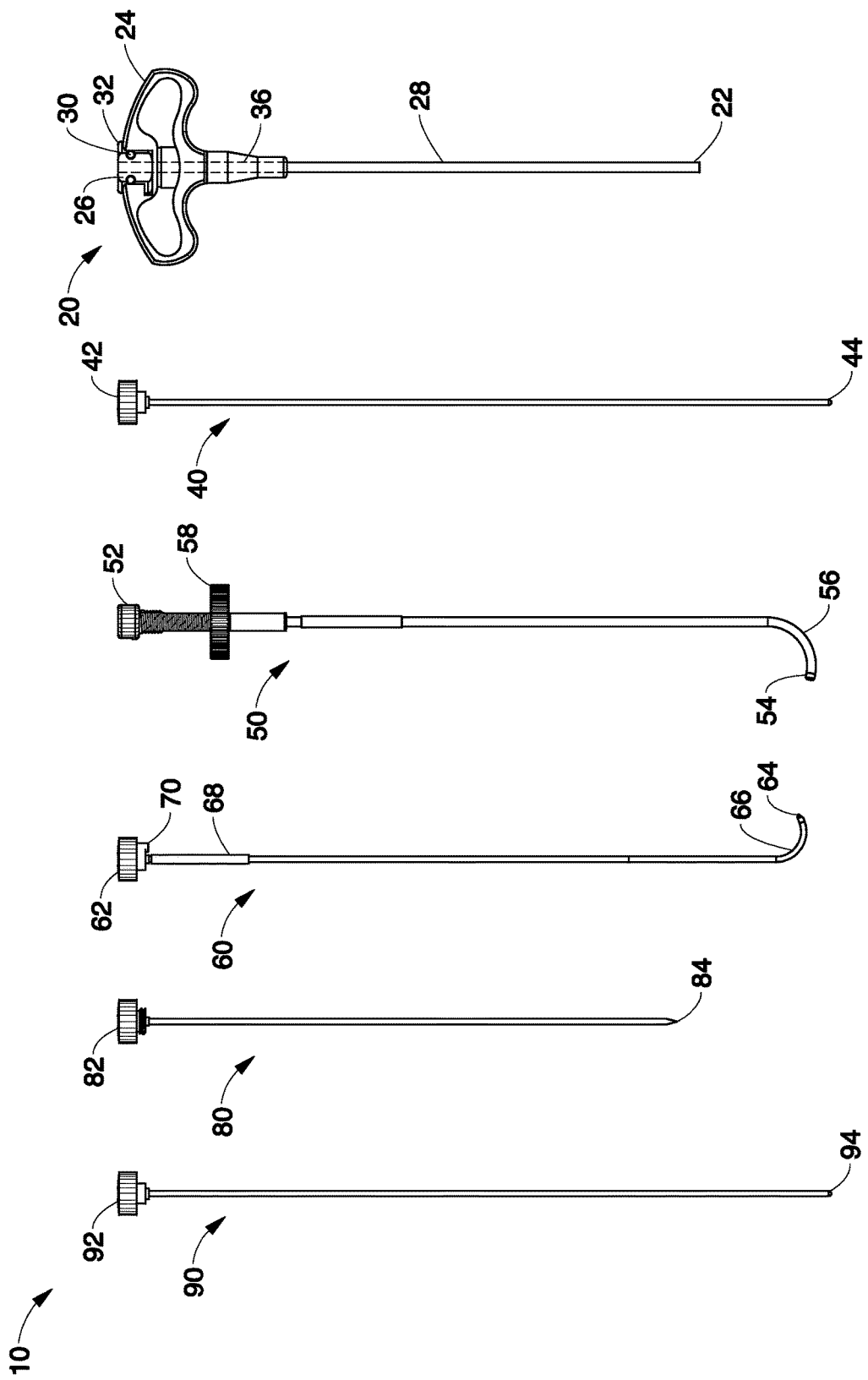
FIG. 1 illustrates an embodiment of a system for generating a curved path in bone.
Figure 2:
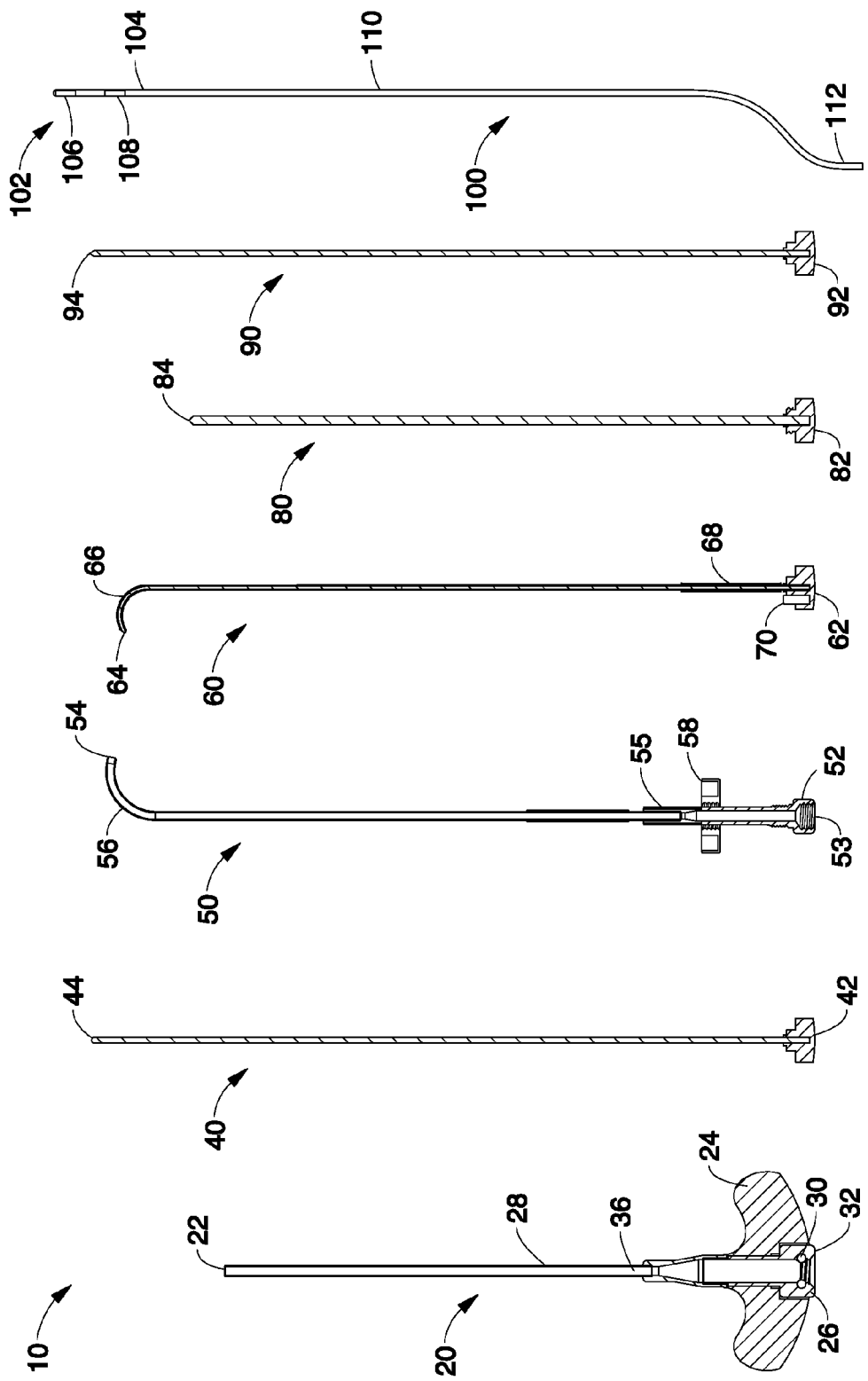
FIG. 2 is a sectional view of an embodiment of the system of FIG. 1.

FIGS. 1 and 2 illustrate an embodiment comprising a system or kit 10 for forming a path through bone. The system comprises a needle trocar 20 (the main body of the instrument set). The trocar 20 comprises an elongate shaft 28 having a handle 24 at its proximal end 32 and a trocar channel 36 passing through to the distal end 22 of the trocar 20. The trocar channel 36 is generally sized to allow the other instruments in the system 10 to be slideably introduced into the patient to a treatment region. System 10 further comprises a straight stylet 80 having a sharp-tipped needle 84 at its distal end that is used with the needle trocar 20 to create the initial path through the soft tissue and cortical shell to allow access to the cancellous bone, a curved cannula 50 that is used to create/maintain the curved path within the bone/tissue. A straightening stylet 40 may be used to straighten out the curve and load the curved cannula 50 into the needle trocar 20. A curved stylet 60 may be used in conjunction with the curved cannula 50 to create the curved path within the bone/tissue, and a channeling stylet 90 is used to create a working channel for a treatment device (such as RF probe 100) beyond the end of the curved path created by the curved cannula 50.

The surgical devices and surgical systems described may be used to deliver numerous types of treatment devices to varying regions of the body. Although embodiments of the devices and systems are particularly useful in navigating through bone, in one embodiment they may also be used to navigate through soft tissue, or through channels or lumens in the body, particularly where one lumen may branch from another lumen.

The following examples illustrate embodiments of the system 10 applied to generating a curved bone path in the vertebral body, and more particularly for creating a bone path via a transpedicular approach to access targeted regions in the spine. In particular, the system 10 may be used to deliver a treatment device to treat or ablate intraosseous nerves, and in particular that basivertebral nerve. Although the system and methods provide significant benefit in accessing the basivertebral nerve, in accordance with several embodiments, the system 10 may similarly be used to create a bone path in any part of the body (such as the humerus, femur, pelvis, fibula, tibia, ulna, radius, etc.)

Figure 3:
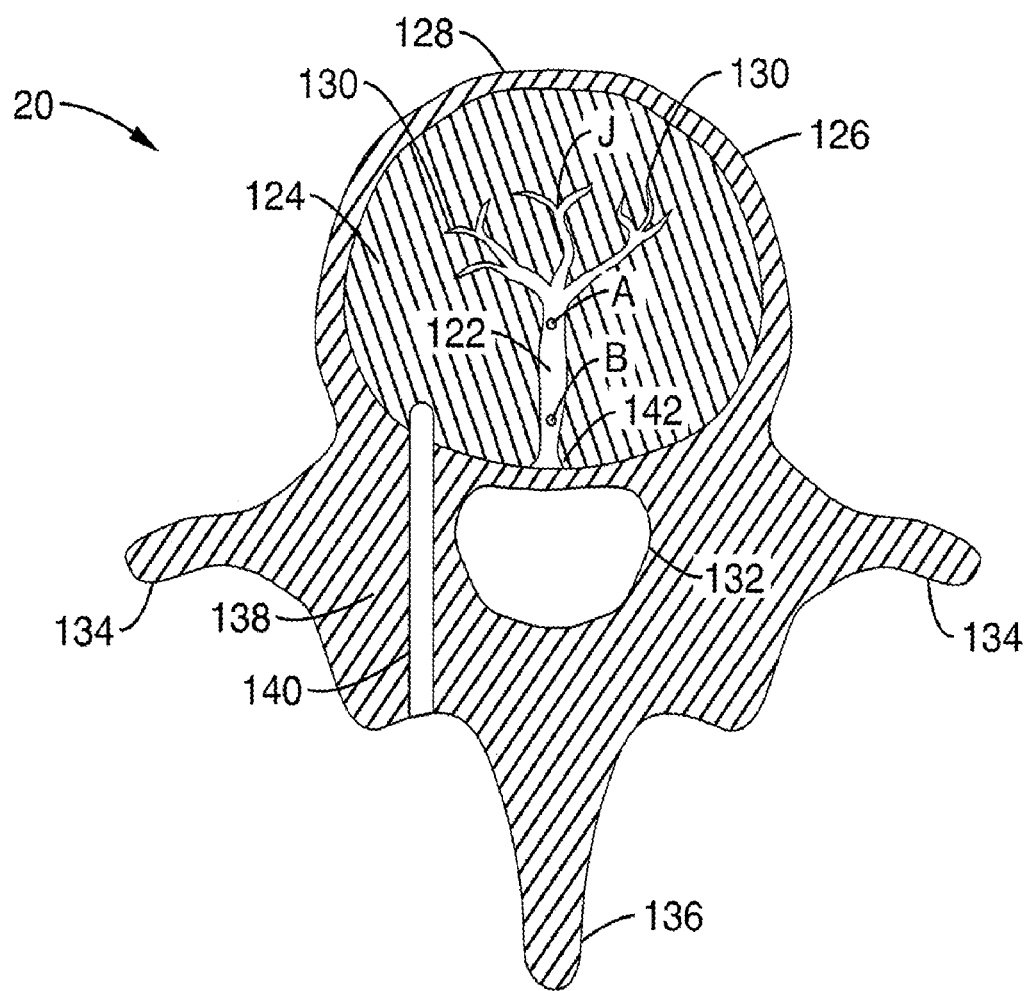
FIG. 3 illustrates a sectioned view of an embodiment of a vertebral body with a path bored through the cortical shell.

FIG. 3 illustrates a cross-sectional view of a vertebra 120. Recently, the existence of substantial intraosseous nerves 122 and nerve branches 130 within human vertebral bodies (basivertebral nerves) has been identified. The basivertebral nerve 122 has at least one exit 142 point at a location along the nerve 122 where the nerve 122 exits the vertebral body 126 into the vertebral foramen 132. Minimally invasive interventional treatments for lower back pain are a promising alternative to existing non-surgical conservative therapy or spinal surgery treatments, including spinal fusion. The basivertebral nerve may provide innervation to the trabecular bone of the vertebral body. The basivertebral nerves accompany the basivertebral vessels that enter the vertebrae through the large posterior neurovascular foramen. The basivertebral nerves may comprise segments having lengths between 5 and 8 mm and diameters of 0.25 to 0.5 mm. The basivertebral nerve is believed to conduct pain receptive signals from intraosseous sources. Accordingly, modulation (e.g., defunctionalization, ablation) of the basivertebral nerve is provided in several embodiments herein to reduce chronic or acute back pain.

In accordance with several embodiments, the basivertebral nerves are at, or in close proximity to, the exit point 142. In some embodiments, the exit point 142 is the location along the basivertebral nerve where the basivertebral nerve exits the vertebra. Thus, the target region of the basivertebral nerve 122 is located within the cancellous portion 124 of the bone (i.e., to the interior of the outer cortical bone region 128), and proximal to the junction J of the basivertebral nerve 122 having a plurality of branches 130. Treatment in this target region is advantageous because only a single portion of the basivertebral nerve 122 need be effectively treated to modulate (e.g., denervate or otherwise affect the entire basivertebral nerve system). Treatment, in accordance with one embodiment, can be effectuated by focusing in the region of the vertebral body located between 60% (point A) and 90% (point B) of the distance between the anterior and posterior ends of the vertebral body. In some embodiments, treatment is located at or proximate (e.g., posterior to) the junction J. In some embodiments, treatment of the basivertebral nerve 122 in locations more downstream than the junction J requires the denervation of each branch 130. The target region may be identified or determined by pre-operative imaging, such as from MRI or CT images. In various embodiments, treatment can be effectuated by focusing in the region of the vertebral body located at a region that is more than 1 cm from the outer cortical wall of the vertebral body, within a region that is centered at or about 50% of the distance from the posterior outer wall of the vertebral body to the anterior outer wall, and/or within a region that is between 10% and 90% (e.g., between about 10% and about 60%, between about 20% and about 80%, between about 35% and about 65%, between about 5% and about 65%, between about 10% and about 55%, or overlapping ranges thereof) of the distance from the posterior outer wall of the vertebral body to the anterior outer wall.

In various embodiments, the junction J is located at a location of the terminus of the vertebral foramen, at the junction between a main trunk of the basivertebral nerve 122 and the initial downstream branches, at a location corresponding to a junction between at least one of the initial downstream branches and its respective sub-branches, or other locations along the basivertebral nerve 122.

In accordance with several embodiments, one approach for accessing the basivertebral nerve involves penetrating the patient's skin with a surgical instrument, which is then used to access the desired basivertebral nerves, e.g., percutaneously. In one embodiment, a transpedicular approach is used for penetrating the vertebral cortex to access the basivertebral nerve 122. A passageway 140 is created between the transverse process 134 and spinous process 136 through the pedicle 138 into the cancellous bone region 124 of the vertebral body 126 to access a region at or near the base of the nerve 122. In one embodiment, a postereolateral approach (not shown) may also be used for accessing the nerve. The transpedicular approach, postereolateral approach, basivertebral foramen approach, and other approaches are described in more detail in U.S. Pat. No. 6,699,242, herein incorporated by reference in its entirety.

FIGS. 4A-4F illustrate an embodiment of a method for accessing the basivertebral nerve with the system 10. First, the straight stylet 80 can be inserted in aperture 26 at the proximal end 32 of needle trocar 20. The straight stylet 80 can be advanced down the trocar channel 36 (see FIG. 2) of the trocar 20 until the proximal stop 82 abuts against handle 24 of the trocar 20, at which point the distal tip 84 of straight stylet protrudes out of the distal end 22 of the trocar 20. In one embodiment, the tip 84 of the straight stylet 80 comprises a sharp tip for piercing soft tissue and bone.

Figure 4I:
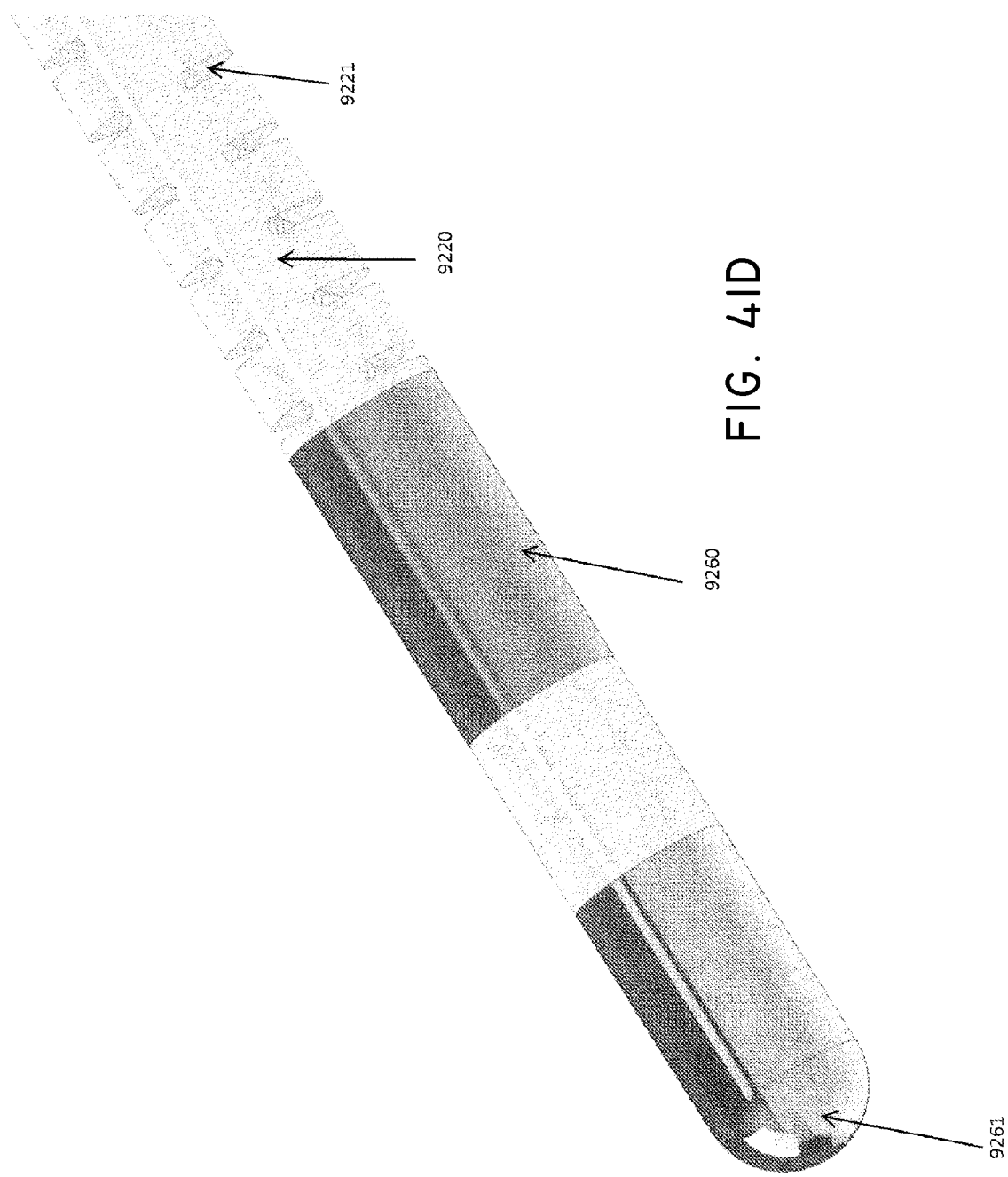
FIGS. 4A-4F illustrate a method for accessing the basivertebral nerve in accordance with several embodiments.
Figure 41E:
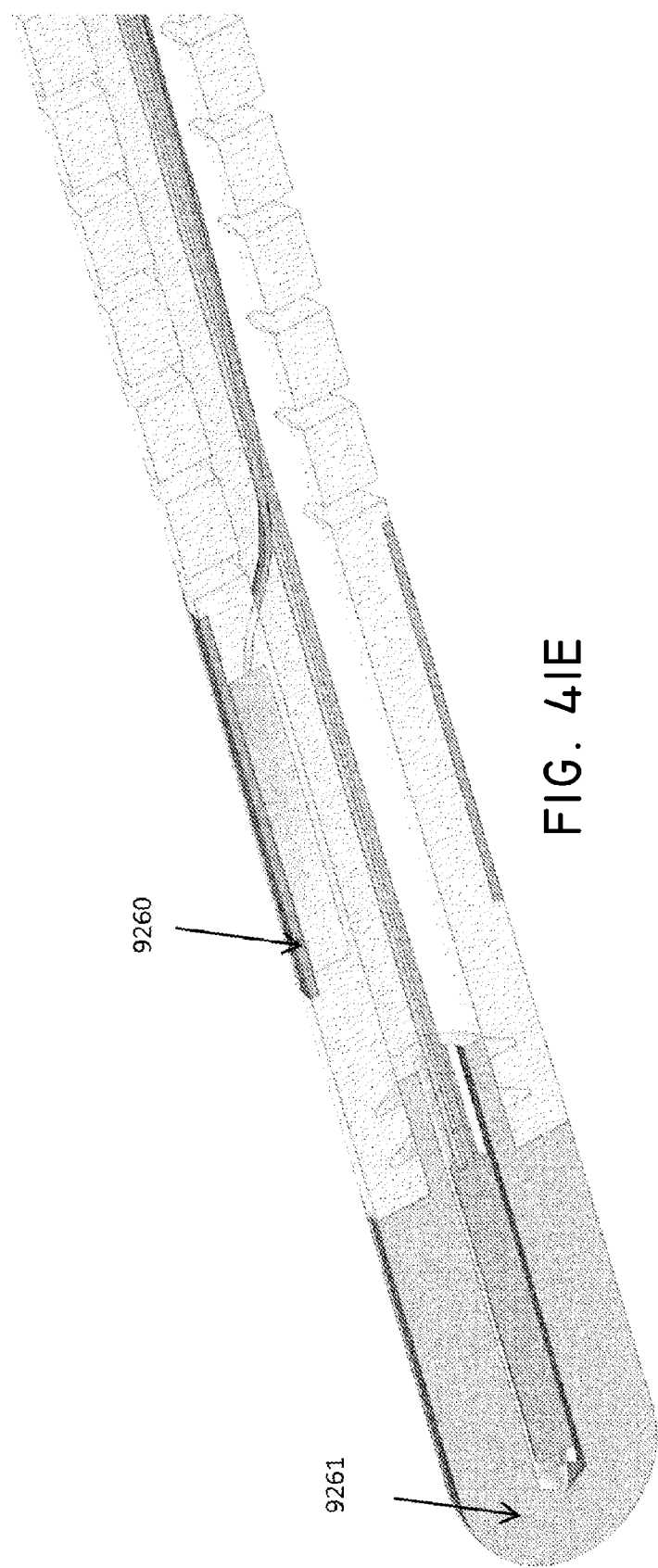

Referring now to FIG. 4A, in some embodiments, the assembly (trocar 20 and straight stylet 80) is advanced through soft tissue to the surface of the bone. Once the proper alignment is determined, the assembly can be advanced through the cortical shell of pedicle 138 and into the cancellous interior 124 of the bone.

In some embodiments, after the proper depth is achieved, the straight stylet 80 is removed from the trocar 20, while the trocar 20 remains stationary within the vertebra 120. The straightening stylet 40 can then be inserted into proximal aperture 52 (see FIG. 2) of the curved cannula 50 and advanced along the central lumen of the curved cannula 50 until the stop 42 of the stylet 40 abuts up to the proximal end of the curved cannula. In some embodiments, this advancement forces the distal tip of the straight stylet through the curved section 56 of the curved cannula 50 to straighten out the curve 56. In some embodiments, the straight stylet comprises a hard, noncompliant material and the distal end 56 of the curved cannula 50 comprises a compliant, yet memory retaining material (e.g. Nitinol, formed PEEK, etc.) such that the curved 56 section yields to the rigidity of the straightening stylet 40 when installed, yet retains its original curved shape when the stylet 40 is removed.

As shown in FIG. 4B, once the straightening stylet 40 is secure and the curved cannula 50 is straight, they can be inserted together into the needle trocar 20 and secured. Proper alignment (e.g. prevent rotation, orient curve direction during deployment) may be maintained by aligning a flat on the upper portion 57 of the curved cannula 50 to an alignment pin secured perpendicularly into the needle trocar 20 handle 24. Other alignment elements may also be used (e.g., visual indicia such as lines, text, shapes, orientations, or coloring). In some embodiments, once the curved cannula 50 is secure, the straightening stylet 40 is removed, while the curved cannula 50 remains stationary within the trocar 20.

Referring to FIG. 4C, in accordance with several embodiments, the curved stylet 60 can then be straightened out by sliding the small tube 68 proximally to distally on its shaft towards the distal tip 64 or from the distal tip 64 proximally on its shaft towards the proximal end 62. In some embodiments, once the curved distal tip 66 is straightened out and fully retracted inside the small tube 68, the curved stylet 60 may be inserted into the proximal aperture 52 of the curved cannula 50, which still resides inside the needle trocar 20. As the curved stylet 60 is advanced into the curved cannula 50, the small tube 68 may be met by a stop 55 (see FIG. 4C). As the curved stylet 60 continues to advance, the small tube 68 may be held inside the handle of the curved cannula 50. This can allow the curve of the stylet 60 to be exposed inside the curved cannula 50. To create the maximum force, the curve of the two parts (50 & 60) may be aligned. To facilitate alignment, the cap on the curved stylet 60 can have an alignment pin 70 which engages with alignment notch 52 on the proximal end of the curved cannula 50. Other alignment elements may also be used (e.g., visual indicia such as lines, text, shapes, orientations, or coloring).

Once the stylet 60 is fully seated and aligned with the curved cannula 50, the tip of the curved stylet 60 may protrude from the tip of the curved cannula 50 by about 1/16 to 3/16 inches. This protrusion can help to drive the curve in the direction of its orientation during deployment.

Referring now to FIG. 4D, in accordance with several embodiments, with the curved stylet 60 and the curved cannula 50 engaged, the locking nut 58 at the top of the curved cannula 50 may be rotated counter clockwise to allow the cannula 50 and stylet 60 to be advanced with relation to the needle trocar 20 such that the proximal end 52 rests or abuts against locking nut 58, advancing the curved cannula 50 and stylet 60 beyond the distal opening of trocar 20 to generate a curved path in the cancellous bone region 124. As the curved cannula 50 and stylet 60 are advanced they can curve at a radius of 0.4 to 1.0 inches through cancellous bone and arc to an angle between approximately 0° to approximately 180° (e.g., from approximately 5° to approximately 110°, from approximately 45° to approximately 110°, from approximately 15° to approximately 145°, from approximately 30° to approximately 120°, from approximately 60° to approximately 90°, from approximately 10° to approximately 45°, overlapping ranges thereof, or any angle within the recited ranges). Once the curved cannula 50 and stylet 60 are deployed to the intended angle, the locking nut at the top of the curved cannula 50 may be engaged with the needle trocar 20 to stop any additional advancement of the curved stylet cannula assembly.

Figure 7B:
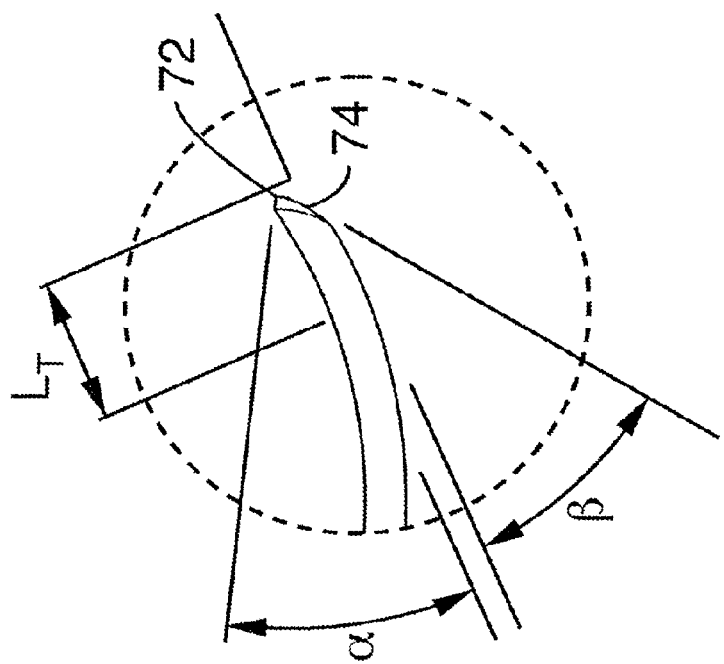
FIGS. 7A-7B show embodiments of a curved stylet.
Figure 7A:
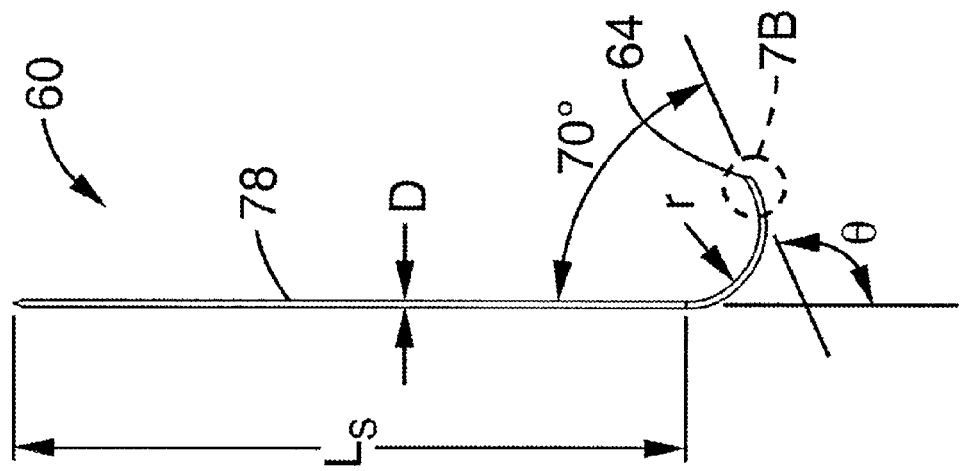

In accordance with several embodiments, FIGS. 7A-7B illustrate the tip of a curved stylet 60, which has been formed with two angles. To help the curve deployment in the proper direction, the curve 66 of the curved stylet 60 may be shaped in a predetermined orientation. The angle on the inside of the curve 72 may be less than the angle on the outside of the curve 74. This disparity in angles helps the stylet cannula assembly (collectively 50, 60) curve in the bone as bone pushes against outside curve face 74, thereby ensuring the curve radius is maintained during deployment, according to one embodiment.

Referring now to FIG. 4E, in accordance with several embodiments, the curved stylet 60 may then be removed and replaced by the channeling stylet 90. The tip 94 of the channeling stylet 90 may be advanced beyond the end 54 of the curved cannula 50 towards the intended target treatment zone.

Referring now to FIG. 4F, in accordance with several embodiments, once the channeling stylet 90 reaches the target treatment zone, it is removed, thereby creating a working channel. In some embodiments, channel 140 generally has a first section 142 that crosses the cortical bone of the pedicle 138, followed by a curved path. These sections may be occupied by curved cannula 50 such that a treatment device fed through the cannula 50 will have to follow the curve of the cannula 50 and not veer off in another direction. The channel 140 may further comprise the linear extension 146 in the cancellous bone 124 to further advance the treatment device toward the treatment site T. In some embodiments, the treatment site T corresponds to a location of a terminus of the nerve 122 (e.g., terminus of the basivertebral foramen or the junction between a main trunk of the basivertebral nerve and its sub-branches). In some embodiments, the treatment site or location T is identified without knowing the precise location of the basivertebral nerve 122.

With the trocar 20 and curved cannula 50 still in place, a treatment device (e.g. treatment probe 100 shown in FIG. 2) with an active element 102 on the distal end 104 of elongate flexible catheter 110 may be delivered to the target treatment location T to perform a localized treatment. In some embodiments, the target treatment location T is identified prior to introduction of the trocar 20 by magnetic resonance (MR) imaging, computed tomography (CT) imaging, or other imaging modalities. The introduction of the trocar 20, curved cannula 50, treatment device, and/or other instruments can be visualized in real time using fluoroscopic or other imaging to ensure proper introduction and orientation within the target treatment location. In accordance with several embodiments, the treatment (e.g., neuromodulation) can be performed at multiple levels of vertebrae (simultaneously or sequentially with one, two, three or more treatment devices). The levels may be adjacent or spaced apart. For example, treatments can be performed at the L4 and L5 levels, at the L3-L5 levels, at the L5 and S1 levels, or at other combinations of lumbar, sacral, cervical or thoracic vertebral levels. In some embodiments, a single treatment system or device (e.g., a generator and one or more radio frequency probes with one or more electrode pairs) or multiple treatment systems or devices (e.g., two or more generators each with one, two, three or more radiofrequency probes) are used to administer the treatment. In one embodiment, multiple treatment probes can be daisy-chained or otherwise reversibly or integrally coupled to (or integral with) each other and/or to a single generator or other energy generation module to simultaneously treat multiple levels of vertebrae that are spaced apart. A "y" shaped device may be used in some embodiments. In various embodiments, the treatment devices comprise one, two, three or more energy sources (e.g., electrodes) that can be connected by one or more connection members or elements to space the energy sources apart to simultaneously treat multiple levels of vertebrae. Simultaneous treatment of two or more vertebrae may be treated with radiofrequency or other therapeutic modalities (ultrasound, radiation, steam, microwave, laser, cryoablation, etc.). Different therapeutic modalities or different energy levels of the same therapeutic modality that work simultaneously are provided in some embodiments.

In one embodiment, the active element 102 is delivered to the treatment site and activated to deliver therapeutic treatment energy. In various embodiments, the treatment device comprises a probe, catheter, antenna, wire, tube, needle, cannula, sleeve, or conduit. The treatment device may comprise an RF delivery probe having bipolar electrodes 106 and 108 that deliver a therapeutic level of heating (e.g., thermal dose) to modulate (e.g., stimulate or ablate) at least a portion of the nerve 122.

In some embodiments, the treatment device comprises a microwave energy delivery device comprising one or more antennas. In some embodiments, the treatment device comprises a chemical ablation or cryoablation device comprising a fluid conduit for delivery (e.g., injection) of fluids, chemicals or agents (e.g., neurolytic agents) capable of ablating, stimulating, denervating, blocking, disrupting, or otherwise modulating nerves. In some embodiments, the treatment device comprises an ultrasound delivery device having one or more transducers or a laser energy delivery device comprising one or more light delivery elements (e.g., lasers, such as fiber optic lasers or vertical cavity surface emitting lasers (VCSELs), or light emitting diodes (LEDs)).

According to several embodiments of the invention, many treatment modalities can be delivered to the treatment site for modulation of nerves or other tissue (e.g., neuromodulation, ablation, temporary or permanent denervation, stimulation, inhibition, blocking, disruption, or monitoring). For example, treatment may be affected by monopolar or tripolar RF, ultrasound, radiation, steam, microwave, laser, or other heating means. These modalities may be delivered to the treatment site through one or more of the embodiments of systems and/or methods disclosed herein, and treatment applied such that the nerve is heated to the desired level for the desired duration (e.g., a sufficient thermal dose is applied) to affect stimulation, denervation, ablation or the desired therapeutic effect.

For example, the ultrasonic energy can be controlled by dosing, pulsing or frequency selection to achieve the desired heating level for the desired duration. Similarly, microwave treatment may be applied using a microwave energy delivery catheter and/or one or more antennas. Microwaves may be produced with a frequency in the range of 300 GHz to 300 MHz, between 1 GHz and 5 GHz, between 2 GHz and 10 GHz, between 10 GHZ and 100 GHz, 100 GHz and 300 GHz, between 50 GHz and 200 GHz, between 200 GHz and 300 GHz, or overlapping ranges thereof. Pulses of between 1-5 seconds, between 2-3 seconds, between 0.5 seconds-2 seconds, between 4-5 seconds, between 5-10 seconds, between 10-30 seconds, or overlapping ranges between, in duration may be generated. In some embodiments, a single pulse, 1-3 pulses, 2-4 pulses, 3-8 pulses, 8-20 pulses, or overlapping ranges between, may be generated.

Radiation therapy may use radiation sources comprising any one of a number of different types, such as, but not limited to, particle beam (proton beam therapy), cobalt-60 based (photon or gamma-ray source such as that found in the GammaKnife), or linear accelerator based (e.g., linac source). The dose of radiation delivered to the patient will typically range between 10 Gy and 70 Gy. However, because the treatment region is contained within the large bony mass of the vertebral body, higher doses may be contemplated, as there is little risk to surrounding tissues that are more vulnerable. The dose may be varied based on the treatment volume, or other variables such as treatment time and dose concentration. A prescription of 35 instances of a 2 Gy dose might be replaced by 15 instances of a 3 Gy dose, a technique known as "hypofractionation." Taken to its logical extreme, this might be replaced with a single 45 Gy dose if the dosage delivered to healthy tissue can be reduced significantly. An identification dose may in some embodiments be used prior to the treatment dose, for example, to elicit some response form the patient relating to the patient's pain. The identification dose is generally a much smaller dose than treatment dose TD, so as not to damage healthy tissue. Doses may range from 0.5 Gy to 5 Gy. However, this range may also change based on considerations such as anatomy, patient, etc.

Additionally or alternatively, the treatment device may comprise a fluid or agent delivery catheter that deposits an agent or fluid, e.g. bone cement, phenol, alcohol, neurotoxin, inhibitory or stimulatory drug, chemical, or medicament, for neuroablation or permanent or temporary denervation, or other therapeutic agent, to the treatment site or location T. Growth factors, stem cells, gene therapy or other biological therapeutic agents may also be delivered.

In some embodiments, cryogenic cooling may be delivered for localized treatment of the basivertebral nerve or an intraosseous nerve using, for example, liquid nitrogen, liquid nitrous oxide, liquid air, or argon gas. Cryotherapy may be delivered in one or more freeze cycles. In several embodiments, two freeze-thaw cycles are used. In some embodiments, 3-5 freeze-thaw cycles are used. In some embodiments, a single freeze-thaw cycle is used In some embodiments, a desired temperature of the tissue is −40° C. to −50° C., −20° C. to −40° C., −35° C. to −45° C., −50° C. to −80° C., or overlapping ranges thereof. The desired temperature may be maintained for 5-20 minutes, 10-15 minutes, or greater than 10 minutes, depending on the temperature and thermal dose desired. Furthermore, treatment may be effected by any mechanical destruction and or removal means capable of severing or denervating the basivertebral nerve. For example, a cutting blade, bur, electrocautery knife or mechanically actuated cutter may be used to effect denervation of the basivertebral nerve.

In addition to or separate from treating (e.g., modulating) the basivertebral nerve or an intraosseous nerve, a sensor may be delivered to the region to preoperatively or postoperatively measure nerve conduction at the treatment region. In this configuration, the sensor may be delivered on a distal tip of a flexible probe that may or may not have treatment elements as well.

In accordance with several embodiments, the goal of the treatment may be ablation, or necrosis of the target nerve or tissue, or some lesser degree of treatment to denervate the basivertebral nerve. For example, the treatment energy or frequency may be just sufficient to stimulate the nerve to block the nerve from transmitting signals (e.g. signals indicating pain) without ablation or necrosis of the nerve. The modulation may be temporary or permanent.

In accordance with several embodiments, the therapeutic modalities described herein (including energy or agent delivery) modulates neurotransmission (e.g., neurotransmitter synthesis, release, degradation and/or receptor function, etc.). In some embodiments, signals of nociception are affected. Effects on neurokinin A, neuropeptide Y, substance P, serotonin and/or other signaling pathways are provided in some embodiments. Calcium and/or sodium channel effects are provided in one embodiment. In some embodiments, G-protein coupled receptors are affected.

Once the treatment is complete, the probe 100 may be withdrawn. The curved cannula 50 may then be withdrawn into the needle trocar 20. The needle trocar 20 with the curved cannula 50 may then be removed and the access site may be closed as prescribed by the physician or other medical professional.

In the above system 10, in accordance with several embodiments, the design of the curves 56 and 66 of the curved cannula 50 and curved stylet 60 is such that a flexible element (e.g., distal portion of the treatment device) can navigate through the angular range of deployment of the curved cannula 50 (e.g., Nitinol or other material tube). The curved cannula 50 allows the flexible element to navigate through a curve within bone without veering off towards an unintended direction. Cancellous bone density varies from person to person. Therefore, creating a curved channel within varying density cancellous bone 124 will generally not predictably or accurately support and contain the treatment device as it tries to navigate the curved channel.

With the system 10, the treatment device 100 may be deployed into the bone through the curved cannula 50 (e.g., Nitinol tube), which supports the flexible element (e.g., distal portion of the treatment device) as it traverses through the curve. When it departs from the tube, it will do so in a linear direction along path 146 towards the target zone. In accordance with several embodiments, this advantageously allows the user to predictably and accurately deploy the treatment device towards the target zone or location T regardless of the density of the cancellous bone.

In some embodiments, a radius of curvature that is smaller than that which can be achieved with a large diameter Nitinol tube may be advantageous. To achieve this, the curved portion of the curved cannula 50 may take one of several forms. In one embodiment, the curved cannula 50 is formed from a rigid polymer (e.g., formed PEEK) that can be heat set in a particular curve. If the polymer was unable to hold the desired curve, an additional stylet (e.g. curved stylet 60) of Nitinol, flexible stainless steel, shape memory material, metallic or metallic-based material, or other appropriate material, may also be used in conjunction with the polymer tube to achieve the desired curve. In some embodiments, the stylet comprises a braided tube, rod, or wire. In some embodiments, the stylet comprises a non-braided tube, rod, or wire, or combinations thereof. This proposed combination of material may encompass any number or variety of materials in multiple different diameters to achieve the desired curve. These combinations only need to ensure that the final outside element (e.g. trocar 20) be "disengageable" from the internal elements and have an inner diameter sufficient to allow the desired treatment device 100 to pass to the treatment region T. In accordance with several embodiments, the treatment region T is in a posterior section (e.g., posterior to a midline) of the vertebral body. The treatment region T may correspond to an expected location of a terminus of a basivertebral foramen.

In one embodiment, the curved cannula 50 may comprise a Nitinol, shape memory material, stainless steel or other metallic tube having a pattern of reliefs or cuts (not shown) in the wall of the tube (particularly on the outer radius of the bend). The pattern of cuts or reliefs could allow the tube to bend into a radius tighter than a solid tube could without compromising the integrity of the tubing wall. The curved portion of the curved cannula 50 may comprise a different material than the main body of the curved cannula or the same material.

Figure 5:
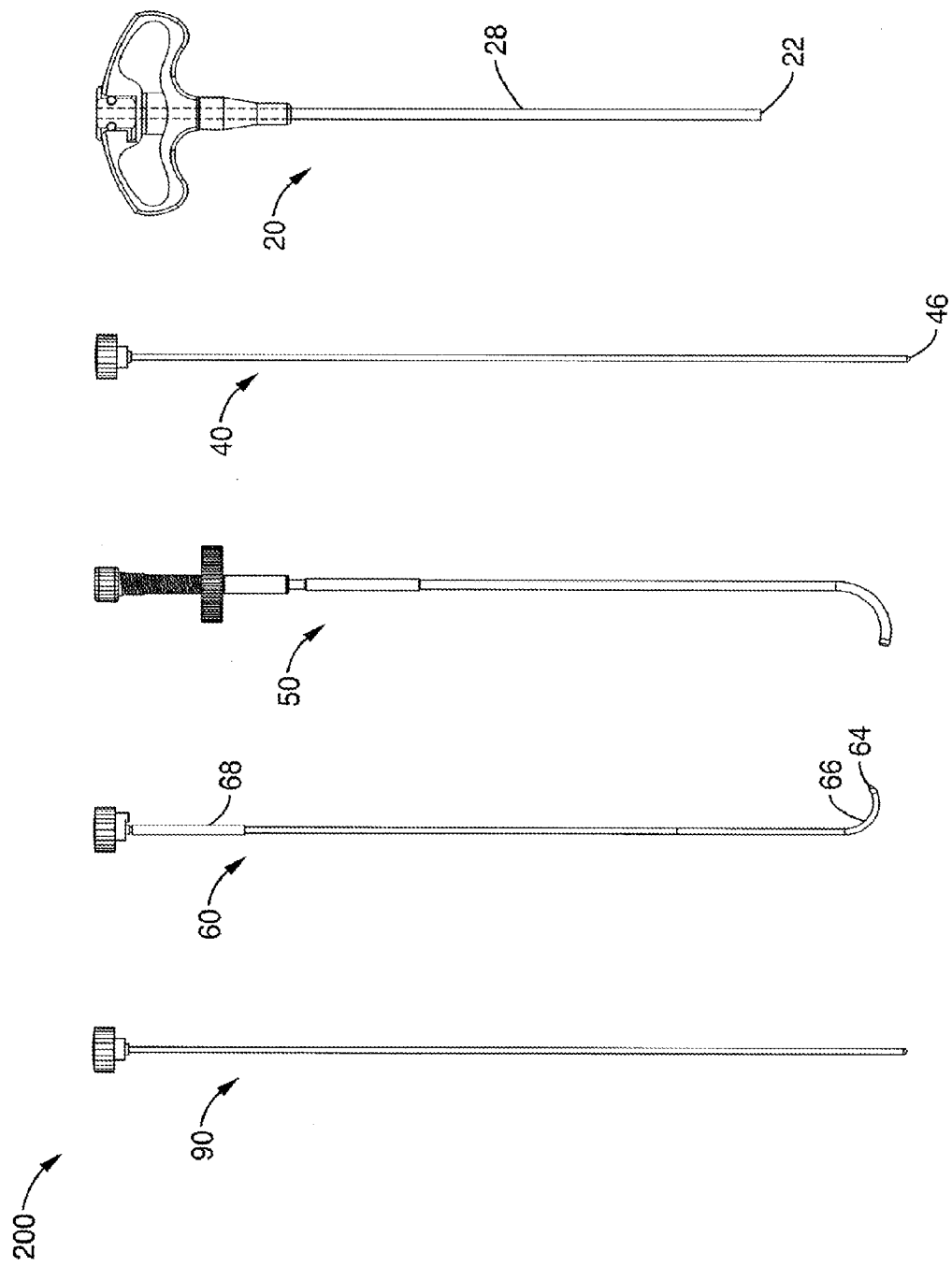
FIG. 5 shows an alternative embodiment of a system for generating a curved path in bone.

FIG. 5 illustrates a second embodiment of the system or kit 200 that may be used to reduce the number of steps required for the procedure. The second embodiment includes a needle trocar 20, straightening stylet 40, used with the needle trocar 20 and the curved cannula 50 to create the initial path through the soft tissue and cortical shell to allow access to the cancellous bone, curved stylet 60 used in conjunction with the curved cannula 50 to create the curved path within the bone/tissue, and channeling stylet 90 used to create a working channel for a treatment device (e.g., probe) beyond the end of the curved path created by the curved stylet.

In an embodiment of the method, the straightening stylet 40 is inserted into the curved cannula 50 and secured. In this embodiment, the straightening stylet 40 has a sharp tip 46 designed to penetrate bone. Once the straightening stylet 40 is secure and the curved cannula 50 is straight, they are inserted into the needle trocar 20 and secured. In tone embodiment, the curved cannula 50 and straightening stylet 40 are inserted into the shaft 28 of the trocar 20 only as far as to have sharp tip 46 of the straightening stylet 40 protrude from the distal end 22 of the trocar 20. Proper alignment is maintained by aligning a flat on the upper portion of the curved cannula 50 with a pin secured perpendicularly into the needle trocar 20 handle. Other alignment elements may also be used (e.g., visual indicia such as lines, text, shapes, orientations, or coloring).

Figure 6:
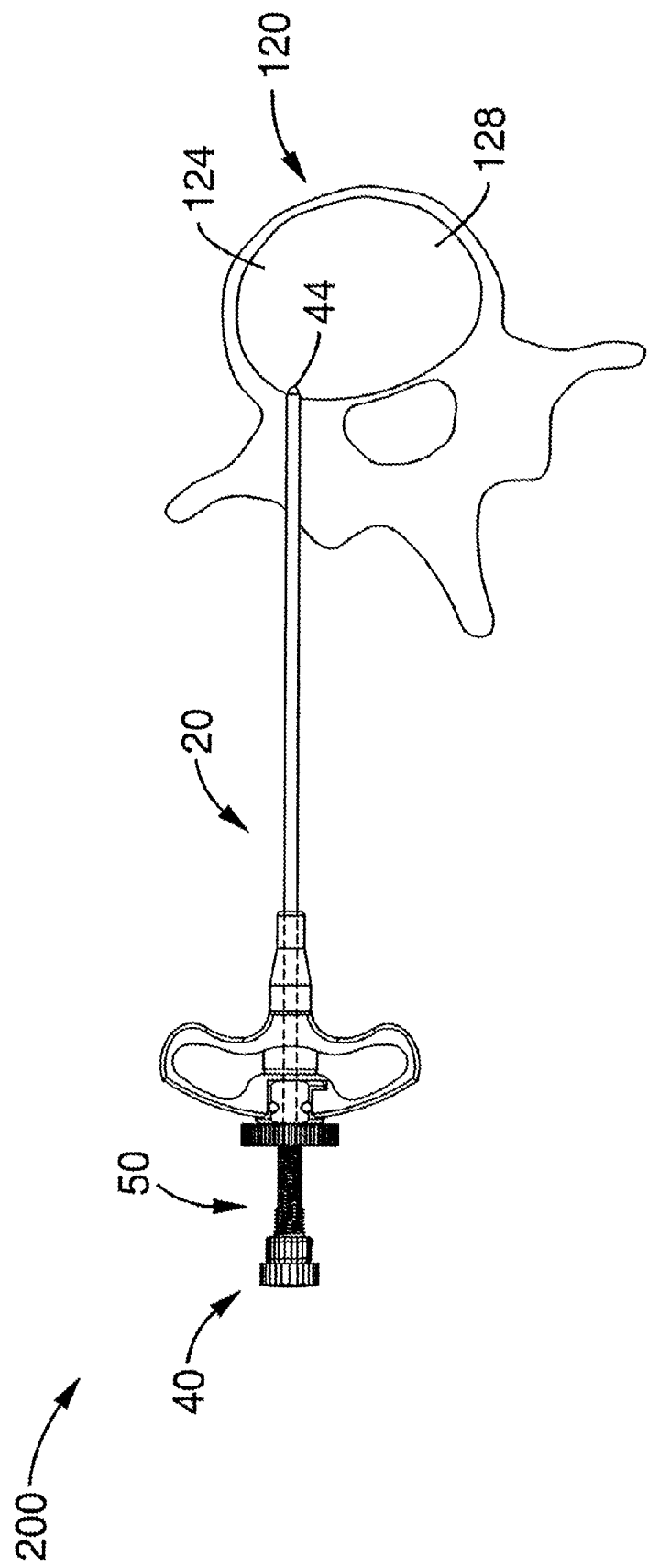
FIG. 6 shows an embodiment of the system of FIG. 5 being installed in a vertebral body.

Referring now to FIG. 6, in accordance with several embodiments, once the curved cannula 50 is secure, the assembly (trocar 20, curved cannula 50, and straightening stylet 40) may be advanced through soft tissue to the surface of the bone. After finding the proper alignment at the pedicle 138 of vertebra 120, the assembly (trocar 20, curved cannula 50, and straightening stylet 40) may be advanced through the cortical shell 128 and into the cancellous interior 124 of the bone.

In accordance with several embodiments, after the proper depth is achieved, the straightening stylet 40 may be removed. The curved stylet 60 may then be straightened out by sliding the small tube 68 on its shaft towards the distal tip 64. In some embodiments, the curved distal tip 66 is straightened out and fully retracted inside the small tube 68, and then the curved stylet 60 is inserted into the curved cannula 50, which still resides inside the needle trocar 20. Once the curved stylet 60 is inserted into the curved cannula 50, the small tube 68 may be met by a stop 55 as illustrated in FIG. 4C. As the curved stylet 60 continues to advance, the small tube 68 may be held inside the handle of the curved cannula 50. This can allow the curve of the stylet 60 to be exposed inside the curved cannula 50.

In several embodiments, to create a maximum force, the curves of the two parts (50 & 60) may be aligned. To ensure alignment, the cap on the curved stylet 60 may have an alignment pin, which engages with a notch on the top of the curved cannula 50. Other alignment elements may also be used (e.g., visual indicia such as lines, text, shapes, orientations, or coloring).

In one embodiment, when the stylet 60 is fully seated and aligned with the curved cannula 50, the tip of the curved stylet 60 may protrude from the tip of the curved cannula 50 by about $\frac{1}{16}$ to $\frac{3}{16}$ inches. This protrusion can help to drive the curved cannula 50 in the direction of its orientation during deployment. Once the curved stylet 60 and the curved cannula 50 are engaged, the lock nut at the top of the curved cannula 50 may be rotated counter clockwise to allow the cannula 50 and stylet 60 to be advanced with relation to the needle trocar 20, as illustrated in FIG. 4D. As the curved cannula and stylet are advanced they generate a curved path toward the treatment location T. Once the curved cannula 50 and stylet 60 are deployed to the intended angle, the lock nut at the top of the curved cannula 50 may be engaged with the needle trocar 20 to stop any additional advancement of the curved stylet cannula assembly.

In accordance with several embodiments, the curved stylet 60 may then be removed and replaced by the channeling stylet 90. In some embodiments, the channeling stylet 90 is advanced beyond the end of the curved cannula 50, as illustrated in FIG. 4E, towards the intended target treatment zone, thereby creating a working channel for the active element to be inserted. Once the channeling stylet 80 reaches the target treatment zone, it can be removed and replaced by the treatment device 100, which can be delivered to the treatment site T and activated.

Once the treatment is complete, the treatment device 100 can be withdrawn. In some embodiments, the curved cannula 50 is then withdrawn into the needle trocar 20. The needle trocar 20 with the curved cannula 50 can then be removed and the access site can be closed as prescribed by the physician or other medical professional.

In accordance with several embodiments, FIGS. 7A and 7B illustrate detailed views of a Nitinol or other shape memory material wire, rod or tube for the curved stylet 60 (proximal end not shown). The wire comprises a shaft 78 having constant diameter D and a length $L_s$ that may vary according to the application and desired depth to the treatment location. The wire has a preformed distal tip that is curved to have a radius r that redirects the distal tip 64 at an angle σ with the shaft. As shown in FIG. 7A, angle σ is shown to be approximately 110°. In accordance with several embodiments, the preformed tip may have an angle ranging from a few degrees (slight deflection off axis), to up to 180° (e.g. directing back toward the proximal end).

As shown in FIG. 7B detailing the distal tip 64, the tip may have a distal extension $L_T$ that extends away from the shaft 78. To promote channeling along a path that follows radius r, the distal tip 64 is configured with dual-plane bevels 74 and 72. Plane 74 is offset at angle β, and plane 72 is offset at angle α. This configuration can allow for the stylet and/or curved cannula to travel through bone in a path correlating to the specified curve in the stylet and/or cannula.

In the example illustrated in FIGS. 7A and 7B, the curved stylet 60 may have a shaft length $L_S$ of approximately 2-5 inches (e.g., 3.6 in.), diameter D of approximately 0.02-0.06 inches (e.g., 0.040 in.), and a distal tip length $L_T$ of about 0.08-0.16 inches (e.g., 0.125 in.), a radius r of about 0.2-0.6 inches (e.g., 0.4 in.), and angle β=35° and angle α=31°. The angles may vary by up to about 10 degrees, up to 15 degrees, or up to 20 degrees in either direction. It should be noted that the above dimensions are for illustration only, and may vary depending on the anatomy and tissue type. For example, modulation devices disclosed herein can be used, in some embodiments, to modulate nerves or treat tissue in other areas of the spine. Non-spinal applications are also contemplated. For example, denervation of renal nerves, cardiac ablation and other non-spinal treatment can be accomplished according to several embodiments described herein.

Any of the embodiments described herein may be provided as a kit of instruments to treat different regions of the body. For example, the location, orientation and angle of the treatment device with respect to the trocar 20 may be varied by providing a set of instruments at varying increments. This may be achieved by varying the curvature (56, 66) in the curved cannula 50 and curved stylet 60. The curvature may be varied by varying the radius of curvature r, the insertion depth (shaft length $L_S$ and tip length $L_T$, and/or the final exit angle σ with respect to the trocar 20 central bore. Thus, the physician or other clinician may select a different kit for treating a lumber spine segment as opposed to a cervical spine segment, as the anatomy will dictate the path that needs to be channeled.

Thus in accordance with several embodiments, when treating different spine segments, a set out of the kit may be selected to match the vertebra (or other region being treated). For example, delivering the treatment device at or near the basivertebral nerve junction or terminus for a lumbar vertebra may have a different angle than for a sacral or cervical vertebra, and may vary from patient to patient. The set may be selected from the kit intraoperatively, or from a pre-surgery diagnostic evaluation (e.g. radiographic imaging of the target region).

Figure 8:
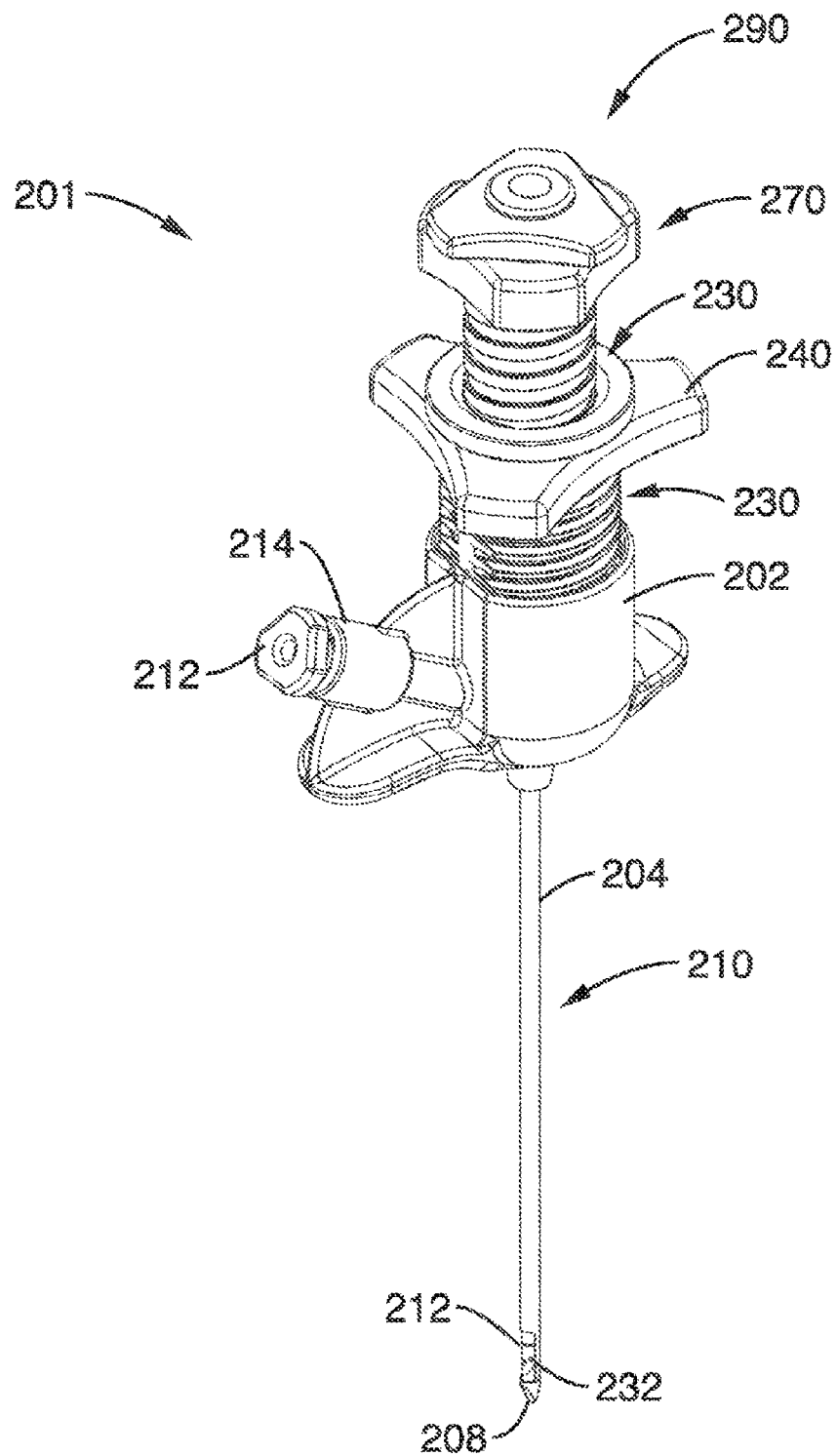
FIG. 8 illustrates a perspective view of an embodiment of a system for generating a curved path in bone.

FIGS. 8-18B illustrate one embodiment of a system 201 for generating a curved path in bon. FIG. 8 shows a perspective view of system 201 in a configuration ready for deployment within a patient's body. System 201 comprises an introducer/trocar 210 having a proximal end housing 202 coupled to an elongate delivery tube 204. The distal end tip 208 has a sharpened and/or beveled tip to facilitate entry into and delivery through at least a portion of a bony mass such as the vertebral body. The proximal end of the assembly (e.g., drive nut 270), may comprise a hard, rigid material to allow the trocar 210 to be tapped into place with a mallet or the like.

The elongate delivery tube 204 comprises a laterally positioned radial opening or window 212 disposed just proximal or at the distal tip 208. The window 212 provides radial access from the central channel 218 of tube 204 so that an instrument or probe (e.g. probe 250 distal end) may be delivered at an angle (e.g. non-axial) with respect to the tube axis or central channel 218.

Figure 9:
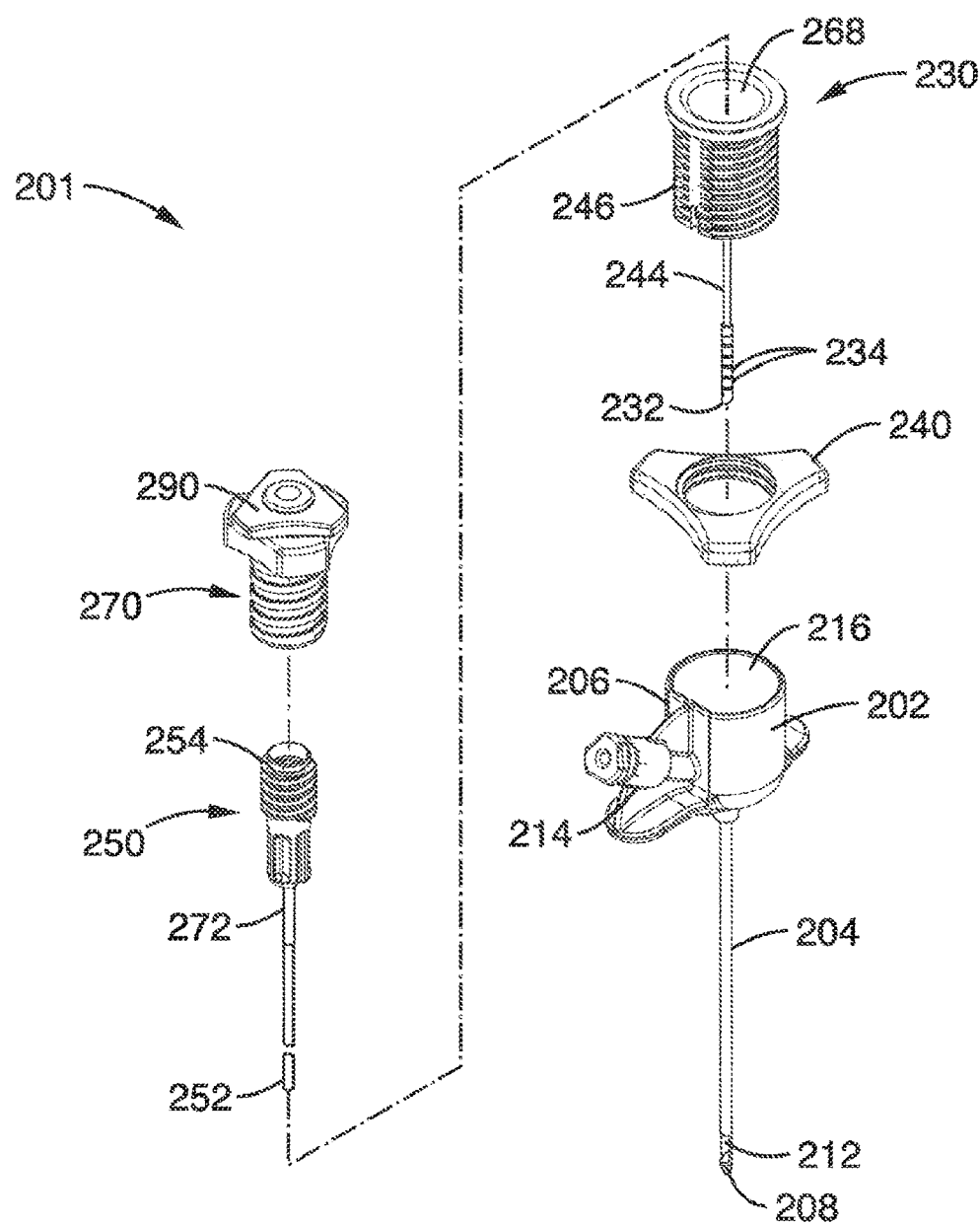
FIG. 9 is an exploded view of the system of FIG. 8.

FIG. 9 illustrates an exploded view of one embodiment of system 201 prior to delivery within a patient. In one embodiment, the trocar 210 is introduced to a location near the target treatment site as a whole assembly shown in FIG. 8. In one embodiment, the trocar may also be introduced to the location by itself, with the additional components being positioned once the trocar 210 is in place. In such a configuration, a stylet (not shown) may be positioned down the central channel 218 of the trocar 204 so as to block the aperture 212 from bone fragments or other tissue matter entering in channel 218. The stylet may have a hard, widened proximal end to allow the trocar 210 to be tapped into place.

In one embodiment, the proximal end 206 of trocar housing 202 comprises a centrally-located, counter-bore or recess 216 that is in communication with trocar channel 218. Trocar recess 216 allows placement and reciprocation of curveable cannula 230 within the trocar recess 216 and trocar central channel 218. The curveable cannula 230 may be held in place at a specified location within the trocar recess 216 via a stop nut 240 that is threaded about proximal body 246 of the curveable cannula 230. The curveable cannula 230 also comprises a central recess 268 within proximal body 246 that is centrally aligned with cannula channel 245. Central recess 268 and cannula channel 245 are configured to receive and allow reciprocation of probe 250, which is threaded into drive nut 270. In several embodiments, the drive nut 270 comprises a hardened proximal surface suitable for applying an impact force to advance one or more of the trocar, curveable cannula, or probe through bone.

Figure 12:
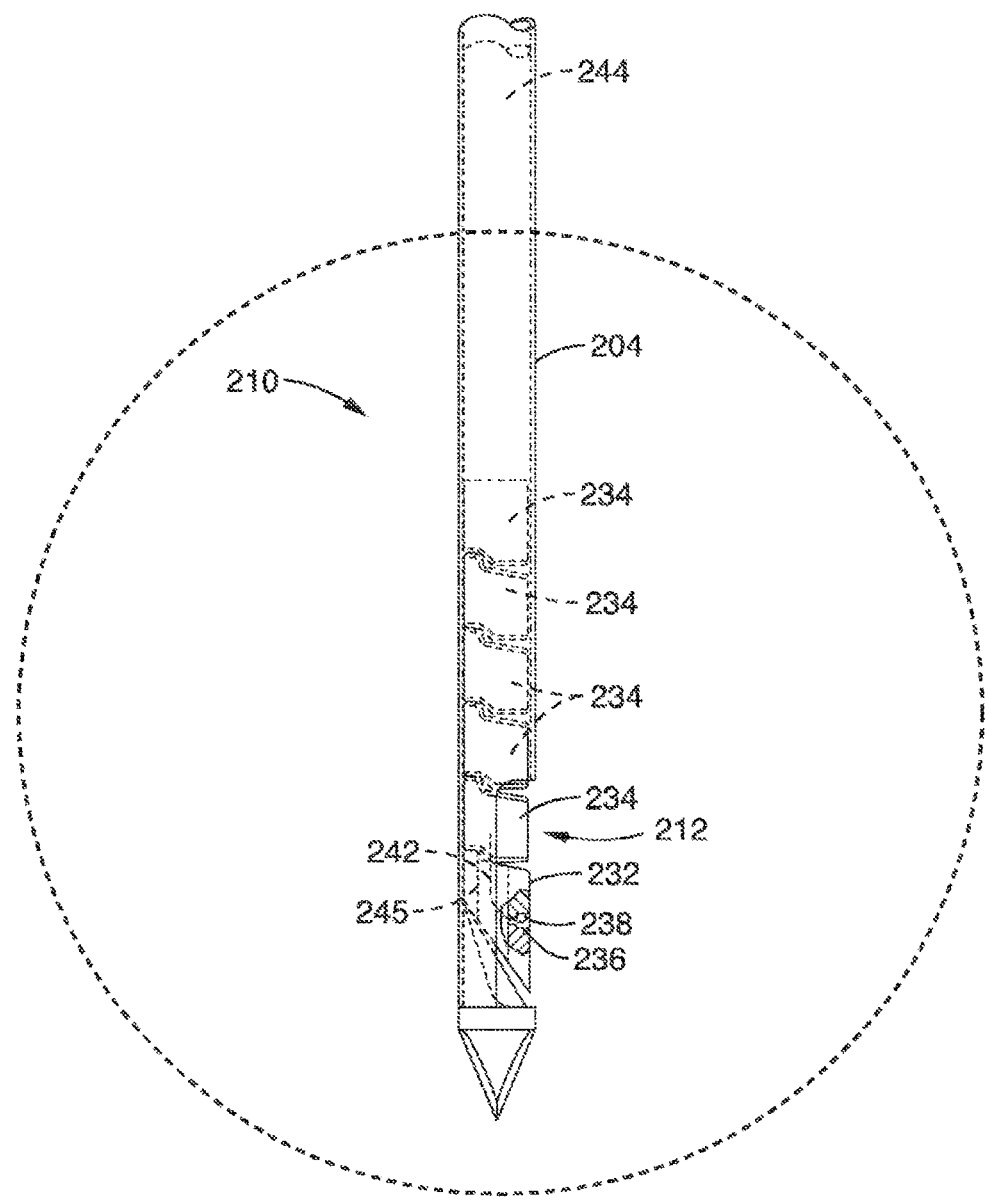
FIG. 12 is a side view of the distal end of an embodiment of the system of FIG. 8 during introduction of the system into the body.
Figure 14:
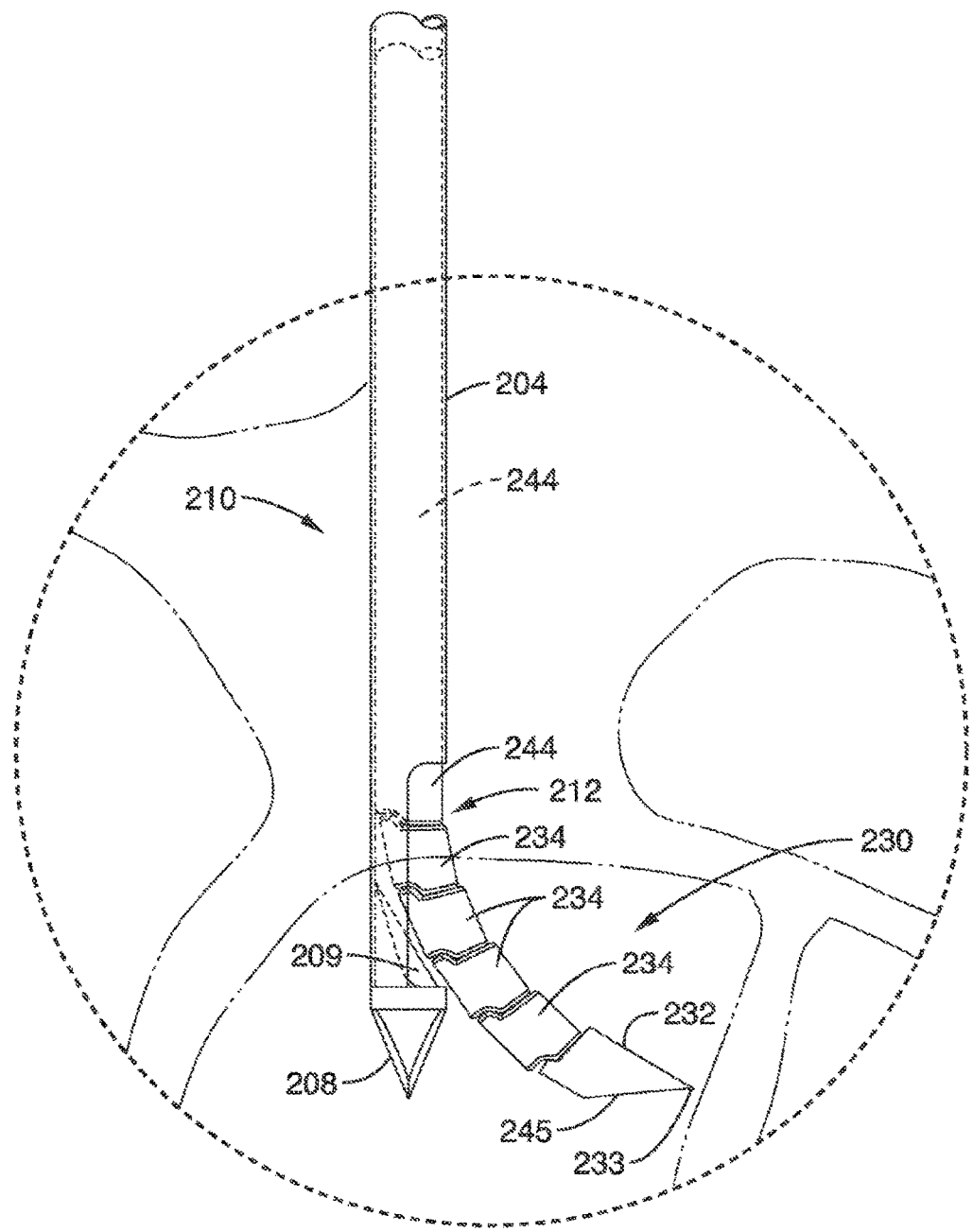
FIG. 14 is a side view of the distal end of an embodiment of the system of FIG. 8 after deploying the curveable cannula into the body.

FIGS. 10A-10E schematically illustrate one embodiment of system 201 in various stages of deployment. 11, 13, 15 and 16 illustrate section views of the proximal end of one embodiment system 201 through the various stages embodied in FIGS. 10A-10E. Correspondingly, FIGS. 12 and 14, illustrate close-up views of the distal end of one embodiment of system 201 through various stages embodied in FIGS. 10A-10E.

Figure 11:
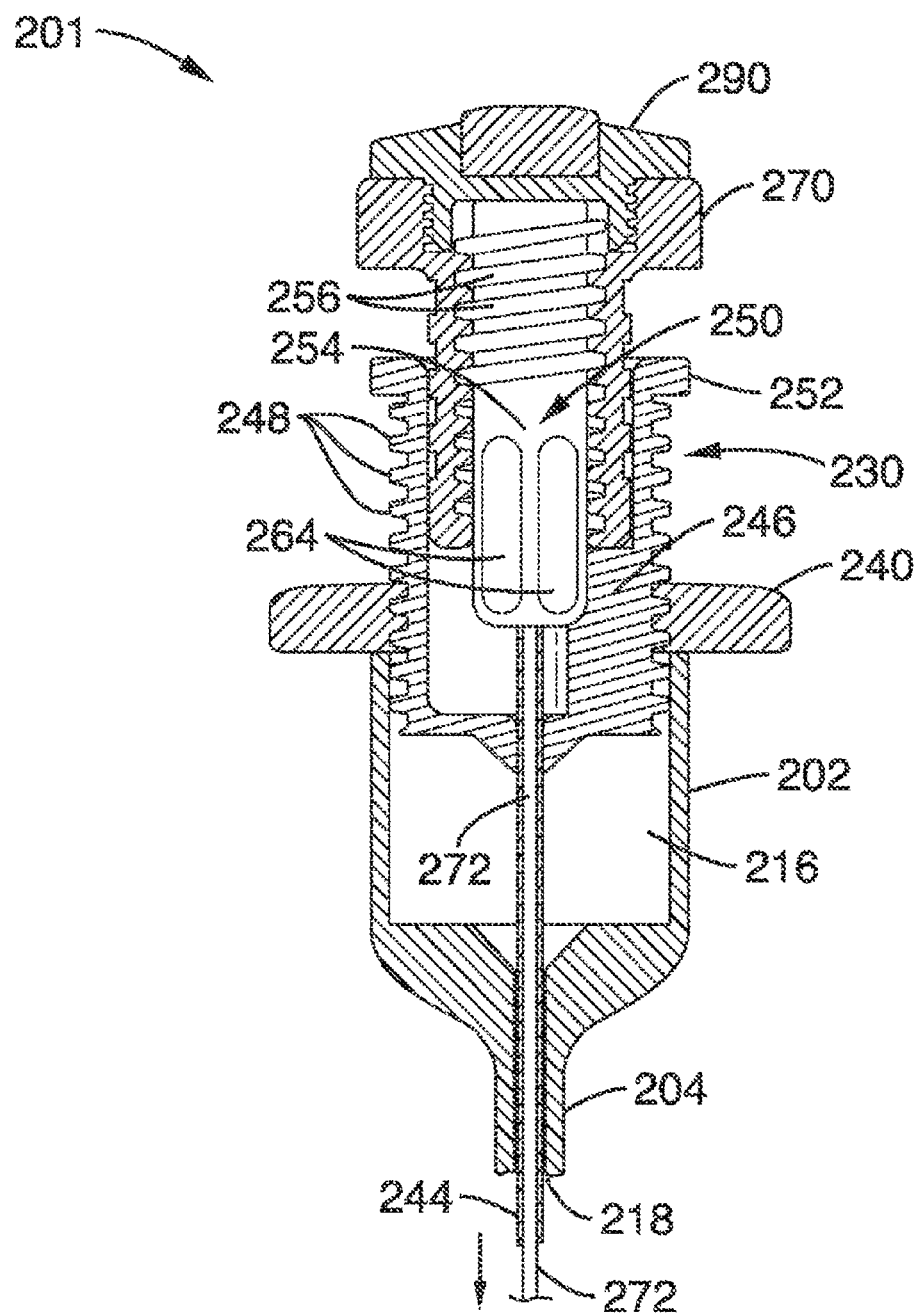
FIG. 11 is a section view of the proximal end of an embodiment of the system of FIG. 8 during introduction of the system into the body.

FIG. 11 illustrates a sectional view of the proximal end of one embodiment of system 201 in an un-deployed state prior to or during insertion of the trocar 210 to the desired treatment location in the patient. For delivery into a vertebral body 120 (e.g. to access the basivertebral nerve), the trocar 210 may be delivered through pedicle 138 via channel 140 (as shown in FIG. 3). Channel 140 may be a pre-drilled hole, or may be generated by insertion of the sharpened tip 208 into the bone. To facilitate insertion, the proximal surface 292 of cap 290 of the drive nut 270 may comprise a rigid material (e.g. stainless steel or the like) so that a mallet or similar device may strike surface 292 to tap the trocar body 204 into place.

During insertion of the trocar 210, in accordance with several embodiments, the stop nut 240 may be threaded distally along external threads 248 of the proximal body 246 of the curveable cannula 230 to restrict motion of the cannula 230 distally down trocar recess 216. This restrained motion may keep the distal end 232 of the cannula 230 from prematurely deploying while the trocar 210 is being delivered.

In accordance with several embodiments, the distal end of the curveable cannula is deformable so as to be delivered in a straight configuration through the trocar and deployed in a curved configuration outward from the radial opening at an angle with respect to the central axis. As shown in FIG. 12, the distal tip 233 of the curveable cannula 230 may comprise a series of tubular mating links 234 each having a central bore to provide a continuous cannula channel 245 along with cannula tube 244. The mating links 234 may be configured to cause the distal tip 233 of the curveable cannula to articulate into a curved shape and be steerable. Cannula channel 245 extends from central cannula recess 268 of the proximal body 246 to the distal link 232 at tip 233. Distal link 232 comprises a beveled tip 233 to facilitate the curveable cannula 230 generating a path through bone as detailed below. Distal link 232 may also comprise a hard material (e.g. stainless steel, thermoplastic, or the like) to provide a rigid leading edge for the curveable cannula 230.

In one embodiment, the mating links 234 are held together with a cord 242 that runs from the proximal body 246 of the curveable cannula 230, and terminates at an aperture 236 in the distal link 232. In some embodiments, the distal end of cord 242 terminates at a ball 238 that is disposed in a counter-bore, countersink, or like retaining surface of the aperture 236 to retain the cord within the distal link 232.

Figures 10A, 10B:
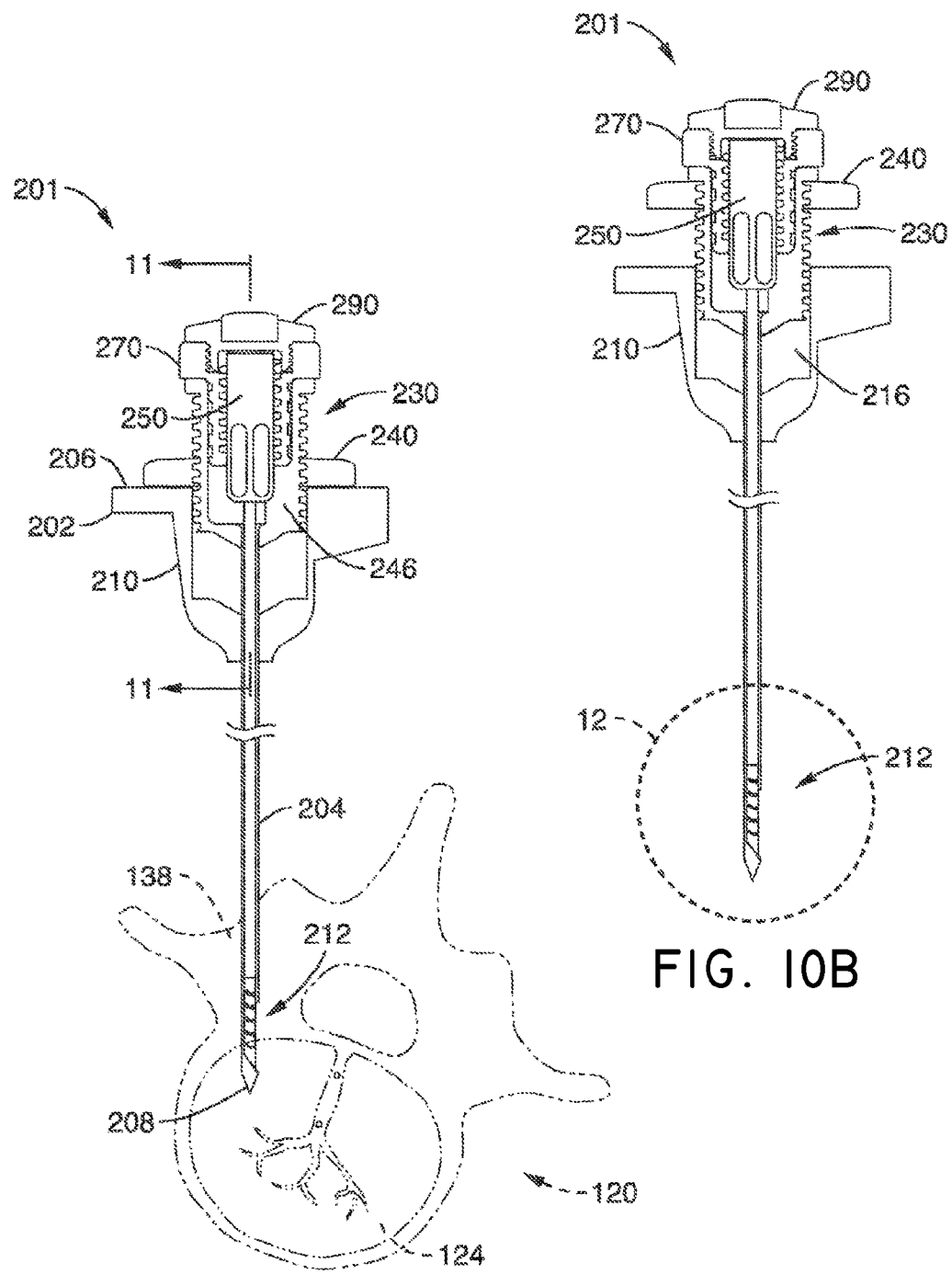
FIGS. 10A-10E show schematic diagrams of embodiments of the system of FIG. 8 at various possible stages of deployment during a procedure.
Figures 10C, 10D:
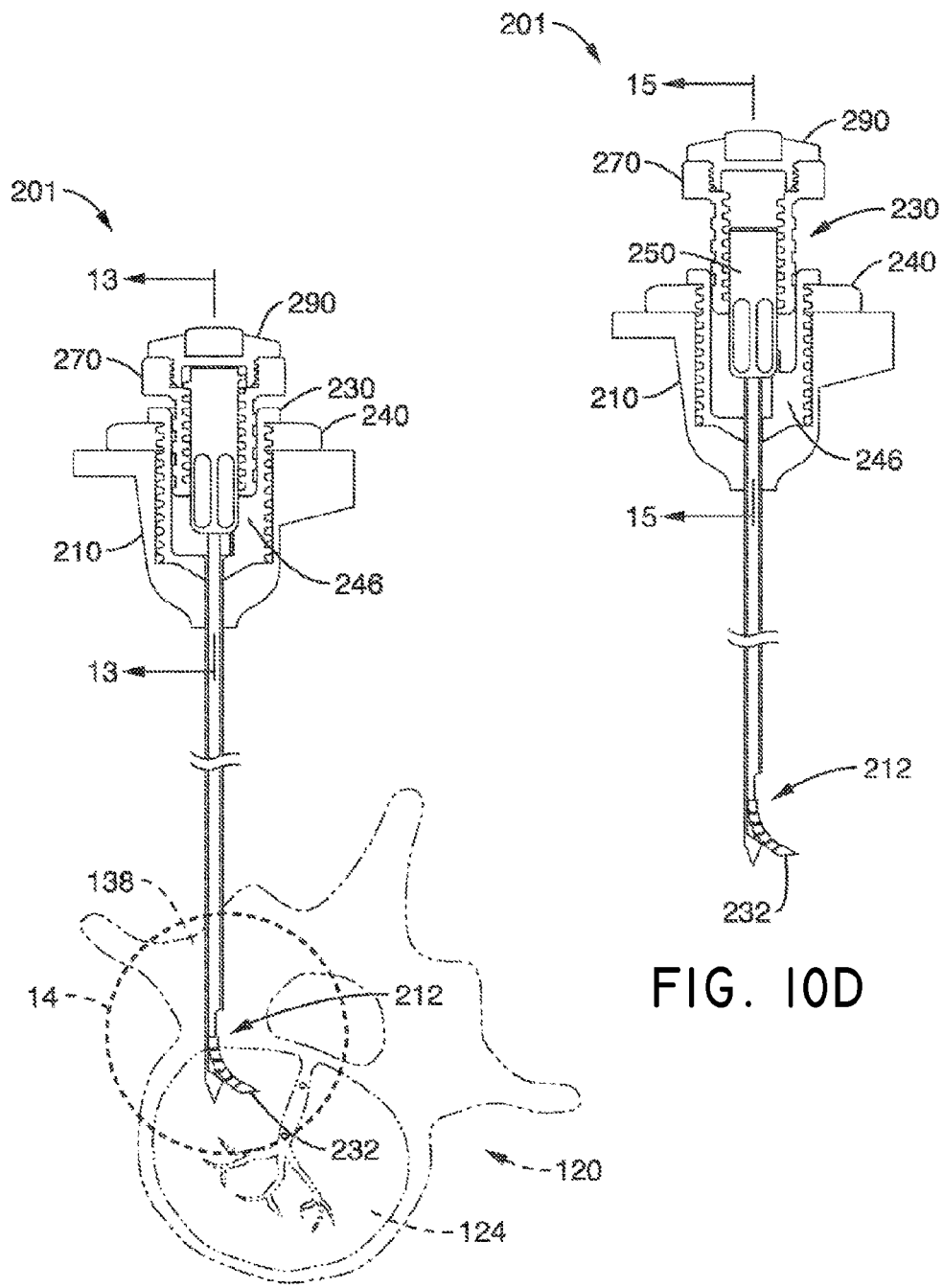
Figure 10E:
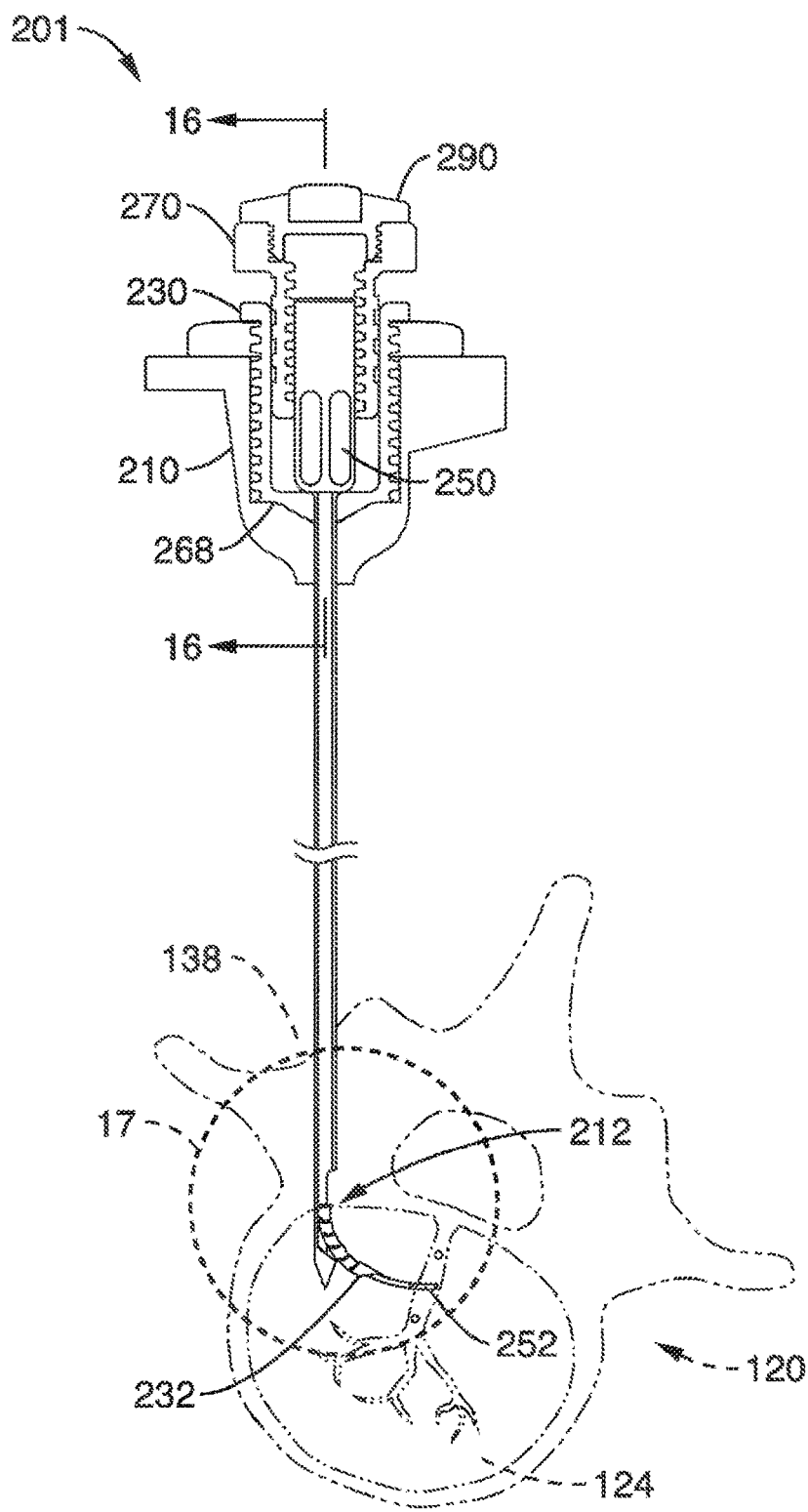

Referring now to FIG. 10B, in accordance with several embodiments, once the trocar 210 is in place, stop nut 240 is threaded proximally along external threads 248 of the proximal end 246 of the curveable cannula 230 to allow motion of the cannula 230 distally downward in recess 214.

Figure 13:
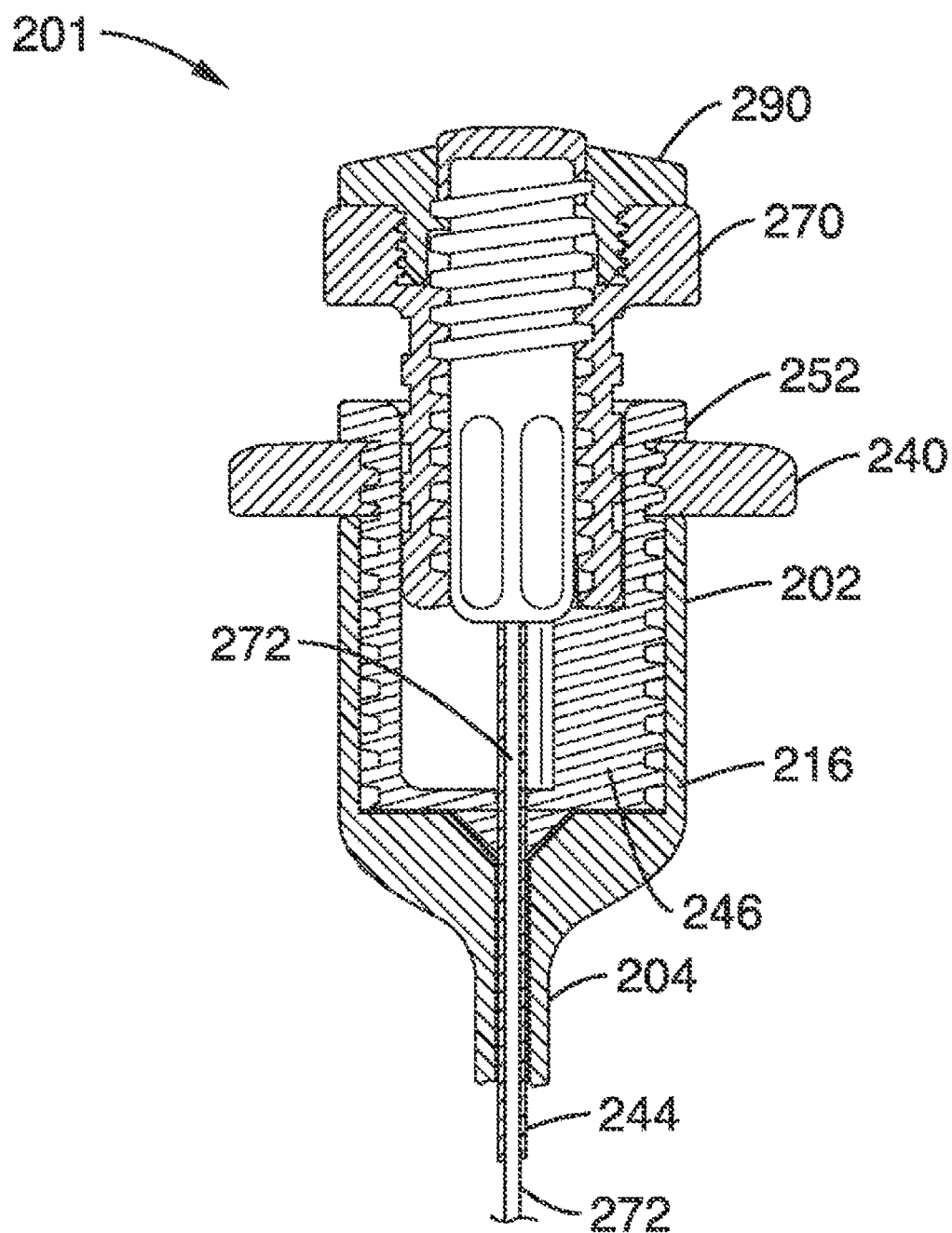
FIG. 13 is a section view of the proximal end of an embodiment of the system of FIG. 8 after deploying the curveable cannula into the body.

In accordance with several embodiments, the proximal body 246 of curveable cannula 230 may then be deployed downward within trocar recess 216, as shown in FIG. 13. As there may be resistance from the bony mass of the vertebral body (or other bony mass), the cannula 230 may be tapped downward by striking the proximal surface of cap 290 (e.g. with a mallet or the like) while holding the trocar at housing 202. In several embodiments, the motion of proximal body 246 pushes tube 244 distally within channel 218 of the trocar body 204. This motion forces the leading edge 232 and trailing mating links 234 out of the radial window 212 in tube 204, as shown in FIG. 14. The distal end of opening or window 212 comprises a ramp 209 to facilitate the leading edge 232 out the window 212 at the proper angle with respect to the trocar tube 204 central axis, and without catching or getting stuck at the distal end of the trocar 210.

In some embodiments, a pull cord 242 is coupled to the distal tip of the curveable cannula 230, the pull cord extending to the proximal end of the trocar 210. In addition to the ramp 209, the curved path of the distal tip 233 is facilitated by tension provided by cord 242, which forces the mating links 232, 234 to arch upon the applied tension. The pull cord may be configured to apply a tensile force to the distal end of the curveable cannula to bias the curveable cannula into a curved configuration. In some embodiments, the cord 242 is coupled to male-threaded dial 212 (see FIG. 8) to act as a pull cord to apply said tension. The dial 212 may be turned clockwise or counterclockwise within internal-threaded arm 214 to increase or relieve the tension on the cord 242, thereby providing steering of the distal tip 233 while the curveable cannula 230 is advanced down trocar body 204 and out window 212 (e.g. increased tension provides a sharper radius, decreased tension provides a more relaxed or no radius.) The tensile force applied to the distal tip of the curveable cannula 230 may be controlled from the proximal end of the trocar to steer the curveable cannula 230 along a desired path.

In an alternative embodiment, cord 242 may comprise a memory material such as a Nitinol wire that fastens the tube 244 and links 232, 234 in a preformed curved-shape. The cord 246 in this configuration stretches to allow the curveable cannula 230 to be delivered into and stowed in a linear form within channel 218, and retracts when not restrained in channel 218 to drive a curved path when exiting window 212.

As shown in FIGS. 13 and 14, in accordance with several embodiments, the curveable cannula 230 is fully deployed, with the proximal end 246 disposed at the bottom of recess 216, and the distal tip 233 in a deployed orientation forming a curved path (along with trailing links 234) through the bone at the treatment site. In this configuration, the probe 250 is restrained from axial motion (in the distal direction) with respect to the curved cannula 230, because it is threaded inside a threaded recess portion of drive nut 270, which is restrained from distal motion by stop 258 in the proximal end 246.

Figure 15:
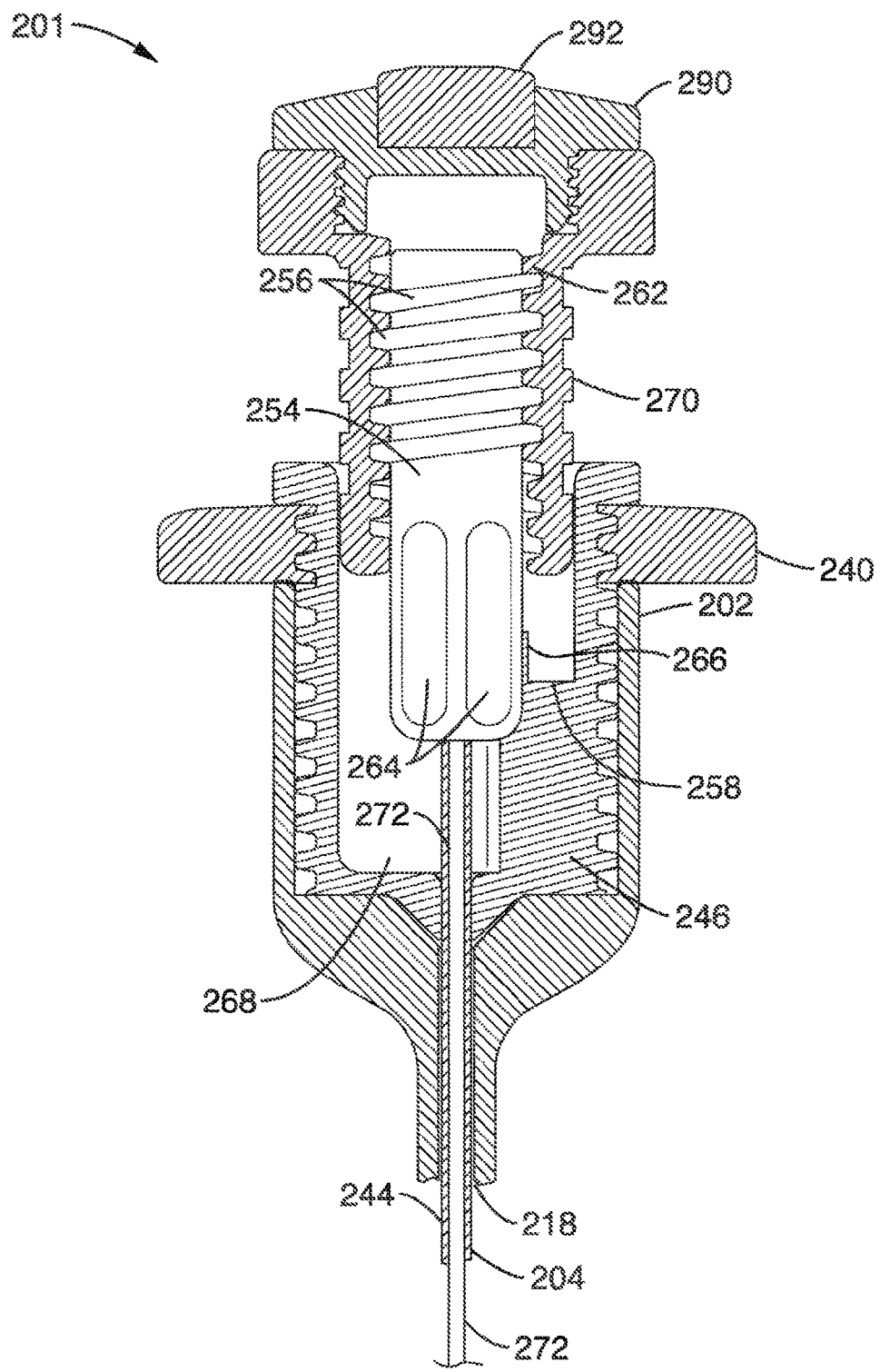
FIG. 15 is a section view of the proximal end of an embodiment of the system of FIG. 8 with the drive nut retracted.

As shown in FIG. 15, in accordance with several embodiments, the drive nut 270 may be raised (proximally advanced out of cavity 268) with respect to the curveable cannula 230 and probe proximal body 254 by rotating the drive nut 270. The proximal body 254 of the probe 250 comprises a male thread 256 that mates with the female internal threads 262 in a distal recess of the drive nut 270. The thread pattern 256/262 may be opposite of the thread pattern between the stop nut 240 and proximal end 246 of the curveable cannula 230 (e.g. right-handed thread vs. left-handed thread), so that rotation of the drive nut 270 does not result in rotation of the curveable cannula 230.

Furthermore, the proximal end 254 of the probe 250 may comprise a plurality of vertical grooves 264, at least one of which interfaces with key 266 of the curveable cannula 230. This interface, in one embodiment, only allows axial motion of the proximal body 264 with the curveable cannula 230, and restricts rotation of the proximal body 264 with the curveable cannula 230. Thus, rotation of the drive nut 270 may only result in proximal translation of the drive nut 270. As seen in FIG. 15, the probe proximal body 254 is now free to move downward in cavity 268.

Figure 16:
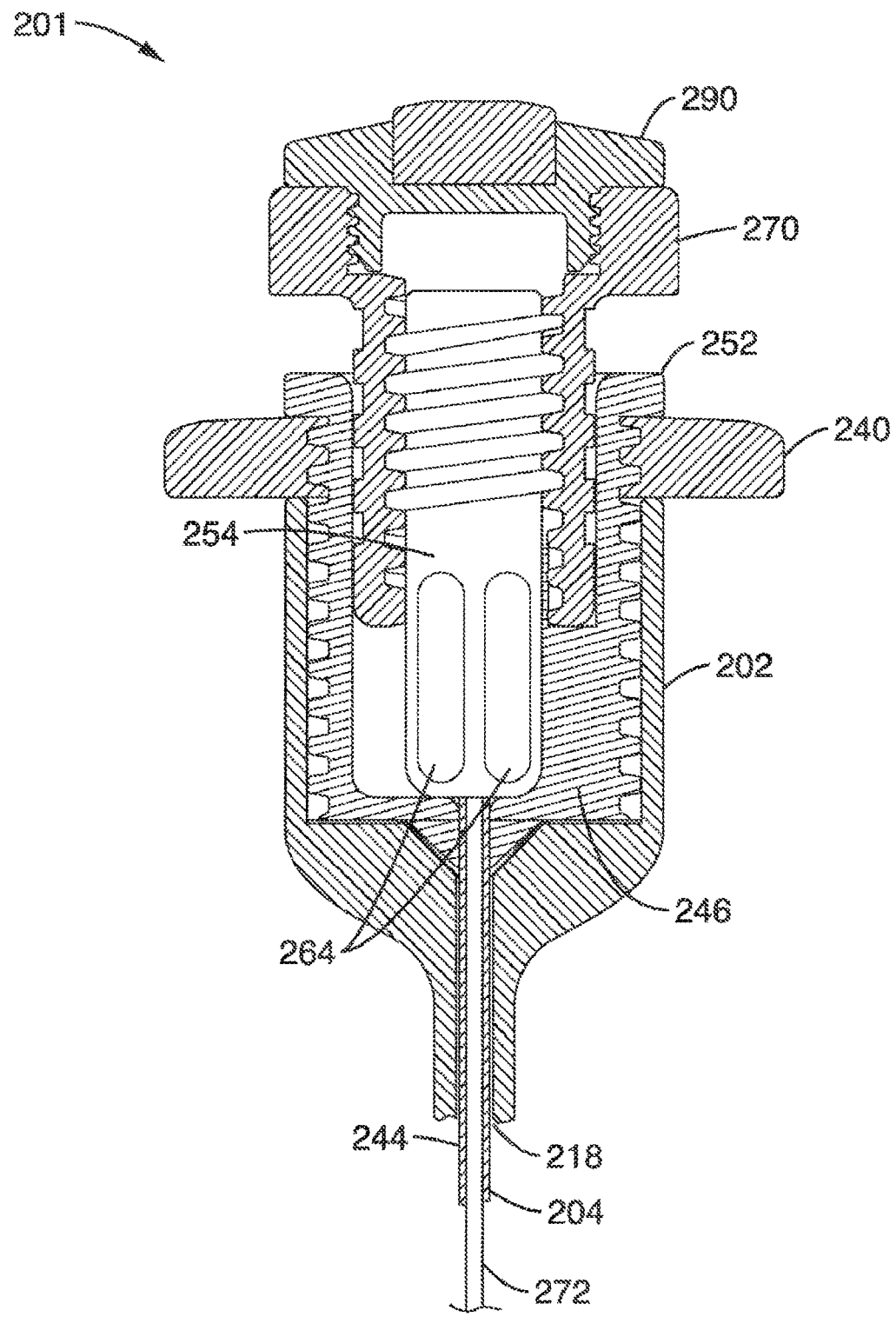
FIG. 16 is a section view of the proximal end of an embodiment of the system of FIG. 8 after deploying the probe into the body.
Figure 17:
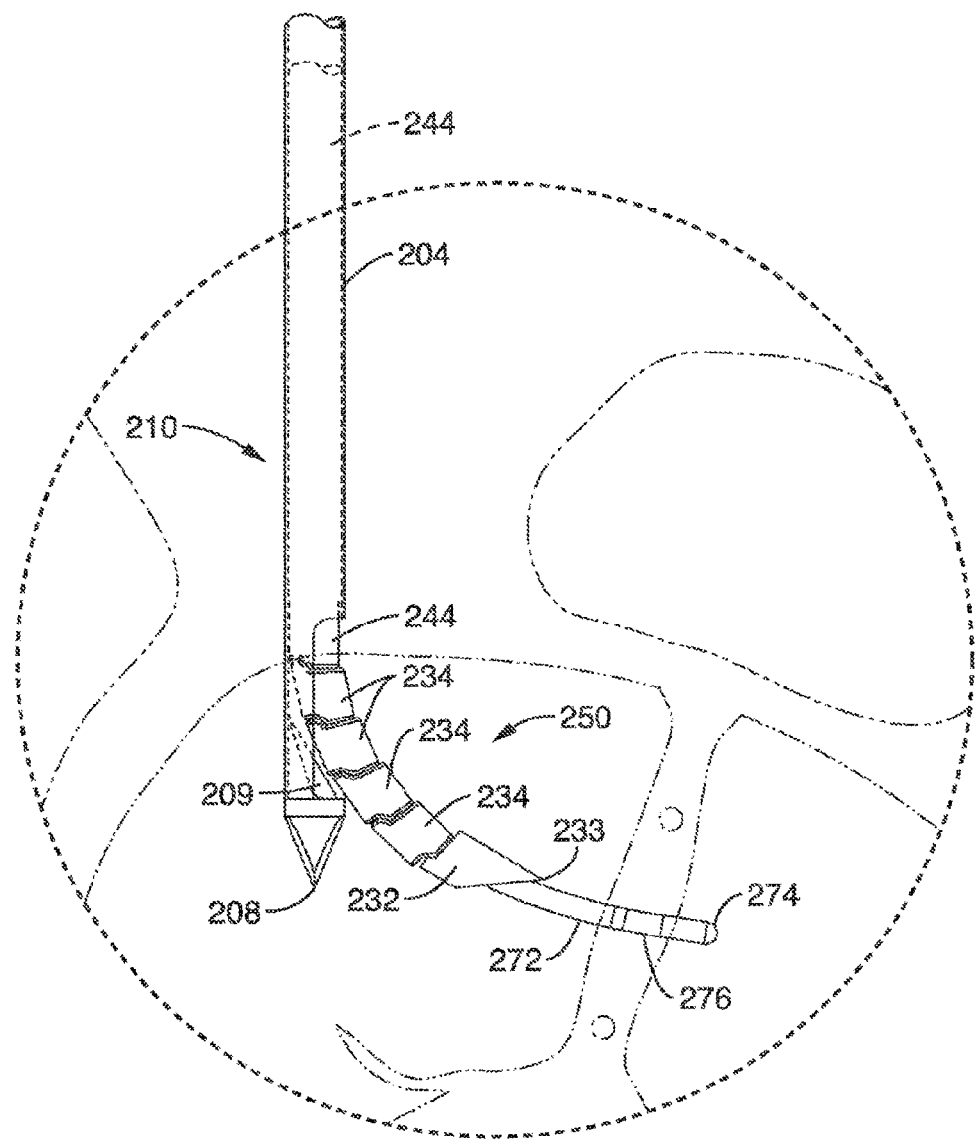
FIG. 17 is a side view of the distal end of an embodiment of the system of FIG. 8 after deploying the probe into the body.

Referring now to FIGS. 16 and 17, in accordance with several embodiments, the system 201 is shown in a fully deployed state, with the distal shaft of the probe 250 advanced beyond distal end 233 of the curveable cannula central channel 245. In several embodiments, this deployment is achieved by advancing the proximal body 254 within the cavity 268 of the curveable cannula 230. In several embodiments, the proximal body 254 and drive nut 270 are advanced as a unit within cavity 268 in accordance with several embodiments, (e.g., by tapping the cap 290), thereby providing an impact force to advance the probe tip 274 out of the cannula 230 and through tissue and/or bone to reach the desired treatment or diagnostic location within the body.

In one embodiment, a channeling stylet (such as stylet 90 shown in kit 10 of FIG. 1) may also be used to create a working channel beyond the end of the curved path created by the curveable cannula 230 prior to deploying a probe for treatment or diagnostic purposes.

Once the distal tip 274 of the probe 250 is positioned at the desired location, treatment of the target tissue may be performed. As shown in FIG. 17, probe distal end 274 may comprise a first electrode 274 configured to deliver a therapeutic amount of RF energy to the target location. In the configuration shown in FIG. 17, the probe 250 comprises a bipolar probe with a return electrode 276, in accordance with several various embodiments, the probe 250 comprises any treatment instrument or device described herein.

Cap 290 may further be configured to include (e.g. a self-contained unit) a power source (e.g. battery) and receptacles (not shown) to couple to the probe 250, thereby supplying the energy to deliver a therapeutic level of energy to the tissue. In this configuration, the cap 290 may have sufficient power to deliver one or more metered doses of energy specifically measured to modulate (e.g., denervate) at least a portion of the basivertebral nerve of a vertebral body.

In accordance with several embodiments, the cap 290 may be threaded (or otherwise releasable coupled) into drive nut 270 to be interchangeable depending on the application or step of the procedure. For example, a cap 290 having a reinforced/hardened surface 292 used for driving the system 201 into the bone may be replaced by another cap having couplings (not shown) for probe 250, an internal power supply (not shown), or couplings for an external power supply/controller (not shown) for delivering energy for treatment and/or diagnosis of a region of tissue. For embodiments wherein a fluid and/or agent is delivered to the target tissue, the cap 290 may be configured to facilitate delivery of the fluid through a probe having one or more fluid delivery channels. In some embodiments, the interchangeable cap 290 is configured to provide access to the probe 250 for providing a therapeutic energy.

FIGS. 18A and 18B are side views one embodiment of the distal end of the system 201 with the curveable cannula 230 in a stowed and deployed position respectively. The distal link 232 and trailing links 234 are configured to have mating/interlocking surfaces that allow the distal end of the cannula to curve in one direction. The more distal link of a mating pair will have an extension 235 that mates with a correspond depression 237 in the link proximal to it. This allows the links to rotate with respect to each other to create a curved distal end as shown in FIG. 18B.

Figure 19A:
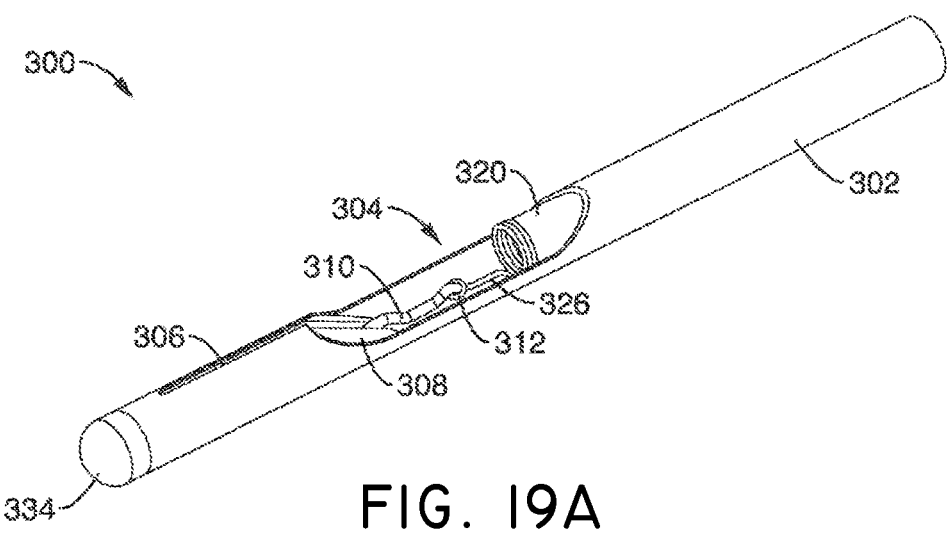
FIG. 19A illustrates a perspective view of an embodiment of an alternative system for generating a curved path in bone.
Figure 19B:
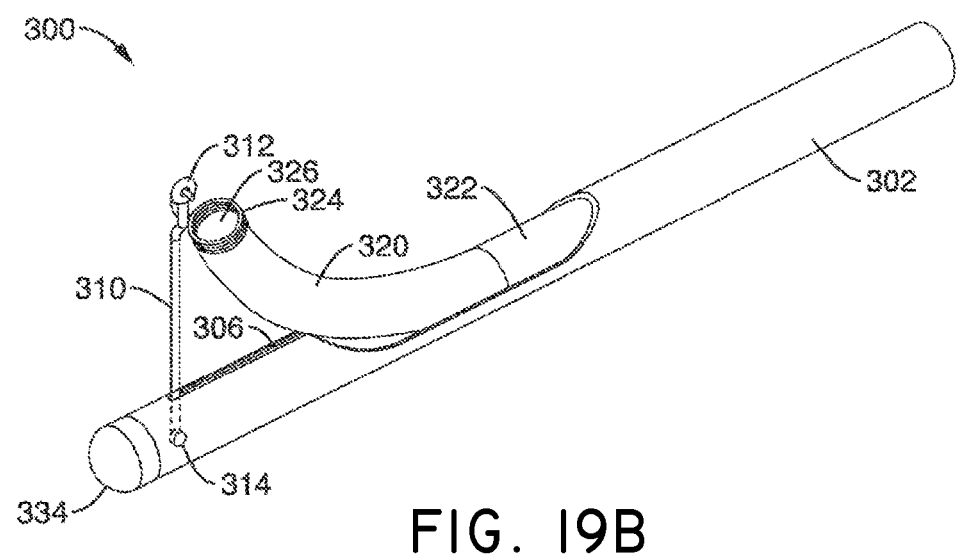
FIG. 19B illustrates the system of FIG. 19A in a deployed configuration.

FIGS. 19A and 19B illustrate an alternative embodiment of system 300 for generating a curved channel through bone. System 300 comprises a tubular trocar body 302, the proximal end (not shown) of which may comprise a portion or all of any of the previously described proximal ends for devices 10, 200, or 201 disclosed herein. The distal tip 334 comprises a leading edge surface for advancing through bone, and a radial or lateral window 304 allowing access to the central channel of the trocar body 302. The window 304 is positioned a short distance proximal to the distal tip 334.

In one embodiment, a curveable cannula 322 is positioned in the trocar 302, the curveable cannula 322 having a distal end 324 coupled via linkage 326 to a pivotable arm 310. The proximal end (not shown) of the curveable cannula may comprise a portion or all of any of the previously described proximal ends for devices 10, 200, or 201 disclosed herein. The pivotable arm 310 has a first end pivotably coupled at joint 314 at a location at or near the distal tip 334 of the trocar 334. In a stowed configuration (illustrated in FIG. 19A), the pivotable arm is configured to lay axially in the trocar 302 within slot 306 that runs from pivot 314 proximally to the radial opening or window 304. The proximal (when stowed) end 312 of the arm 310 is coupled to the linkage 326.

As shown in FIG. 19B, in accordance with several embodiments, the cannula 322 may be advanced laterally outward from window 304 by simply advancing the cannula 322 distally down the trocar 302. The pivotable arm 310 constrains the motion of the curveable end 320 of the cannula to a curved path of specified radius (determined by the length of arm 310. Once the pivotable arm has reached full rotation (shown approximately 90 degrees in FIG. 19B, however such angle may be specified to be any desired amount), the cannula end 320 has created a curved path outward from the trocar toward the desired treatment site. A probe, stylet or similar device (such as curved stylet 60, channeling stylet 90, or probe 100 of FIG. 1) may be positioned at the opening of the distal end 320 to facilitate generating the curved bore without allowing tissue or bone to enter the cannula. The probe or treatment and/or diagnostic device may then be routed through the cannula end 320 to a region of tissue or bone that is off-axis from the trocar body 302.

FIGS. 20 through 26 illustrate several embodiments of the invention comprising a system or kit 400 for forming a path through bone. The system 400 comprises a slotted needle trocar 410 (e.g., the main body of the instrument set) that functions as an introducer into a vertebral body. The slotted needle trocar 410 comprises an elongate shaft 414 having a slotted handle 412 at its proximal end and a trocar channel 418 passing through to the distal end 416 of the trocar 410. The trocar channel 418 is generally sized to allow the other instruments in the system 400 (e.g. curved cannula, therapy device, etc.) to be slideably introduced into a patient to a desired treatment region (e.g., a vertebral body identified as a source of back pain).

In one embodiment, system 400 further comprises a straight stylet 450 having an elongate shaft 454 configured to be received in trocar channel 418 of slotted needle trocar 410. Elongate shaft 454 has a sharp-tipped distal end 456 that, when installed fully within the slotted needle trocar 410, extends slightly beyond the distal end 416 of the trocar tube 410 (see FIG. 21) to close opening 418 and provide a leading edge to create the initial path through the soft tissue and cortical shell, thereby allowing access to the cancellous bone of the vertebral body.

In one embodiment, cannula stylet 450 comprises a pair of key protrusions 458 that are orthogonally oriented with respect to the length of the stylet handle 452. The key protrusions are configured to lock with key slots 426 on the trocar handle 412 via rotation of the stylet handle 452 after full insertion in the trocar 410. When the stylet handle 452 is fully rotated to the orientation shown in FIG. 21, the key protrusions 458 lock the stylet 450 from linear motion with respect to the trocar 410.

With the stylet 450 locked into place with respect to the trocar handle 412, the stylet 450 and slotted needle trocar 410 may be configured to be inserted in unison into the patient's tissue. In accordance with several embodiments, this step may be performed prior to insertion into the patient or after insertion into the patient.

In one embodiment, the stylet handle 452 comprises a raised striking surface 460 made of a hard, rigid material (e.g. stainless steel or similar metallic or plastic material) to allow the trocar 410 to be tapped into place with a mallet or the like, particularly when piercing the hard cortical shell of the vertebral body.

Figure 20:
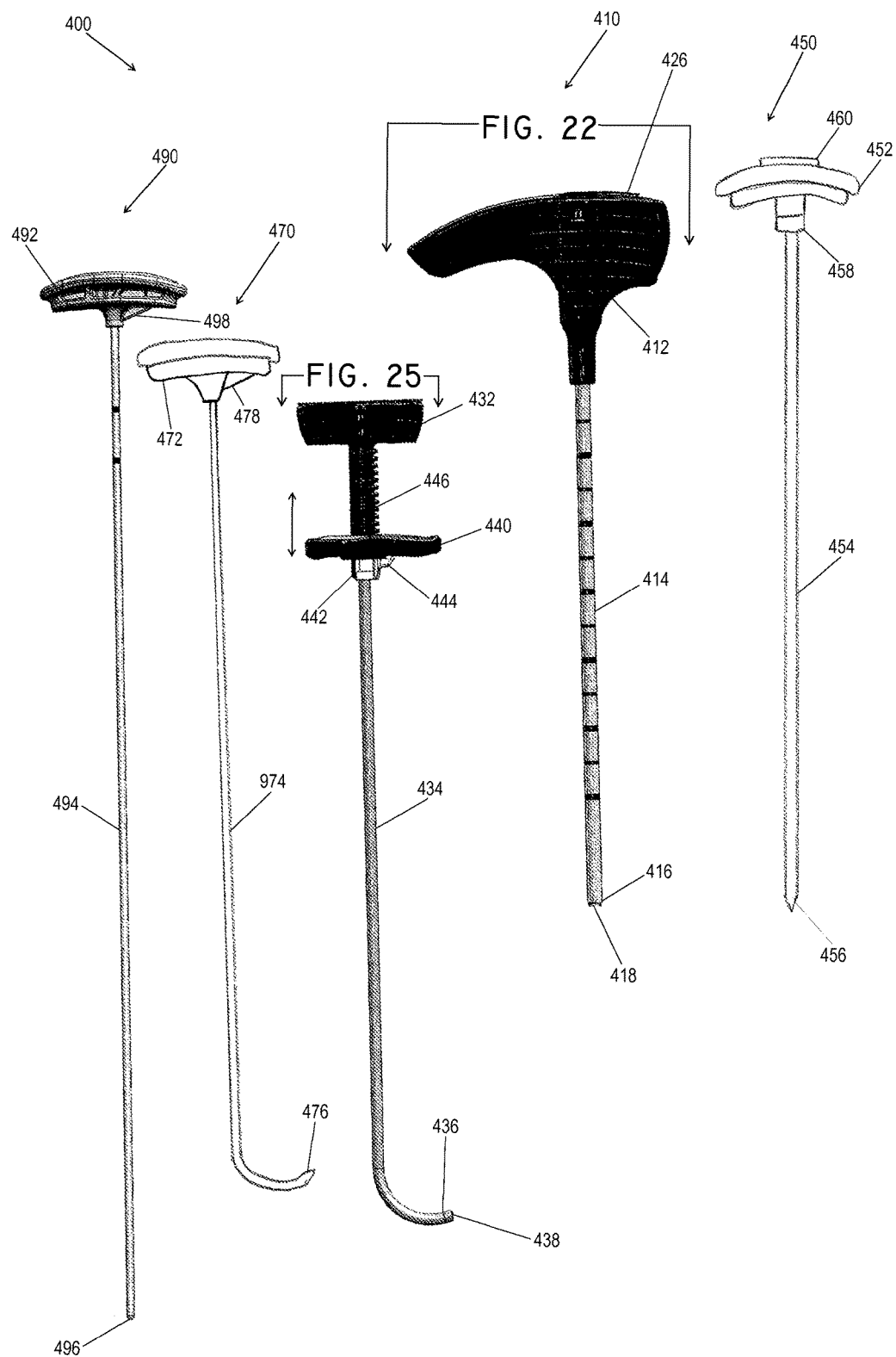
FIG. 20 is a side view of system or kit having a slotted trocar for forming a path through bone.
Figure 21:
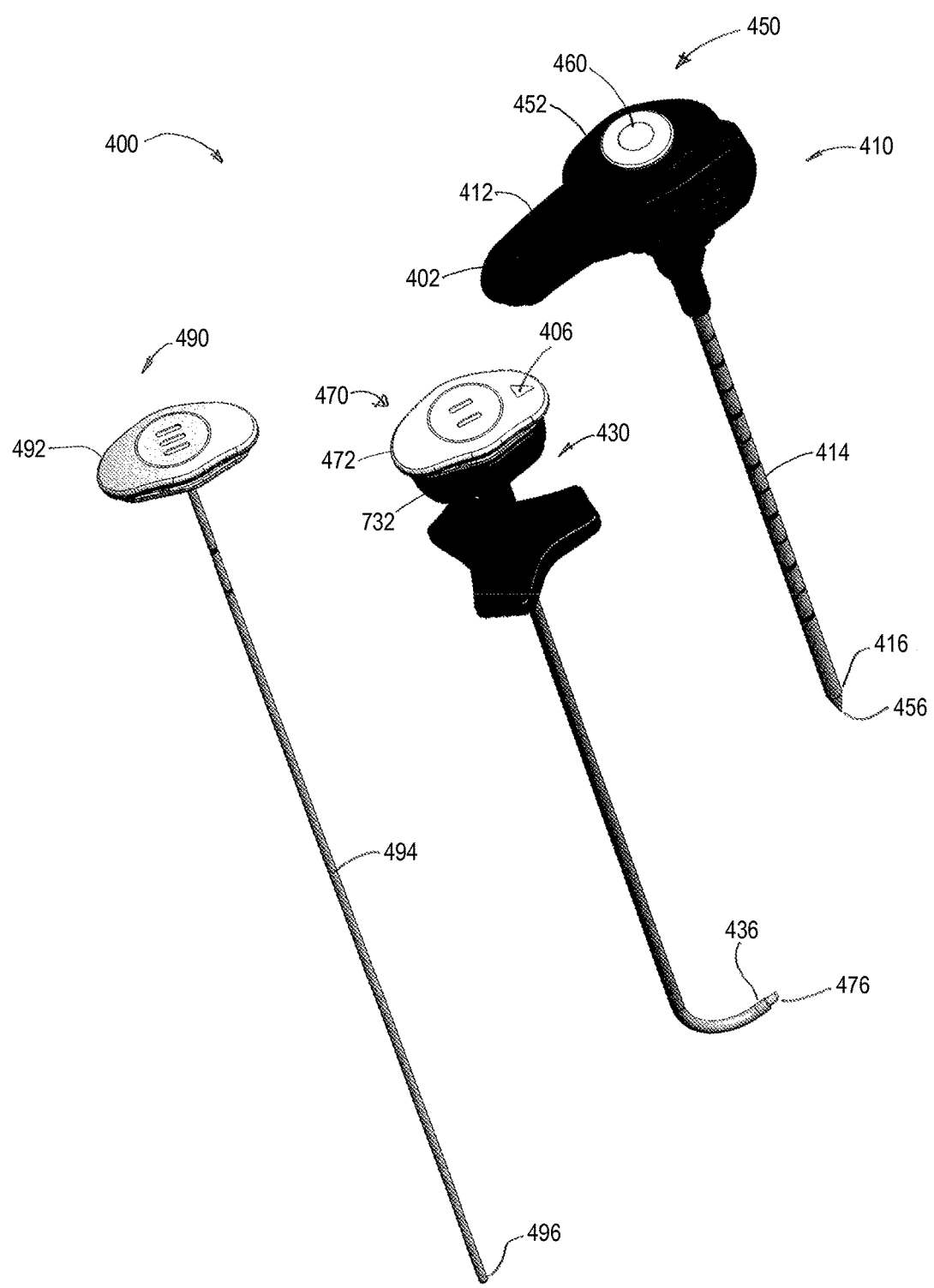
FIG. 21 is a perspective view of an embodiment of the system of FIG. 20 with stylets installed within the trocar and curved cannula.
Figures 22, 23:
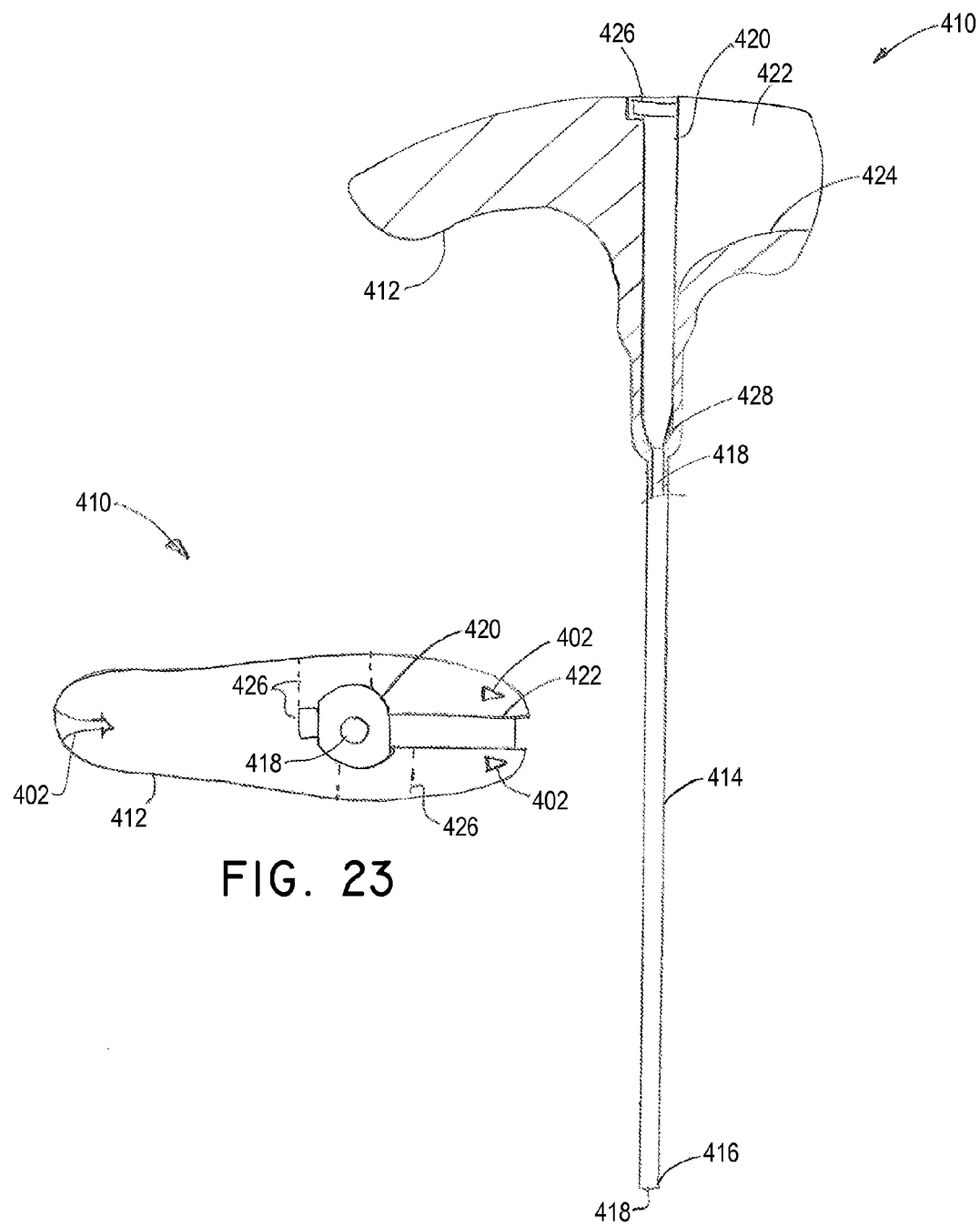
FIG. 22 is a section view of an embodiment of the trocar of FIG. 20.
FIG. 23 is a top view of an embodiment of the trocar of FIG. 20.

In accordance with several embodiments, FIGS. 20 and 21 illustrate exploded views of system 400 prior to delivery within a patient. FIG. 22 illustrates a sectional view of the proximal end of slotted needle trocar 410 in an un-deployed state prior to or during insertion of the trocar 410 to the desired treatment location in the patient. For delivery into a vertebral body 120 (e.g., to access a basivertebral nerve), the slotted needle trocar 410 may be delivered through pedicle 138 via channel 140 (as shown in FIG. 3). Channel 140 may be a pre-drilled hole, or may be generated by insertion of the sharpened tip 208 into the bone. To facilitate insertion, the striking surface 460 of stylet 450 may be tapped with a mallet or the like to drive the slotted needle trocar 410 into place.

In one embodiment, system 400 further comprises a curved cannula 430 that is used to create and/or maintain a curved path within the bone and/or tissue when extended past the distal end 416 of trocar 410. Curved cannula 430 may comprise a slotted handle 432 that is proximal to a threaded tube 446 and elongate straight tubular body 434 section and a preformed, curved distal end 436. In accordance with several embodiments, the curved distal end 436 of tubular body 434 is made of a shape memory material (e.g., Nitinol) that allows the curved distal end to be bent into a straight configuration, and retain its curved shape upon release of a restraint.

Referring to FIGS. 22 and 23, in accordance with several embodiments, the handle 412 of slotted needle trocar 410 comprises a centrally-located bore or recess 420 that is in communication with trocar channel 418. Trocar recess 420 allows placement and movement of curved cannula 430 within the trocar recess 420 and trocar channel 418. The trocar recess 420 may have a tapered section 428 at the bottom of handle 412 so that no sharp edges are present to hang up instruments entering central channel 418 to catch or hang up on. In communication with the trocar recess 420 is a lateral slot 422 running through the handle 412 generally orthogonally or radially to the axis of the trocar recess 420 and central channel 418. The lateral slot 422 may have a curvilinear lower surface 424 that is configured to allow the curved distal end 436 of the curved cannula 430 to be inserted in the trocar 410 without having to pre-straighten the curved cannula 430.

In one embodiment, the curved cannula 430 is held in place at a specified location within the trocar recess 420 and trocar channel 418 via a stop nut 440 that is threaded about proximal body 446 of the curved cannula 430. With the stop nut 440 in the position shown in FIG. 20, the distal end 436 of the curved cannula 430 can be restrained from moving past opening 418 at distal end 416 of the slotted needle trocar 410. When the curved cannula 430 is prepared for delivery beyond the distal end 416 of the slotted needle trocar 410 (e.g., after installation of curved stylet 470 is complete), the stop nut can be rotated up threaded body 446 to allow downward motion of the curved cannula 430 within the slotted needle trocar 410. Stop 442 and key 444 interface with the trocar 410 to help ensure the trajectory of the curved distal end 436 is correctly oriented.

In accordance with several embodiments, FIGS. 24A through 24C illustrate insertion of the curved cannula distal end 436 into the slotted needle trocar 410. In accordance with several embodiments, this step is performed after the trocar 410 has been positioned at the proper location within the vertebral body (e.g. as shown in FIG. 3 to generate passageway 140 between the transverse process 134 and the spinous process 136 through the pedicle 138 into the cancellous bone region 124 of the vertebral body 126). With the trocar 410 in position, the straight stylet 450 may be removed to open the central channel 418 for additional instrumentation.

As shown in FIG. 24A, in one embodiment, the curved distal end 436 of the curved cannula body 434 is inserted laterally into the lateral slot 422 until it contacts the far wall of trocar recess 420 and the curvilinear bottom surface 424 of the lateral slot 422. The lateral slot 422 and curvilinear bottom surface 424 may advantageously allow the cannula 430 to be installed at an angle with respect to the central channel 418 (e.g., the straight portion 434 of the cannula 430 is inserted orthogonal, or substantially off-axis, from the axis of the trocar channel 418), which allows a significant portion of the curved distal end 436 to enter tapered region 428 and trocar channel 418 prior to contacting the trocar channel 418).

In one embodiment, the curvilinear bottom surface 424 comprises a radius substantially matching the natural radius of curved distal end 436. The curvilinear bottom surface 424 having such a matching radius may advantageously promote an evenly distributed loading along the curved distal end 436 while the curved distal end 436 is advanced into the tapered section 428 and straightened into trocar channel 418.

In order to ensure proper trajectory of the curved cannula 430, the indicia arrows 404 of the curved cannula handle 432 (see FIG. 26) may be lined up in the same direction as corresponding indicia arrows 402 on the trocar handle 412. In some embodiments, other indicia may be used (e.g., slots, lines, notches, ribs, or laser markings).

Referring now to FIG. 24B, in accordance with several embodiments, an inward and/or downward force is applied on the curved cannula 430 to advance the curved distal end 436 and tube body 434 into the trocar recess 420 and central channel 418, which straightens the curved cannula 430 to a more vertical orientation.

Referring to FIG. 24C, in one embodiment, the cannula tube body 434 is in a substantially vertical orientation once the entirety of the curved end 436 is disposed within the central channel 418 (and thus deflected to a substantially straight configuration). Further downward force may be applied to the curved cannula 430 until the stop nut 440 reaches the top of the trocar handle 412. The key protrusion 444 below the stop nut 440 may further acts to guide the proper orientation of the curved cannula 430 as it is restrained to travel linearly down lateral slot 422.

Figure 25:
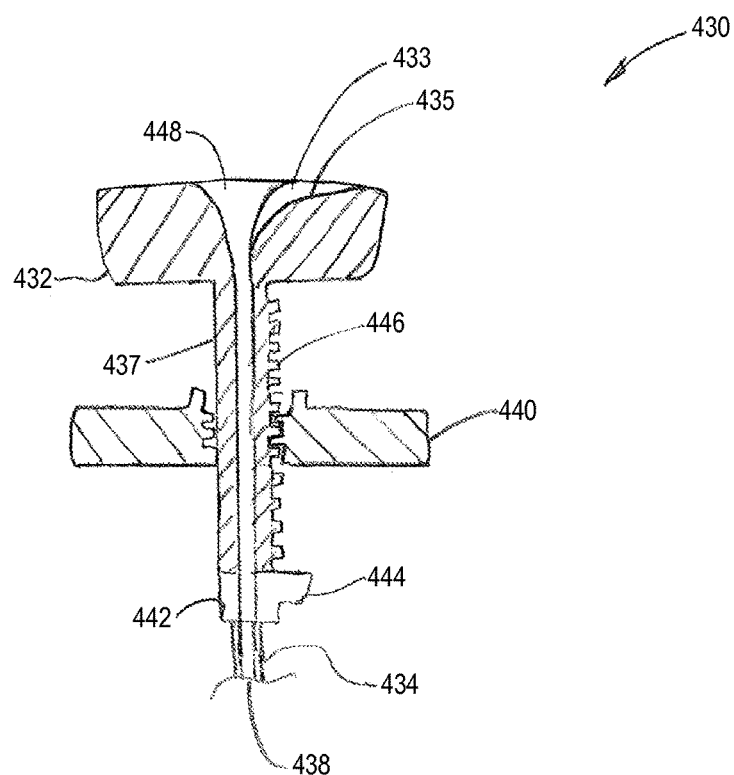
FIG. 25 is a sectional view of an embodiment of the slotted curved cannula of FIG. 20.
Figure 26:
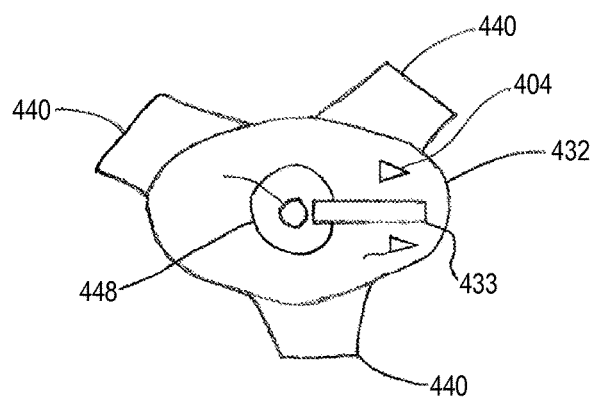
FIG. 26 is a top view of an embodiment of the slotted curved cannula of FIG. 20

Referring to FIGS. 25 and 26, the curved stylet 470 may then be installed into the curved cannula 430. The curved stylet 470 comprises a straight proximal stylet body 474 and a curved distal end 476. In accordance with several embodiments, the curved stylet 470 comprises a preformed, deformable memory material that, when installed in the curved cannula 430, provides additional rigidity and inertia to the curved distal end 426 of the cannula 430. In some embodiments, the curved stylet 470 also provides a leading edge for the curved cannula 430 as it generates a curved path beyond the distal end 416 of the trocar.

In one embodiment, the curved cannula 430 comprises a central recess 448 within cannula handle 432 that is in communication with and centrally aligned with cannula channel 438. Central recess 448 and cannula channel 438 may be configured to receive and allow reciprocation of curved stylet 470 (and a treatment probe that may be deployed subsequently). Similar to the trocar handle 412, the cannula handle 432 may comprise a lateral slot 433 that is in communication with the central recess 448. In one embodiment, lateral slot 433 comprises a curved lower surface 435 that facilitates insertion of the curved tip 476 of the stylet body 474 into the central recess 448 and cannula channel 438 (e.g., similar to the illustration in FIGS. 24A-24C showing insertion of the curved cannula 430 into the trocar 410). In one embodiment, the curvilinear bottom surface 435 of the cannula handle 432 comprises a radius substantially matching the radius of the preformed curved distal end 476 of the curved stylet 470.

In accordance with several embodiments, to facilitate proper orientation of the curved end 476 of stylet 450 with the curved distal end 436 of the curved cannula 430, arrow indicia 406 (see FIG. 21) are disposed on the curved stylet handle 472 to provide visualization of orientation with respect to the arrow indicia 404 of the curved cannula 430. In some embodiments, other indicia may be used (e.g., slots, lines, notches, ribs, or laser markings). In one embodiment, key tab 478 limits full extension of the curved stylet 470 into the curved cannula 430 unless lined up with the slot 433.

With the curved stylet 470 installed into the curved cannula 430, the lock nut 440 may be raised along proximal body 446 of curved cannula 430, and the curved stylet 470 and curved cannula 430 assembly may be further extended down trocar central channel 418 so that the curved distal end 476 generates a curved path beyond the distal end 416 of the trocar 410.

In accordance with several embodiments, when the curved path is created, the curved stylet 470 is removed. A treatment probe (such as the treatment probes described herein) may then be delivered through the curved cannula 430 to the treatment site.

In some embodiments, a channeling stylet 490 is used to create a working channel beyond the end of the curved path created by the curveable cannula 430 prior to deploying a treatment probe for a diagnostic device. In one embodiment, the elongate body 494 of the channeling stylet 490 is inserted in the recess 448 of the cannula handle 432 and delivered through the cannula channel 438 so that the distal end 496 of the channeling stylet 490 extends beyond the curved distal end 436 of the curved cannula 430 a specified distance, creating a hybrid curved and straight channel through the cancellous bone. The channeling stylet 490 may then be removed, and a treatment probe may be installed in its place to deliver therapeutic treatment to the target treatment site.

Several embodiments of the invention are shown in FIG. 27 through FIG. 35C. In accordance with several embodiments, the apparatus may vary as to configuration and as to details of the parts, and the method may vary as to the specific steps and sequence, without departing from the basic concepts as disclosed herein.

In accordance with several embodiments, surgical devices and surgical systems described herein may be used to deliver numerous types of treatment modalities to varying regions of the body. In addition to the particular usefulness of several embodiments in navigating through bone. The systems and methods may also be used to navigate through soft tissue, or through channels or lumens in the body, particularly where one lumen may branch from another lumen.

The following examples illustrate several embodiments of a system 510 for generating a curve bone path in the vertebral body, and more particularly, for creating a bone path via a transpedicular approach to access targeted regions in the spine. In particular, the system 510 may be used to deliver a treatment device to treat or modulate (e.g., ablate) intraosseous nerves, and in particular the basivertebral nerve. In accordance with several embodiments, in addition to the system and methods providing significant benefit in accessing the basivertebral nerve, the systems and methods may similarly be used to create a bone path in any part of the body.

Figure 27:
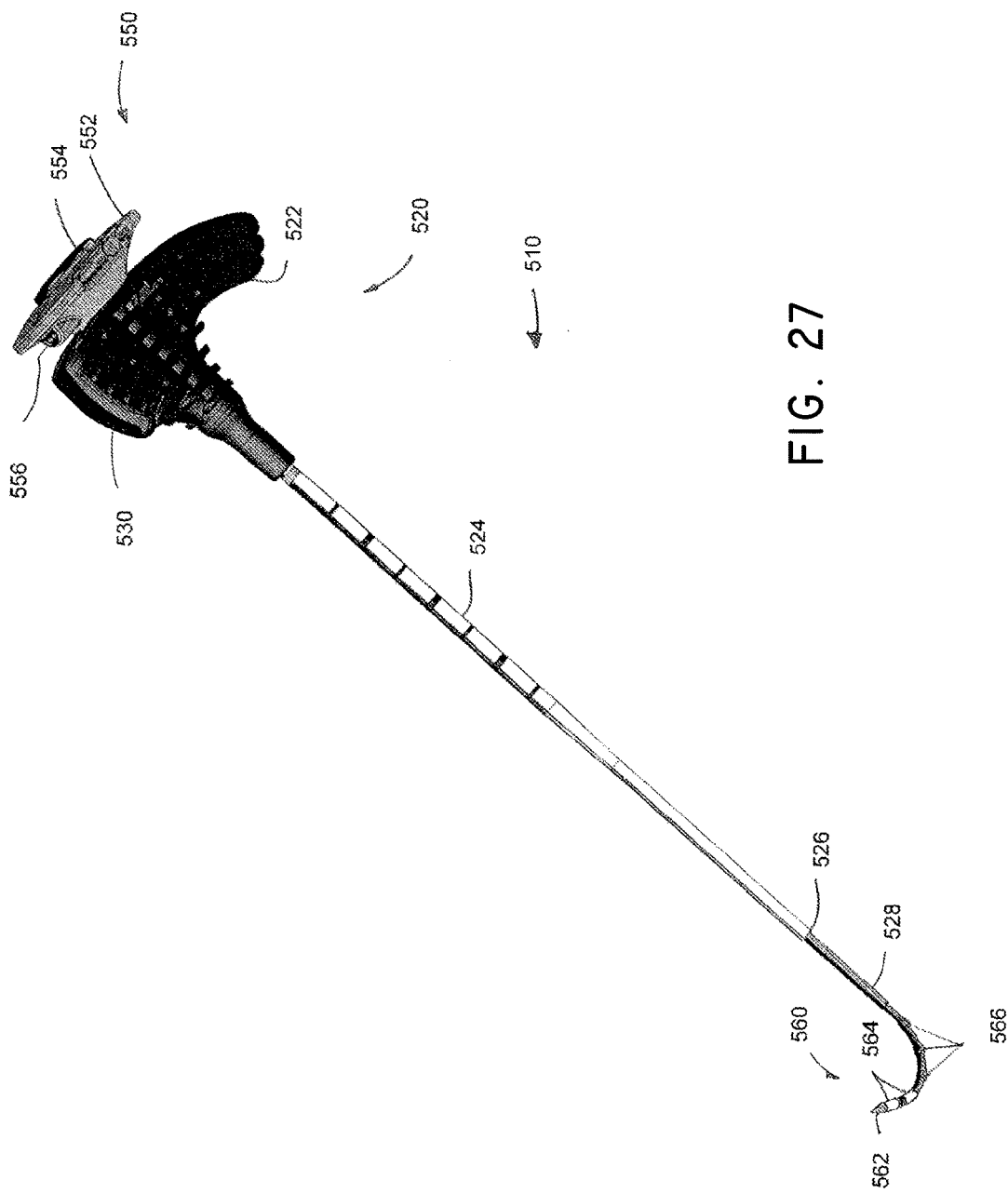
FIG. 27 is perspective view of an embodiment of a self-guiding curveable treatment device.

Referring to FIG. 27, one embodiment of the system 510 comprises a slotted needle trocar 520 (the main body of the instrument set) that functions as an introducer into the vertebral body. The slotted needle trocar 520 comprises an elongate shaft or hypotube 524 having a slotted handle 522 at its proximal end and a trocar channel 528 passing through to the distal end 526 of the trocar 520. The trocar channel 528 may generally be sized to allow the elongate body 558 of a curved probe 550 to be slideably introduced into a patient to a desired treatment region.

Figure 28:
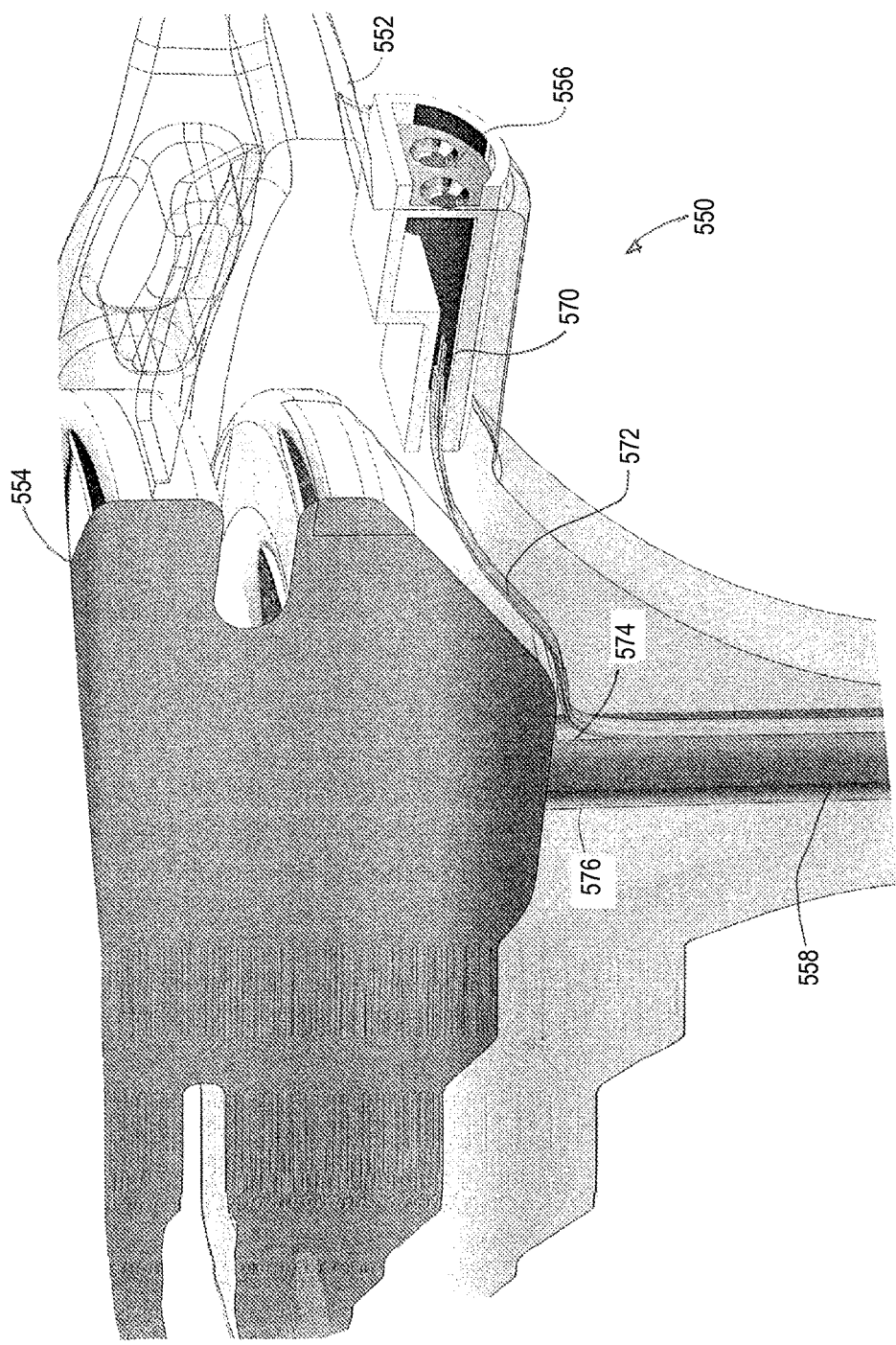
FIG. 28 is a sectioned view of an embodiment of the curveable treatment probe of FIG. 27.

FIG. 28 shows a cross-sectional view of one embodiment of the proximal end of the treatment probe 550, which comprises a handle 552 having a striking surface 554, a radio frequency generator (RFG) cable connection 556, and a dual-lead flex conduit 572 having a proximal end 570 coupling the RFG cable connection 556 to one or more electrodes 554 via a slot 574 in a stylet 558, which may be coupled to striking surface 554 at proximal end 576. The stylet 558 comprises a straight proximal end 576, and curved distal end 560. In one embodiment, RFG cable connection 556 may be configured for coupling a power source to power operation of electrodes 554. In accordance with several embodiments, other couplings may be used for connecting cables to the device.

Figures 29, 30:
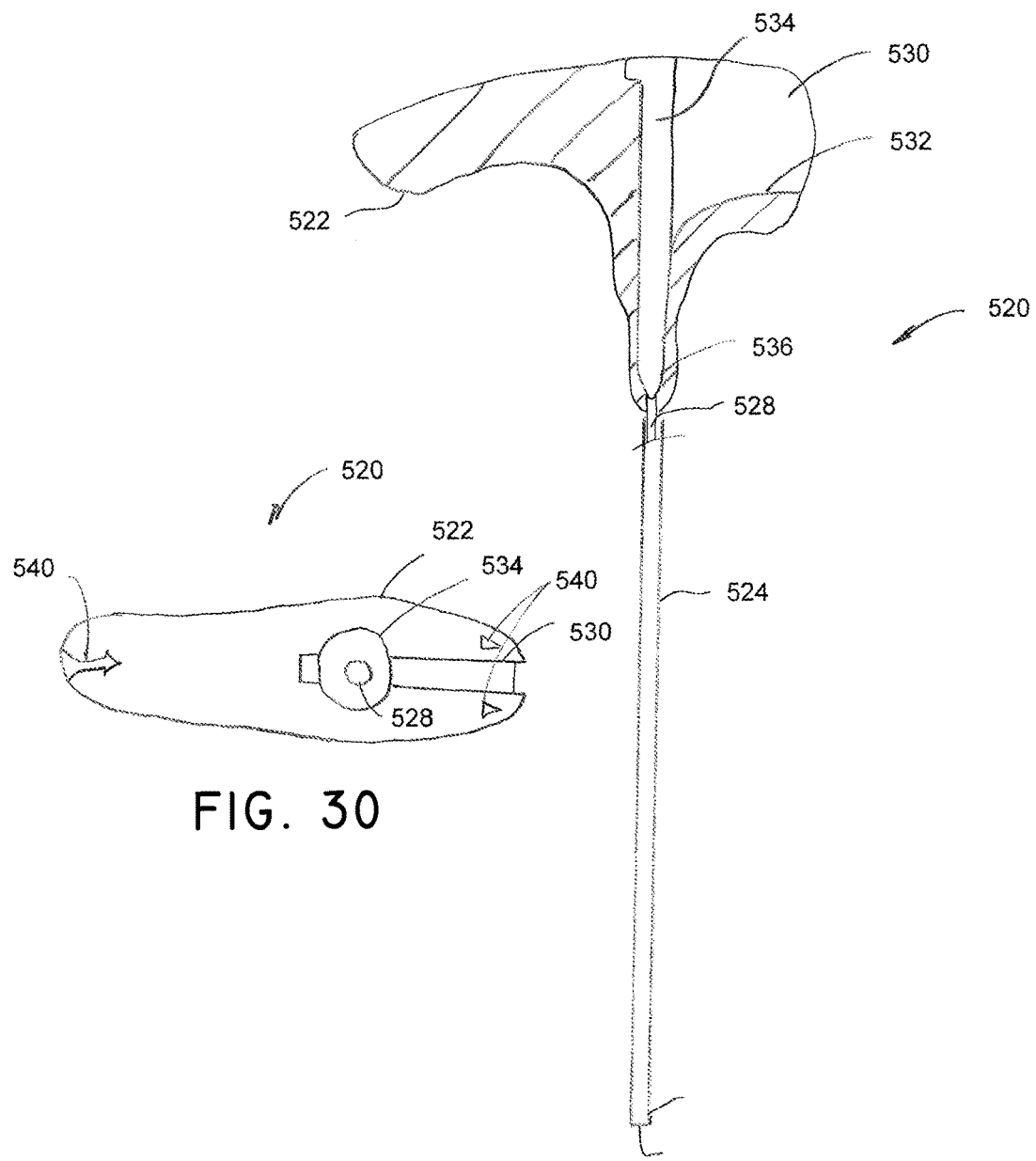
FIG. 29 is a sectioned view of an embodiment of the slotted trocar of FIG. 27.
FIG. 30 is a top view of an embodiment of the slotted trocar of FIG. 27.

Referring to FIGS. 29 and 30, one embodiment of the handle 522 of slotted needle trocar 520 comprises a centrally-located bore or recess 534 that is in communication with trocar channel 528. Trocar recess 534 facilitates placement and reciprocation of treatment probe 550 within the trocar recess 534 and trocar central channel 528. The trocar recess 534 tapers at the bottom of handle 536 (e.g., so that no sharp edges are present to hang up instruments entering trocar channel 528).

In one embodiment, in communication with the trocar recess 534 is a lateral slot 530 running through the handle 522 generally orthogonally to the axis of the trocar recess 534 and trocar channel 528. The lateral slot comprises a curvilinear lower surface 532 that may be configured to allow the curved distal end 560 of the treatment probe 550 to be inserted in the trocar 520 without having to pre-straighten the curved distal end 560 of the treatment probe 550. Indicia 540 may be positioned on the top of the handle 522 to guide proper orientation of the treatment probe 550.

In accordance with several embodiments, FIGS. 31A through 31C illustrate insertion of the curved distal end 560 of treatment probe 550 into the trocar 520. In accordance with several embodiments, this step is performed after the trocar 520 has been positioned at the proper location within the vertebral body (e.g., as shown in FIGS. 59A and 59B to pierce the cortical shell and generate passageway 640 in the vertebra 620).

As shown in FIG. 31A, in accordance with several embodiments, the curved distal end 560 of the treatment probe 550 is inserted laterally into the lateral slot 530 until it contacts the far wall of recess 534 and the curvilinear bottom surface 532 of the slot 530. The slot 530 and curvilinear bottom surface 532 allow the stylet 558 to be installed at an angle with respect to the trocar channel 528 (e.g., the straight portion 574 of the stylet 558 is inserted orthogonal, or substantially off-axis, from the axis of the trocar channel 528), which may allow for the tip 562 and a significant portion of the curved distal end 560 of treatment probe 550 to enter trocar channel 528 prior to contacting the walls of trocar channel 528).

In one embodiment, the curvilinear bottom surface 532 may comprise a radius significantly matching the natural radius of curved distal end 560 of the treatment probe 560. The curvilinear bottom surface 532 having such a matching radius may advantageously promote an evenly distributed loading along the curved distal end 650 while the curved distal end 560 is advanced into and straightened into trocar channel 528.

To ensure proper trajectory of the probe 550 in one embodiment, the indicia arrows (not shown) of the probe handle 552 may be lined up in the same direction as indicia arrows 540 (FIG. 30) on the trocar handle 522. In some embodiments, other indicia may be used (e.g., slots, lines, notches, ribs, or laser markings, or combinations thereof).

Referring now to FIG. 31B, in accordance with several embodiments, an inward and/or downward force is applied on the probe 550 to advance the stylet 558 into the recess 534 and trocar channel 528, which straightens the curved end 560 of stylet 558 to a more vertical orientation.

Referring to FIG. 31C, in accordance with several embodiments, the stylet 558 is in a substantially vertical orientation once the entirety of the curved end 560 is disposed within the trocar channel 528 (and thus deflected to a substantially straight configuration). Further downward force may be applied to the treatment probe 550 until the distal tip reaches the end 526 of tube 524.

Figure 32:
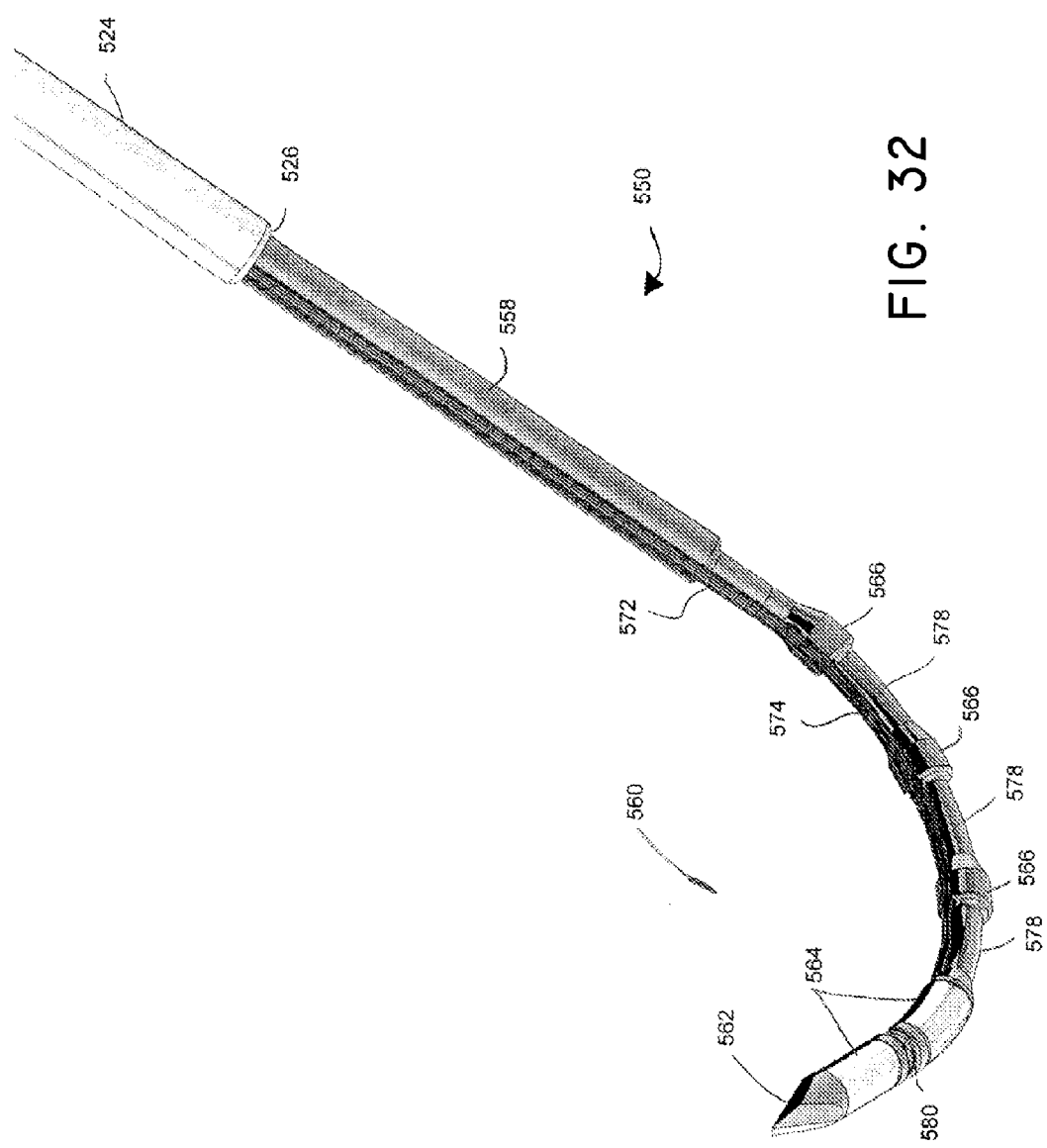
FIG. 32 shows a perspective view of an embodiment of the distal end of the treatment device of FIG. 27 in a fully deployed state.

FIG. 32 shows a perspective view of one embodiment of the distal end of the treatment probe 550 in a fully deployed state. Stylet 558 comprises a preformed curved distal end 560 having a beveled or sharpened distal tip 562. In accordance with several embodiments, stylet 558, and in particular distal end 560, comprise a compliant, yet memory retaining material such as memory metal (e.g., Nitinol), or polymer (e.g. PEEK, DELRIN, NYLON, VALOX, etc.), or a combination of both (e.g., Nitinol core inside thermoplastic exterior), such that the curved distal end 560 yields to the rigidity of the inner walls of trocar channel 528 when installed, yet retains its original curved shape when the curved end 560 of stylet 558 is removed from, or outside of, the trocar 520.

The distal end 560 of stylet 558 may be pre-curved to create an angular range of approximately 0° to approximately 180° (e.g., from approximately 45° to approximately 110°, or from approximately 75° to approximately 100°), when fully deployed from the trocar 520.

In several embodiments, the curved distal end 560 comprises a plurality of circumferentially relieved sections 578 separated by a plurality of bosses 566. The bosses 566 have an outside diameter that corresponds closely to the inside diameter of the trocar channel 528 of hypotube 524 (e.g., the diameter of each boss 566 will be approximately 0.025" to 0.060" smaller than the diameter of the trocar channel 528). The circumferentially relieved sections 578 may allow for the curved distal end 560 to conform to the straight confines of the trocar channel 528, while promoting retention of the curved distal end 560 to its preformed curved state. In one embodiment, the stylet 552 is machined with groove 574 and recesses 578, 582 prior to heat setting the curve 560.

Figure 33:
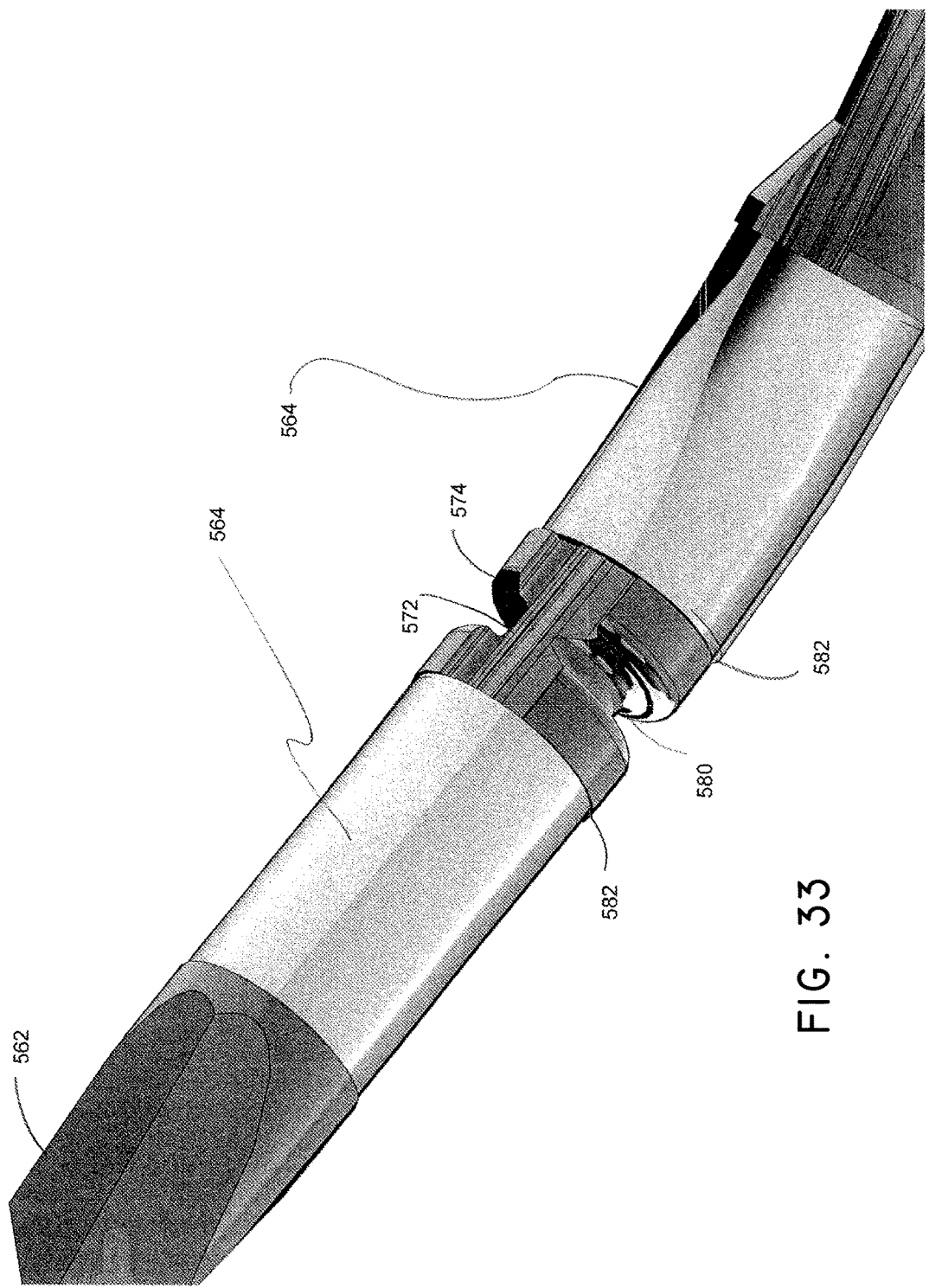
FIG. 33 shows a perspective view of the distal end of an embodiment of the curveable treatment probe of FIG. 27.

FIG. 33 shows a close-up view of one embodiment of the distal end 560 of the curveable treatment probe 550. Channel or slot 574 extends distally on stylet 558 to house flex circuit 572 along the length of the stylet 558. The curved distal end 560 of stylet 558 comprises a pair of recesses 582 configured to house a pair of electrodes 564 (e.g., tubular electrodes) flush to the diameter of bosses 566 on either side of grove 580. An insulation layer (not shown) may be disposed between the first and second electrodes 564 and the stylet 552. The dual lead flex circuit 572 is electrically coupled to each electrode 564 for application as a bipolar RF applicator. The electrodes 564 may also be coated (e.g., with parylene, etc.) for insulation. In some embodiments the electrodes may be of a different type or shape (e.g., elliptical or flat).

Figure 34:
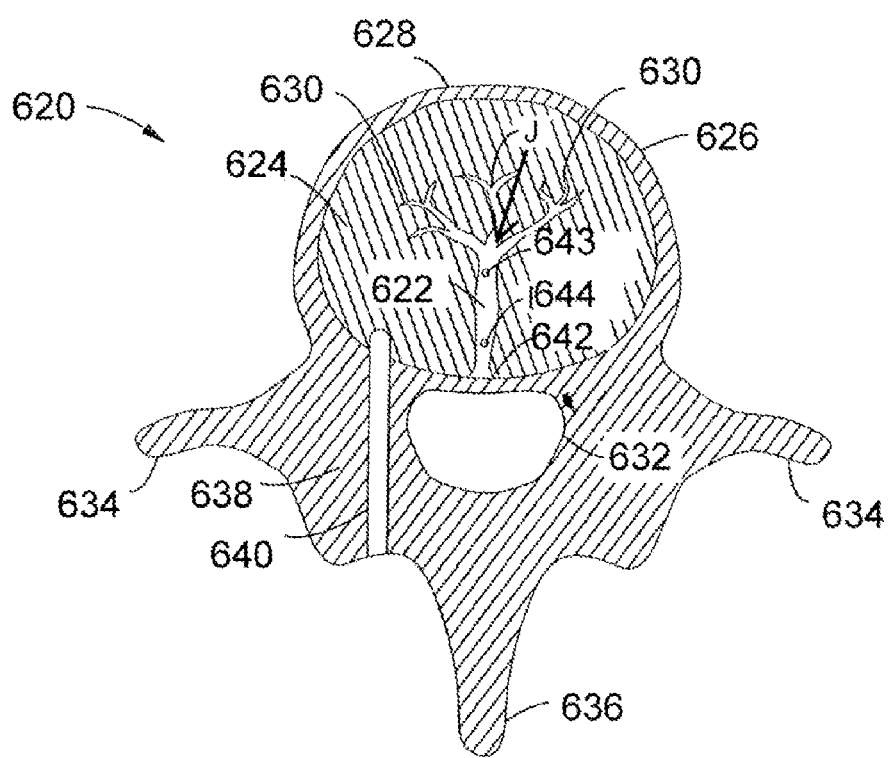
FIG. 34 illustrates a sectioned view of an embodiment of a vertebral body with a path bored through the cortical shell.

FIG. 34 illustrates a cross-sectional view of a vertebra 620. The existence of substantial intraosseous nerves 622 (e.g., basivertebral nerves), and nerve branches 630 within human vertebral bodies has been identified. The basivertebral nerve 622 has at least one exit 642 point at a location along the nerve 622 where the nerve 622 exits the vertebral body 626 into the vertebral foramen 632.

In accordance with several embodiments, the basivertebral nerves are at, or in close proximity to, the exit point 642. Thus, the target region of the basivertebral nerve 622 is located within the cancellous portion 624 of the bone (i.e., to the interior of the outer cortical bone region 628), and proximal to the junction J of the basivertebral nerve 622 having a plurality of branches 630 (e.g. between points A and B along nerve 622). Treatment in this region may be advantageous because only a single portion of the basivertebral nerve 622 need be effectively treated to denervate or affect the entire system. Typically, treatment in accordance with this embodiment can be effectuated by focusing in the region of the vertebral body located between 60%, 643, and 90%, 644, of the distance between the anterior and posterior ends of the vertebral body. In contrast, treatment of the basivertebral nerve 622 in locations more downstream than the junction J may require the denervation of each branch 630.

In accordance with several embodiments for accessing the basivertebral nerve, the patient's skin is penetrated with a surgical instrument which is then used to access the desired basivertebral nerves, i.e., percutaneously. In one embodiment, a transpedicular approach is used for penetrating the vertebral cortex to access the basivertebral nerve 622. A passageway 640 is created between the transverse process 634 and spinous process 636 through the pedicle 638 into the cancellous bone region 124 of the vertebral body 626 to access a region at or near the base of the nerve 622. It is appreciated that a postereolateral approach (not shown) may also be used for accessing the nerve.

Figure 35C:
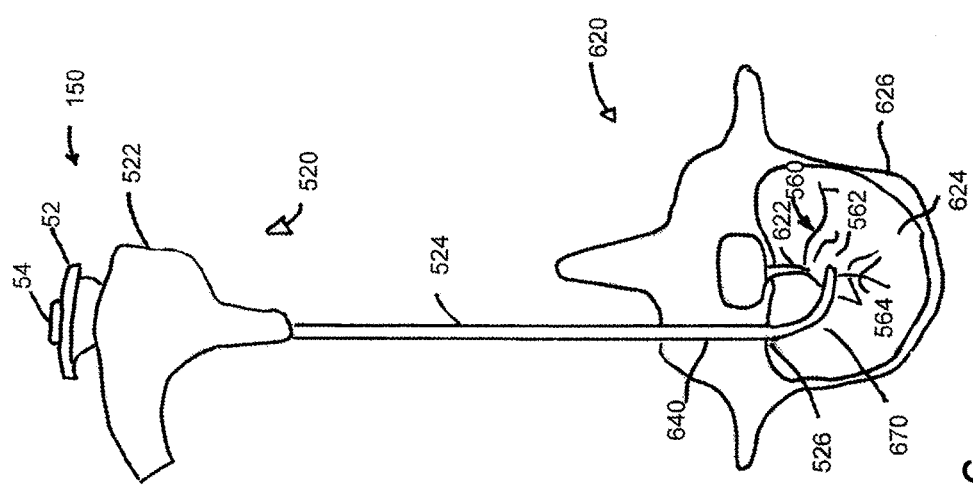

In accordance with several embodiments, FIGS. 35A-C illustrate a method for accessing the vertebral cortex and treating the basivertebral nerve of a vertebra with the system 10 in accordance with several embodiments of invention.

As shown in FIG. 35A, a straight stylet 650 may be inserted into proximal recess 534 of trocar 520 and advanced such that sharpened tip 654 of the stylet body 652 protrudes from the trocar distal end 56. The straight stylet 650 may have protrusions 658 just below stylet handle 556 for locking the stylet 650 to the trocar handle 522. When the stylet 650 is fully seated within trocar 520, the tip 654 of the straight stylet 650 may protrude from the distal end 526 of the trocar 220 (e.g., by about 1/16 to 3/16 inches). The protrusion or tip 654 may help to drive the trocar 520 through the cortical shell 628 in the direction of the cancellous bone 624 of vertebral body 626.

Referring now to FIG. 35B, the trocar 520 and stylet 650 may be advanced into the desired location within the vertebral body 626. The stylet 650 comprises a striking surface 660 to drive the trocar 510 into the vertebra 620 by piercing the cortical shell 628 and generating straight passageway 640 between the transverse process 634 and spinous process 636 through the pedicle 638 into the cancellous bone region 624 of the vertebral body 626. With the trocar 520 in position, the straight stylet 650 may be removed to open the trocar channel 528 for delivery of additional instrumentation.

In an alternative embodiment, the tip 562 of probe may be used as the stylet for piercing the cortical shell 628 and generating path 640 through vertebra 620. In this configuration, the probe tip 662 is only advanced slightly from distal end 526 of trocar hypotube 524 to act as stylet for advancement of trocar. A releasable collar (not shown) may be used between probe handle 552 and trocar handle 522 to restrict advancement of the curved distal end 560 past distal opening 526 of the trocar body 524. In one embodiment the trocar 520 is then driven to the proper location within the vertebral body 626 with striking surface 554 to generate passageway 640 between the transverse process 634 and spinous process 636 through the pedicle 638 into the cancellous bone region 624 of the vertebral body 626.

Referring now to FIG. 35C, with the trocar 510 in place, the treatment probe 550 may be advanced along the trocar channel 528 such that the curved distal end 560 exiting the distal opening 526 generates a curved path 670 through the cancellous bone 624.

In accordance with several embodiments, treatment energy may then be delivered via bipolar electrodes 564 to the target treatment location T at the basivertebral nerve 622 to perform a localized treatment via delivery of a therapeutic level of heating to stimulate or ablate the basivertebral nerve 622.

In one embodiment, the RF energy is delivered to the treatment site via electrodes 564, and activated to deliver therapeutic treatment energy. In one embodiment, the treatment probe comprises an RF delivery probe having bipolar electrodes.

In accordance with several embodiments, any number of treatment modalities may be delivered to the treatment site for therapeutic treatment. For example, treatment may be affected by monopolar, tripolar or sesquipolar RF, ultrasound, radiation, steam, microwave, laser, or other heating means. In one embodiment, the treatment device comprises a fluid delivery catheter that deposits an agent (e.g., bone cement, or other therapeutic agent) to the treatment site T.

In accordance with several embodiments, cryogenic cooling (not shown) may be delivered for localized treatment of the basivertebral nerve. Furthermore, treatment may be affected by any mechanical destruction and or removal means capable of severing or denervating the basivertebral nerve. For example, a cutting blade, bur or mechanically actuated cutter (not shown) typically used in the art of orthoscopic surgery may be used to affect denervation of the basivertebral nerve.

In addition to or separate from treating the basivertebral nerve, a sensor (not shown) may be delivered to the region to preoperatively or postoperatively measure nerve conduction at the treatment region. In this configuration, the sensor may be delivered on a distal tip of a flexible probe that may or may not have treatment elements as well.

In other embodiments, the goal of the treatment may be ablation, or necrosis of the target nerve or tissue, or some lesser degree of treatment to denervate the basivertebral nerve. For example, the treatment energy or frequency may be just sufficient to stimulate the nerve to block the nerve from transmitting signal (e.g. signals indicating pain).

Once the treatment is complete, the curved probe 550 may be withdrawn into the cannula. The needle trocar 550 with the curved cannula 550 is then removed and the access site is closed as prescribed by the physician.

In accordance with several embodiments, the above systems 10, 200, 201, 300, 400, and 510 may be provided as a kit of instruments to treat different regions of the body. As one example, the varying of location, orientation, and angle may be achieved by varying the curvature in the curved or curveable cannula (e.g., 230, 322, 430, or 550). The curvature may be varied by varying the radius of curvature, the insertion depth (shaft length and tip length), and/or the final exit angle with respect to the trocar channel 528. Thus, the physician may select a different kit for treating a lumber spine segment as opposed to a cervical spine segment, as the anatomy may dictate the path that needs to be channeled.

In accordance with several embodiments, each of the components in the systems 10, 200, 201, 300, 400 and 510 may have any length, shape, or diameter desired or required to provide access to the treatment and/or diagnostic region (e.g. intraosseous nerve or basivertebral nerve trunk) thereby facilitating effective treatment and/or diagnostic of the target region. For example, the size of the intraosseous nerve to be treated, the size of the passageway in the bone (e.g. pedicle 138 or 638) for accessing the intraosseous nerve, and the location of the bone (and thus the intraosseous nerve) are factors that that may assist in determining the desired size and shape of the individual instruments. In several embodiments, the treatment device (e.g., RF probe) has a diameter between 1 mm and 5 mm (e.g., between 1 mm and 3 mm, between 2 mm and 4 mm, between 3 mm and 5 mm, 1 mm, 2 mm, 3 mm, 4 mm, 5 mm, or any diameter between the recited ranges).

In accordance with several embodiments, the systems 10, 200, 201, 300, 400, and 510 described above may be used with a number of different treatment modalities for therapeutic treatment of the target region, which may be spinal or non-spinal. For example, in one embodiment, it is desirable to operate the treatment devices or probes in system 10, 200, 201, 300, 400, and 510 in a manner that ablates the tissue of the target region (e.g. basivertebral nerve) to produce heat as described in U.S. Pat. No. 6,699,242, herein incorporated by reference in its entirety.

In another embodiment, the treatment device is configured to deliver therapeutic treatment that is targeted to block nerve conduction without ablating the nerve, i.e. thermal treatment is delivered to the nerve (e.g. via thermal therapy, agent or the like) that results in denervation of the basivertebral nerve without necrosis of tissue. This may be achieved via delivery of a lesser amount of energy or agent to the tissue site (either in the form of less exposure time, concentration, intensity, thermal dose etc.) than is required for ablation, but an amount sufficient to achieve some amount of temporary or permanent denervation.

In accordance with several embodiments, the probe described herein may comprise non-therapy devices, such as diagnostic devises (e.g. ultrasound, cameras, or the like) to diagnose a region of tissue independent of or in connection with treatment of the region of tissue.

In several embodiments, individual elements of any of the systems 10, 200, 201, 300, 400, and 510 detailed above may be used interchangeably where applicable. For example, the curved stylet 60 shown in systems 10 and 200 may be temporarily implemented in place of the probe of systems 201 and 300 to provide additional curving bias to the curveable cannula (230, 320) while the cannula is being driven into the bone. Furthermore, the channeling stylet 90 may be used to further generate a channel beyond the curved path provided by the curveable cannula (230, 320).

Several embodiments of a steerable devices or systems (e.g., including a distal treatment probe and a proximal handle) for actuating curvature/steering of the distal probe are shown in FIGS. 36 through 42. It is further envisioned that any of the distal probe designs are interchangeable with the proximal handle designs so that no one handle design is specific to a distal probe design, and vice-versa. In accordance with at least one embodiment, the system is configured to generate a curved path in bone, and in particular a path entering the vertebra from the pedicle and curving into the vertebral body to the treatment location at the basivertebral nerve plexus. In accordance with several embodiments, the steerable systems described herein are robust enough to travel through bone as well as articulate within the bone.

Figure 36A:
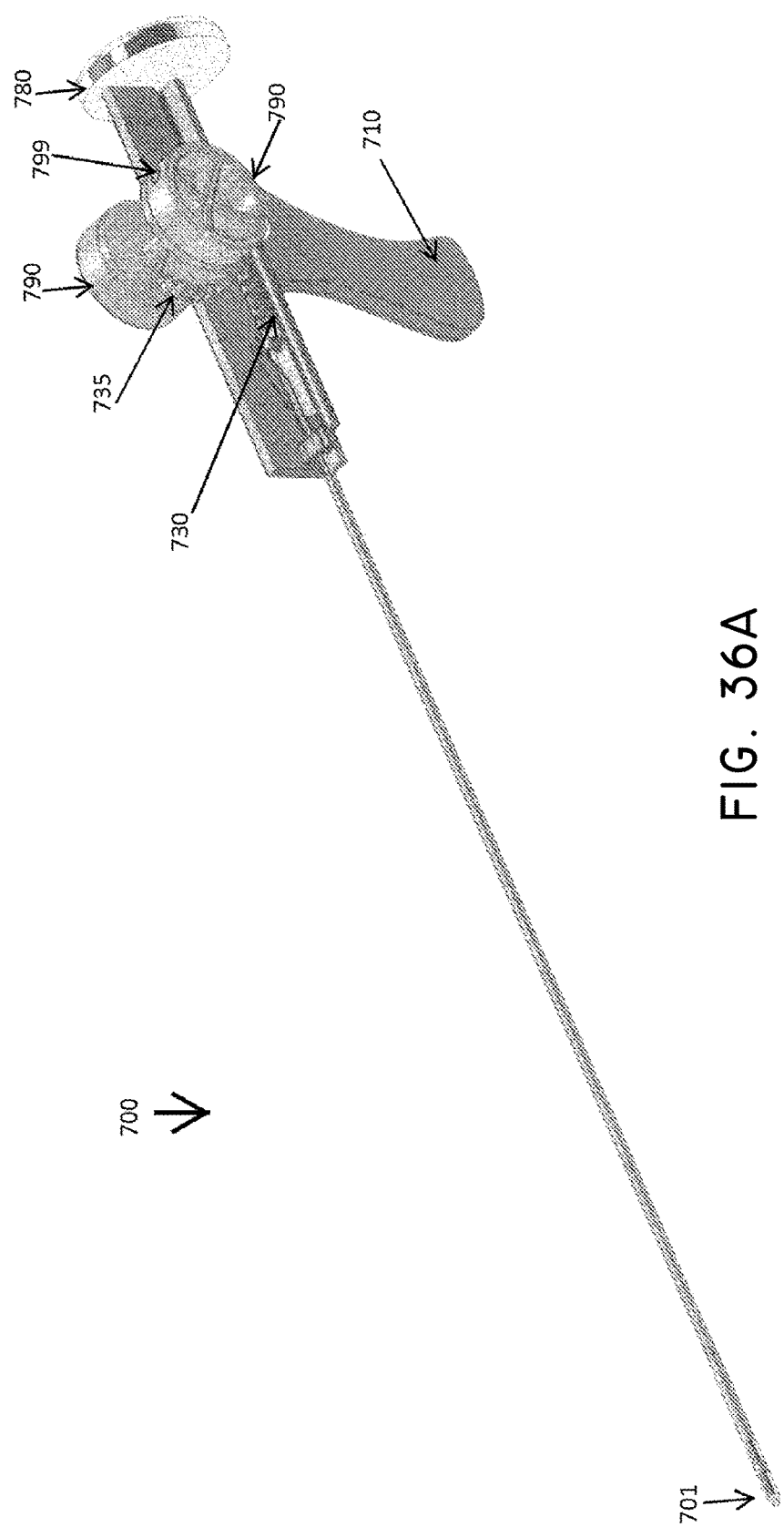
FIGS. 36A-36D illustrate an embodiment of a steerable probe with a proximal handle having a thumb wheel.

FIGS. 36A-36D illustrate an embodiment of a steerable probe 700 with a proximal handle 710 having a thumb wheel 790 that is configured to operate steering of a distal end 701 of the probe. In one embodiment, the proximal handle 710 includes one or two thumb wheels 790 which are interconnected. In one embodiment, rotation of the thumb wheel 790 drives linear motion of a pull wire 711 via a rack 730 and pinion 735. In some embodiments, the steerable probe 700 comprises electrode wiring 713, electrode lead 715, engagement teeth 731, 736 between the rack 730 and pinion 735, and a pull wire 711 embedded within the rack 730. The bottom side of the rack 730 may have a series of notches 732 that interface with a protrusion 750 in the handle 710 to generate a resistive "click type" motion of the thumb wheel 790. As shown in FIG. 36A, the thumb wheel 790 may have one or more markings or indicia 799 of various degrees of curvature for the distal end 701. In one embodiment, the proximal end of the handle 710 includes a strike surface 780 for hammering the distal end 701 through cortical bone.

Figure 36B:
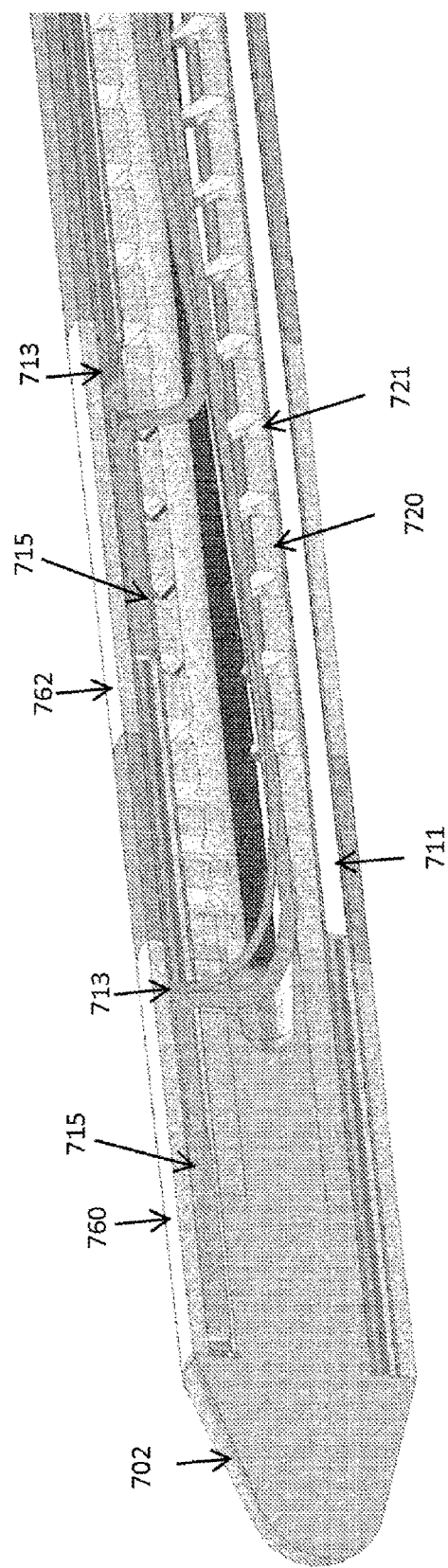
Figure 36C:
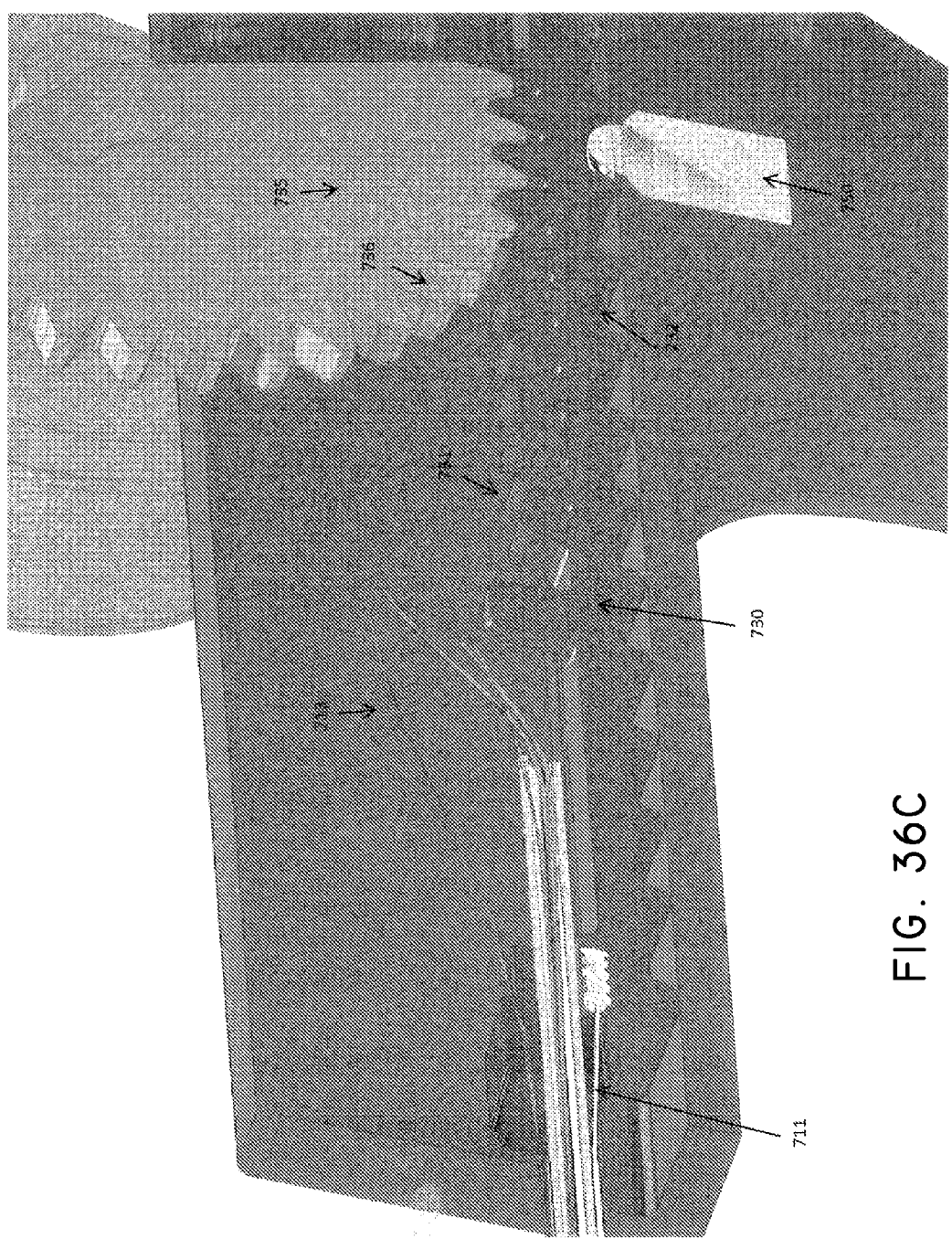
Figure 36D:
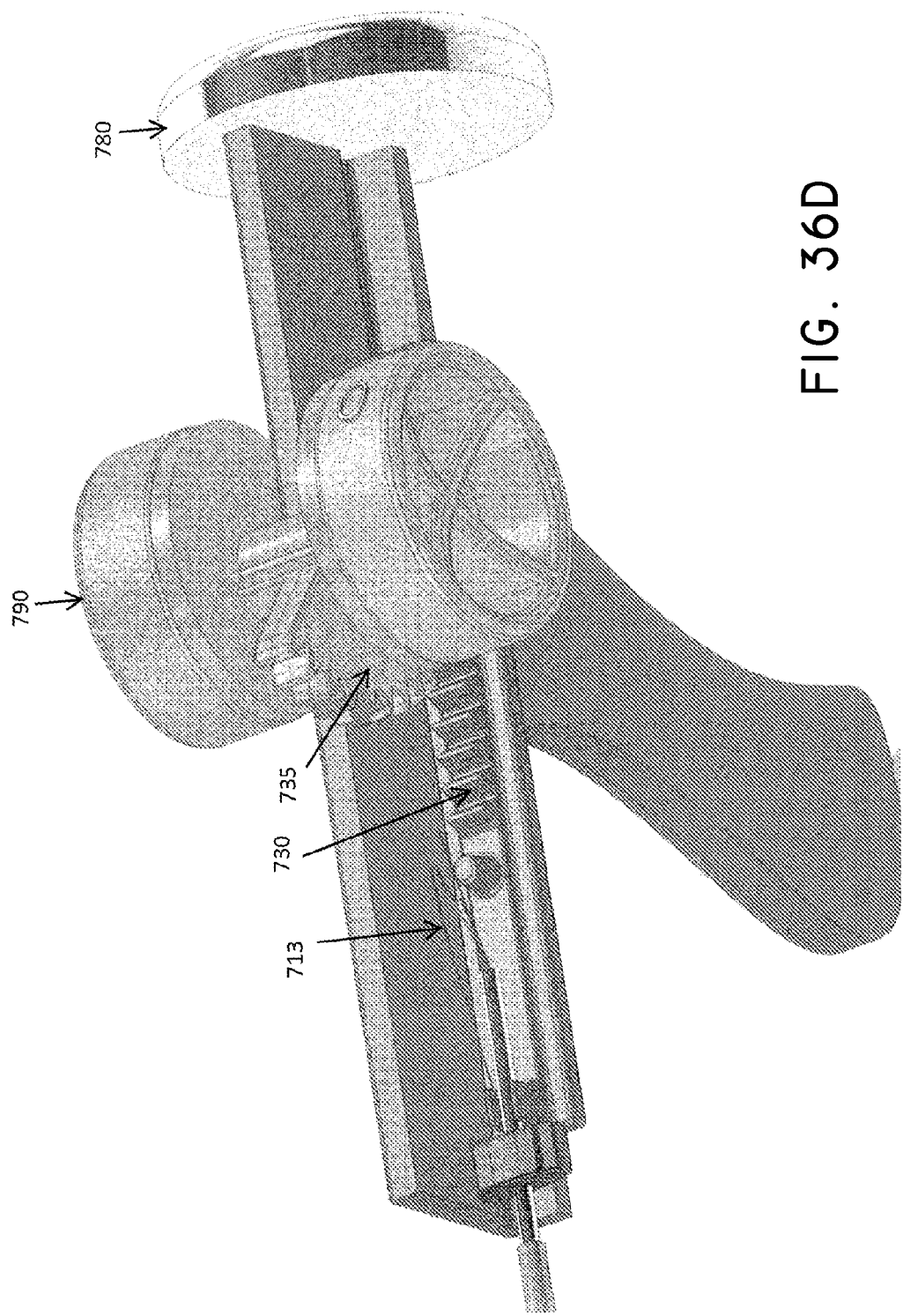

As shown in FIG. 36B, one embodiment of the steerable probe 700 may include tubular electrodes 760, 762, a pull wire 711 and a central tube 720 (e.g., a hypotube) that is laterally slotted 721 to allow the tube 720 to bend upon actuation of the pull wire 711, while still providing axial rigidity to allow the distal end 701 to be tapped through bone.

Figure 37A:
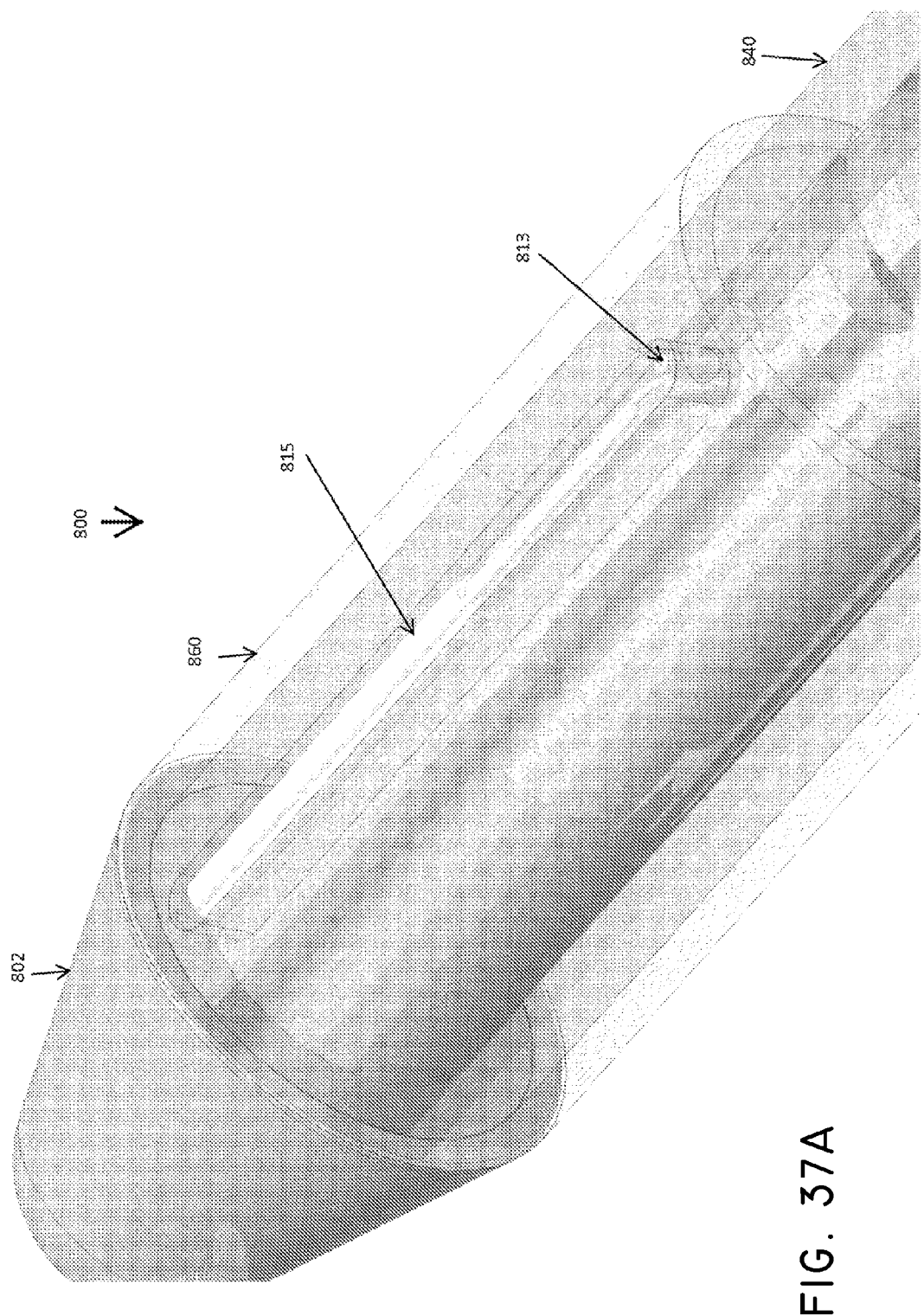
FIGS. 37A-37C illustrate an embodiment of a steerable probe having a slotted hypotube.
Figure 37B:
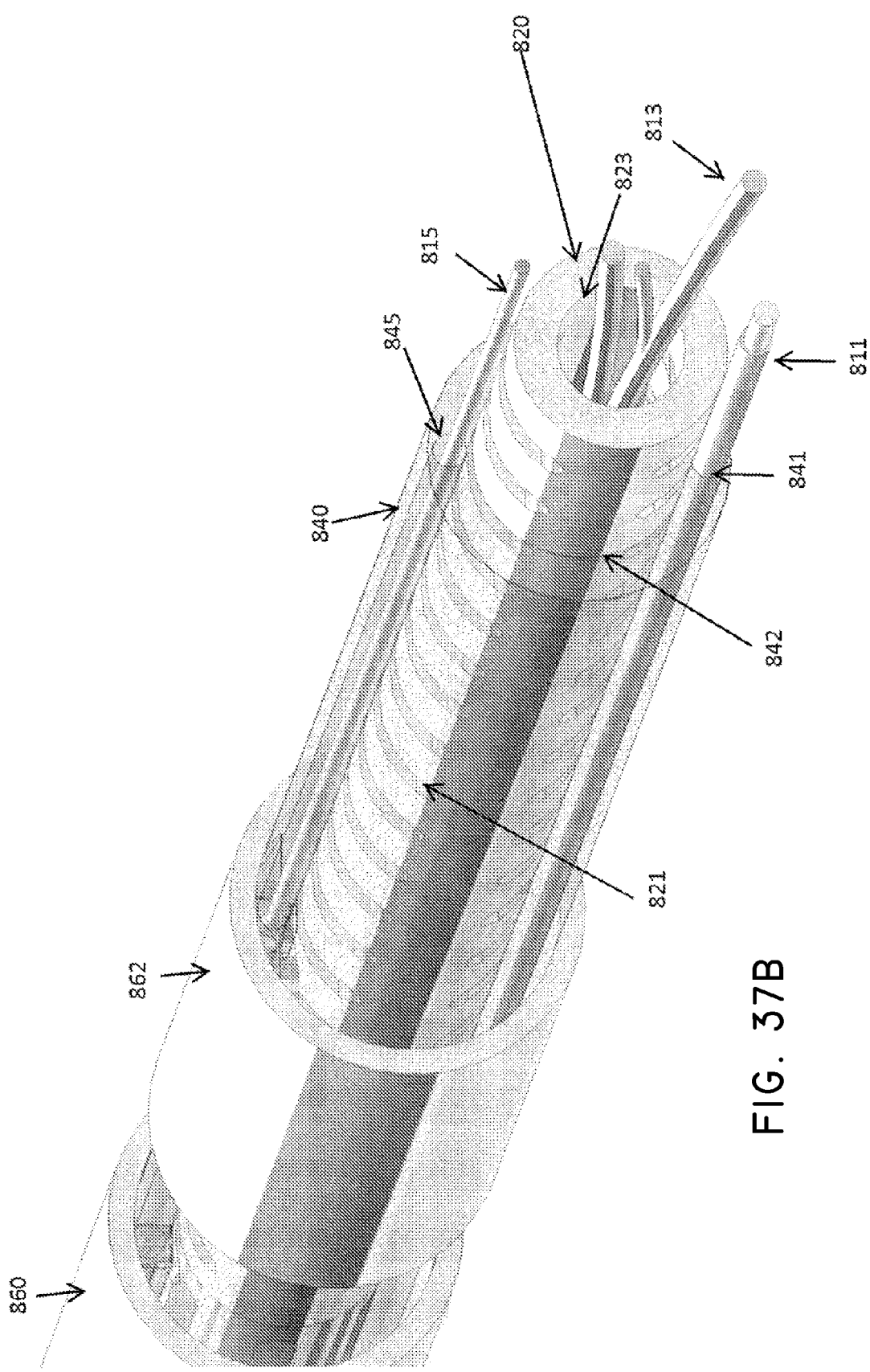
Figure 37C:
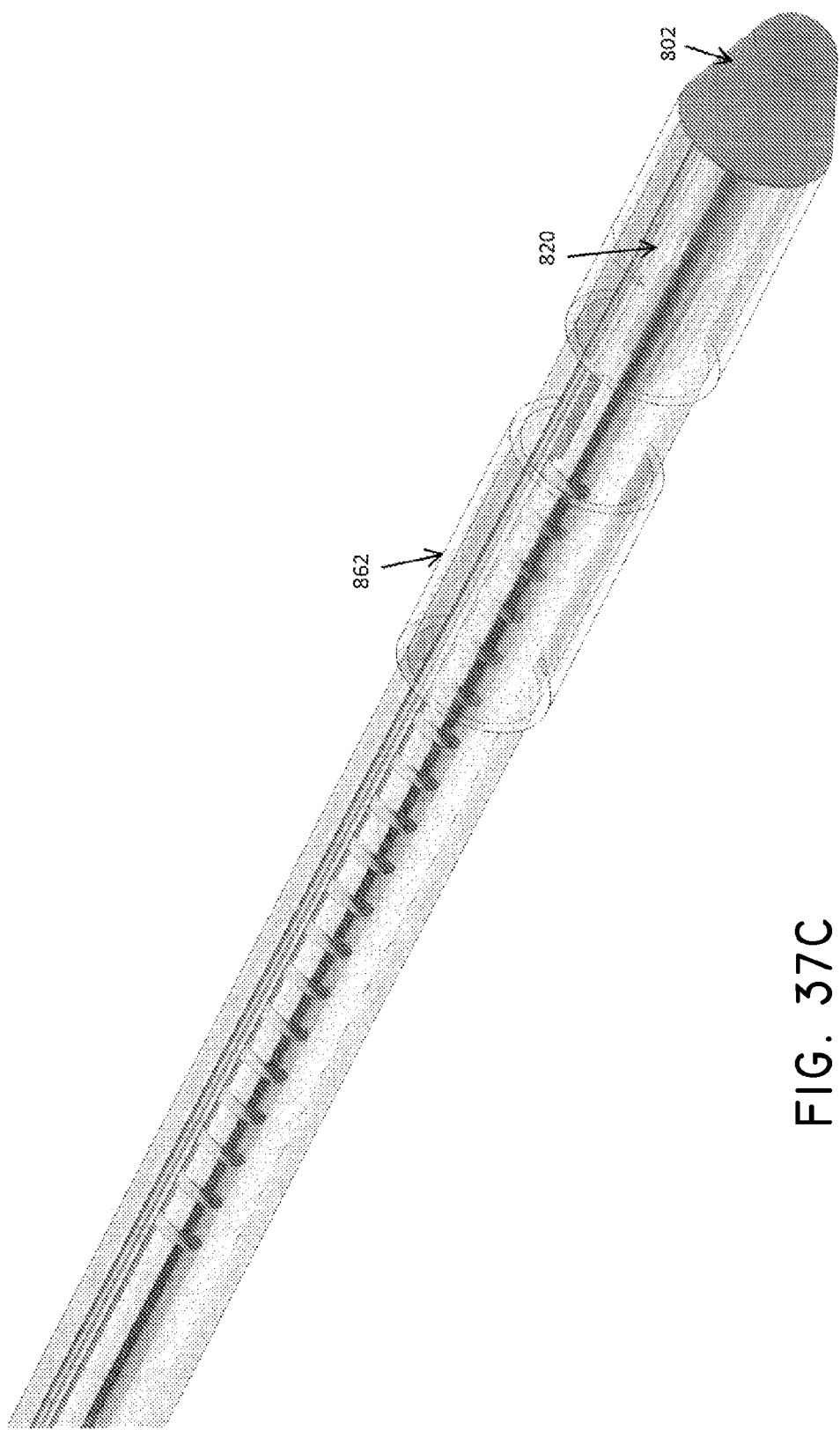

FIGS. 37A-37C illustrates an embodiment of a steerable probe 800 with a hypotube 820 that is laterally slotted 821 to allow the hypotube 820 to bend upon actuation of pull wire 811, along with slots and/or relief for wiring. The distal end of the steerable probe 800 may include a conical distal tip 802 and tubular electrodes 860, 862. FIG. 37B illustrates a side view of the steerable probe 800 showing electrode wiring 813 within a lumen 823 of the hypotube 820. In various embodiments, the hypotube 820 comprises stainless steel or DELRIN® material. In various embodiments of manufacture, an outer layer 840 of PEBAX® (a block copolymer which offers a wide range of performances among thermoplastic elastomers) or other copolymer or thermoplastic elastomer material is deposited between the electrodes 860, 862 and formed to have a diameter that is flush with the outer diameter of the electrodes 860, 862. In some embodiments, the outer layer 840 comprises a lumen 841 for the pull wire 811, a lumen 845 for electrode lead wiring 815, and a central channel 842 (e.g., for the hypotube 820). In some embodiments, the outer layer 840 comprises a pocket to house electrode lead wiring 815 and/or electrode wiring 813. In some embodiments, the hypotube 820 includes an oval slot for electrode lead wiring 815 and/or electrode wiring 813. In some embodiments, the outer layer 840 comprises an overmolded tip onto hypotube 820 near the distal tip 802, as shown in FIG. 37C.

Figure 38A:
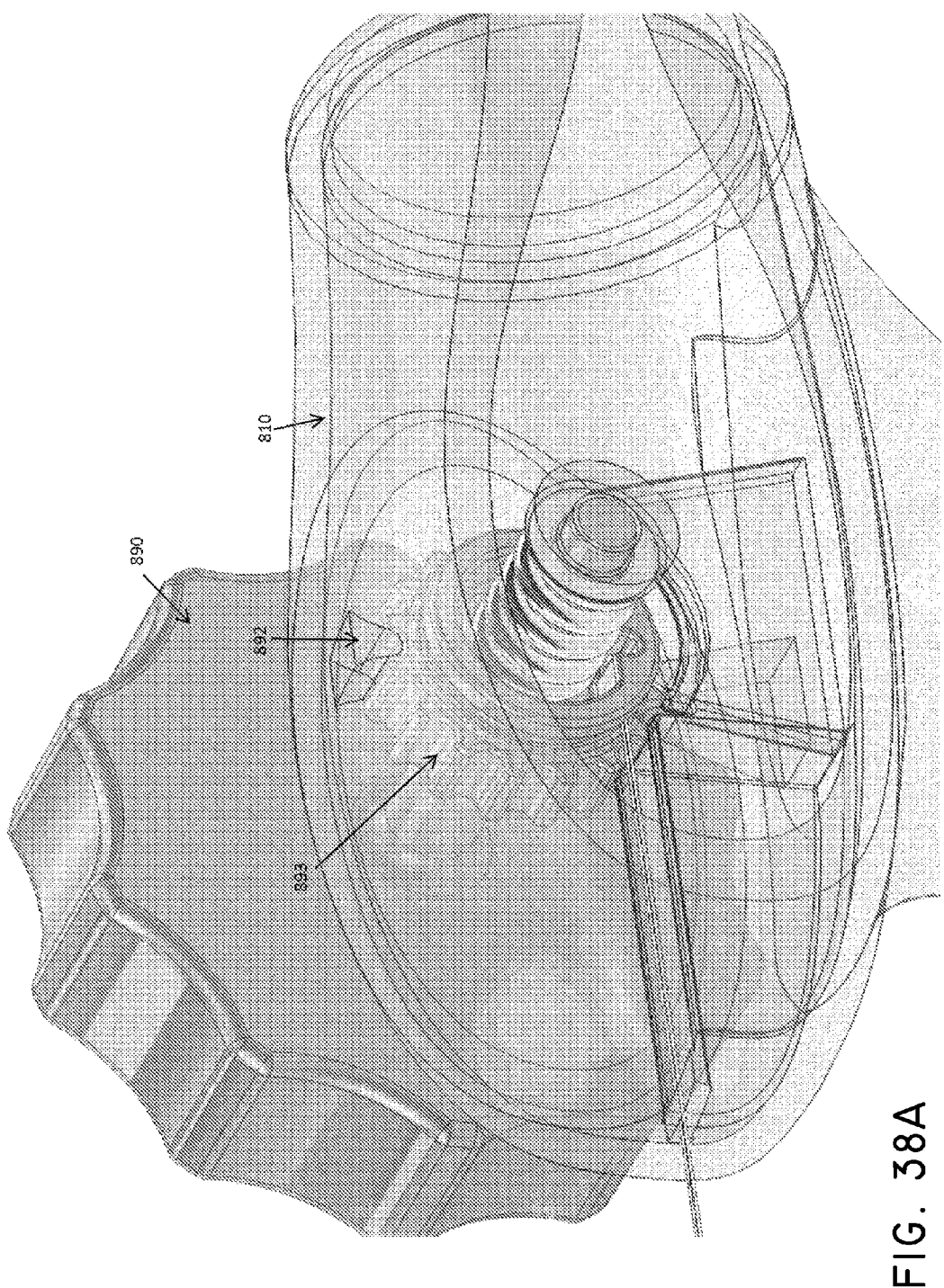
FIGS. 38A-38C illustrate embodiments of a steerable probe proximal handle having an ergonomic design and a thumb wheel.
Figure 38B:
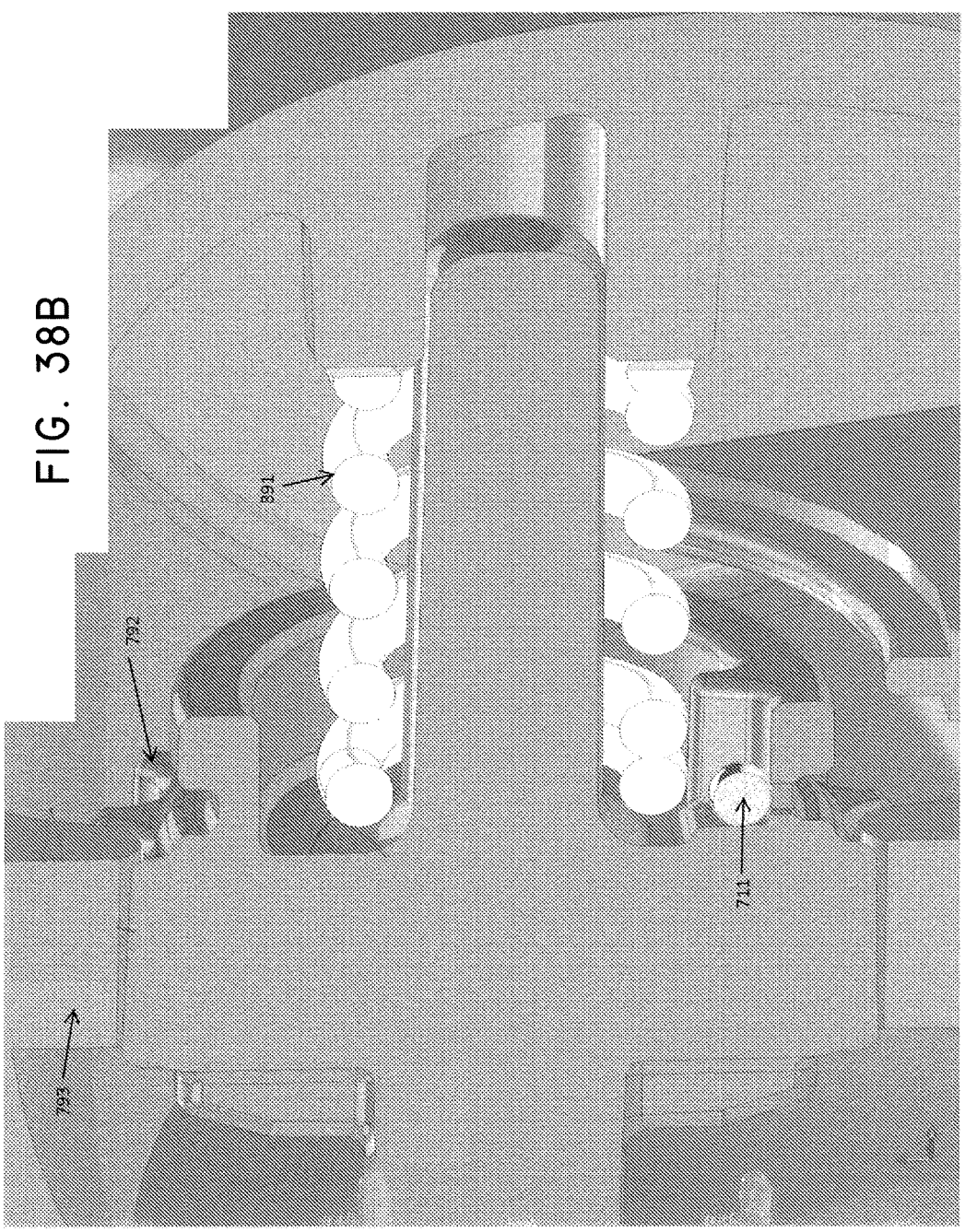
Figure 38C:
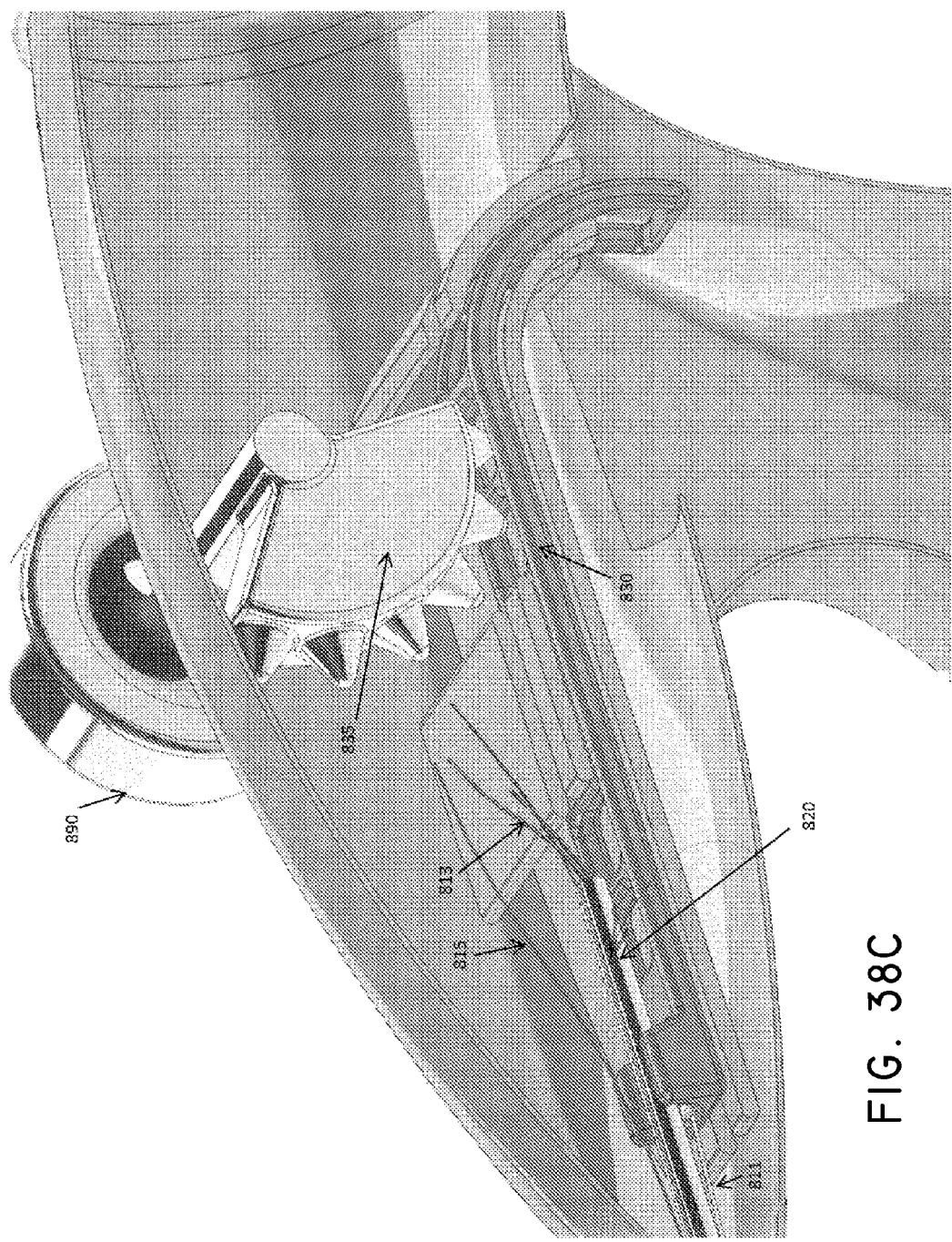

FIGS. 38A-38C illustrate embodiments of a steerable device proximal handle 810 with a more ergonomic design and a larger thumb wheel 890. Rotation of the thumb wheel 890 may be configured to operate steering of the distal end 801 of a probe, and in some embodiments, bend the tip 802. In one embodiment, the thumb wheel 890 is spring loaded axially via a spring 891 to retain the thumb wheel 890 in a radially locked position with respect to handle 810 (e.g. via pall notched wheel 892 and detent 893). Referring to FIG. 38B, in accordance with several embodiments, to actuate curvilinear motion of the distal end 801 of the probe, the thumb wheel 890 is pushed inward toward the proximal handle 810 to compress the spring 891 and disengage the detent 893 from the pall notched wheel 892, thereby allowing for rotation of the thumb wheel 890. The thumb wheel 890 drives linear motion of a pull wire 811. In some embodiments, the pull wire 811 is embedded within the pall notched wheel 892.

FIG. 38B illustrates an embodiment where the linear motion of the pull wire 811 is driven by the notched wheel 892. In some embodiments, the pull wire 811 is embedded within the rack 830. FIG. 38C illustrates an embodiment where the linear motion of the pull wire 811 is driven via a rack 830 and pinion 835. In one embodiment, the hypotube 820 is fixed with respect to the rack 830 and the pull wire 811 is retracted and/or extended based on radial motion of thumb wheel 890, which drives pinion 835. The rack 830 and pinion 835 may be interchangeable with other components in different embodiments.

Figure 39A:
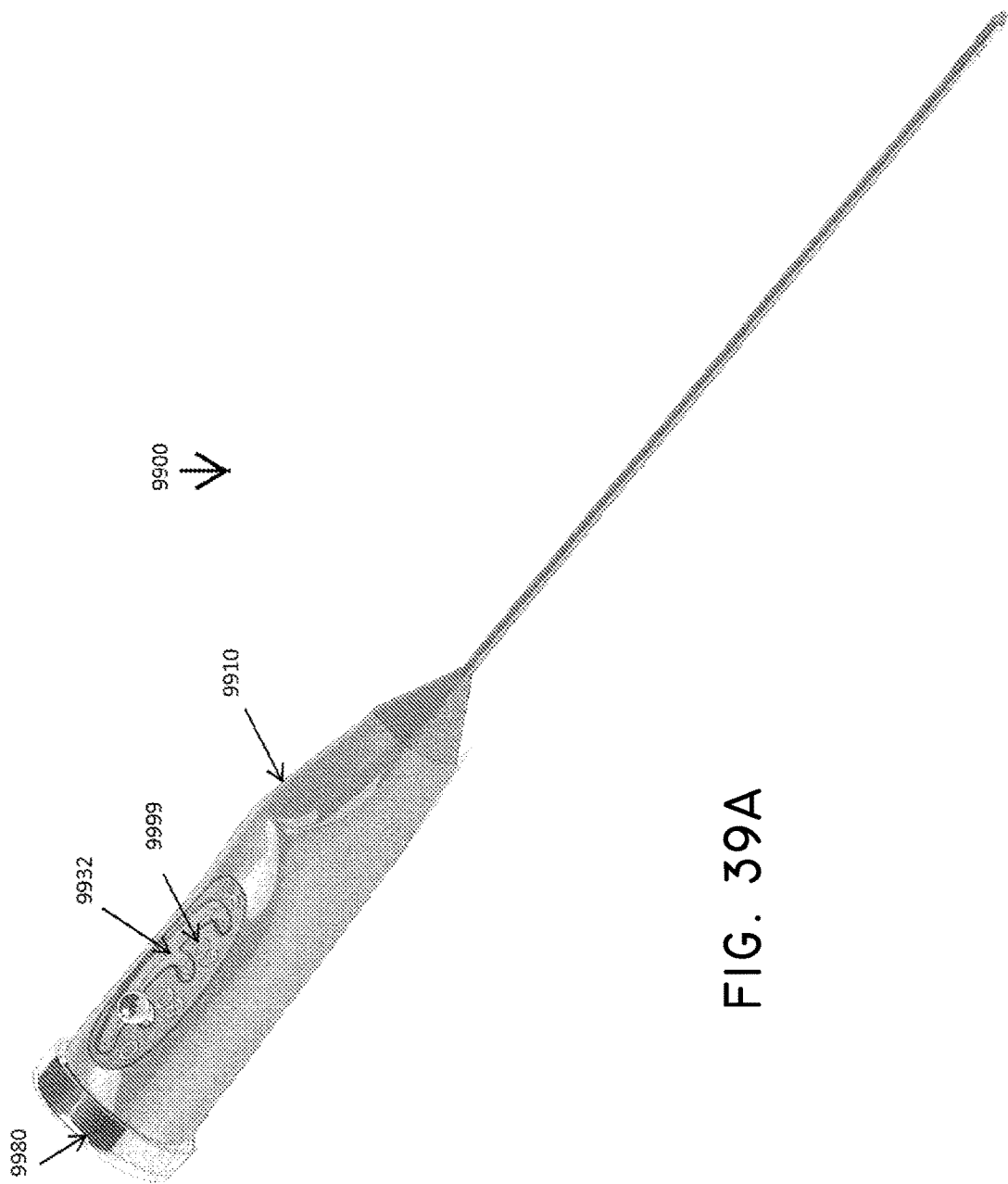
FIGS. 39A-39D illustrate embodiments of a steerable probe proximal handle with preset angles in a "stick shift" type configuration.
Figure 39B:
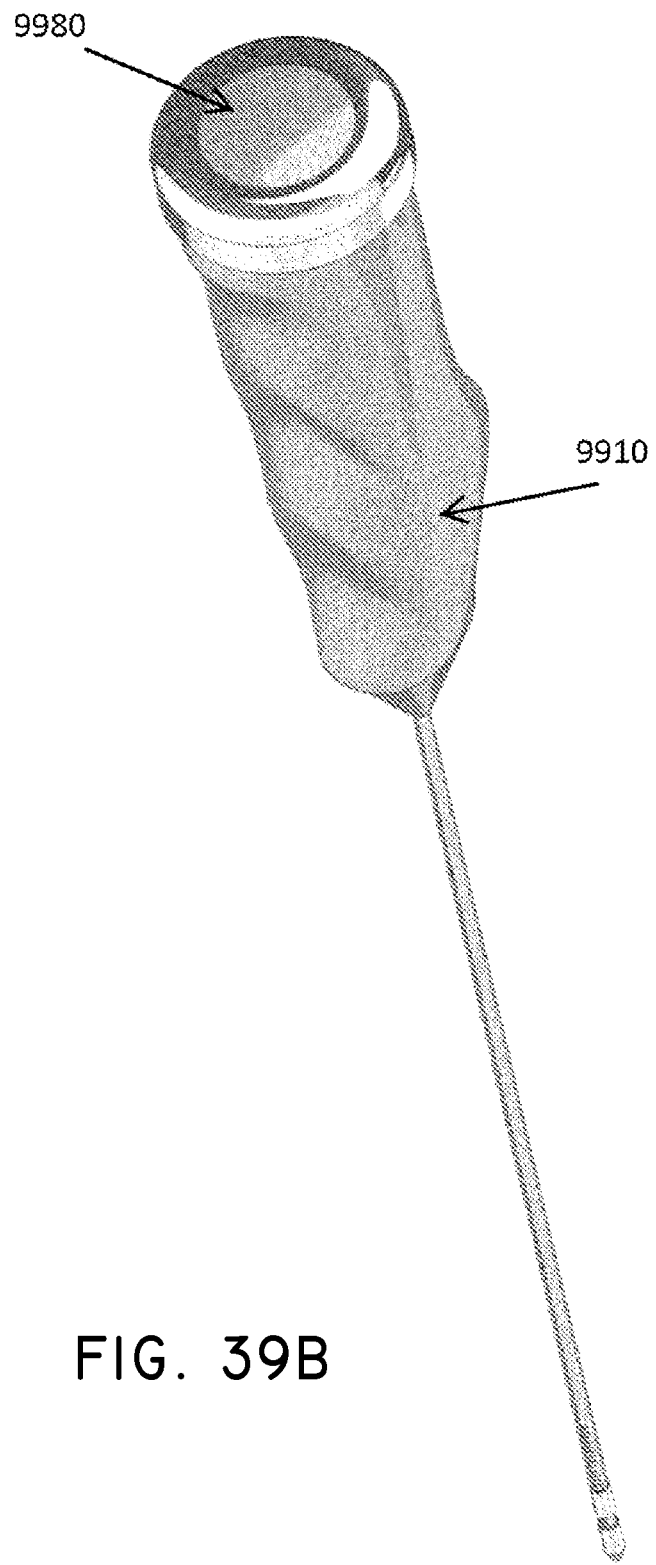
Figure 39C:
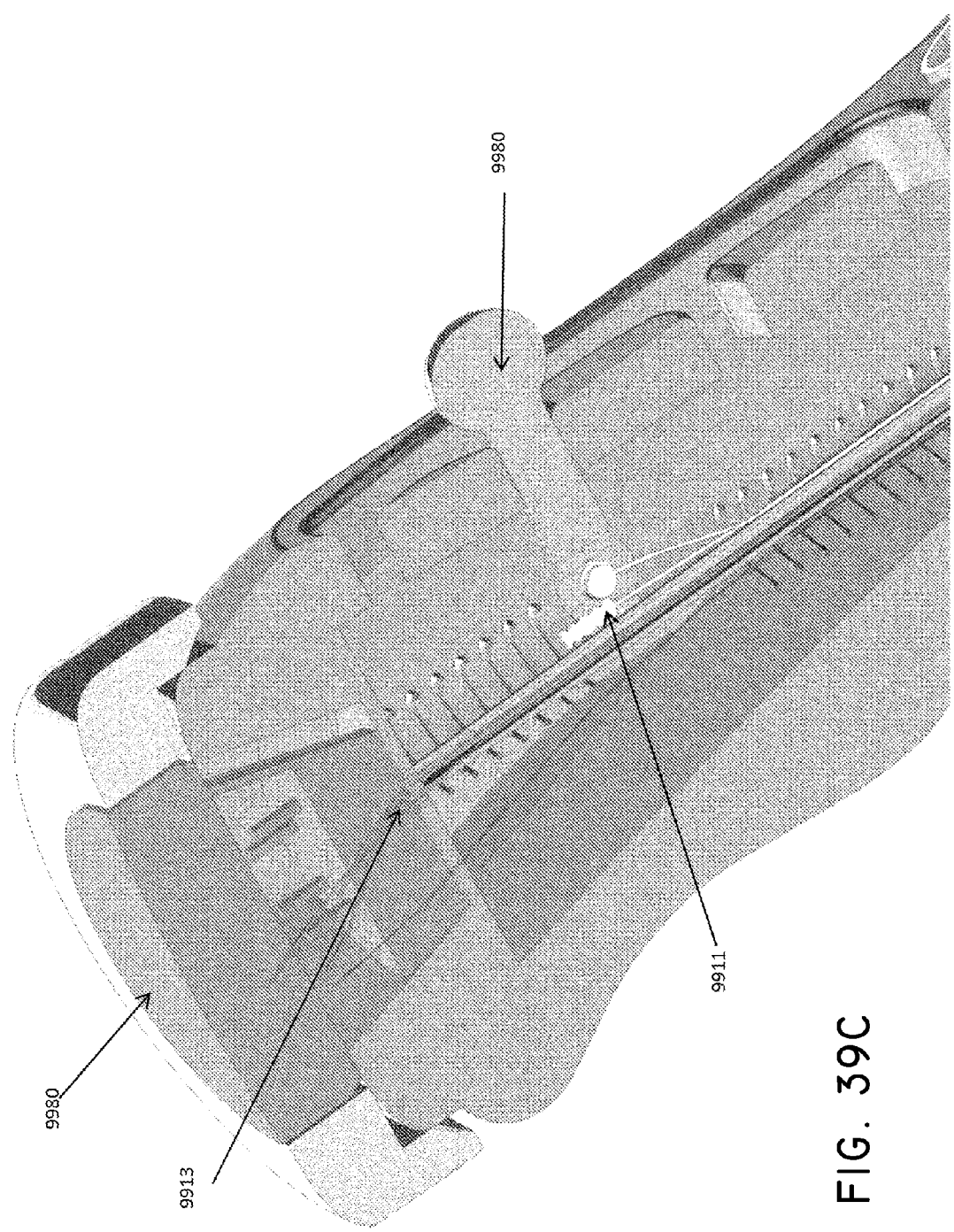
Figure 39D:
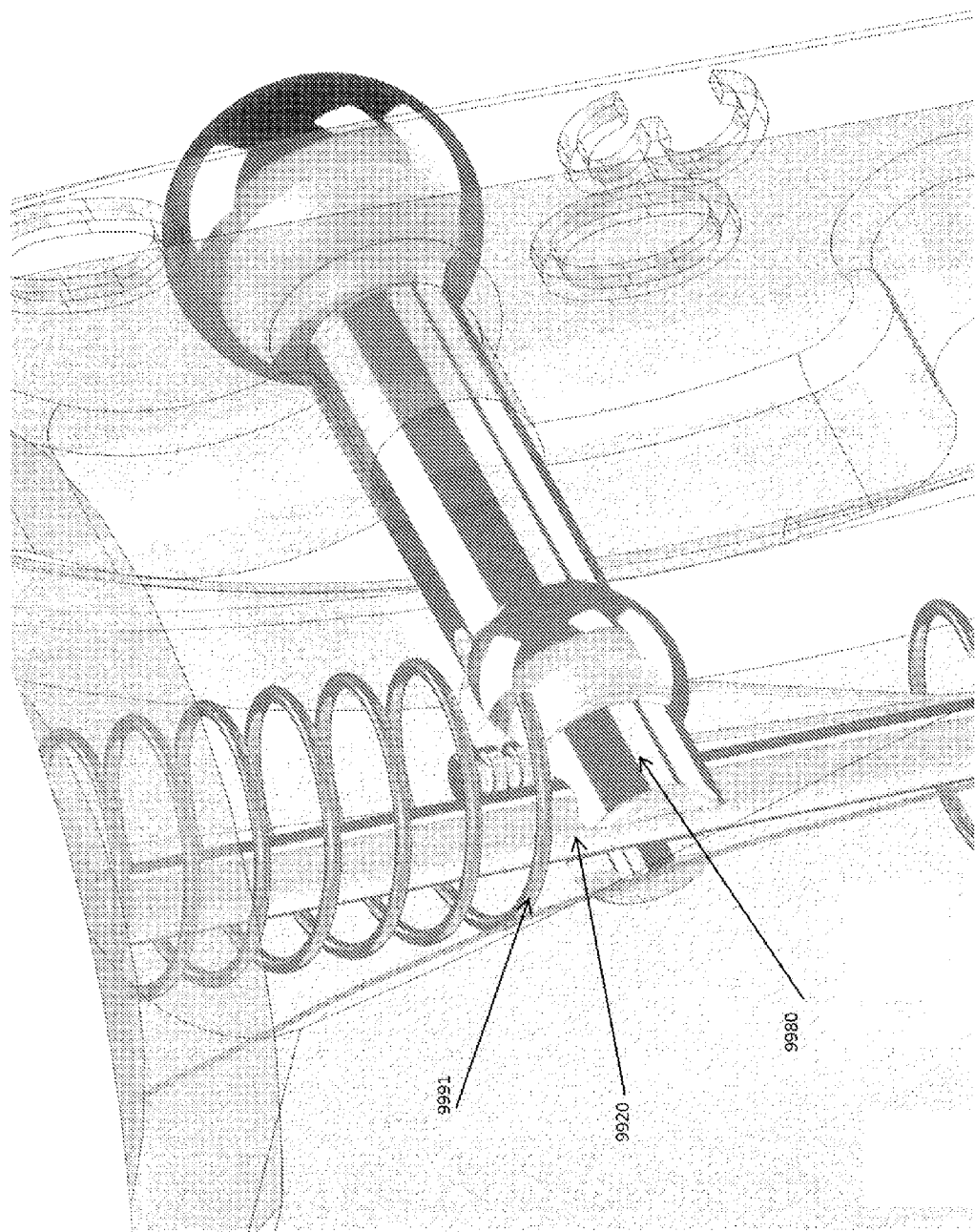

FIGS. 39A-39D illustrate an embodiment of a steerable probe 9900 proximal handle 9910, which may have markings or indicia 9999 of preset angles of curvature for the distal end (e.g., 0, 30, 60, and 90 degrees) in "stick shift" type configuration. As illustrated in FIG. 39D, the knob 9980 is mounted on the hypotube 9920 and is freely rotatable to navigate the curved slots 9932. The knob 9980 may be spring loaded via springs 9991 to restrain/retain the knob 9980 in respective slots 9932 at given increments. In some embodiments, a pull wire 9911 is embedded within the knob 9980. In some embodiments, the pull wire 9911 has a bulbous end that is retained within the knob 9980, as illustrated in FIG. 39D. As the knob 9980 is moved, the pull wire 9911 may be retracted to allow the distal end to bend upon actuation of pull wire 9911. Several embodiments may include a strike surface 9980 located at proximal end of handle 9910 (e.g., for hammering the distal end through cortical bone). In several embodiments, leads 9913 may be wired through a center piece of the strike surface 9980.

In one embodiment, not shown, an actuation knob is spring loaded to restrain/retain the knob in respective slots at given increments (e.g., in an "escalating ladder" embodiment). The handle 9910 may have a stationary rail and a spring retainer that slides along the stationary rail. As the knob is moved toward the 90 degree marking, the pull wire may be retracted to allow the distal end to bend upon actuation of the pull wire. This escalating ladder embodiment may allow the knob to come to rest at certain preset locations on the handle 9910. In one embodiment, the steerable probe 9900 comprises curved slots 9932.

Figure 40A:
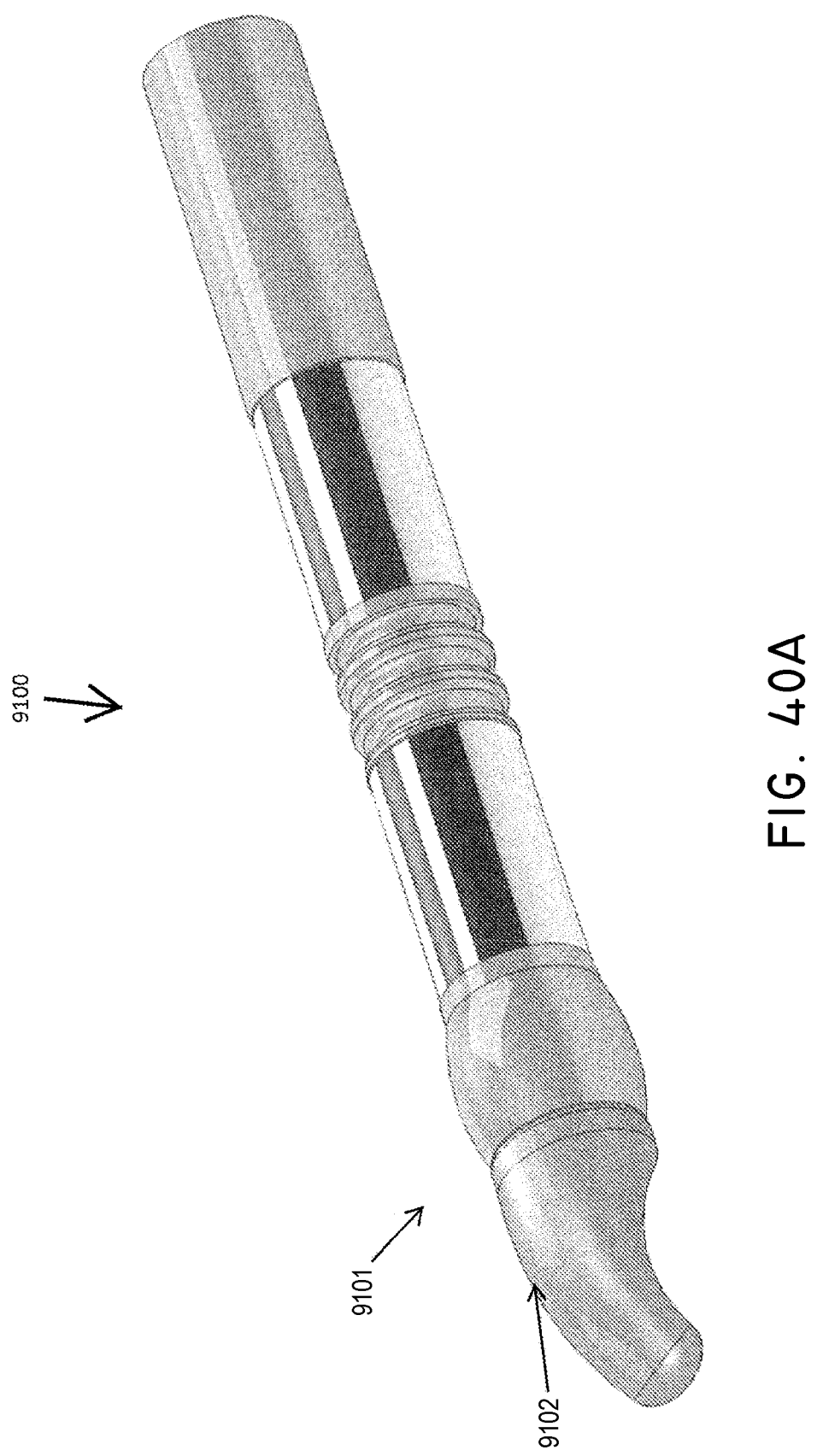
FIGS. 40A-40C illustrate embodiments of a steerable probe distal end and show a distal end with a furled ceramic distal tip for guiding the probe in a curved path in bone.
Figure 40B:
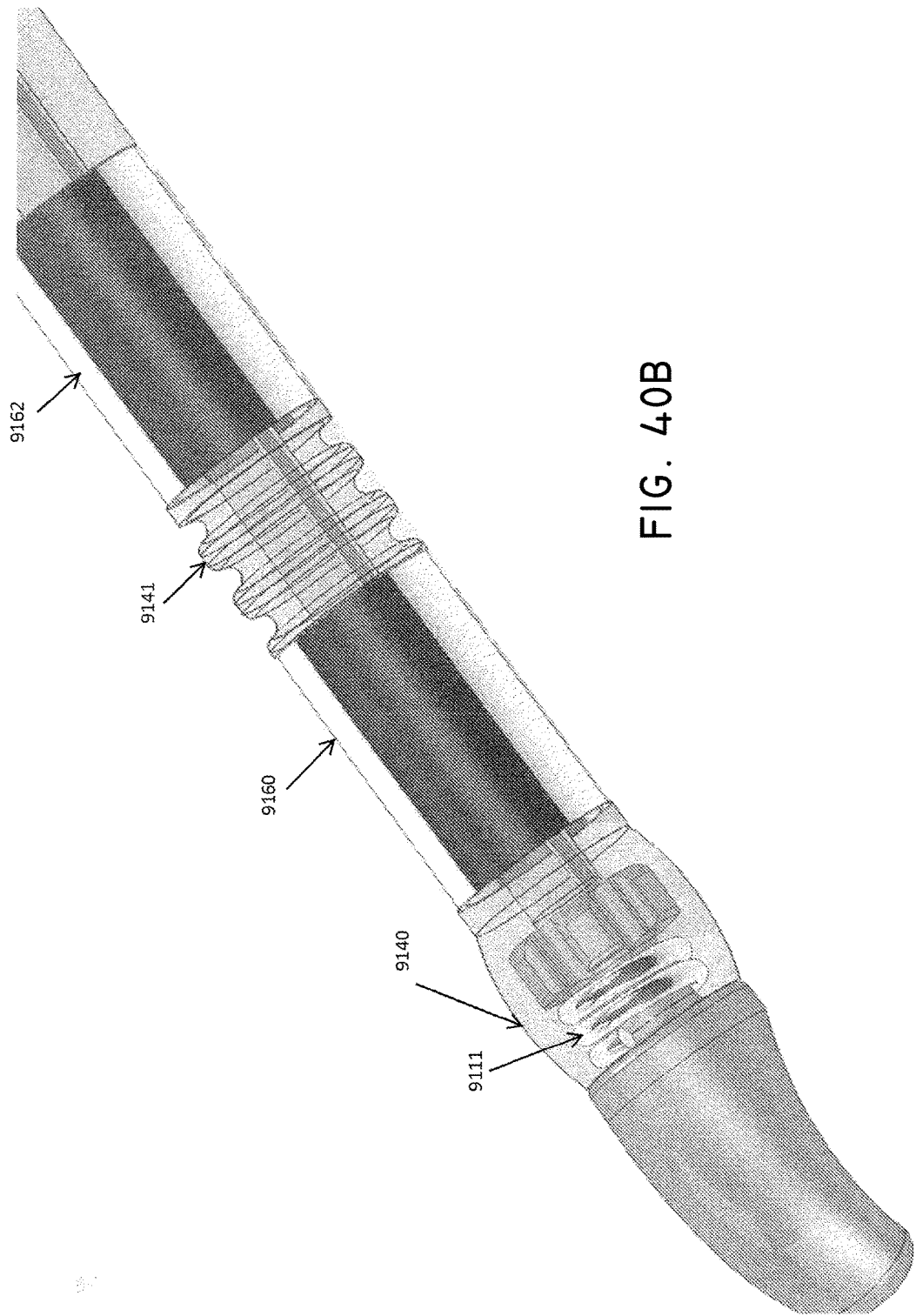
Figure 40C:
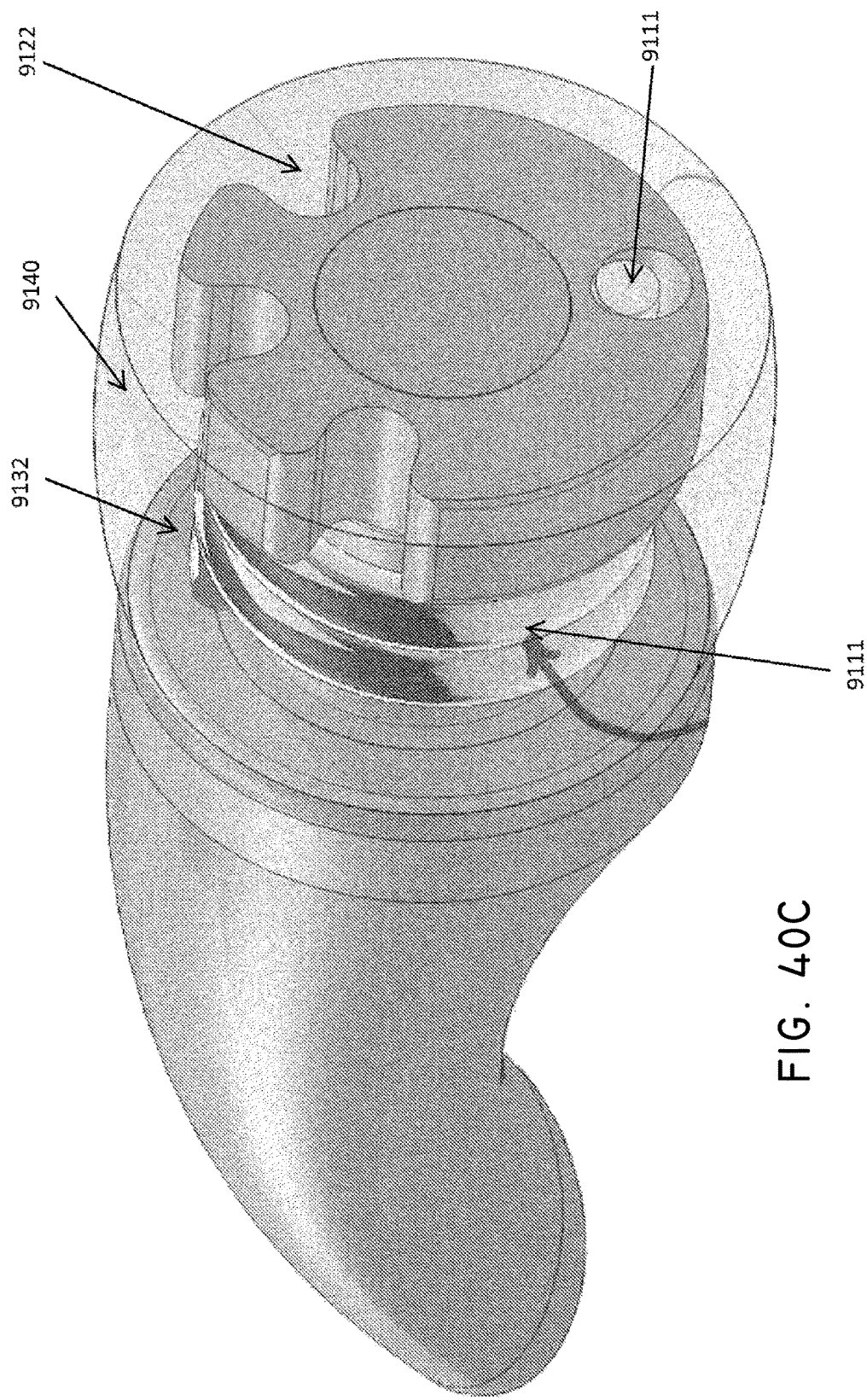

FIGS. 40A-40C illustrate several embodiments of the distal end 9101 of a steerable probe 9100. In accordance with several embodiments, the distal end 9101 may have a furled ceramic distal tip 9102 for guiding a probe through a curved path in bone. In addition, a laser-welded pull wire 9111 may be wrapped around a distal end of the furled tip 9102 just proximal to the curvature at a relieved circumferential channel 9132. The proximal end of the furled tip 9102 may comprise reflow channels 9122 for coupling to the polymeric outer structure 9140. In one embodiment, the polymeric (e.g., PEBAX®) outer structure 9140 forms a singular unit with separate lumens for a pull wire and/or electrode wiring (not shown). The polymeric outer structure 9140 may comprise lateral circumferential grooves 9141 between the electrodes 9160, 9162 to promote lateral bending. In one embodiment, this configuration may be inserted into a vertebral channel after the cortical shell has been pierced by a sharp stylet or the like. In one embodiment, at least two instruments are necessary to generate a curved path to the treatment site (e.g., a sharp stylet and a sleeve for guiding instruments).

Figure 41A:
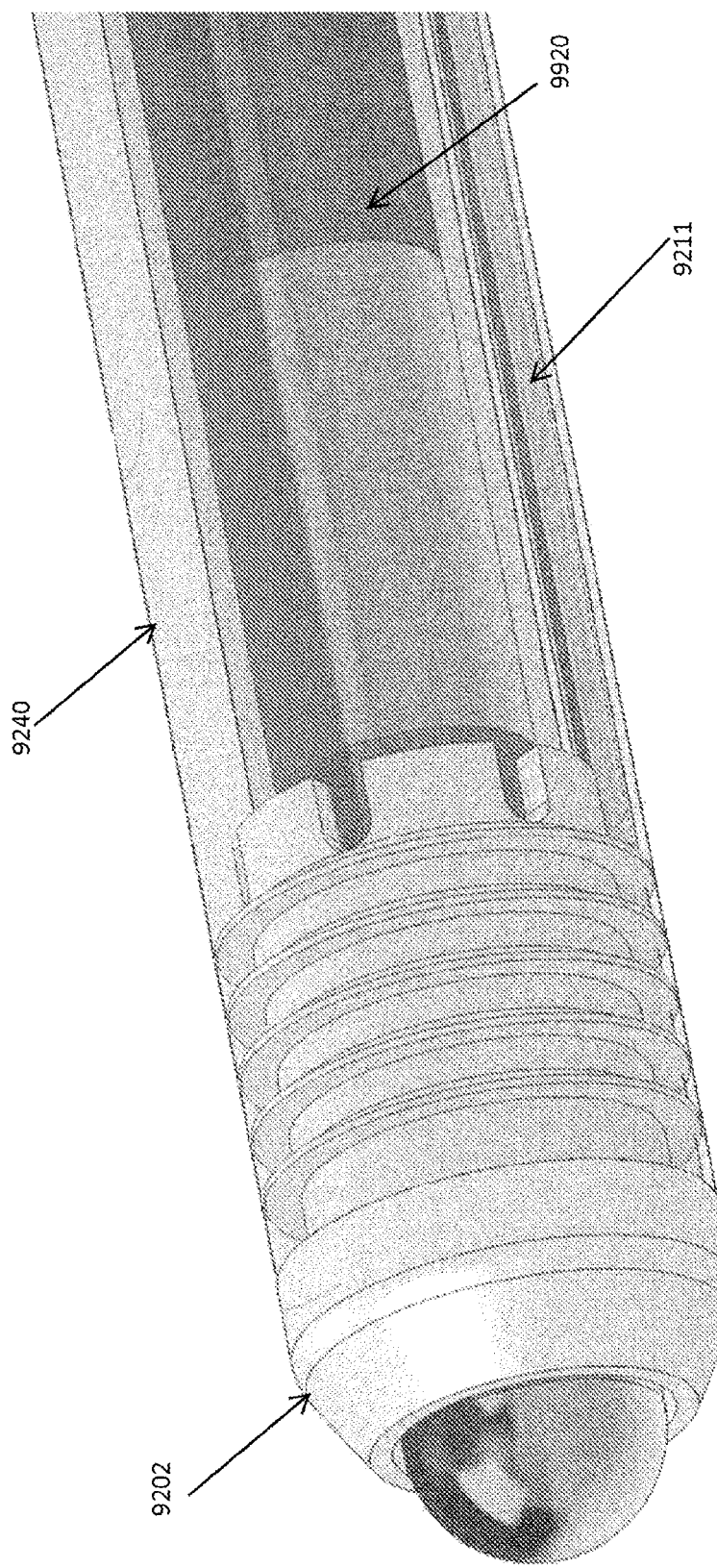
Figure 41B:
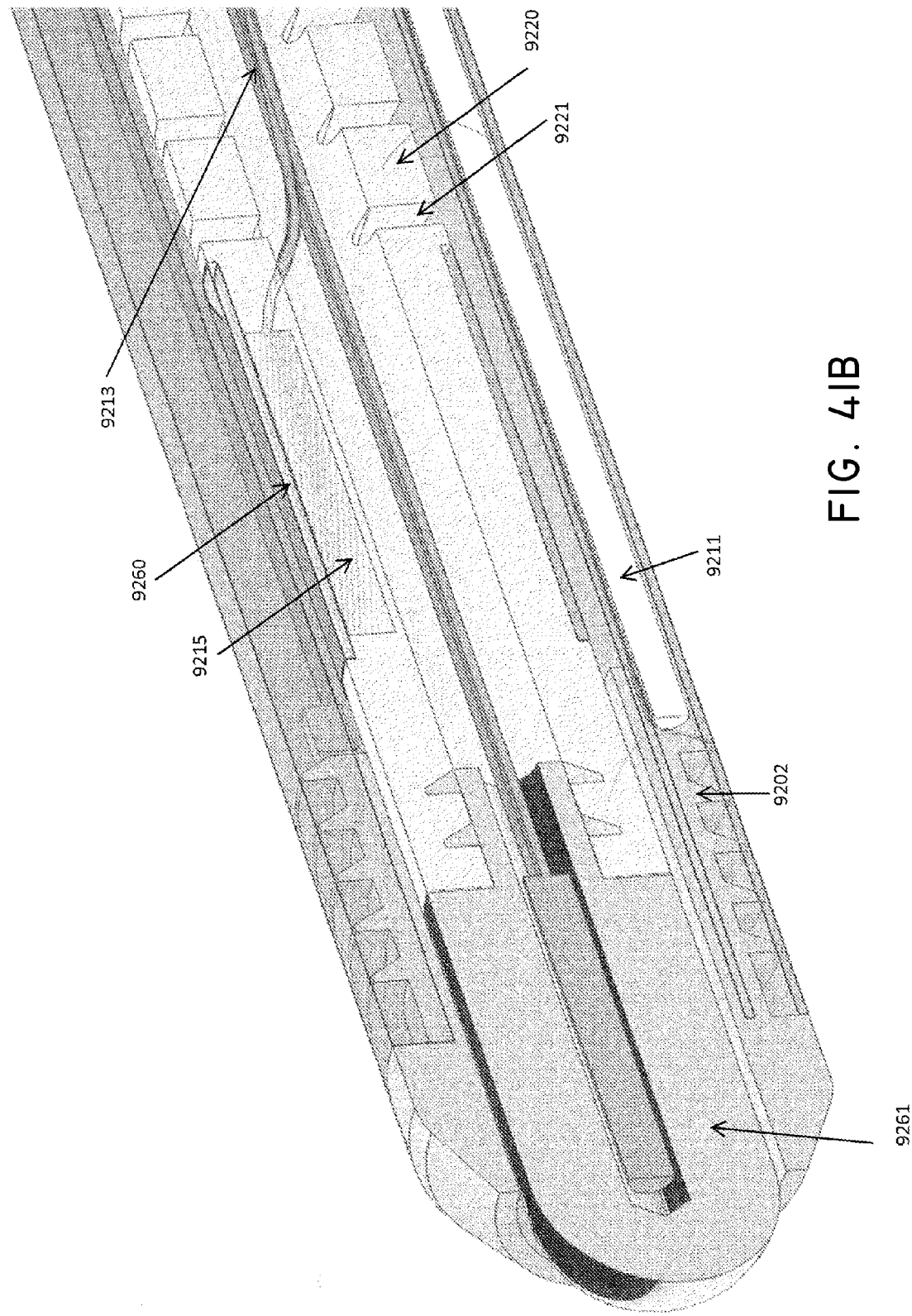
Figure 41C:
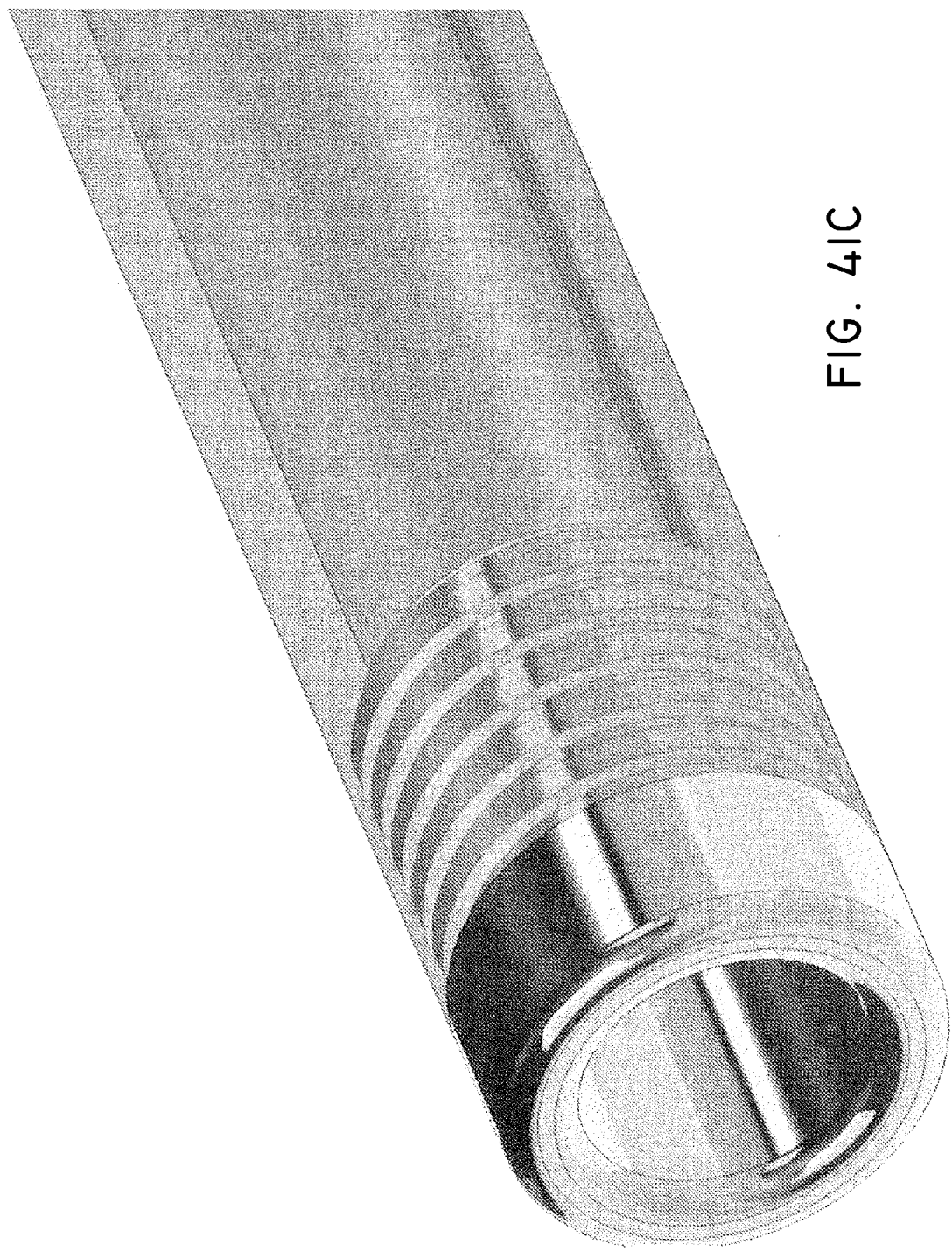

FIGS. 41A-41E illustrate an embodiment of a steerable probe distal end 9201 comprising a steerable sleeve 9240 and a passively-steered treatment probe 9220. In one embodiment, the steerable sleeve 9240 comprises a bendable tube (e.g., PEBAX®) having a trocar channel sized to receive the treatment probe 9220, and a lumen in the sidewall for receiving and allowing reciprocation of the guidewire 9211. In one embodiment, the guidewire 9211 is laser welded to an endcap 9202 that is disposed at the distal end 9201 of the tube 9240. In one embodiment, the endcap 9202 is stainless steel. In one embodiment, the endcap 9202 has a spherical radius, as illustrated in FIG. 41C. In one embodiment, the treatment probe 9220 comprises an elongate shaft (e.g., DELRIN®, also known as polyoxymethylene, acetal, polyacetal, and polyformaldehyde) having lateral slots 9221 to promote bending in one direction (or multiple directions in another embodiment). FIG. 41B illustrates one embodiment of tubular electrodes 9260 of a steerable probe 9200. In one embodiment, the elongate shaft comprises a spherical electrode tip 9261, wherein the elongate shaft has a relief proximal to the distal tip for housing a tubular electrode 9260. The elongate shaft may comprise a central channel for electrode wiring 9213 and electrode lead 9215. In other embodiments, the elongate shaft may be comprised of a different thermoplastic which demonstrates high stiffness and low friction characteristics (e.g., Celcon® or Hostaform®).

In one embodiment, during operation, the treatment probe 9220 is configured to be disposed within the steerable sleeve 9240 so that the spherical tip of the electrode 9261 protrudes out of the distal end of the central channel of the sleeve 9240, and acts as a stylet while the probe 9220 and sleeve 9240 are guided in a curved path to the treatment site. Prior to delivery of the treatment probe 9220, a sharp stylet (not shown) may be inserted in the sleeve 9240 for piercing the outer cortical shell of the vertebral body. The stylet may then be removed and the treatment probe 9220 may be inserted for delivery to the treatment site via a steered, curved path. Upon reaching the treatment site, the sleeve 9240 may be retracted (or probe 9220 advanced) to expose the second of two bipolar electrodes for treatment.

Figure 42A:
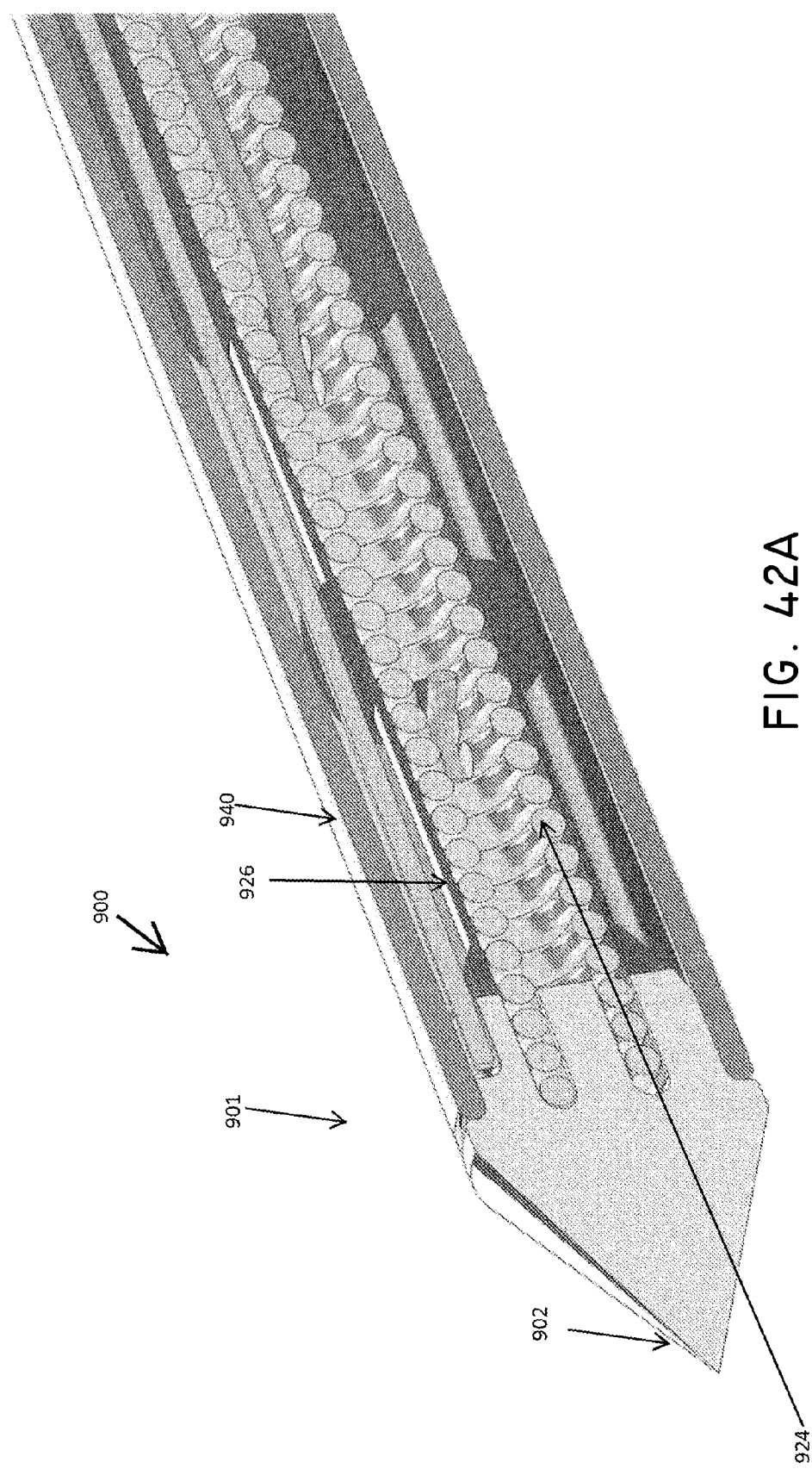
FIGS. 42A-42B illustrate an embodiment of a steerable probe system comprising a one-instrument design with a steerable inner probe and a retractable sleeve.
Figure 42B:
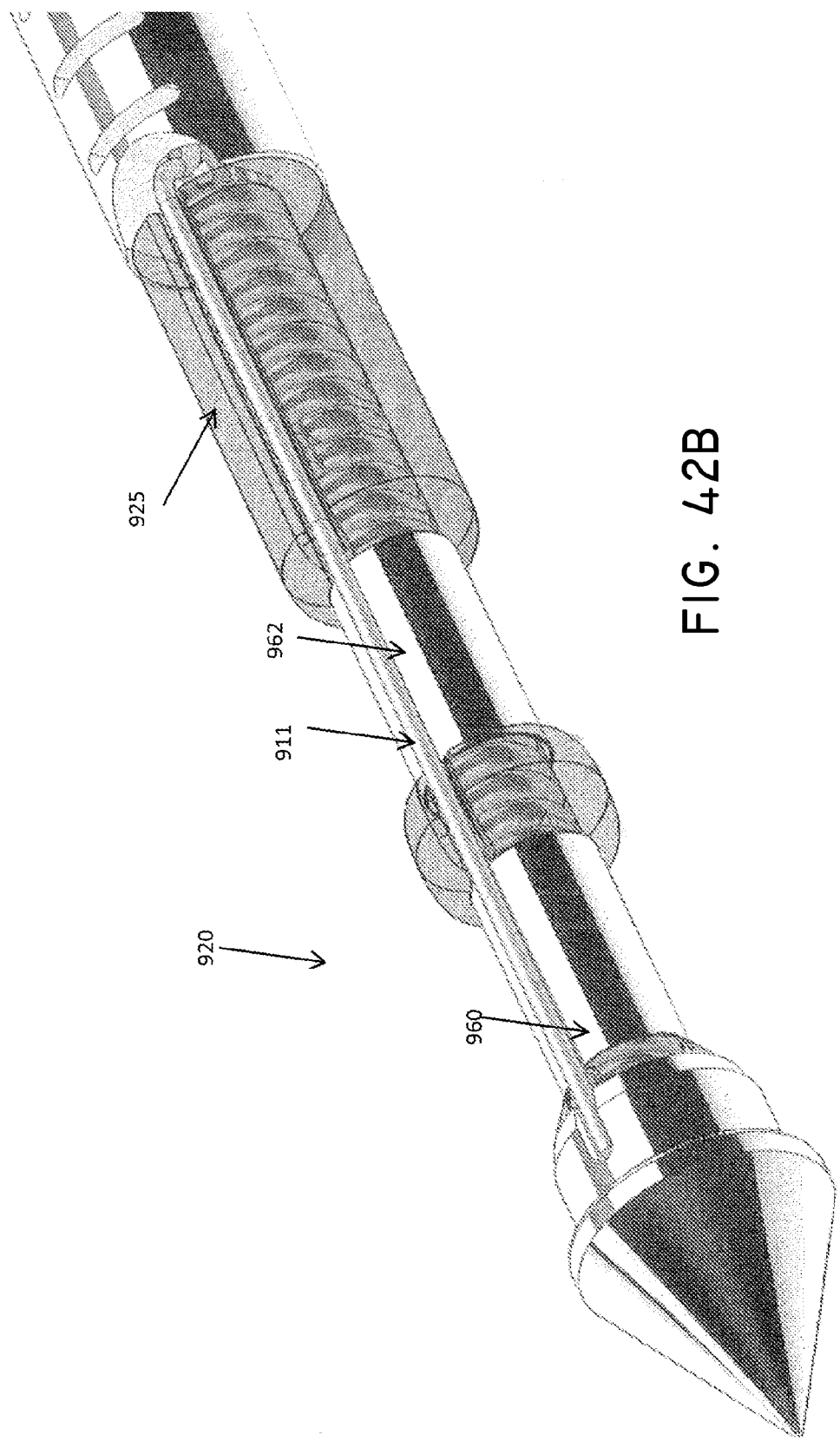

FIGS. 42A-42B illustrate an embodiment of a steerable probe 900 with a steerable probe distal end 901 comprising a single-instrument design with a steerable inner probe 920 and a retractable sleeve 940. The steerable probe 900 comprises a sharp distal tip 902 for piercing a cortical shell and channeling a path through cancellous bone. In one embodiment, attached proximal to the sharp distal tip 902 is a helical tubular segment 924 that provides lateral bendability, while being axially stiff when the sheath is in the position shown in FIG. 42B. As shown in FIG. 42A, a pull wire 911 may be coupled to the distal tip 902, with channeling through polymer spacers 925. In one embodiment, two spaced apart tubular electrodes 960, 962 surround a helical segment 924 just proximal to the distal end and have a layer of polymer 926 disposed between the electrodes 960, 962 and the helical segment 924 as shown in FIG. 42A. The sheath 940 may be disposed in the distal position as illustrated in FIG. 42A for channeling, and then retracted to allow for electrodes to be exposed for treatment.

Figure 42C:
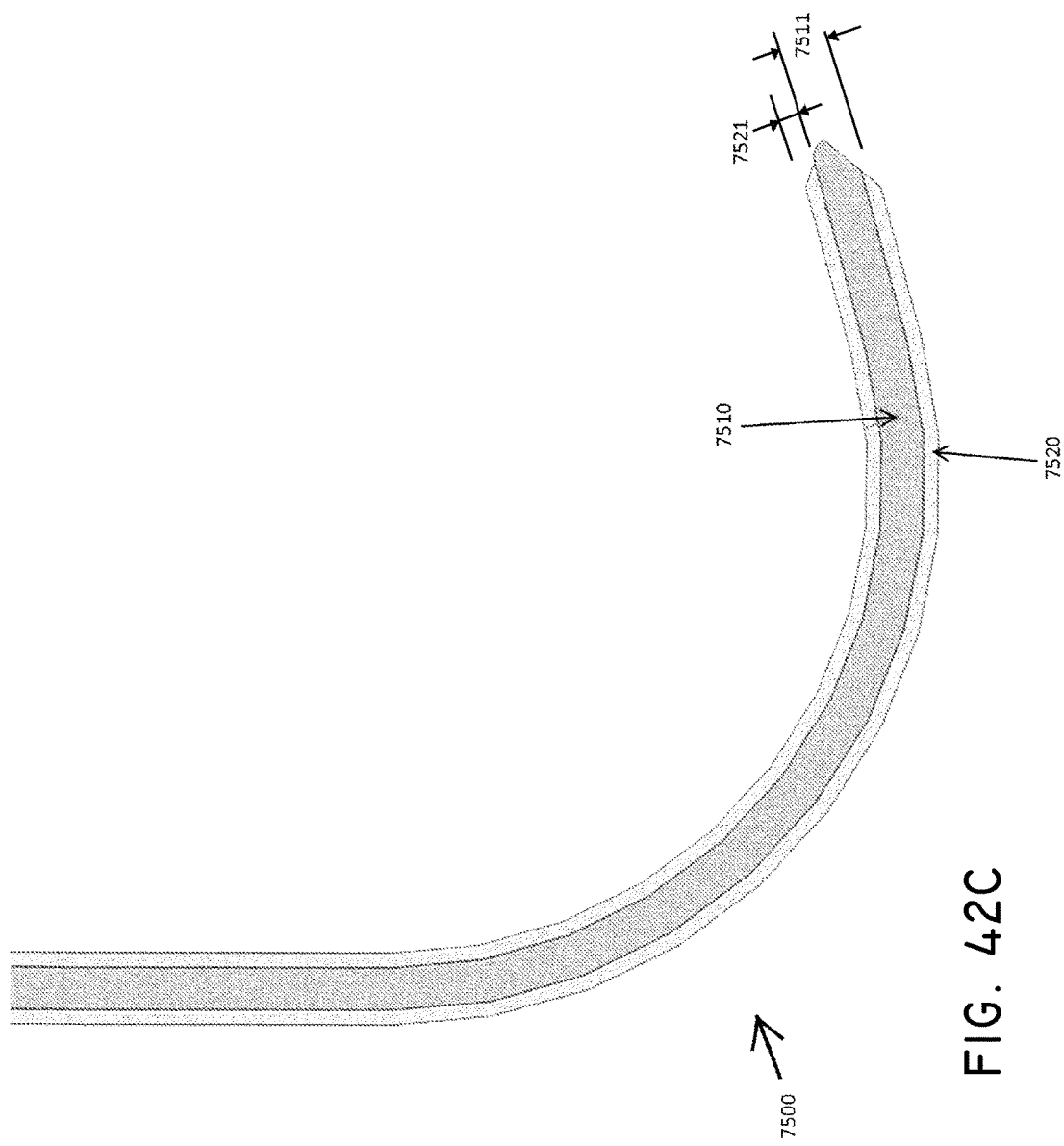
FIG. 42C illustrates an embodiment of a curved stylet.

FIG. 42C illustrates an embodiment of a curved stylet 7500 (e.g., J-shaped stylet) capable of use with any of the systems (e.g., bone channeling, intraosseous nerve access and/or neuromodulation systems) described herein. The curved stylet 7500 comprises an inner core 7510 and an outer tube 7520. In several embodiments, the inner core 7510 comprises an elastic metal alloy (e.g., nitinol, stainless steel, etc.). The diameter 7511 of the inner core 7510 may be in the range of about 0.010" to about 0.080" (e.g., 0.010" to 0.050", 0.015" to 0.045", 0.020" to 0.080", 0.025" to 0.075", 0.030" to 0.080", 0.050" to 0.080", 0.010" to 0.030", or overlapping ranges thereof). In one embodiment, the diameter 7511 is constant along the entire length of the inner core 7510. In several embodiments, the outer tube 7520 comprises a polymer (e.g., PEEK, PEBAX®, polyolefin, etc.). The range of wall thickness 7521 of the outer tube 7520 may be in the range of about 0.005" to about 0.040". In some embodiments, the overall diameter of the stylet 7500 is about 0.090". In one embodiment the overall diameter of the stylet 7500 is constant along the entire length of the stylet 7500, advantageously allowing the stylet 7500 to conform to the inner diameter along the entire length of a cannula (e.g., any of the curved or curveable cannulas described herein). If the overall diameter were to be increased, then the range of the wall thickness and diameter of inner core may also both increase. In accordance with several embodiments, the stiffness of the stylet 7500 can advantageously be altered by manipulating the diameter 7511 of the inner core 7510, manipulating the wall thickness 7521 of the outer tube 7520, or a combination of both. In some embodiments, the distal tip of the stylet 7500 is angled but not sharp. In one embodiment, the distal tip of the stylet 7500 is at least partially rounded or blunt. In some embodiments, outer tube 7520 extends laterally beyond inner core 7510 and surrounds the distal tip of the inner core 7510. When the stylet 7500 is disposed within a cannula, lumen or hypotube of any previous embodiment, the stylet 7500 may be in contact with and provide lateral support for the cannula, lumen or hypotube.

In general, it may be desirable to operate embodiments of the invention in a manner that produce a peak temperature in the target tissue of between about 80° C. and 95° C. When the peak temperature is below 80° C., the off-peak temperatures may quickly fall below about 45° C. When the peak temperature is above about 95° C., the bone tissue exposed to that peak temperature may experience necrosis and produce charring. This charring reduces the electrical conductivity of the charred tissue, thereby making it more difficult to pass RF current through the target tissue beyond the char and to resistively heat the target tissue beyond the char. In some embodiments, the peak temperature is between 86° C. and 94° C., between 80° C. and 90° C., 85° C., overlapping ranges thereof, or any temperature value between 80° C. and 95° C.

It may be desirable to heat the volume of target tissue to a minimum temperature of at least 42° C., in accordance with several embodiments. When the tissue experiences a temperature above 42° C., nerves within the target tissue may be desirably damaged. However, it is believed that denervation is a function of the total quantum of energy delivered to the target tissue; i.e., both exposure temperature and exposure time determine the total dose of energy delivered.

Typically, the period of time that an intraosseous nerve is exposed to therapeutic temperatures is in general related to the length of time in which the electrodes are activated. In some embodiments, the electrodes, when the peak temperature is between 80° C. and 95° C., may be activated between 10 and 20 minutes, between 10 and 15 minutes, 12 minutes, 15 minutes, less than 10 minutes, greater than 20 minutes, or any duration of time between 10 and 20 minutes, to achieve the minimum target tissue temperature such that the nerve tissue is modulated (e.g., denervated). However, since it has been observed that the total heating zone remains relatively hot even after power has been turned off (and the electric field eliminated), the exposure time can include a period of time in which current is not running through the electrodes.

In general, the farther apart the electrodes, the greater the likelihood that the ION will be contained within the total heating zone. Therefore, in some embodiments the electrodes are placed at least 5 mm apart or at least 10 mm apart. However, if the electrodes are spaced too far apart, the electric field takes on an undesirably extreme dumbbell shape. Therefore, in many embodiments, the electrodes are placed apart a distance of between 1 mm and 25 mm, between 5 mm and 15 mm, between 10 mm and 15 mm between 3 mm and 10 mm, between 8 mm and 13 mm, between 10 mm and 18 mm, between 12 mm and 20 mm between 20 and 25 mm, between 1 mm and 3 mm, or any integer or value between 1 mm and 25 mm.

In some embodiments, it is desirable to heat the target tissue so that at least about 1 cc of bone tissue experiences the minimum temperature. This volume corresponds to a sphere having a radius of about 0.6 cm. Alternatively stated, it is desirable to heat the target tissue so the minimum temperature is achieved by every portion of the bone within 0.6 cm of the point experiencing the peak temperature.

In accordance with several embodiments, it is desirable to heat the target tissue so that at least about 3 cc of bone experiences the minimum temperature. This volume corresponds to a sphere having a radius of about 1 cm (e.g., 0.7 cm, 0.8 cm. 0.9 cm, 1.0 cm, 1.1 cm, 1.2 cm, 1.3 cm, 1.4 cm).

Some embodiments provide a steady-state heated zone having a peak temperature of between 80° C. and 95° C. (e.g., between 86° C. and 94° C., between 80° C. and 90° C., or overlapping ranges thereof), and heat at least 1 cc of bone (e.g., at least 2 cc of bone, at least 3 cc of bone, at least 4 cc of bone, at least 5 cc of bone) to a temperature of at least 50° C. (e.g., 60° C.).

In accordance with several embodiments, a method of therapeutically treating a vertebral body having a basivertebral nerve comprises providing an energy device having an active and a return electrode, inserting the active electrode into the vertebral body, inserting the return electrode into the vertebral body, and applying a sufficiently high frequency voltage difference between the active and return electrodes to generate a current therebetween to produce a total heating zone having a diameter of at least 0.5 cm and a steady state temperature of at least 50° C.

As noted above, a peak temperature below about 100° C. or below about 105° C. is desirable in order to prevent charring of the adjacent tissue, steam formation and tissue popping. In some embodiments, this is accomplished by providing the power supply with a feedback means that allows the peak temperature within the heating zone to be maintained at a desired target temperature, such as 90° C. In some embodiments, the peak temperature is in the range of 85° C. to 95° C. In other embodiments, the peak temperature is between about 70° C. and 90° C.

In some embodiments, between about 24 watts and 30 watts of power is first supplied to the device in order to rapidly heat the relatively cool bone, with maximum amperage being obtained within about 10-15 seconds. In other embodiments, between about 28 watts and 32 watts of power, between about 20 watts and 26 watts of power, between 30 watts and 40 watts of power, between 15 watts and 24 watts of power, overlapping ranges thereof, or any power level within the ranges, is first supplied to the device.

In some embodiments, the maximum amperage may be obtained within 5-10 seconds, within about 15-25 seconds, within about 7-12 seconds, within about 13-18 seconds, overlapping ranges thereof, or any duration within the recited ranges. As the bone is further heated to the target temperature, the feedback means gradually reduces the power input to the device to between about 6-10 watts. In some embodiments, the power input is reduced to between 4-7 watts, about 8-12 watts, between 2-6 watts, between about 7-15 watts, or overlapping ranges thereto.

Cooling may be employed for any of the neuromodulation devices (e.g., energy delivery devices) described herein. In several embodiments, a cooling balloon or other cooling device or fluid (e.g., heat removal elements, heat sinks, cooling fluid circulating through one or more lumens of the neuromodulation device) is used for cooling the treatment zone or location or the area surrounding the treatment zone or location.

If the active electrode has no active cooling means, it may become subject to conductive heating by the heated tissue, and the resultant increased temperature in the electrode may adversely affect performance by charring the adjacent bone tissue. Accordingly, in some embodiments, a cool tip active electrode may be employed. The cooled electrode helps maintain the temperature of the electrode at a desired temperature. Cooled tip active electrodes are known in the art. Alternatively, the power supply may be designed to provide a pulsed energy input. It has been found that pulsing the current favorably allows heat to dissipate from the electrode tip, and so the active electrode stays relatively cooler.

In various embodiments, the neuromodulation device comprises an electrosurgical probe having a shaft with a proximal end, a distal end, and at least one active electrode at or near the distal end. A connector may be provided at or near the proximal end of the shaft for electrically coupling the active electrode to a high frequency voltage source. In some embodiments, a return electrode coupled to the voltage source is spaced a sufficient distance from the active electrode to substantially avoid or minimize current shorting therebetween. The return electrode may be provided integral with the shaft of the probe or it may be separate from the shaft In some embodiments, the electrosurgical probe or catheter comprises a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft.

In several embodiments, the shaft is a rigid needle that is introduced through a percutaneous penetration in the patient. However, for endoscopic procedures within the spine, the shaft may have a suitable diameter and length to allow the surgeon to reach the target site (e.g., a disc) by delivering the shaft through the thoracic cavity, the abdomen or the like. Thus, the shaft may have a length in the range of about 5.0 to 30.0 cm (e.g., about 5-10, 10-15, 10-20, or 10-30 cm, or overlapping ranges thereof), and a diameter in the range of about 0.2 mm to about 10 mm (e.g., about 0.2-1, 1-2, 2-4, 2-6, 6-8, or 5-10 mm, or overlapping ranges thereof). In any of these embodiments, the shaft may also be introduced through rigid or flexible endoscopes.

The probe may include one or more active electrode(s) for applying electrical energy to tissues within the spine. The probe may include one or more return electrode(s), or the return electrode may be positioned on the patient's back, as a dispersive pad. In either embodiment, sufficient electrical energy is applied through the probe to the active electrode(s) to either necrose the blood supply or nerves within the vertebral body.

The electrosurgical instrument may also be a catheter that is delivered percutaneously and/or endoluminally into the patient by insertion through a conventional or specialized guide catheter, or the invention may include a catheter having an active electrode or electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The catheter shaft may include a plurality of wires or other conductive elements running axially therethrough to permit connection of the electrode or electrode array and the return electrode to a connector at the proximal end of the catheter shaft. The catheter shaft may include a guide wire for guiding the catheter to the target site, or the catheter may comprise a steerable guide catheter. The catheter may also include a substantially rigid distal end portion to increase the torque control of the distal end portion as the catheter is advanced further into the patient's body. Specific deployment means will be described in detail in connection with the figures hereinafter.

In some embodiments, the electrically conductive wires may run freely inside the catheter bore in an unconstrained made, or within multiple lumens within the catheter bore.

The tip region of the instrument may comprise many independent electrode terminals designed to deliver electrical energy in the vicinity of the tip. The selective application of electrical energy is achieved by connecting each individual electrode terminal and the return electrode to a power source having independently controlled or current limited channels. The return electrode(s) may comprise a single tubular member of conductive material proximal to the electrode array. Alternatively, the instrument may comprise an array of return electrodes at the distal tip of the instrument (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing or preventing energy delivery to surrounding (non-target) tissue, such as the spinal cord.

Temperature probes associated with the apparatus may be disposed on or within the electrode carrier; between the electrodes (may be preferred in bipolar embodiments); or within the electrodes (may be preferred for monopolar embodiments). In some embodiments wherein the electrodes are placed on either side of the ION, a temperature probe is disposed between the electrodes or in the electrodes. In alternate embodiments, the deployable portion of the temperature probe comprises a memory metal.

The electrode terminal(s) may be supported within or by an inorganic insulating support positioned near the distal end of the instrument shaft. The return electrode may be located on the instrument shaft, on another instrument or on the external surface of the patient (i.e., a dispersive pad). In some embodiments, the close proximity of the dual needle design to the intraosseous nerve makes a bipolar design more preferable because this minimizes the current flow through non-target tissue and surrounding nerves. Accordingly, the return electrode may be either integrated with the instrument body, or another instrument located in close proximity thereto. The proximal end of the instrument(s) may include the appropriate electrical connections for coupling the return electrode(s) and the electrode terminal(s) to a high frequency power supply, such as an electrosurgical generator.

In some embodiments, the active electrode(s) have an active portion or surface with surface geometries shaped to promote the electric field intensity and associated current density along the leading edges of the electrodes. Suitable surface geometries may be obtained by creating electrode shapes that include sharp edges, or by creating asperities or other surface roughness on the active surface(s) of the electrodes. Electrode shapes can include the use of formed wire (e.g., by drawing round wire through a shaping die) to form electrodes with a variety of cross-sectional shapes, such as square, rectangular, L or V shaped, or the like. The electrodes may be tip electrodes, ring electrodes, plate electrodes, cylindrical electrodes, frustoconical electrodes, or any other shape electrodes. Electrode edges may also be created by removing a portion of the elongate metal electrode to reshape the cross-section. For example, material can be ground along the length of a round or hollow wire electrode to form D or C shaped wires, respectively, with edges facing in the cutting direction. Alternatively, material can be removed at closely spaced intervals along the electrode length to form transverse grooves, slots, threads or the like along the electrodes. In other embodiments, the probe can be sectored so that a given circumference comprises an electrode region and an inactive region. In some embodiments, the inactive region is masked.

The return electrode is, in several embodiments, spaced proximally from the active electrode(s) a suitable distance. In most of the embodiments described herein, the distal edge of the exposed surface of the return electrode is spaced about 1 to 25 mm (or any distance therebetween) from the proximal edge of the exposed surface of the active electrode(s), in dual needle insertions. Of course, this distance may vary with different voltage ranges, the electrode geometry and depend on the proximity of tissue structures to active and return electrodes. In several embodiments, the return electrode has an exposed length in the range of about 1 to 20 mm, about 2 to 6 mm, about 3 to 5 mm, about 1 to 8 mm, about 4 to 12 mm, about 6 to 16 mm, about 10 to 20 mm, 4 mm, 5 mm, 10 mm, or any length between 1 and 20 mm. The application of a high frequency voltage between the return electrode(s) and the electrode terminal(s) for appropriate time intervals effects modifying the target tissue. In several embodiments, the electrodes have an outer diameter of between 1 and 2 mm (e.g., between 1 and 1.5 mm, between 1.2 and 1.8 mm, between 1.5 and 1.7 mm, between 1.6 and 2 mm, 1.65 mm, or any outer diameter between the recited ranges). In several embodiments, the electrodes have an inner diameter of between 0.5 and 1.5 mm (e.g., between 0.5 and 0.8 mm, between 0.75 and 0.9 mm, between 0.8 and 1 mm, between 1 mm and 1.5 mm, 0.85 mm, or any inner diameter between the recited ranges).

Embodiments may use a single active electrode terminal or an array of electrode terminals spaced around the distal surface of a catheter or probe. In the latter embodiment, the electrode array usually includes a plurality of independently current limited and/or power-controlled electrode terminals to apply electrical energy selectively to the target tissue while limiting the unwanted application of electrical energy to the surrounding tissue and environment resulting from power dissipation into surrounding electrically conductive fluids, such as blood, normal saline, and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the catheter to form a single wire that couples to a power source.

In one configuration, each individual electrode terminal in the electrode array is electrically insulated from all other electrode terminals in the array within said instrument and is connected to a power source which is isolated from each of the other. electrode terminals in the array or to circuitry which limits or interrupts current flow to the electrode terminal when low resistivity material (e.g., blood) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In one embodiment, lower impedance paths may automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode terminal(s) due to oxide layers which form selected electrode terminals (e.g., titanium or a resistive coating on the surface of me till, such as platinum).

In one embodiment of the invention, the active electrode comprises an electrode array having a plurality of electrically isolated electrode terminals disposed over a contact surface, which may be a planar or non-planar surface and which may be located at the distal tip or over a lateral surface of the shaft, or over both the tip and lateral surface(s). The electrode array may include at least two or more electrode terminals and may further comprise a temperature sensor. In one embodiment, each electrode terminal may be connected to the proximal connector by an electrically isolated conductor disposed within the shaft. The conductors permit independent electrical coupling of the electrode terminals to a high frequency power supply and control system with optional temperature monitor for operation of the probe. The control system may advantageously incorporate active and/or passive current limiting structures, which are designed to limit current flow when the associated electrode terminal is in contact with a low resistance return path back to the return electrode.

In one embodiment, the use of such electrode arrays in electrosurgical procedures may be particularly advantageous as it has been found to limit the depth of tissue necrosis without substantially reducing power delivery. The voltage applied to each electrode terminal causes electrical energy to be imparted to any body structure which is contacted by, or comes into close proximity with, the electrode terminal, where a current flow through all low electrical impedance paths may be limited. Since some of the needles are hollow, a conductive fluid could be added through the needle and into the bone structure for the purposes of lowering the electrical impedance and fill the spaces in the cancellous bone to make them better conductors to the needle.

It should be clearly understood that embodiments of the invention are not limited to electrically isolated electrode terminals, or even to a plurality of electrode terminals. For example, the array of active electrode terminals may be connected to a single lead that extends through the catheter shaft to a power source of high frequency current. Alternatively, the instrument may incorporate a single electrode that extends directly through the catheter shaft or is connected to a single lead that extends to the power source. The active electrode(s) may have ball shapes, twizzle shapes, spring shapes, twisted metal shapes, cone shapes, annular or solid tube shapes or the like. Alternatively, the electrode(s) may comprise a plurality of filaments, rigid or flexible brush electrode(s), side-effect brush electrode(s) on a lateral surface of the shaft, coiled electrode(s) or the like.

The voltage difference applied between the return electrode(s) and the electrode terminal(s) can be at high or radio frequency (e.g., between about 50 kHz and 20 MHz, between about 100 kHz and 2.5 MHz, between about 400 kHz and 1000 kHz, less than 600 kHz, between about 400 kHz and 600 kHz, overlapping ranges thereof, 500 kHz, or any frequency within the recited ranges. The RMS (root mean square) voltage applied may be in the range from about 5 volts to 1000 volts, in the range from about 10 volts to 200 volts, between about 20 to 100 volts, between about 40 to 60 volts, depending on the electrode terminal size, the operating frequency and the operation mode of the particular procedure. Lower peak-to-peak voltages may be used for tissue coagulation, thermal heating of tissue, or collagen contraction and may be in the range from 50 to 1500, from 100 to 1000, from 120 to 400 volts, from 100 to 250 volts, from 200 to 600 volts, from 150 to 350 volts peak-to-peak, overlapping ranges thereof, or any voltage within the recited ranges. As discussed above, the voltage may be delivered continuously with a sufficiently high frequency (e.g., on the order of 50 kHz to 20 MHz) (as compared with e.g., lasers claiming small depths of necrosis, which are generally pulsed about 10 to 20 Hz). In addition, the sine wave duty cycle (i.e., cumulative time in anyone-second interval that energy is applied) may be on the order of about 100%, as compared with pulsed lasers which typically have a duty cycle of about 0.0001%. In various embodiments, the current ranges from 50 to 300 mA (e.g., from 50 to 150 mA, from 100 to 200 mA, from 150 to 300 mA, overlapping ranges thereof, or any current level within the recited ranges).

A power source may deliver a high frequency current selectable to generate average power levels ranging from several milliwatts to tens of watts per electrode, depending on the volume of target tissue being heated, and/or the maximum allowed temperature selected for the instrument, tip. The power source allows the user to select the power level according to the specific requirements of a particular procedure.

The power source may be current limited or otherwise controlled so that undesired heating of the target tissue or surrounding (non-target) tissue does not occur. In one embodiment, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909. Additionally, current limiting resistors may be selected. In several embodiments, microprocessors are employed to monitor the measured current and control the output to limit the current.

The area of the tissue treatment surface can vary widely, and the tissue treatment surface can assume a variety of geometries, with particular areas and geometries being selected for specific applications. The geometries can be planar, concave, convex, hemispherical, conical, linear "in-line" array or virtually any other regular or irregular shape. Most commonly, the active electrode(s) or electrode terminal(s) can be formed at the distal tip of the electrosurgical instrument shaft, frequently being planar, disk-shaped, ring-shaped, or hemispherical surfaces for use in reshaping procedures or being linear arrays for use in cutting. Alternatively or additionally, the active electrode(s) may be formed on lateral surfaces of the electrosurgical instrument shaft (e.g., in the manner of a spatula), facilitating access to certain body structures in endoscopic procedures.

The devices may be suitably used for insertion into any hard tissue in the human body. In some embodiments, the hard tissue is bone. In other embodiments, the hard tissue is cartilage. In some embodiments when bone is selected as the tissue of choice, the bone is a vertebral body. In several embodiments, devices are adapted to puncture the hard cortical shell of the bone and penetrate at least a portion of the underlying cancellous bone. In some embodiments, the probe advances into the bone to a distance of at least ⅓ of the cross-section of the bone defined by the advance of the probe. Some method embodiments are practiced in vertebral bodies substantially free of tumors. In others, method embodiments are practiced in vertebral bodies having tumors and may be used in conjunction with treatment of tumors.

EXAMPLE

The following Example illustrates some embodiments of the invention and is not intended in any way to limit the scope of the disclosure. Moreover, the methods and procedures described in the following examples, and in the above disclosure, need not be performed in the sequence presented.

A pilot human clinical study was performed to determine efficacy of a minimally invasive technique involving ablation of the basivertebral nerve in providing relief to patients with chronic lower back pain.

In the present study, a radiofrequency device was used to ablate the nerves within the vertebral bone that transmit pain signals. The study involved treatment of 16 human patients with chronic (greater than 6 months) isolated lower back pain who were unresponsive to at least 3 months of non-surgical conservative care. The patients treated and observed in the study were an average of 47.6 years old and had undergone an average of 32.4 months of conservative treatment. The patients all had Oswestry Disability Index (ODI) scores greater than 30 and either pathologic changes or positive provocative discography at the targeted degenerated disc level.

In accordance with several embodiments, the intraosseous course of the basivertebral foramen for the targeted vertebral bodies was visualized and mapped using MRI imaging (e.g., anteroposterior and lateral still images). CT or other imaging techniques can also be used. In the study, treatment was performed using intraoperative fluoroscopy and a transpedicular approach; however, other visualization and approach techniques can be used. The treatment device used during the study was a bipolar radiofrequency probe with a curved obturator. In the study, the bipolar RF probe was inserted through a bone biopsy needle and guided to the target treatment location under fluoroscopy. The bipolar RF probe was then used to ablate the basivertebral nerve in a controlled manner. The RF energy delivered in the study had a frequency of 500 kHz, the temperature at the electrodes was 85° C., and the duration of treatment varied between 5 and 15 minutes. In accordance with several embodiments, the RF energy delivered may be between 400 and 600 kHz (e.g., 450 kHz, 500 kHz, 550 kHz), the temperature at the electrodes may be between 80° C. and 100° C. (e.g., 85° C., 90° C., 95° C.), and the duration of treatment may be between 4 and 20 minutes (e.g., 6 minutes, 8 minutes, 10 minutes, 12 minutes, 15 minutes).

In accordance with several embodiments, the treatment was limited to the L3, L4, L5 and S1 vertebrae. Two-level and three-level intraosseous ablation treatments were performed on various patients. The multiple levels treated during the study were at adjacent levels. Twelve patients were treated at the L4 and L5 levels, two patients were treated at L3 through L5 levels, and two patients were treated at the L5 and S1 levels.

Radiographs found no fractures during the follow-up period, and no remodeling of bone was observed. Thirteen of the sixteen patients reported "profound and immediate relief." The treatment procedure resulted in improved ODI scores and Visual Analogue Pain Scale (VAS) values, which were sustained at one year. ODI scores were significantly improved at six weeks, three months, six months, and twelve months. The mean decrease in ODI scores at 1 year was 31 points. VAS values decreased from a preoperative average of 61.1 to an average of 45.6 at the 1-year follow-up. No device-related serious adverse events were reported. Accordingly, in one embodiment, basivertebral nerve ablation is a safe, simple procedure that is applicable during the early stages of treatment for patients with disabling back pain.

Conditional language, for example, among others, "can," "could," "might," or "may," unless specifically stated otherwise, or otherwise understood within the context as used, is generally intended to convey that certain embodiments include, while other embodiments do not include, certain features, elements and/or steps.

Although certain embodiments and examples have been described herein, aspects of the methods and devices shown and described in the present disclosure may be differently combined and/or modified to form still further embodiments. Additionally, the methods described herein may be practiced using any device suitable for performing the recited steps. Some embodiments have been described in connection with the accompanying drawings. However, it should be understood that the figures are not drawn to scale.

Distances, angles, etc. are merely illustrative and do not necessarily bear an exact relationship to actual dimensions and layout of the devices illustrated. Components can be added, removed, and/or rearranged. Further, the disclosure (including the figures) herein of any particular feature, aspect, method, property, characteristic, quality, attribute, element, or the like in connection with various embodiments can be used in all other embodiments set forth herein.

For purposes of this disclosure, certain aspects, advantages, and novel features of the inventions are described herein. Embodiments embodied or carried out in a manner may achieve one advantage or group of advantages as taught herein without necessarily achieving other advantages. The headings used herein are merely provided to enhance readability and are not intended to limit the scope of the embodiments disclosed in a particular section to the features or elements disclosed in that section. The features or elements from one embodiment of the disclosure can be employed by other embodiments of the disclosure. For example, features described in one figure may be used in conjunction with embodiments illustrated in other figures.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "delivering a therapeutic dose of energy" include "instructing the delivery of a therapeutic dose of energy."

Various embodiments of the invention have been presented in a range format. It should be understood that the description in range format is merely for convenience and brevity and should not be construed as an inflexible limitation on the scope of the invention. The ranges disclosed herein encompass any and all overlap, sub-ranges, and combinations thereof, as well as individual numerical values within that range. For example, description of a range such as from about 5 to about 30 minutes should be considered to have specifically disclosed subranges such as from 5 to 10 degrees, from 10 to 20 minutes, from 5 to 25 minutes, from 15 to 30 minutes etc., as well as individual numbers within that range, for example, 5, 10, 15, 20, 25, 12, 15.5 and any whole and partial increments therebetween. Language such as "up to," "at least," "greater than," "less than," "between," and the like includes the number recited. Numbers preceded by a term such as "about" or "approximately" include the recited numbers. For example, "about 10%" includes "10%." For example, the terms "approximately", "about", and "substantially" as used herein represent an amount close to the stated amount that still performs a desired function or achieves a desired result.

What is claimed is:

1. A system for channeling a path into bone, comprising:
   an introducer having a proximal end, a distal end and a central channel,
   wherein the central channel is disposed along a central axis of the introducer and extends from the proximal end toward the distal end,
   wherein the introducer comprises a distal opening at or near the distal end of the introducer, the distal opening being in communication with the central channel,
   wherein the introducer is configured to be deployed through a cortical bone region and into a cancellous bone region of a vertebral body;
   a curved cannula sized to be received in said central channel and delivered from the proximal end of the introducer toward said distal opening,
   wherein the curved cannula comprises a straight tubular body and a curved distal end configured to be extended laterally outward from the distal opening of the introducer in a curved path extending away from the introducer,
   wherein the curved path is generated through at least a portion of the cancellous bone region of the vertebral body,
   wherein the curved cannula comprises a cannula channel configured to allow a treatment device to be delivered through the cannula channel; and
   a treatment device configured to be delivered through the cannula channel of the curved cannula to a location at or beyond the curved path,
   wherein the proximal end of the introducer comprises a handle comprising:
      a proximal recess,
      wherein the proximal recess is in communication with the central channel to allow reciprocation of the curved cannula within the central channel; and
      a lateral slot in communication with said proximal recess, the lateral slot extending radially outward from the proximal recess at a proximal surface of the handle,
      wherein the lateral slot is configured to allow insertion of the curved cannula such that a central axis of the straight tubular body is at an angle with respect to the central axis of the introducer when the curved distal end of the curved cannula is inserted into the proximal recess.

2. The system of claim 1, wherein the curved distal end of the curved cannula is deformable so as to be delivered in a straight configuration through the introducer and deployed in a curved configuration outward from the distal opening at an angle with respect to the central axis of the introducer.

3. The system of claim 1, wherein the lateral slot comprises a curvilinear bottom surface configured to allow the curved distal end of the curved cannula to be slideably advanced into the proximal recess and the central channel without having to pre-straighten the curved cannula.

4. The system of claim 3, wherein the curvilinear bottom surface comprises a radius substantially matching a radius of the curved distal end of the curved cannula, thereby promoting evenly distributed loading along the curved distal end while the curved distal end is advanced into the proximal recess and the central channel.

5. The system of claim 1, further comprising
   a curved stylet comprising a straight proximal body and a preformed curved distal end.

6. The system of claim 5, wherein a proximal end of the curved cannula comprises a cannula handle comprising:
   a central recess,
   wherein the central recess is in communication with the cannula channel to allow reciprocation of the curved stylet within the cannula channel; and a lateral cannula slot in communication with said central recess, the lateral cannula slot extending radially outward from the central recess at a proximal surface of the cannula handle, wherein the lateral cannula slot is configured to allow insertion of the curved stylet such that a central axis of the straight proximal body is at an angle with respect to a central axis of the cannula channel when the preformed curved distal end of the curved stylet is inserted into the central recess.

7. The system of claim 6, wherein the lateral cannula slot comprises a curvilinear bottom surface configured to allow the preformed curved distal end of the curved stylet to be slideably, advanced into the central recess and the cannula channel, and wherein the curvilinear bottom surface of the cannula handle comprises a radius substantially matching a radius of the preformed curved distal end of the curved stylet.

8. The system of claim 6:
wherein the curved cannula comprises a stop nut threaded about a threaded portion, the threaded portion being distal to the cannula handle and proximal to the straight tubular body;
wherein the stop nut is configured to have a first position on the threaded portion, said stop nut being configured to restrain advancement of the curved cannula within the introducer such that the curved distal end of the cannula does not extend past the distal end of the introducer when the stop nut is in the first position.

9. A system for channeling a path into bone, comprising:
an introducer comprising a proximal end, a distal end and a central channel,
wherein the central channel is disposed along a central axis of the introducer and extends from the proximal end toward the distal end,
wherein the introducer comprises a distal opening at or near the distal end of the introducer, the distal opening being in communication with the central channel;
a curved cannula sized to be received in said central channel and delivered from the proximal end of the introducer toward said distal opening,
wherein the curved cannula comprises a straight tubular body at a proximal end and a curved distal end,
wherein the curved distal end is configured to be extended laterally outward from the distal opening of the introducer in a curved path extending away from the introducer,
wherein the proximal end of the introducer comprises a handle comprising:
a proximal recess,
wherein the proximal recess is in communication with the central channel to allow reciprocation of the curved cannula within the central channel; and
a lateral slot in communication with said proximal recess, the lateral slot extending radially outward from the proximal recess at a proximal surface of the handle,
wherein the lateral slot is configured to allow insertion of the curved cannula such that a central axis of the straight tubular body is at an angle with respect to the central axis of the introducer when the curved distal end of the curved cannula is inserted into the proximal recess.

10. The system of claim 9, wherein the curved distal end of the curved cannula is deformable so as to be delivered in a straight configuration through the introducer and deployed in a curved configuration outward from the distal opening of the introducer at an angle with respect to the central axis.

11. The system of claim 9, wherein the lateral slot comprises a curvilinear bottom surface configured to allow the curved distal end of the curved cannula to be slideably advanced into the proximal recess and the central channel.

12. The system of claim 11, wherein the curvilinear bottom surface comprises a radius substantially matching a radius of the curved distal end of the curved cannula.

13. The system of claim 9, further comprising:
a curved stylet comprising a straight proximal body and a preformed curved distal end,
wherein the curved cannula comprises a cannula channel configured to allow delivery of a treatment device to a location within the bone beyond the curved path.

14. The system of claim 13, wherein the proximal end of the curved cannula comprises a cannula handle comprising:
a central recess,
wherein the central recess is in communication with the cannula channel to allow reciprocation of the curved stylet within the cannula channel; and
a lateral cannula slot in communication with said central recess, the lateral cannula slot extending radially outward from the central recess at a proximal surface of the cannula handle,
wherein the lateral cannula slot is configured to allow insertion of the curved stylet such that a central axis of the straight proximal body is at an angle with respect to a central axis of the cannula channel when the preformed curved distal end of the curved stylet is inserted into the central recess.

15. The system of claim 14, wherein the lateral cannula slot comprises a curvilinear bottom surface configured to allow the preformed curved distal end of the curved stylet to be slideably advanced into the central recess and the cannula channel, wherein the curvilinear bottom surface of the cannula handle comprises a radius substantially matching a radius of the preformed curved distal end of the curved stylet.

16. The system of claim 14:
wherein the curved cannula comprises a stop nut threaded about a threaded portion of the curved cannula, the threaded portion being distal to the cannula handle and proximal to the straight tubular body;
wherein the stop nut is configured to have a first position on the threaded portion, said stop nut being configured to restrain advancement of the curved cannula within the introducer such that the curved distal end of the curved cannula does not extend past the distal end of the introducer when the stop nut is in the first position.

17. A method for channeling a path into a vertebral body of a patient, comprising:
inserting an introducer into the vertebral body, the introducer comprising a proximal end, a distal end and a central channel,
wherein the central channel is disposed along a central axis of the introducer and extends from the proximal end toward the distal end,
wherein the introducer comprises a distal opening at or near the distal end of the introducer, the distal opening being in communication with the central channel,
wherein the proximal end of the introducer comprises a handle comprising a proximal recess in communication with the central channel and a lateral slot in communication with said proximal, recess, the lateral slot extending radially outward from the proximal recess at a proximal surface of the handle, wherein the central channel is sized to receive a curved cannula, the curved cannula comprising a straight tubular body at a proximal end of the curved cannula and a curved distal end, wherein the curved distal end of the curved cannula is deformable so as to be delivered in a straight configuration through the introducer;

inserting the curved distal end of the curved cannula into said proximal recess through the lateral slot and such that a central axis of the straight tubular body is at an angle with respect to the central axis of the introducer;

advancing the curved cannula into the proximal recess, thereby straightening the curved distal end;

advancing the curved cannula within said central channel from the proximal end of the introducer toward the distal opening of the introducer; and extending the curved distal end laterally outward from the distal opening to generate a curved path radially outward from the introducer.

18. The method of claim 17, further comprising delivering a treatment device through the curved cannula to a location beyond the curved path.

19. The method of claim 17, wherein the curved cannula comprises a cannula channel, the proximal end of the curved cannula comprising a cannula handle comprising a central recess in communication with the cannula channel and a lateral cannula slot in communication with said central recess, the lateral cannula slot extending radially outward from the central recess at a proximal surface of the cannula handle, the method further comprising:

inserting a curved stylet into the curved cannula;

the curved stylet comprising a straight proximal body and a preformed curved distal end;

inserting the preformed curved distal end of the curved stylet into the central recess through the lateral cannula slot such that a central axis of the straight proximal body is at an angle with respect to a central axis of the cannula channel of the curved cannula;

advancing the curved stylet into the central recess, thereby straightening the preformed curved distal end;

advancing the curved stylet within said curved cannula from the proximal end to the distal opening of the introducer; and wherein generating the curved path radially outward from the introducer comprises extending the curved distal end of the curved cannula and the preformed curved distal end of the curved stylet in unison laterally outward from the distal opening of the introducer.

20. The method of claim 19:

wherein the curved cannula comprises a stop nut threaded about a threaded portion of the curved cannula, the threaded portion being distal to the cannula handle and proximal to the straight tubular body;

wherein the stop nut is configured to have a first position on the threaded portion;

wherein the curved stylet is advanced within said curved cannula with said stop nut in the first position to restrain advancement of the curved cannula within the introducer such that the curved distal end of the curved cannula does not extend past the distal end of the introducer, wherein the stop nut comprises a second position on the threaded portion configured to allow further translation of the curved cannula with respect to the introducer, the method further comprising:

rotating the stop nut to the second position prior to extending the curved distal end laterally outward from the distal opening.

* * * * *